(12) United States Patent
Wegert et al.

(10) Patent No.: US 10,214,520 B2
(45) Date of Patent: Feb. 26, 2019

(54) SUBSTITUTED AZASPIRO(4.5)DECANE DERIVATIVES

(71) Applicant: Gruenenthal GmbH, Aachen (DE)

(72) Inventors: Anita Wegert, Aldenhoven (DE); Sven Kuehnert, Dueren (DE); Rene Michael Koenigs, Erkelenz (DE); Bert Nolte, Bad Muenstereifel (DE); Klaus Linz, Rheinbach (DE); Stephanie Harlfinger, Basel (DE); Babette-Yvonne Koegel, Langerwehe-Hamich (DE); Paul Ratcliffe, Aachen (DE); Fritz Theil, Berlin (DE); Olga Groeger, Berlin (DE); Birgit Braun, Berlin (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 15/326,138

(22) PCT Filed: Jul. 14, 2015

(86) PCT No.: PCT/EP2015/001445
§ 371 (c)(1),
(2) Date: Jan. 13, 2017

(87) PCT Pub. No.: WO2016/008582
PCT Pub. Date: Jan. 21, 2016

(65) Prior Publication Data
US 2017/0210734 A1  Jul. 27, 2017

(30) Foreign Application Priority Data

Jul. 15, 2014 (EP) .................... 14002439

(51) Int. Cl.
| | | |
|---|---|---|
| *C07D 209/54* | (2006.01) | |
| *C07D 417/06* | (2006.01) | |
| *C07D 209/96* | (2006.01) | |
| *A61K 31/403* | (2006.01) | |
| *A61K 31/4178* | (2006.01) | |
| *A61K 31/4439* | (2006.01) | |
| *A61K 31/454* | (2006.01) | |
| *A61K 31/506* | (2006.01) | |
| *A61K 31/541* | (2006.01) | |
| *C07D 401/06* | (2006.01) | |
| *C07D 401/12* | (2006.01) | |
| *C07D 403/12* | (2006.01) | |
| *C07D 405/06* | (2006.01) | |
| *C07D 409/04* | (2006.01) | |
| *C07D 409/06* | (2006.01) | |
| *C07D 409/14* | (2006.01) | |

(52) U.S. Cl.
CPC .......... *C07D 417/06* (2013.01); *A61K 31/403* (2013.01); *A61K 31/4178* (2013.01); *A61K 31/4439* (2013.01); *A61K 31/454* (2013.01); *A61K 31/506* (2013.01); *A61K 31/541* (2013.01); *C07D 209/54* (2013.01); *C07D 209/96* (2013.01); *C07D 401/06* (2013.01); *C07D 401/12* (2013.01); *C07D 403/12* (2013.01); *C07D 405/06* (2013.01); *C07D 409/04* (2013.01); *C07D 409/06* (2013.01); *C07D 409/14* (2013.01)

(58) Field of Classification Search
CPC .. C07D 209/54; C07D 209/96; C07D 405/06; A61K 31/403
USPC ............. 544/238, 322, 336; 546/200, 270.4, 546/276.7; 548/126, 311.4, 408, 411; 514/409
See application file for complete search history.

(56) References Cited

U.S. PATENT DOCUMENTS

| | | |
|---|---|---|
| 5,091,567 A | 2/1992 | Geibel et al. |
| 5,977,102 A | 11/1999 | Himmelsbach et al. |
| 6,573,386 B1 | 6/2003 | Goenczi et al. |
| 7,157,456 B2 | 1/2007 | Straub et al. |
| 2002/0058687 A1 | 5/2002 | Marfat |
| 2005/0187281 A1 | 8/2005 | Hinze et al. |
| 2005/0192333 A1 | 9/2005 | Hinze et al. |
| 2006/0004034 A1 | 1/2006 | Hinze et al. |
| 2007/0117824 A1 | 5/2007 | Berk et al. |
| 2007/0213351 A1 | 9/2007 | Sundermann et al. |
| 2008/0221141 A1 | 9/2008 | Friderichs et al. |
| 2009/0111842 A1 | 4/2009 | Merla et al. |
| 2009/0156593 A1 | 6/2009 | Zemolka et al. |
| 2009/0247505 A1 | 10/2009 | Zemolka et al. |
| 2009/0247561 A1 | 10/2009 | Zemolka et al. |
| 2009/0286833 A1 | 11/2009 | Oberboersch et al. |

(Continued)

FOREIGN PATENT DOCUMENTS

| | | |
|---|---|---|
| WO | WO 97/32882 A1 | 9/1997 |
| WO | WO 02/085838 A1 | 10/2002 |

(Continued)

OTHER PUBLICATIONS

Damasio, Antonio R., Alzheimer's Disease and Related Dementias, Cecil Textbook of Medicine, 20th Edition, 2:1992-1996 (1996).*
Jordan, V. Craig, Tamoxifen: A Most Unlikely Pioneering Medicine, Nature Reviews: Drug Discovery, 2(3):205-213 (2003).*
Layzer, Degenerative Diseases of the Nervous System, Cecil Textbook of Medicine, 20th Edition, vol. 2, pp. 2050-2057 (1996).*
Marcantoni E., et al., "Cerium(III) Chloride, a Novel Reagent for Nonaqueous Selective Conversion of Dioxolanes to Carbonyl Compounds", J. Org. Chem., vol. 62, No. 12, 1997, American Chemical Society, pp. 4183-4184 (Two (2) pages).
Majumdar et al., "Thiourea: A Novel Cleaving Agent for 1, 3-Dioxolanes", J. Org. Chem., vol. 64, No. 15, Jul. 2, 1999, American Chemical Society, pp. 5682-5685 (Four (4) pages).

(Continued)

*Primary Examiner* — Deepak R Rao
(74) *Attorney, Agent, or Firm* — Norris McLaughlin, PA

(57) ABSTRACT

The invention relates to substituted spirocyclic cyclohexane derivatives which have an affinity for the μ opioid receptor and/or the ORL1 receptor, processes for the preparation thereof, medicaments containing these compounds and the use of these compounds for the preparation of medicaments.

15 Claims, No Drawings

(56) References Cited

U.S. PATENT DOCUMENTS

| | | | |
|---|---|---|---|
| 2010/0009986 | A1 | 1/2010 | Zemolka et al. |
| 2010/0048553 | A1 | 2/2010 | Schunk et al. |
| 2010/0048554 | A1 | 2/2010 | Schunk et al. |

FOREIGN PATENT DOCUMENTS

| | | | |
|---|---|---|---|
| WO | WO 2004/043967 A1 | 5/2004 | |
| WO | WO 2005/063769 A1 | 7/2005 | |
| WO | WO 2005/066183 A1 | 7/2005 | |
| WO | WO 2006/018184 A2 | 2/2006 | |
| WO | WO 2006/031610 A2 | 3/2006 | |
| WO | WO 2006/034015 A1 | 3/2006 | |
| WO | WO 2006/108565 A1 | 10/2006 | |
| WO | WO 2007/019987 A1 | 2/2007 | |
| WO | WO 2007/030061 A1 | 3/2007 | |
| WO | WO 2007/070826 A1 | 6/2007 | |
| WO | WO 2007/079930 A1 | 7/2007 | |
| WO | WO 2007/124903 A1 | 11/2007 | |
| WO | WO 2007/127763 A2 | 11/2007 | |
| WO | WO 2008/009415 A2 | 1/2008 | |
| WO | WO 2008/009416 A1 | 1/2008 | |
| WO | WO 2008/034731 A1 | 3/2008 | |
| WO | WO 2008/036755 A1 | 3/2008 | |
| WO | WO 2008/101659 A1 | 8/2008 | |
| WO | WO 2008/101660 A1 | 8/2008 | |
| WO | WO 2008/129007 A1 | 10/2008 | |
| WO | WO 2009/111056 A1 | 9/2009 | |
| WO | WO 2009/118169 A1 | 10/2009 | |
| WO | WO 2009/118173 A1 | 10/2009 | |
| WO | WO 2013/057320 A1 | 4/2013 | |

OTHER PUBLICATIONS

Alberati, D., et al., "4-Substituted-8-(1-Phenyl-Cyclohexyl)-2,8-Diaza-Spiro[4.5]Decan-1-One as a Novel Class of Highly Selective GlyT1 Inhibitors with Superior Pharmacological and Pharmacokinetic Parameters", Bioorganic & Medicinal Chemistry Letters, 16, Jun. 9, 2006, pp. 4321-4325 (Five (5) pages).

Wang, J., et al., "Discovery of Spiro-Piperidine Inhibitors and Their Modulation of the Dynamics of the M2 Proton Channel from Influenza A Virus", JACS Articles, J. Am. Chem., Soc., vol. 131, No. 23, May 26, 2009, pp. 8066-8076 (Eleven (11) pages).

Bhandari, K., et al., "A Convenient Method for the Reduction of Amides to Their Corresponding Amines", Communications to the Editor, Chemistry & Industry, Sep. 3, 1990, pp. 547-548 (Two (2) pages).

Hutchins, R. O., et al., "Tetraalkylammonium Trihydridocyanoborates. Versatile, Selective Reagents for Reductive Aminations in Nonpolar Media", J. Org. Chem., 1981, vol. 46, No. 17, 1981, pp. 3571-3574 (Four (4) pages).

Setaki, D., et al., "Synthesis, Conformational Characteristics and Anti-Influenza Virus A Activity of Some 2-Adamantylsubstituted Azacycles", Bioorganic Chemistry, Aug. 1, 2006, 34, pp. 248-273 (Twenty-six (26) pages).

Stamatiou, et al., "Novel 3-(2-Adamantyl)Pyrrolidines with Potent Activity Against Influenza A Virus-Identification of Aminoadamantane Derivatives Bearing Two Pharmacophoric Amine Groups", Bioorganic & Medicinal Chemistry Letters, 11, 2001, Elsevier Science Ltd., pp. 2137-2142 (Six (6) pages).

Posner, G. H., et al., "Nitroolefins in One-Flask, Tandem, A+B+C Coupling Reactions Producing Heterocycles", Tetrahedron vol. 46, No. 21, 1990, Pergamon Press Plc, pp. 7509-7530 (Twenty-two (22) pages).

Flintoft, R. J., et al., "Alkylation of Ketone and Ester Lithium Enolates with Nitroethylene", Tetrahedron Letters, 40, 1999, Elsevier Science Ltd., pp. 4485-4488 (Four (4) pages).

Krafft, E. A., et al., "A Straightfoward and Efficiently Scaleable Synthesis of Novel Racemic 4-Substituted-2,8-Diazaspiro[4.5]Decan-1-One Derivatives", Synthesis 2005, Oct. 28, 2005, No. 19, pp. 3245-3252 (Eight (8) pages).

Van Leusen, D., et al., "Synthetic Uses of Tosylmethyl Isocyanide (TosMIC)", Organic Reactions, 57, Chapter 3, 2001, pp. 417-679 (Ninety-four (94) pages).

Whitlock, G. A., et al., "Novel 2-Imidazoles as Potent and Selective $\alpha_{1A}$ Adrenoseptor Partial Agonists", Bioorganic & Medicinal Chemistry Letters, 18, Mar. 29, 2008, Elsevier Ltd., pp. 2930-2934 (Five (5) pages).

Geffken, D., et al., "Synthese and Eigenschaften von 2-Hydroxycarbohydroximsaeure-estern", with English abstract, Arch. Parm. 1988, Weinheim, 321, pp. 45-49 (Five (5) pages).

Lagerlund, O., et al., "Aminocarbonylations of Alkenyl Phosphates, Chlorides, Bromides, and Triflates with $Mo(Co)_6$ as a Solid CO Source", Tetrahedron, 65, (2009), pp. 7646-7652 (Seven (7) pages).

Meyers, A. I., et al., "The Synthesis of Chiral $\alpha$, $\beta$-Unsaturated and Aryl Oxazolines from Ketones and Arols Via Their Inflates and Pd-Catalyzed CO and Amino Alcohol Coupling", Tetrahedron Letters, vol. 33, No. 9, 1992, pp. 1181-1184 (Four (4) pages).

Van Der Mey, M., et al., "Novel Selective PDE4 Inhibitors. 3. In Vivo Antiinflammatory Activity of a New Series of N-Substituted cis-Tetra-and cis-Hexahydrophthalazinones", Journal of Medicinal Chemistry, May 14, 2002, vol. 45, No. 12, pp. 2520-2525 (Six (6) pages).

Murray, T. J., et al., "Synthesis of Heterocyclic Compounds Containing Three Contiguous Hydrogen Bonding Sites in All Possible Arrangements", Tetrahedron, vol. 51, No. 2., 1995, pp. 635-648 (Fourteen (14) pages).

Wadsworth, W. S., et al., "Ethyl Cyclohexylideneacetate", Organic Syntheses, Coll. vol. 5, p. 547 (1973); vol. 4.5, p. 44 (1965) (Three (3) pages).

Bryans, J. S., et al., "Identification of Novel Ligands for the Gabapentin Binding Site on the $\alpha_2$ $\delta$ Subunit of a Calcium Channel and Their Evaluation as Anticonvulsant Agents", Journals of Medicinal Chemistry, Apr. 29, 1998, vol. 41, No. 11, pp. 1838-1845 (Eight (8) pages).

Ardati, A., et al., "Interaction of [$^3$H] Orphanin FQ and $^{125}$I-Tyr14-Orphanin FQ with the Orphanin FQ Receptor: Kinetics and Modulation by Cations and Guanine Nucleotides", Molecular Pharmacology, 1997, vol. 51, The American Society for Pharmacology and Experimental Therapeutics, pp. 816-824 (Nine (9) pages).

D'Amour, F., et al., "A Method for Determining Loss of Pain Sensation", J. Pharm. Exp. Ther. 1941, pp. 74-79 (Six (6) pages).

Kim, S. H., et al., "An Experimental Model for Peripheral Neuropathy Produced by Segmental Spinal Nerve Ligation in the Rat", Pain, vol. 50, 1992, Elsevier Science Publishers B.V., pp. 355-363 (Nine (9) pages).

Halfpenny, P. R., et al., "Highly Selective ,Opioid Analgesics. 3. Synthesis and Structure-Activity Relationships of Novel N-[2-(1-Pyrrolidinyl)-4- or -5-substituted-cyclohexyl]arylacetamide Derivatives", Journal of Medicinal Chemistry, 1990, vol. 33, No. 1, pp. 286-291, XP-002952674 (Six (6) pages).

Girolamo Calo et al., « Pharmacology of Nociceptin and its Receptor: A Novel Therapeutic Target, British Journal of Pharmacology, 2000, pp. 1261-1283, vol. 29, Macmillian Publishers Ltd.

Miyuki Nishi et al., "Unrestrained Nociceptive Response and Disregulation of Hearing Ability in Mice Lacking the Nociceptin orphaninFQ Receptor", The EMBO Journal, 1997, pp. 1858-1864, vol. 16, No. 8, Oxford University Press.

Toshiya Manabe et al., "Facilitation of Long-term Potentiation and Memory in Mice Lacking Nociceptin Receptors", Nature, 1998, vol. 394, Macmillan Publishers Ltd.

FDA mulls drug to slow late-stage Alzheimer's [online], [retrieved on Sep. 23, 2003]. Retrieved from the Internet, URL; http://www.cnn.com/2003/HEAL TH/conditions/09/24/alzheimers.drug.ap/indexhtml>.

International Search Report (PCT/ISA/210) issued in PCT Application No. PCT/EP2015/001445 dated Sep. 28, 2015 (Three (3) pages).

Written Opinion (PCT/ISA/237) issued in PCT Application No. PCT/EP2015/001445 dated Sep. 28, 2015 (Five (5) pages).

Reimann, E., et al., "Stereoselektive Synthese und Pharmakologische Pruefung von trans-3-Methil-10b-carbethoxy-1,2,3,4,4a,5,6,10b-

(56) References Cited

OTHER PUBLICATIONS octahydrobenzo(f)isochinolin", with English abstract, Arch. Pharm., Weinheim, Germany, 1998, vol. 321, No. 12, pp. 935-941 (Seven (7) pages).

Marko, I. E., et al., "Cer(IV)-Katalysierte Hydrolyse von Acetalen und Ketalen unter Schwach Basischen Bedingungen", Angew. Chem., Jul. 19, 1999, 111, No. 21, pp. 3411-3413 (Three (3) pages).

Ates, A., et al., "Mild and Chemoselective Catalytic Deprotection of Ketals and Acetals Using Cerium (IV) Ammonium Nitrate", Tetrahedron, vol. 59, 2003, pp. 8989-8999 (Eleven (11) pages).

Lipshutz, B. H. et al., "Pd(II)-Catalyzed Acetal/Ketal Hydrolysis/Exchange Reactions", Tetrahedron Letters, vol. 26, No. 6, 1985, Pergamon Press Ltd., pp. 705-708 (Four (4) pages).

* cited by examiner

SUBSTITUTED AZASPIRO(4.5)DECANE DERIVATIVES

The present invention relates to substituted spirocyclic cyclohexane derivatives which have an affinity for the μ opioid receptor and the ORL1 receptor, processes for the preparation thereof, medicaments containing these compounds and the use of these compounds for the preparation of medicaments.

Spirocyclic cyclohexane derivatives which have an affinity for the μ opioid receptor and the ORL1 receptor are known in the prior art. In this connection reference may be made to, for example, the full scope of WO2004/043967, WO2005/063769, WO2005/066183, WO2006/018184, WO2006/108565, WO2007/124903, WO2008/009416, WO2008/101659, WO2009/118169 and WO2009/118173.

However, the known compounds are not satisfactory in all respects and there is a need for further compounds with comparable or better properties.

Thus, in suitable binding assays the known compounds sometimes show a certain affinity for the hERG ion channel, for the L-type calcium ion channel (phenylalkylamine, benzothiazepine, dihydropyridine binding sites) or for the sodium channel in the BTX assay (batrachotoxin), which can in each case be interpreted as an indication of cardiovascular side effects. Numerous of the known compounds furthermore show only a low solubility in aqueous media, which can have an adverse effect, inter alia, on the bioavailability. The chemical stability of the known compounds moreover is often only inadequate. Thus, the compounds sometimes do not show an adequate pH, UV or oxidation stability, which can have an adverse effect, inter alia, on the storage stability and also on the oral bioavailability. The known compounds furthermore in some cases have an unfavourable PK/PD (pharmacokinetic/pharmacodynamic) profile, which can manifest itself e.g. in too long a duration of action.

The metabolic stability of the known compounds also appears to be in need of improvement. An improved metabolic stability can indicate an increased bioavailability. A weak or non-existent interaction with transporter molecules involved in the uptake and excretion of drugs is also to be evaluated as an indication of an improved bioavailability and at all events low drug interactions. Furthermore, the interactions with the enzymes involved in the breakdown and excretion of drugs should be as low as possible, since such test results likewise indicate that at all events low drug interactions or none at all are to be expected.

The known compounds furthermore sometimes show an only low selectivity for the kappa opioid receptor, which is responsible for side effects, in particular dysphoria, sedation, diuresis. The known compounds moreover sometimes show a very high affinity for the μ opioid receptor, which appears to be connected with other side effects, in particular respiratory depression, constipation and addiction.

The invention is based on the object of providing compounds which are suitable for pharmaceutical purposes and have advantages over the compounds of the prior art.

This object is achieved by the subject matter of the claims.

It has been found, surprisingly, that substituted spirocyclic cyclohexane derivatives which have an affinity for the μ opioid receptor and the ORL1 receptor can be prepared.

The invention relates to compounds of the general formula (1)

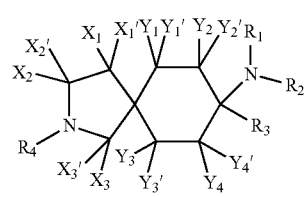

(I)

wherein $Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —NO$_2$, —CHO, —R$_0$, —O(=O)R$_0$, —O(=O)H, —C(=O)—OH, —O(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —S(=O)$_{1-2}$—NHR$_0$, —S(=O)$_{1-2}$—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; preferably in each case independently of each other are chosen from the group consisting of —H, —F, —Cl, —CN, —C$_{1-8}$-aliphatic, —C$_{1-8}$-aliphatic-NHC$_{1-8}$-aliphatic, —C$_{1-8}$-aliphatic-N(C$_{1-8}$-aliphatic)$_2$, —S—C$_{1-8}$-aliphatic, —S-aryl, -aryl, —C$_{1-8}$-aliphatic-aryl; or $Y_1$ and $Y_1'$, or $Y_2$ and $Y_2'$, or $Y_3$ and $Y_3'$, or $Y_4$ and $Y_4'$ together represent =O;

$X_1$, $X_1'$, $X_2$, $X_2'$, $X_3$ and $X_3'$ in each case independently of each other represent —H, —F, —Cl, —Br, —I, —NO$_2$, —CF$_3$, —OR$_5$, —SR$_5$, —SO$_2$R$_5$, —S(=O)$_2$OR$_5$, —CN, —COOR$_5$, —CONR$_5$, —NR$_6$R$_7$, or —R$_0$; or $X_1$ and $X_1'$, or $X_2$ and $X_2'$, or $X_3$ and $X_3'$ together represent =O;

or $X_1$ and $X_2$ or $X_2$ and $X_3$ together represent —(CH$_2$)$_{2-6}$—, wherein individual hydrogen atoms can also be replaced by —F, —Cl, —Br, —I, —NO$_2$, —CF$_3$, —OR$_5$, —CN or —C$_{1-6}$-aliphatic; or $X_1$ and $X_1'$ or $X_2$ and $X_2'$ or $X_3$ and $X_3'$ in each case together represent a C$_{3-6}$-cycloaliphatic, wherein individual hydrogen atoms can also be replaced by —F, —Cl, —Br, —I, —NO$_2$, —CF$_3$, —OR$_5$, —CN or —C$_{1-6}$-aliphatic;

$R_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

$R_1$ and $R_2$ independently of each other represent —H or —R$_0$; or $R_1$ and $R_2$ together represent —CH$_2$CH$_2$OCH$_2$CH$_2$—, —CH$_2$CH$_2$NR$_8$CH$_2$CH$_2$— or —(CH$_2$)$_{3-6}$—;

$R_3$ represents —R$_0$;

$R_4$ represents —R$_{11}$, —O(=O)R$_{11}$, —O(=O)OR$_{12}$, —C(=O)N(R$_{12}$)$_2$; —O(=O)—O—OC(=O)—R$_{12}$—S(=O)R$_{11}$ or —S(=O)$_2$R$_{11}$;

$R_5$ in each case independently represents —H or —R$_0$;

$R_6$ and $R_7$ independently of each other represent —H or —R$_0$; or $R_6$ and $R_7$ together represent —CH$_2$CH$_2$OCH$_2$CH$_2$—, —CH$_2$CH$_2$NR$_{10}$CH$_2$CH$_2$— or —(OH$_2$)$_{3-6}$—;

$R_8$ represents —H, —R$_0$ or —O(=O)R$_0$;

$R_9$ represents —H, —R$_0$ or —OR$_5$, or —NR$_6$R$_7$;

$R_{10}$ represents —H or —C$_{1-6}$-aliphatic;

$R_{11}$ represents a) —$C_{1-6}$-alkyl, —$C_{3-6}$-cycloalkyl, or —$C_{1-3}$-alkyl-$C_{3-6}$-cycloalkyl, wherein in the $C_{3-6}$-cycloalkyl group a ring carbon atom can be replaced by an oxygen atom and —$C_{1-6}$-alkyl, —$C_{3-6}$-cycloalkyl or —$C_{1-3}$-alkyl-$C_{3-6}$-cycloalkyl is mono- or polysubstituted by substituents independently of each other selected from the group consisting of —$NO_2$, —CHO, =O, —O(=O)$R_0$, —O(=O)H, —C(=O)—OH, —O(=O)$OR_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3$H, —S(=O)$_{1-2}$$R_0$, —S(=O)$_{1-2}$$NH_2$, —S(=O)$_{1-2}$—$NHR_0$, —S(=O)$_{1-2}$—N($R_0$)$_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NH—C(=O)N($R_0$)$_2$, —Si($R_0$)$_3$ and —PO($OR_0$)$_2$; or b) unsubstituted or mono- or polysubstituted —$C_{7-12}$-alkyl, —$C_{7-12}$-cycloalkyl or $C_{3-12}$-cycloheteroalkyl having up to 3 hetero atoms in the ring selected from the group of O, N and S, with the proviso that heterocycles having only one oxygen atom as a hetero atom are excluded, or c) -aryl, -heteroaryl, —$C_{4-8}$-cycloalkyl-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl, and $R_{12}$ represents H, —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;

wherein

"aliphatic" in each case is a branched or unbranched, saturated or a mono- or polyunsaturated, unsubstituted or mono- or polysubstituted, aliphatic hydrocarbon radical;

"cycloaliphatic" in each case is a saturated or mono- or polyunsaturated, unsubstituted or mono- or polysubstituted, alicyclic, mono- or multicyclic hydrocarbon radical, the number of ring carbon atoms of which is preferably in the stated range (i.e. "$C_{3-8}$-"cycloaliphatic preferably has 3, 4, 5, 6, 7 or 8 ring carbon atoms);

wherein with respect to "aliphatic" and "cycloaliphatic" —$C_{7-12}$-alkyl, —$C_{7-12}$-cycloalkyl or $C_{3-12}$-cycloheteroalkyl "mono- or polysubstituted" is understood as meaning substitution once or several times of one or more hydrogen atoms, e.g. substitution once, twice, three times or completely by substituents independently of each other chosen from the group consisting of —F, —Cl, —Br, —I, —CN, —$NO_2$, —CHO, =O, —$R_0$, —O(=O)$R_0$, —O(=O)H, —C(=O)—OH, —O(=O)$OR_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NH—C(=O)N($R_0$)$_2$, —Si($R_0$)$_3$, —PO($OR_0$)$_2$;

"aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl;

"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system;

wherein with respect to "aryl" and "heteroaryl", "mono- or polysubstituted" is understood as meaning substitution once or several times of one or more hydrogen atoms of the ring system by substituents chosen from the group consisting of —F, —Cl, —Br, —I, —CN, —$NO_2$, —CHO, =O, —$R_0$, —C(=O)$R_0$, —C(=O)H, —C(=O)OH, —C(=O)$OR_0$, —C(=O)$NH_2$, —C(=O)$NHR_0$, —C(=O)—N($R_0$)$_2$, —OH, —O($CH_2$)$_{1-2}$O—, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3$H, —S(=O)$_{1-2}$$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NHC(=O)N($R_0$)$_2$, —Si($R_0$)$_3$, —PO($OR_0$)$_2$; wherein N ring atoms optionally present can in each case be oxidised (N-oxide);

in the form of an individual stereoisomer or mixture thereof, the free compounds and/or their physiologically acceptable salts and/or solvates.

Where various radicals are combined, for example $Y_1$, $Y_1'$, $Y_2$, $Y_2'$, $Y_3$, $Y_3'$, $Y_4$ and $Y_4'$, and where radicals on substituents thereof are combined, such as e.g. —$OR_0$, —OC(=O)$R_0$, —OC(=O)$NHR_0$, a substituent, e.g. $R_0$, can assume different meanings for two or more radicals, for example —$OR_0$, —OC(=O)$R_0$, —OC(=O)$NHR_0$, within a substance.

The compounds according to the invention show good binding to the ORL1 receptor and/or the μ opioid receptor.

The compounds according to the invention preferably have a $K_i$ value on the μ opioid receptor of at most 500 nM, more preferably at most 100 nM or at most 50 nM, still more preferably at most 10 nM, most preferably at most 1.0 nM and in particular at most 0.5 nM.

Methods for determination of the $K_i$ value on the μ opioid receptor are known to the person skilled in the art. The determination is preferably carried out as described in connection with the examples.

The compounds according to the invention preferably have a $K_i$ value on the ORL1 receptor of at most 500 nM, more preferably at most 100 nM or at most 50 nM, still more preferably at most 10 nM, most preferably at most 1.0 nM and in particular at most 0.75 nM.

Methods for determination of the $K_i$ value on the ORL1 receptor are known to the person skilled in the art. The determination is preferably carried out as described in connection with the examples.

It has been found, surprisingly, that the compounds according to the invention having affinity for the ORL1 and μ opioid receptor preferably have a pharmacological profile which has significant advantages compared with the other opioid receptor ligands:

1. The compounds according to the invention show an activity in acute pain models which is sometimes comparable to that of the usual level 3 opioids. At the same time, however, they are distinguished by a clearly better tolerability compared with conventional μ opioids.
2. In contrast to the usual level 3 opioids, the compounds according to the invention show a clearly higher activity in mono- and polyneuropathy pain models, which is to be attributed to a synergism of the ORL1 and μ opioid component.

3. In contrast to the usual level 3 opioids, the compounds according to the invention show a substantial, preferably a complete separation of antiallodynic or antihyperalgesic action and antinociceptive effect in neuropathic animals.
4. In contrast to the usual level 3 opioids, the compounds according to the invention show a clear intensification of action against acute pain in animal models for chronic inflammation pain (inter alia carrageenan- or CFA-induced hyperalgesia, visceral inflammation pain).
5. In contrast to the usual level 3 opioids, side effects typical of μ opioids (inter alia respiratory depression, opioid-induced hyperalgesia, physical dependency/withdrawal, emotional dependency/addiction) are clearly reduced or preferably are not to be observed with the compounds according to the invention in the therapeutically active dose range.

On the basis of the reduced μ opioid side effects on the one hand and the increased activity on chronic, preferably neuropathic pain on the other hand, the mixed ORL1/μ agonists are thus distinguished by clearly increased safety margins compared with pure μ opioids. This results in a clearly increased "therapeutic window" in the treatment of states of pain, preferably chronic pain, still more preferably neuropathic pain.

A preferred embodiment of the invention relates to compounds of the general formula (2), i.e. $Y_1'$, $Y_2'$, $Y_3'$ and $Y_4'$ are each —H:

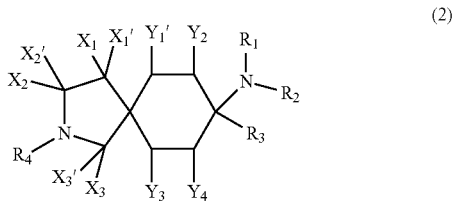

(2)

In a preferred embodiment of the compound (2) according to the invention $Y_1$, $Y_2$, $Y_3$ and $Y_4$ are not —H. In another preferred embodiment of the compound (2) according to the invention three of the radicals $Y_1$, $Y_2$, $Y_3$ and $Y_4$ are not —H and the remaining radical is —H. In another preferred embodiment two of the radicals $Y_1$, $Y_2$, $Y_3$ and $Y_4$ are not —H and the remaining two radicals are —H. In a further preferred embodiment of the compound (2) according to the invention one of the radicals $Y_1$, $Y_2$, $Y_3$ and $Y_4$ is not —H and the remaining radicals are —H.

In a particularly preferred embodiment of the compound (2) according to the invention $Y_1$, $Y_2$, $Y_3$ and $Y_4$ each represent —H.

Particularly preferred compounds of the general formula (1) or (2) are those wherein $R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$.

Particularly preferred compounds of the general formula (2) are those wherein $R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, —OH, —$OCH_3$, —$OC_2H_5$ and —$N(CH_3)_2$;

$R_4$ represents —$R_{11}$ or —O(=O)$R_{11}$; and $X_1$, $X_1'$, $X_2$, $X_2'$, $X_3$, $X_3'$ in each case independently of each other represent —H, —F, —Cl, —Br, —I, —$NO_2$, —$CF_3$, —$OR_5$, —$SR_5$, —$SO_2R_5$, —$S(=O)_2OR_5$, —CN, —$COOR_5$, —$CONR_5$, —$NR_6R_7$, or —$R_0$; or $X_1$ and $X_1'$, or $X_2$ and $X_2'$, or $X_3$ and $X_3'$ together represent =O.

Particularly preferred compounds are those of the general formula (3), i.e. $Y_1$, $Y_1'$, $Y_2$, $Y_2'$, $Y_3$, $Y_3'$, $Y_4$ and $Y_4'$ are each —H:

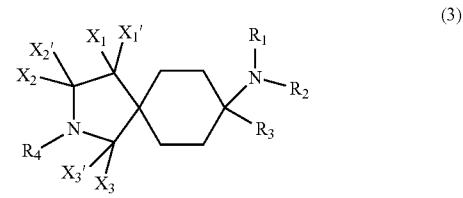

(3)

Preferred embodiments of the compounds of the general formula (3) have the general formula (3.1):

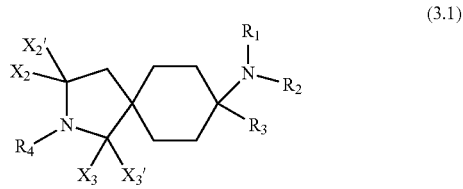

(3.1)

These embodiments relate to compounds of the general formula (3) in which $X_1$ and $X_1'$ are —H.

Particularly preferred compounds of the general formula (3.1) are those wherein $X_2$, $X_2'$, $X_3$ and $X_3'$ represent H; or $X_2$ and $X_2'$, or $X_3$ and $X_3'$ together represent =O;

$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$;

$R_1$ represents $CH_3$;

$R_2$ represents —H or —$CH_3$; or $R_1$ and $R_2$ together form a ring and represent —(C$H_2$)$_{3-4}$—; and $R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, —OH, —$OCH_3$, —$OC_2H_5$ and —$N(CH_3)_2$;

$R_4$ represents —$R_{11}$ or —O(=O)$R_{11}$;

$R_5$ in each case independently represents —H or $R_0$;

$R_6$ and $R_7$ independently of each other represent —H or $R_0$; or $R_6$ and $R_7$ together represent —CH$_2$CH$_2$OCH$_2$CH$_2$—, —CH$_2$CH$_2$NR$_{10}$CH$_2$CH$_2$— or —(OH$_2$)$_{3-6}$—;

$R_9$ represents —$R_0$, —OR$_5$, or —NR$_6$R$_7$;

$R_{10}$ represents —H or —C$_{1-6}$-aliphatic, and $R_{11}$ represents C$_{3-12}$-cycloheteroalkyl having up to 3 hetero atoms in the ring selected from the group of O, N and S, with the proviso that heterocycles having only one oxygen atom as a hetero atom are excluded, -aryl, -heteroaryl, —C$_{4-8}$-cycloalkyl-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

and $R_{12}$ represents H, —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, or —C$_{1-8}$-aliphatic-heteroaryl.

Preferred embodiments of the compounds of the general formula (3.1) have the general formula (3.1.1), (3.1.2), (3.1.3), (3.1.4), (3.1.5) or (3.1.6):

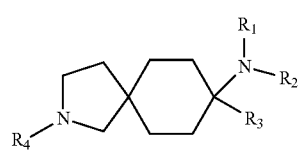

(3.1.1)

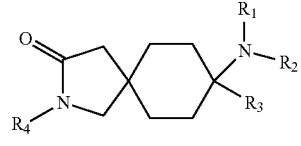

(3.1.2)

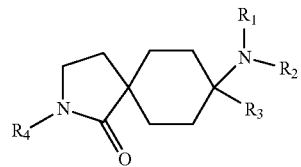

(3.1.3)

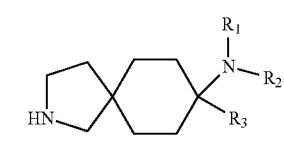

(3.1.4)

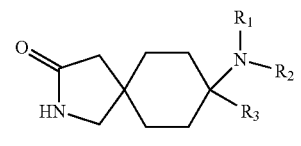

(3.1.5)

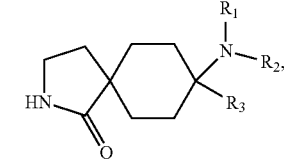

(3.1.6)

preferably, according to general formula 3.1.2.

Preferred embodiments of the compounds of the general formula (3) have the general formula (3.2)

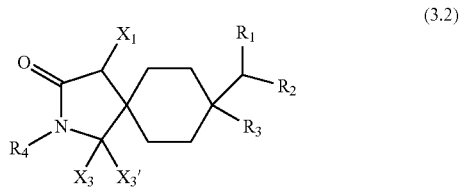

(3.2)

In the compounds according to the general formula 3.2 $X_1$ is preferably $R_0$ or —OR$_0$, wherein $R_0$ in particular represents C$_{1-6}$-aliphatic, C$_{1-6}$-aliphatic-C$_{3-8}$-cycloaliphatic, aryl, heteroaryl, C$_{1-6}$-aliphatic-aryl or C$_{1-6}$-aliphatic-heteroaryl, in particular represents C$_{1-6}$-alkyl, C$_{1-6}$-alkyl-C$_{3-8}$-cycloaliphatic, aryl, heteroaryl, C$_{1-6}$-alkyl-aryl or C$_{1-6}$-alkyl-heteroaryl, in each case unsubstituted or mono- or polysubstituted by substituents independently of each other chosen from —F, —Cl, —Br, —CN, OH, SH, C$_{1-3}$-alkyl, C$_{1-3}$-alkoxy, in particular methoxy, aryl, in particular C$_{1-3}$-alkyl, C$_{1-3}$-alkoxy, in particular methoxy, aryl, in particular phenyl, C$_{1-3}$-alkyl-aryl, in particular benzyl, aryloxy, in particular phenoxy, which in turn are in each case unsubstituted or mono- or polysubstituted by substituents independently of each other chosen from the group consisting of —F, —Cl, —Br, —CN, OH, methyl, methoxy, phenyl, benzyl or phenoxy.

A further preferred embodiment relates to compounds of the general formula (4.1), i.e. $R_1$ and $R_2$ are in each case —CH$_3$.

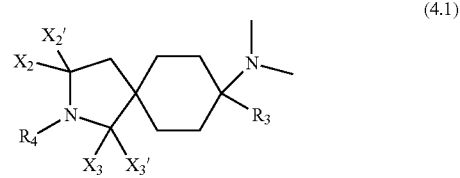

(4.1)

Preferred embodiments of the compounds of the general formula (4.1) have the general formula (4.1.1), (4.1.2), (4.1.3), (4.1.4), (4.1.5), (4.1.6) or (4.1.7):

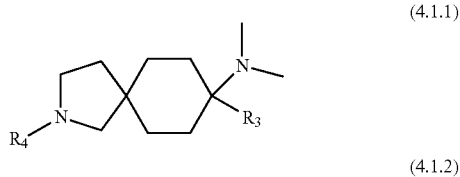

(4.1.1)

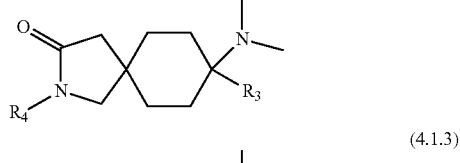

(4.1.2)

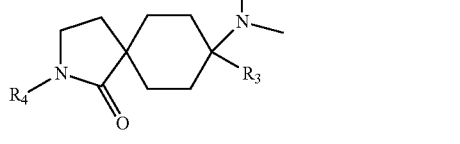

(4.1.3)

-continued (4.1.4)

(4.1.5)

(4.1.6)

(4.1.7)

preferably according to general formulas (4.1.2) or (4.1.7), especially (4.1.2).

In further preferred embodiments of the invention, the compound has the general formula (5)

(5)

wherein:

$X_1$ is selected from —H, benzyl or $C_{1-3}$-alkoxy-substituted-$C_{1-4}$-alkyl;

$X_2$ and $X_2'$ either are both —H, or together represent =O, preferably $X_2$ and $X_2'$ together represent =O;

$R_1$ is methyl and $R_2$ is —H or -methyl; preferably $R_1$ and $R_2$ are methyl;

$R_3$ represents —$C_{1-8}$-aliphatic, -aryl, -heteroaryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Br, —CN, —$CH_3$, —$C_2H_5$, —$NH_2$, —$NO_2$, —SH, —$CF_3$, OH, —$OCH_3$, —$OC_2H_5$ and —$N(CH_3)_2$; preferably $R_3$ represents -phenyl or -thienyl, pyridinyl, or pyrazinyl, in each case unsubstituted or mono-substituted by —F, —$CH_3$; -ethyl, -n-propyl, -n-butyl, -vinyl, or -allyl, unsubstituted or mono- or polysubstituted by —$OCH_3$, —OH or —$OC_2H_5$, in particular by —$OCH_3$ or —$OC_2H_5$; and $R_4$ is a group according to general formula (6)

(6)

wherein
n=1, 2, 3 or 4
$R_{40}$, $R_{40}'$ and $R_{41}$, independently of each other are either H or substituted or unsubstituted $C_{1-3}$-alkyl.

Preferably, $Y_1$, $Y_1'$, $Y_2$, $Y_2'$, $Y_3$, $Y_3'$, $Y_4$ and $Y_4'$ in each case independently of each other are chosen from the group consisting of —H, —F, —Br, —CN, —$NH_2$, —NH—$C_{1-6}$-aliphatic, —NH—$C_{3-8}$-cycloaliphatic, —$N(C_{1-6}$-aliphatic$)_2$, —$N(C_{3-8}$-cycloaliphatic$)_2$, —$N(C_{1-6}$-aliphatic-OH$)_2$, —$NO_2$, —NH—$C_{1-6}$-aliphatic-$C_{3-8}$-cycloaliphatic, —NH—$C_{1-6}$-aliphatic-aryl, aliphatic-heteroaryl, —NH-aryl, —NH-heteroaryl, —SH, S—$C_{1-6}$ aliphatic, —S—$C_{3-8}$-cycloaliphatic, —S—$C_{1-6}$-aliphatic-$C_{3-8}$-cycloaliphatic, S—$C_{1-6}$ aliphatic aryl, —S—$C_{1-6}$-aliphatic-heteroaryl, —S-aryl, —S-heteroaryl, —OH, —O—$C_{1-6}$-aliphatic, —O—$C_{3-8}$-cycloaliphatic, —O—$C_{1-6}$-aliphatic-OH, —O—$C_{1-6}$-aliphatic-$C_{3-8}$-cycloaliphatic, —O—$C_{1-6}$-aliphatic-aryl, —O—$C_{1-6}$-aliphatic-heteroaryl, —O-aryl, —O-heteroaryl, —O—C(=O)$C_{1-6}$-aliphatic, —O—C(=O)$C_{3-8}$-cycloaliphatic, —O—C(=O)$C_{1-6}$-aliphatic-OH, —O—C(=O)$C_{1-6}$-aliphatic-$C_{3-8}$-cycloaliphatic, —O—C(=O)$C_{1-6}$-aliphatic-aryl, —O—C(=O)$C_{1-6}$-aliphatic-heteroaryl, —O—C(=O)aryl, —O—C(=O)heteroaryl, —$C_{1-6}$-aliphatic, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, -aryl, -heteroaryl, —C(=O)$C_{1-6}$-aliphatic, —C(=O)$C_{3-8}$-cycloaliphatic, —C(=O)$C_{1-6}$-aliphatic-$C_{3-8}$-cycloaliphatic, —C(=O)$C_{1-6}$-aliphatic-aryl, —C(=O)$C_{1-6}$-aliphatic-heteroaryl, —C(=O)aryl, —C(=O)heteroaryl, —$CO_2H$, —$CO_2$—$C_{1-6}$-aliphatic, —$CO_2$—$C_{3-8}$-cycloaliphatic, —$CO_2$—$C_{1-6}$-aliphatic-$C_{3-8}$-cycloaliphatic, —$CO_2$—$C_{1-6}$-aliphatic-aryl, —$CO_2$—$C_{1-6}$-aliphatic-heteroaryl, —$CO_2$-aryl, —$CO_2$-heteroaryl; or $Y_1$ and $Y_1'$, or $Y_2$ and $Y_2'$, or $Y_3$ and $Y_3'$, or $Y_4$ and $Y_4'$ together represent =O.

More preferably, $Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —$C_{1-6}$-aliphatic, —$C_{1-6}$-aliphatic-NH$C_{1-6}$-aliphatic, —$C_{1-6}$-aliphatic-N($C_{1-8}$-aliphatic$)_2$, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, —S—$C_{1-8}$-aliphatic, —S-aryl, -aryl or -heteroaryl.

Particularly preferably, $Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —$C_{1-6}$-alkyl, —$C_{2-6}$-alkenyl, —$C_{1-6}$-alkyl-NH—$C_{1-6}$-alkyl, —$C_{1-6}$-alkyl-N($C_{1-6}$-alkyl$)_2$, -aryl, —$C_{1-6}$-alkyl-aryl, —S—$C_{1-6}$-alkyl and —S-aryl.

In a preferred embodiment at least one of the radicals $Y_1$, $Y_1'$, $Y_2$, $Y_2'$, $Y_3$, $Y_3'$, $Y_4$ and $Y_4'$ is not —H and the remaining radicals represent —H.

Particularly preferably, $Y_1$, $Y_1'$, $Y_2$, $Y_2'$, $Y_3$, $Y_3'$, $Y_4$ and $Y_4'$ each represent —H.

Preferably, $X_1$, $X_1'$, $X_2$, $X_2'$, $X_3$ and $X_3'$ in each case independently of each other represent —H, —F, —Cl, —Br, —I, —$NO_2$, —$NR_6R_7$, —$C_{1-6}$-aliphatic, —$C_{3-8}$-cycloaliphatic, -aryl, -heteroaryl, —$C_{1-6}$-aliphatic-aryl, —$C_{1-6}$-aliphatic-heteroaryl or —$C_{1-6}$-aliphatic-$C_{3-8}$-cycloaliphatic, or $X_1$ and $X_1'$, or $X_2$ and $X_2'$, or $X_3$ and $X_3'$ together represent =O; or $X_1$ and $X_2$, or $X_2$ and $X_3$ together represent —(CH$_2$)$_{2-6}$.

Preferred compounds are in particular also those in which $X_1$, $X_1'$, $X_2$, $X_2'$, $X_3$ and $X_3'$ in each case independently of each other represent —H, —C$_{1-5}$-aliphatic, -aryl or -aryl linked via a —C$_{1-3}$-aliphatic group (bridge); or $X_1$ and $X_1'$, or $X_2$ and $X_2'$, or $X_3$ and $X_3'$ together represent =O.

Particularly preferably, $X_1$, $X_1'$, $X_2$, $X_2'$, $X_3$ and $X_3'$ in each case independently of each other represent —H, —CH$_3$, -phenyl or -benzyl, in particular —H, or $X_1$ and $X_1'$, or $X_2$ and $X_2'$, or $X_3$ and $X_3'$ together represent =O.

Very particularly preferably, $X_1$, $X_1'$, $X_2$, $X_2'$, $X_3$ and $X_3'$ represent H; or $X_2$ and $X_2'$, or $X_3$ and $X_3'$ together represent =O.

In a preferred embodiment $X_2$ and $X_2'$ together represent =O, and $X_1$, $X_1'$, $X_3$ and $X_3'$ represent —H.

In a preferred embodiment $X_2$ and $X_2'$ together represent =O; $X_1$=R$_0$ or —OR$_0$, and $X_1'$, $X_3$ and $X_3'$ represent —H. Preferably, $X_1$ here represents the same radical as described above in connection with the compounds according to the general formula 3.2.

In another preferred embodiment $X_3$ and $X_3'$ together represent =O, and $X_1$, $X_1'$, $X_2$ and $X_2'$ represent —H.

In a further preferred embodiment $X_1$, $X_1'$, $X_2$, $X_2'$, $X_3$ and $X_3'$ represent H.

$R_0$ preferably in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl or —C$_{1-8}$-aliphatic-heteroaryl. In this context —C$_{1-8}$-aliphatic-C$_{3-12}$-cycloaliphatic, —C$_{1-8}$-aliphatic-aryl or —C$_{1-8}$-aliphatic-heteroaryl means that the radicals —C$_{3-12}$-cycloaliphatic, -aryl or -heteroaryl are in each case bonded via a divalent —C$_{1-8}$-aliphatic-bridge. Preferred examples for —C$_{1-8}$-aliphatic-aryl are —CH$_2$—C$_6$H$_5$, —CH=CH—C$_6$H$_5$ and —CH$_2$CH$_2$—C$_6$H$_5$. A preferred example for —C$_{1-8}$-aliphatic-heteroaryl is —CH$_2$-pyridyl. A preferred example for —C$_{1-8}$-aliphatic-C$_{3-12}$-cycloaliphatic is —CH$_2$-cyclopentyl.

Preferably, $R_1$ and $R_2$ independently of each other represent —H; —C$_{1-6}$-aliphatic; —C$_{3-8}$-cycloaliphatic, —C$_{1-6}$-aliphatic-aryl, —C$_{1-6}$-aliphatic-C$_{3-8}$-cycloaliphatic or —C$_{1-6}$-aliphatic-heteroaryl; or the radicals $R_1$ and $R_2$ together form a ring and denote —CH$_2$CH$_2$OCH$_2$CH$_2$—, —CH$_2$CH$_2$NR$_8$CH$_2$CH$_2$— or —(OH$_2$)$_{3-6}$—.

More preferably, $R_1$ and $R_2$ independently of each other represent —H; —C$_{1-5}$-aliphatic; or the radicals $R_1$ and $R_2$ together form a ring and denote —CH$_2$CH$_2$OCH$_2$CH$_2$—, —CH$_2$CH$_2$NR$_8$—CH$_2$CH$_2$— or —(OH$_2$)$_{3-6}$—, wherein $R_5$ preferably denotes —H or —C$_{1-5}$-aliphatic.

Particularly preferred compounds are those wherein $R_1$ and $R_2$ independently of each other represent —CH$_3$ or —H, wherein $R_1$ and $R_2$ do not simultaneously denote —H; or $R_1$ and $R_2$ form a ring and denote —(CH$_2$)$_{3-4}$—.

Very particularly preferred compounds are those wherein $R_1$ and $R_2$ represent —CH$_3$.

Preferably, $R_3$ represents —C$_{1-8}$-aliphatic, —C$_{3-8}$-cycloaliphatic, -aryl, -heteroaryl; or represents -aryl, -heteroaryl or —C$_{3-8}$-cycloaliphatic in each case bonded via a —C$_{1-3}$-aliphatic group.

Preferably, $R_3$ represents —C$_{1-8}$-aliphatic; in each case saturated or unsaturated, unsubstituted or mono- or polysubstituted by —OH, —OCH$_3$ or —OC$_2$H$_5$; -aryl, -heteroaryl; in each case unsubstituted or mono- or polysubstituted by —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or represents —C$_{5-6}$-cycloaliphatic bonded via a —C$_{1-3}$-aliphatic group.

Most preferably, $R_3$ represents -aryl, -heteroaryl; in each case unsubstituted or mono- or polysubstituted by —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or represents a —C$_{5-6}$-cycloaliphatic bonded via a —C$_{1-3}$-aliphatic group.

Particularly preferably, $R_3$ represents -vinyl, -ethyl, -allyl, -propyl, -butyl, -pentyl, -hexyl, -heptyl, -cyclopentyl, -cyclohexyl, -phenyl, -benzyl, -naphthyl, -anthracenyl, -thiophenyl (-thienyl), -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, in each case unsubstituted or mono- or polysubstituted; or —C$_{5-6}$-cycloaliphatic, -phenyl, -naphthyl, -anthracenyl, -thiophenyl, -benzothiophenyl, pyridyl, -furyl, -benzofuranyl, -benzodioxolanyl, -indolyl, -indanyl, -benzodioxanyl, -pyrrolyl, -pyrimidyl, -triazolyl or -pyrazinyl bonded via a saturated, unbranched —C$_{1-3}$-aliphatic group and in each case unsubstituted or mono- or polysubstituted.

Still more preferably, $R_3$ represents -propyl, -butyl, -pentyl, -hexyl, -phenyl, -phenethyl, -thiophenyl (-thienyl), -pyridyl, -triazolyl, -benzothiophenyl or -benzyl, in each case substituted or unsubstituted, particularly preferably -propyl, -3-methoxypropyl, -butyl, -pentyl, -hexyl, -phenyl, -3-methylphenyl, -3-fluorophenyl, -benzo[1,3]-dioxolyl, -thienyl, -5-methylthiophen-2-yl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

Most preferably, $R_3$ represents -phenyl, -benzyl, -phenethyl, in each case unsubstituted or mono- or polysubstituted on the ring; —C$_{1-5}$-aliphatic, —C$_{4-6}$-cycloaliphatic, -pyridyl, -thienyl, -thiazolyl, -imidazolyl, -1,2,4-triazolyl or -benzimidazolyl, unsubstituted or mono- or polysubstituted.

Particularly preferably, $R_3$ represents -phenyl, -benzyl, -phenethyl, -thienyl, -pyridyl, -thiazolyl, -imidazolyl, -1,2,4-triazolyl, -benzimidazolyl or -benzyl, unsubstituted or mono- or polysubstituted by —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; -ethyl, n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, in each case unsubstituted or mono- or polysubstituted by —OH, —OCH$_3$ or —OC$_2$H$_5$.

Particularly preferably, $R_3$ represents -phenyl or -thienyl, -pyrazolyl, -pyridinyl, or pyrazinyl, in each case unsubstituted or monosubstituted by —F, —Cl, —CH$_3$; -ethyl, -n-propyl, -n-butyl, -vinyl, or -allyl, unsubstituted or mono- or polysubstituted by —OCH$_3$, —OH or —OC$_2$H$_5$, in particular by —OCH$_3$ or —OC$_2$H$_5$.

Most preferably, $R_3$ represents -phenyl, 3-methoxyphenyl, -benzyl, 1-methyl-pyrazol-1-yl, pyridin-2-yl, pyrazin-2-yl, -thienyl, 5-methylthiophen-2-yl, 5-fluorothiophen-2-yl, 5-chlorothiophen-2-yl or 3-methoxy propyl.

Preferably, $R_4$ represents —R$_{11}$ or —O(=O)R$_{11}$, wherein $R_{11}$ preferably represents a) —C$_{1-6}$-alkyl which is mono- or polysubstituted by substituents independently of each other selected from the group consisting of —O(=O)—OH, —O(=O)OR$_0$, —O(=O)NH$_2$, —O(=O)NHR$_0$, —O(=O)N(R$_0$)$_2$, —OH, —OR$_0$, —OC(=O)R$_0$, —OC(=O)OR$_0$, —OC(=O)

NHR₀, —OC(=O)N(R₀)₂, —S(=O)₁₋₂—R₀, —S(=O)₁₋₂NH₂, —NH₂, —NHR₀, —N(R₀)₂ and —N⁺(R₀)₃, —N⁺(R₀)₂O⁻; or c) -aryl, -heteroaryl, —C₁₋₈-aliphatic-aryl or —C₁₋₈-aliphatic-heteroaryl.

Particularly preferably, R₁₁ represents a) —C₁₋₃-alkyl which is mono- or polysubstituted by substituents independently of each other selected from the group consisting of —O(=O)—OH, —O(=O)OR₀, —O(=O)NH₂, —O(=O)NHR₀, —O(=O)N(R₀)₂, —OH, —OR₀, —OC(=O)R₀, —OC(=O)OR₀, —OC(=O)NHR₀, —OC(=O)N(R₀)₂, —S(=O)₁₋₂—R₀, —S(=O)₁₋₂NH₂, —S(=O)₁₋₂—NHR₀, —S(=O)₁₋₂—N(R₀)₂, —NH₂, —NHR₀, —N(R₀)₂ and —N⁺(R₀)₃, —N⁺(R₀)₂O⁻, wherein R₀ independently of each other is selected from the group consisting of C₁₋₃-alkyl, C₃₋₆-cycloalkyl, aryl, or heteroaryl, in each case unsubstituted or mono- or polysubstituted by substituents selected from the group consisting of —F, —Cl, —Br, —CN, —OH, —O—C₁₋₃-alkyl, in particular —O—CH₃, —NH₂, —NHC₁₋₃-alkyl, —N(C₁₋₃-alkyl)₂; or represents c) C₁₋₄-aliphatic-aryl or C₁₋₄-aliphatic-heteroaryl.

In particularly preferred embodiments of the invention R₄ is a moiety selected from the moieties defined in "List 1" below:

"List 1":

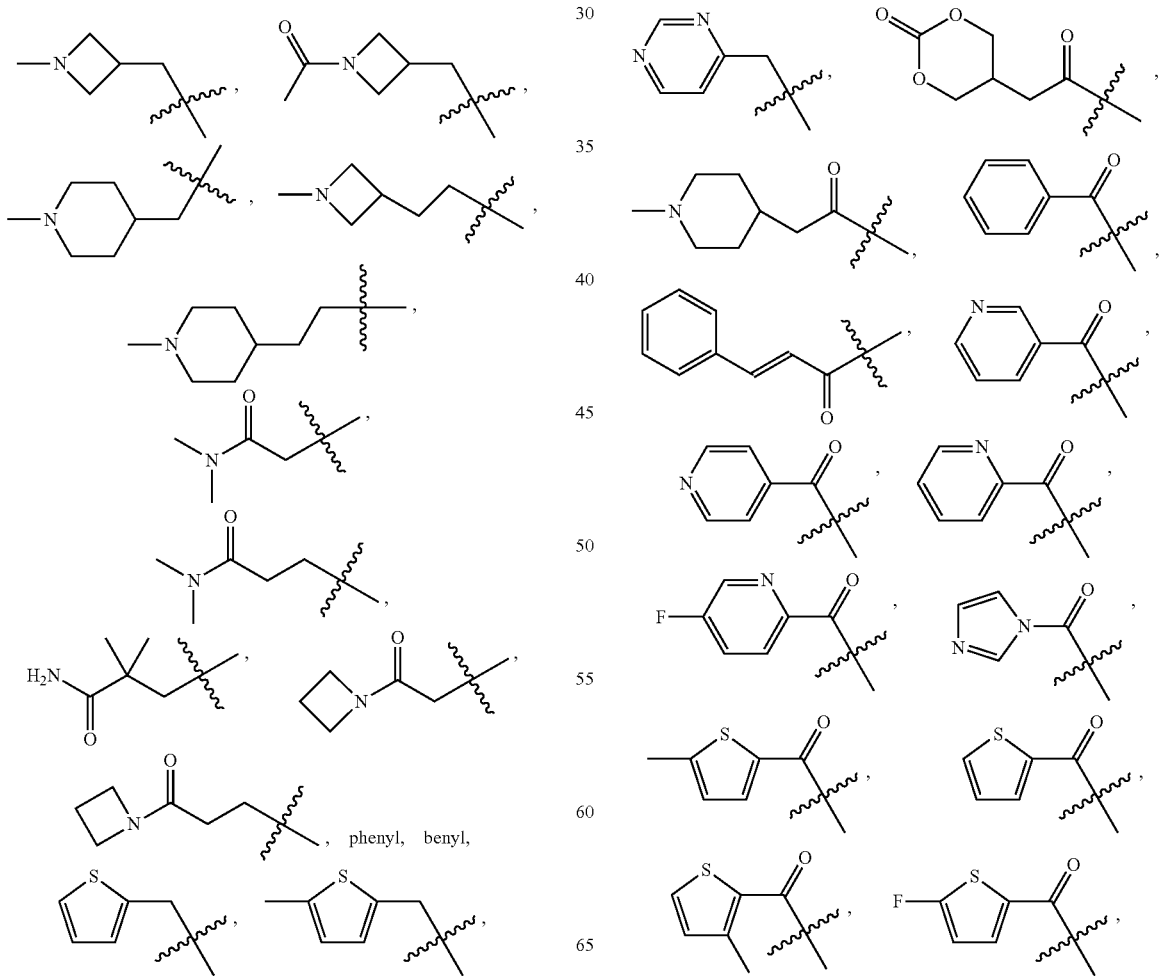

phenyl, benyl,

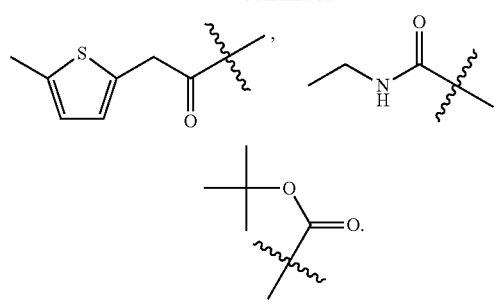
In also particularly preferred embodiments, $R_4$ is a moiety selected from the moieties defined in "List 2" below:
"List 2":
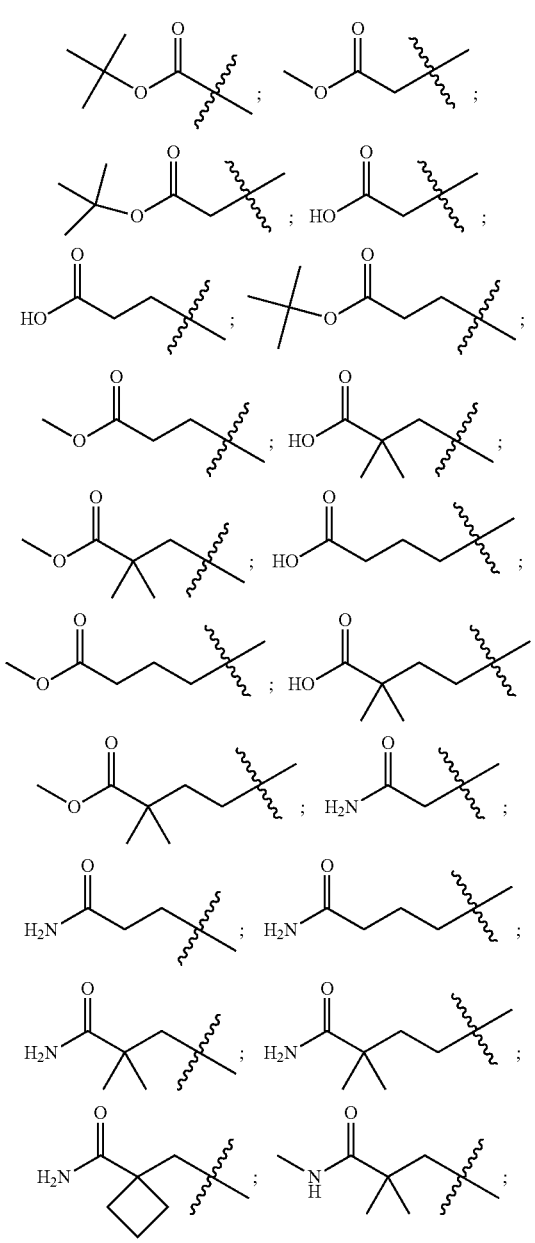
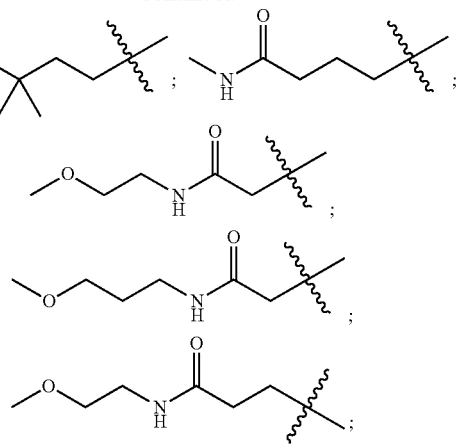
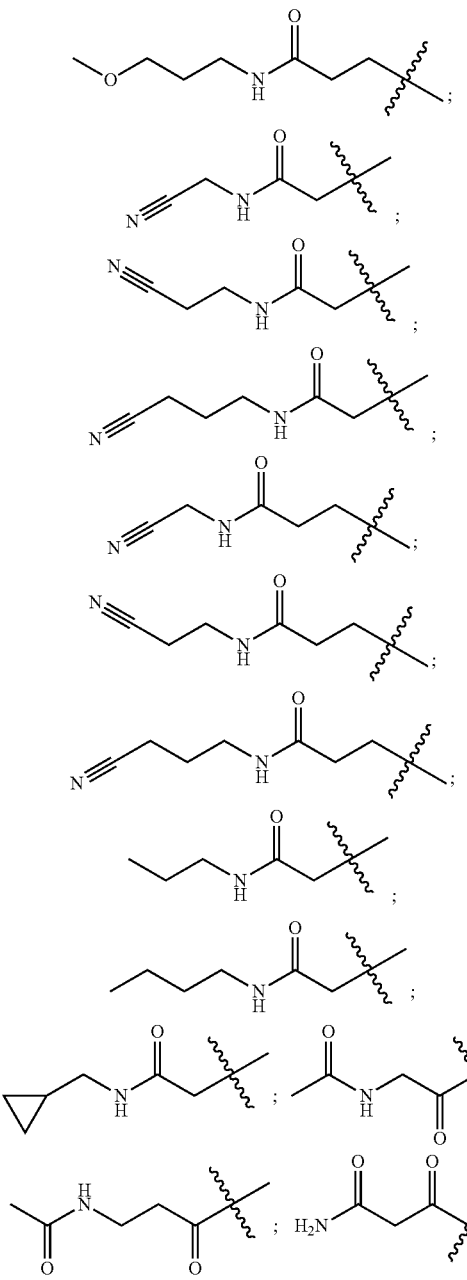

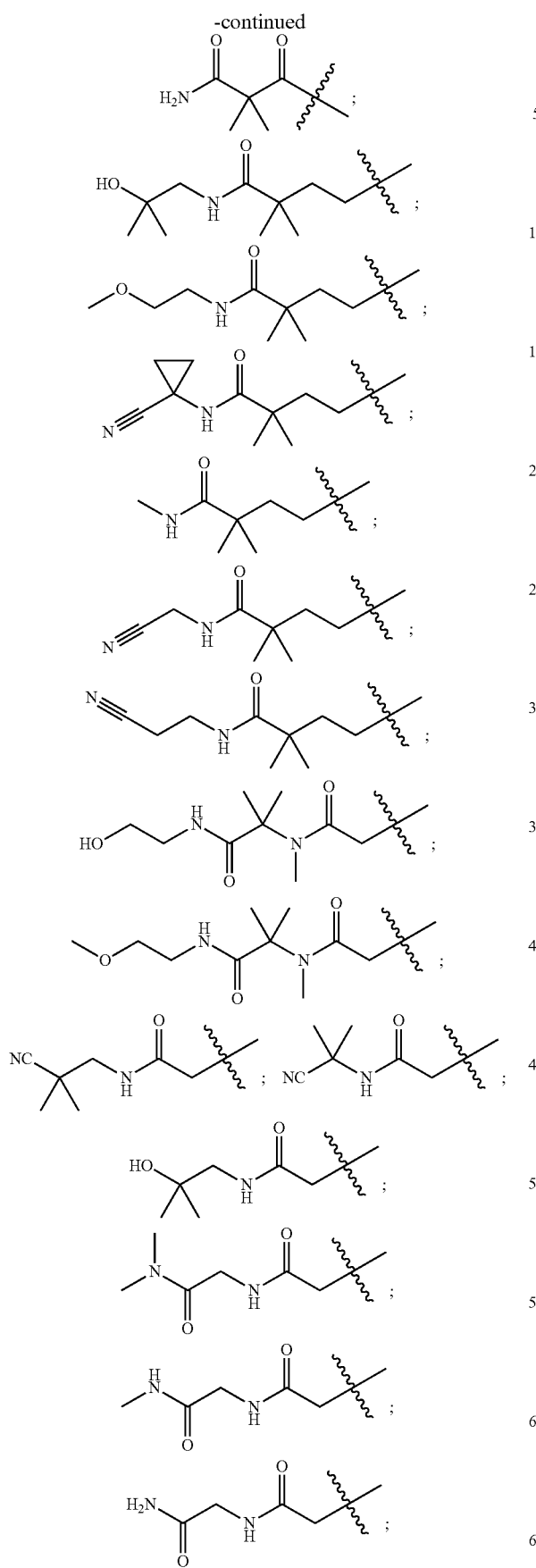
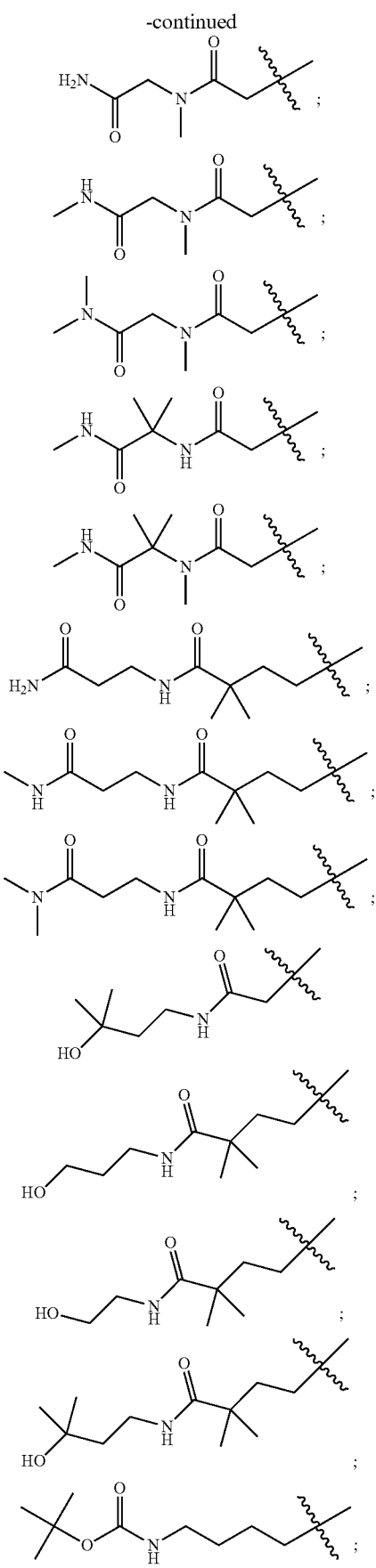

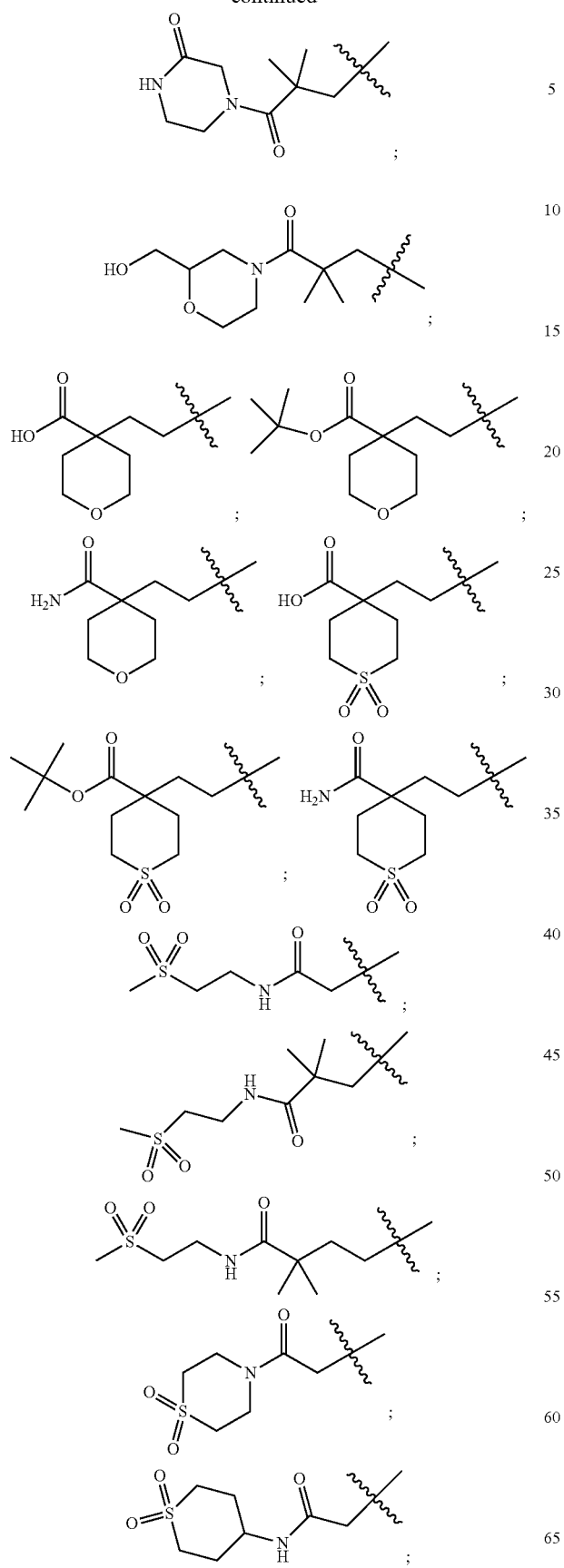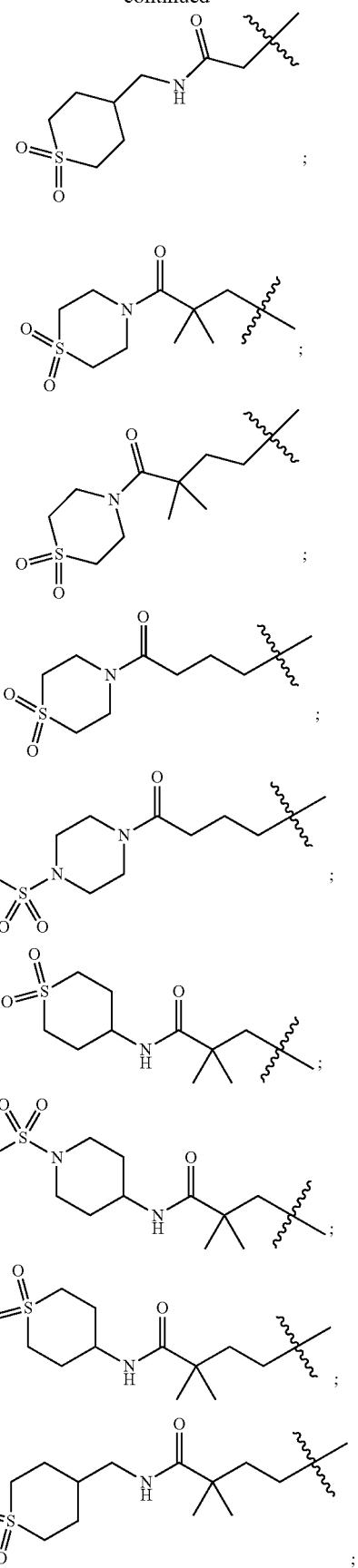

-continued
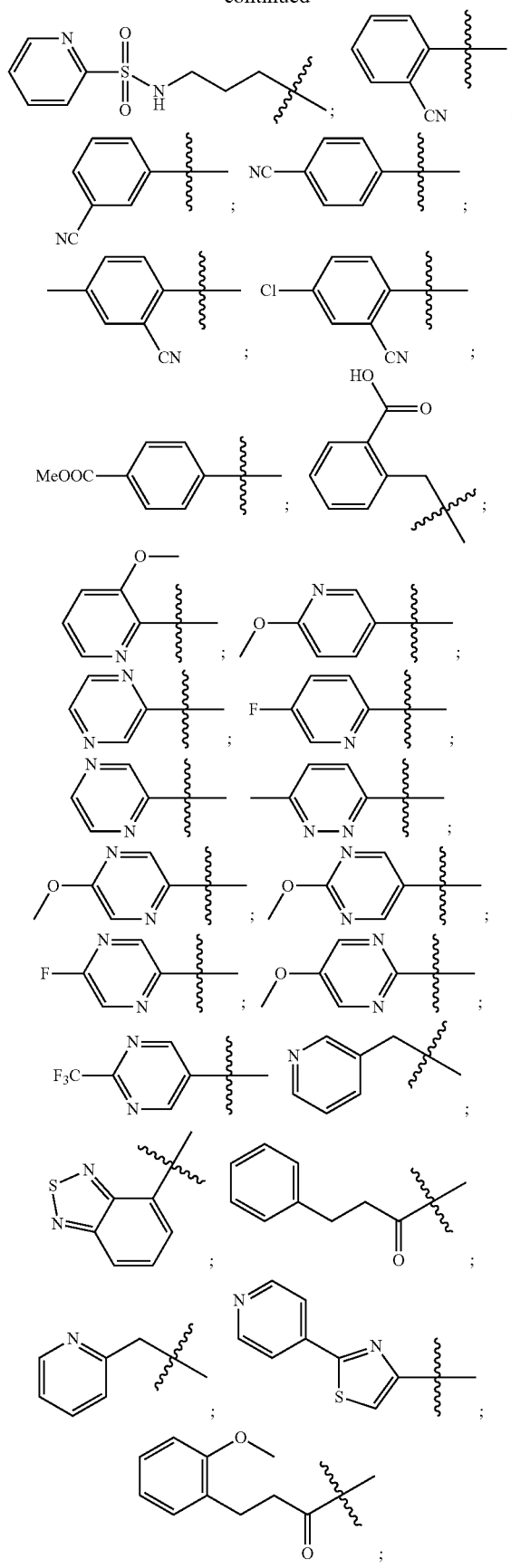
-continued
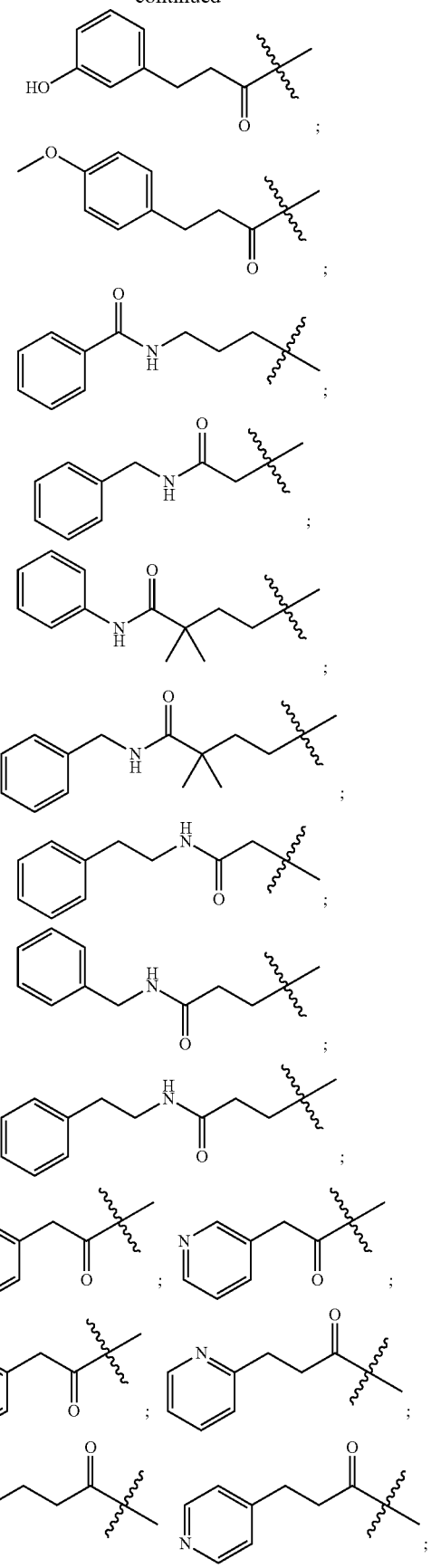

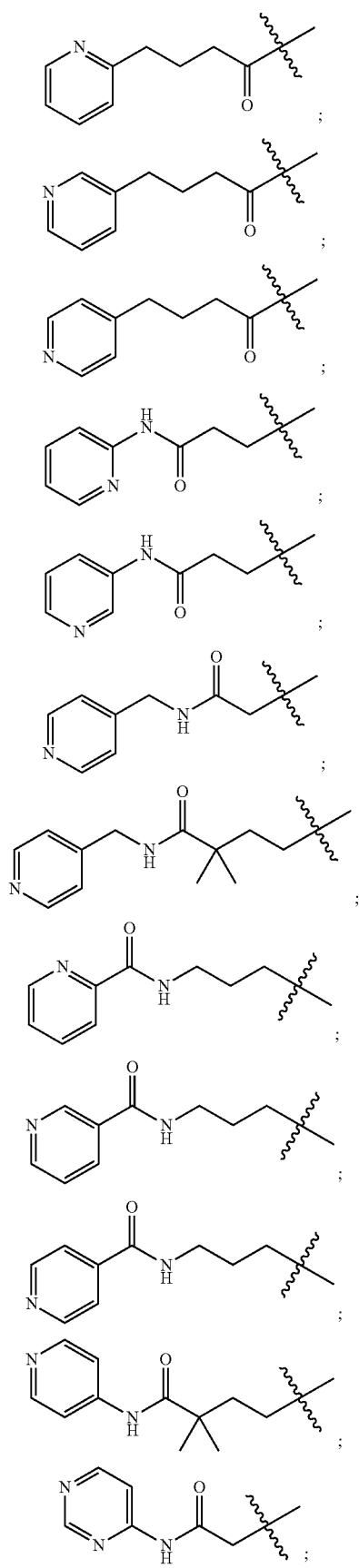
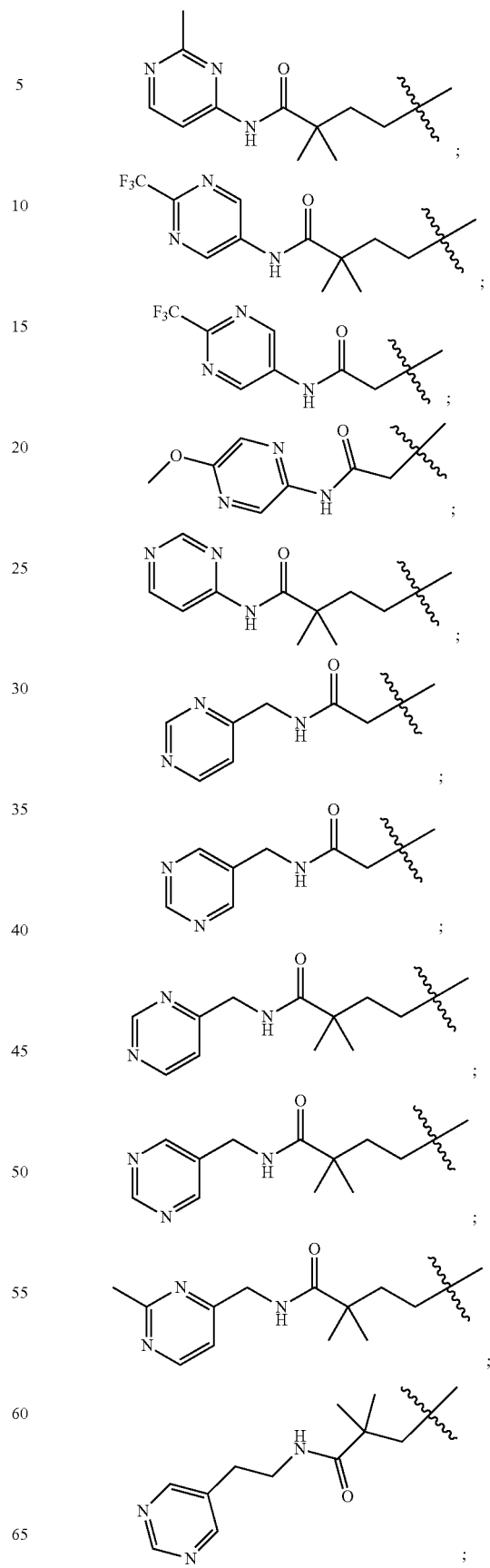

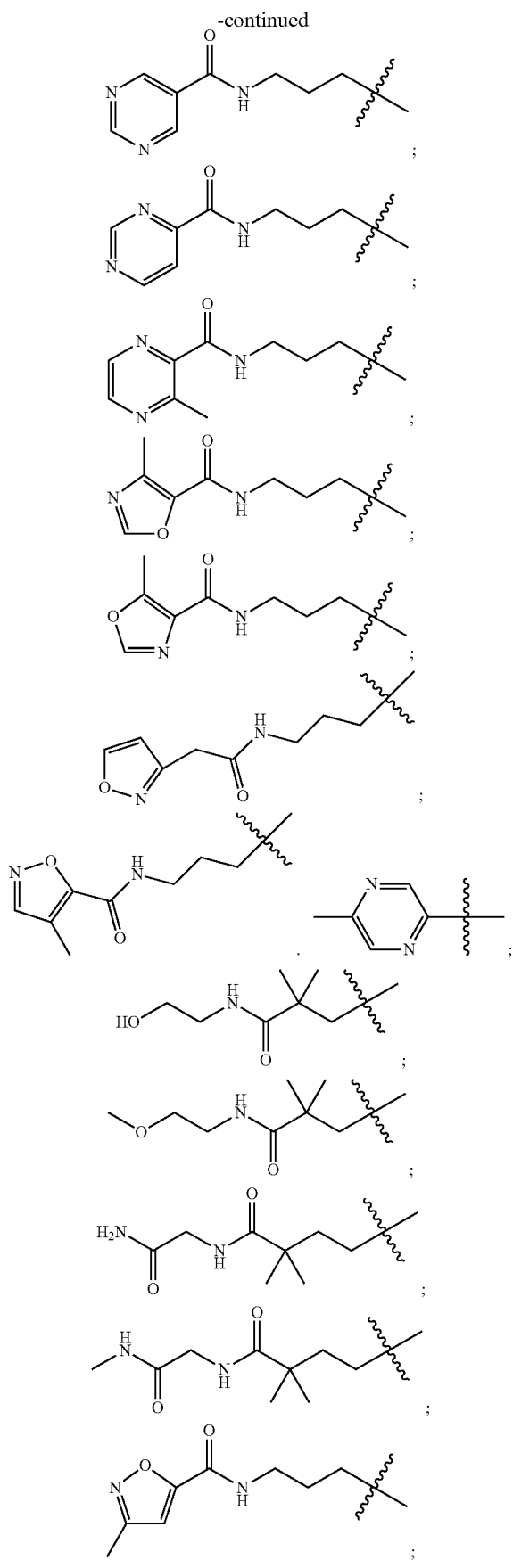

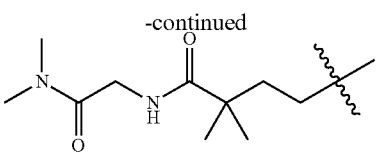

In further preferred embodiments R₄ represents aryl or heteroaryl, in each case unsubstituted or mono- or polysubstituted. In particular, $R_4$ can be selected from the group consisting of phenyl, pyridyl, pyrimidine, thiazole and benzo[c][1,2,5]thiadiazole, in each case unsubstituted or mono- or polysubstituted by substituents from the group consisting of —F, —Cl, —CN, —CF₃, —CH₃, methoxy, pyridyl, or pyrimidinyl.

In further preferred embodiments $R_4$ represents $C_{1-3}$-alkyl which is monosubstituted by a radical —NHR₀, wherein $R_0$ is selected from $C_{1-3}$-alkyl-aryl or $C_{1-3}$-alkyl-heteroaryl, in particular —O(=O)-aryl or —O(=O)-heteroaryl, in each case unsubstituted or mono- or polysubstituted, preferably by one or more radicals independently of each other selected from the group of —F, —Cl, —Br, —CN, —OH, —O—$C_{1-3}$-alkyl, in particular —O—CH₃, —NH₂, —NHC₁₋₃-alkyl, —N(C₁₋₃-alkyl)₂.

In further preferred embodiments $R_4$ represents $C_{1-3}$-alkyl which is monosubstituted by a radical —S(=O)$_{1-2}$—NHR₀, —S(=O)$_{1-2}$—N(R₀)₂, wherein $R_0$ is selected from $C_{1-3}$-alkyl-aryl or $C_{1-3}$-alkyl-heteroaryl, in particular —O(=O)-aryl or —O(=O)-heteroaryl, in each case unsubstituted or mono- or polysubstituted, preferably by one or more radicals independently of each other selected from the group of —F, —Cl, —Br, —CN, —OH, —O—$C_{1-3}$-alkyl, in particular —O—CH₃, —NH₂, —NHC₁₋₃-alkyl, —N(C₁₋₃-alkyl)₂.

In further preferred embodiments $R_4$ represents $C_{1-3}$-alkyl which is monosubstituted by a radical —O(=O)NHR₀, preferably selected from the group consisting of $C_{1-6}$-alkyl, $C_{1-3}$-alkyl-aryl or $C_{1-3}$-alkyl-heteroaryl, in each case unsubstituted or mono- or polysubstituted, preferably by one or more radicals independently of each other selected from the group of —F, —Cl, —Br, —CN, —OH, —O—$C_{1-3}$-alkyl, in particular —O—CH₃, —NH₂, —NHC₁₋₃-alkyl, —N(C₁₋₃-alkyl)₂, —O(=O)OH, —O(=O)NH(C₁₋₃-alkyl), —O(=O)N(C₁₋₃-alkyl)₂ or —O(=O)NH₂.

Preferably, $R_5$ represents —H, —$C_{1-5}$-aliphatic, —$C_{3-8}$-cycloaliphatic, -aryl, or -heteroaryl; or represents an -aryl, —$C_{3-8}$-cycloaliphatic or -heteroaryl in each case bonded via a —$C_{1-3}$-aliphatic group.

Preferably, $R_6$ and $R_7$ independently of each other represent —H, —$C_{1-5}$-aliphatic, —$C_{3-8}$-cycloaliphatic, -aryl, or -heteroaryl, or represent an -aryl, —$C_{3-8}$-cycloaliphatic or -heteroaryl in each case bonded via a —$C_{1-3}$-aliphatic group; or $R_6$ and $R_7$ together form —CH₂CH₂OCH₂CH₂—, —CH₂CH₂N—R₁₀CH₂CH₂— or —(OH₂)$_{3-6}$—. Particularly preferably, $R_6$ and $R_7$ independently of each other represent —H, —$C_{1-5}$-aliphatic; or $R_6$ and $R_7$ together form —CH₂CH₂OCH₂CH₂—, —CH₂CH₂N—R₁₀CH₂CH₂— or —(CH₂)$_{3-6}$—.

Preferably, $R_5$ represents —H, —$C_{1-5}$-aliphatic, —$C_{3-8}$-cycloaliphatic, -aryl, or -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, or —O(=O)—$C_{1-6}$-aliphatic.

Preferably, $R_9$ represents —H, —$C_{1-5}$-aliphatic, —$C_{3-8}$-cycloaliphatic, -aryl- or -heteroaryl, or -aryl, —$C_{3-8}$-cycloaliphatic or -heteroaryl, in each case bonded via —$C_{1-3}$-aliphatic, or represents —OR₅ or —NR₆R₇.

Particularly preferably, $R_9$ is -methyl, -ethyl, -propyl, -butyl, -pentyl, -hexyl, -heptyl, -cyclopentyl, -cyclohexyl, -phenyl, -benzyl, -naphthyl, -anthracenyl, -thiophenyl (-thienyl), -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, in each case unsubstituted or mono- or polysubstituted; a -cyclopentyl or -cyclohexyl bonded via a —$CH_2$— group; an -aryl or -heteroaryl, preferably phenyl, bonded via —$CH_2$—, —$CH_2CH_2$— or —CH═CH—; or $NR_6R_7$ Particularly preferably, $R_{10}$ represents —H or —$C_{1-5}$-aliphatic.

In preferred embodiments $R_{12}$ represents H, $C_{1-6}$-alkyl, $C_{1-3}$-alkyl-aryl or $C_{1-3}$-alkyl-heteroaryl.

In further preferred embodiments of the invention, the compounds have a core structure as defined by general formulas 3.1.2. or 3.2., preferably 3.1.2, wherein $R_4$ is selected from the group of moieties defined in "List 1" and "List 2" above, $X_3$ and $X_3'$ are —H, $X_1$ is either —H, -benzyl or -methoxymethyl, $R_1$ and $R_2$ independently of each other are either —H or -methyl, wherein preferably, $R_1$ and $R_2$, are not —H at the same time, $R_3$ is selected from the group consisting of -phenyl, pyridinyl, pyrazinyl, or -thienyl, in each case unsubstituted or monosubstituted by —F, —Cl, —$CH_3$; -ethyl, -n-propyl, -n-butyl, -vinyl, or -allyl, unsubstituted or mono- or polysubstituted by —$OCH_3$, —OH or —$CO_2H_5$, in particular by —$OCH_3$ or —$OC_2H_5$, preferably $R_3$ is selected from -phenyl, -benzyl, -thienyl, 5-methylthiophen-2-yl, 5-fluorothiophen-2-yl, 5-chlorothiophen-2-yl, pyridine-2-yl, pyrazin-2-yl or 3-methoxy-propyl;

For the purpose of the description, hydrocarbon radicals are divided into aliphatic hydrocarbon radicals on the one hand and aromatic hydrocarbon radicals on the other hand. Aliphatic hydrocarbon radicals are in their turn divided into non-cyclic aliphatic hydrocarbon radicals on the one hand (="aliphatic") and cyclic aliphatic hydrocarbon radicals, i.e. alicylic hydrocarbon radicals, on the other hand (="cycloaliphatic"). Cycloaliphatics can be monocyclic or multicyclic. Alicyclic hydrocarbon radicals ("cycloaliphatic") include both pure aliphatic carbocycles and aliphatic heterocycles, i.e.—if not expressly specified —"cycloaliphatic" includes pure aliphatic carbocycles (e.g. cyclohexyl), pure aliphatic heterocycles (e.g. piperidyl or piperazyl) and non-aromatic, multicyclic, optionally mixed systems (e.g. decalinyl, decahydroquinolinyl).

Aromatic hydrocarbon radicals are in their turn divided into carbocyclic aromatic hydrocarbons on the one hand (="aryl") and heterocyclic aromatic hydrocarbons on the other hand (="heteroaryl").

The assignment of multicyclic, at least partially aromatic systems preferably depends on whether at least one aromatic ring of the multicyclic system contains at least one hetero atom (conventionally N, O or S) in the ring. If at least one such hetero atom is present in this ring, the system is preferably a "heteroaryl" (even if a further carbocyclic aromatic or non-aromatic ring with or without a hetero atom is present optionally as an additionally present ring of the multicyclic system); if such a hetero atom is present in none of the optionally several aromatic rings of the multicyclic system, the system is preferably "aryl" (even if a ring hetero atom is present in an optionally additionally present non-aromatic ring of the multicyclic system).

Within the cyclic substituents, the following priority of assignment accordingly preferably applies: heteroaryl>aryl>cycloaliphatic.

For the purpose of the description, monovalent and polyvalent, e.g. divalent hydrocarbon radicals are not differentiated with respect to terminology, i.e. "$C_{1-3}$-aliphatic" includes, depending on the sense, e.g. both —$C_{1-3}$-alkyl, —$C_{1-3}$-alkenyl and —$C_{1-3}$-alkynyl, and e.g. —$C_{1-3}$-alkylene-, —$C_{1-3}$-alkenylene- and —$C_{1-3}$-alkynylene-.

Preferably, "aliphatic" is in each case a branched or unbranched, saturated or a mono- or polyunsaturated, unsubstituted or mono- or polysubstituted, aliphatic hydrocarbon radical. If aliphatic is mono- or polysubstituted, the substituents independently of each other are chosen from the group consisting of —F, —Cl, —Br, —I, —CN, —$NO_2$, —CHO, ═O, —$R_0$, —O(═O)$R_0$, —O(═O)OH, —O(═O)O$R_0$, —C(═O)$NH_2$, —C(═O)$NHR_0$, —C(═O)N($R_0$)$_2$, —OH, —$OR_0$, —OC(═O)H, —OC(═O)$R_0$, —OC(═O)O$R_0$, —OC(═O)—$NHR_0$, —OC(═O)N($R_0$)$_2$, —SH, —$SR_0$, —$SO_3H$, —S(═O)$_{1-2}$$R_0$, —S(═O)$_{1-2}$$NH_2$, —$NH_2$, —$NHR_0$, —N($R_0$)$_2$, —$N^+$($R_0$)$_3$, —$N^+$($R_0$)$_2O^-$, —NHC(═O)$R_0$, —NHC(═O)$OR_0$, —NHC(═O)$NH_2$, —NHC(═O)$NHR_0$, —NHC(═O)N($R_0$)$_2$, —NHS(═O)$_{1-2}$$R_0$, —Si($R_0$)$_3$, —PO(O$R_0$)$_2$. "Aliphatic" thus includes acyclic saturated or unsaturated hydrocarbon radicals, which can be branched or straight-chain, i.e. alkanyls, alkenyls and alkynyls. In this context alkenyls have at least one C═C double bond and alkynyls have at least one C≡C triple bond. Preferred unsubstituted monovalent aliphatics include —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, —$CH_2CH_2CH_2$—$CH_2CH_3$ and —$CH_2CH_2$—$CH_2CH_2CH_2CH_3$; but also —CH═$CH_2$, —C≡CH, —$CH_2CH$═$CH_2$, —CH═$CHCH_3$, —$CH_2C$≡CH, —C≡$CCH_3$ and —CH═$CHCH$═$CH_2$. Preferred unsubstituted divalent aliphatics include —$CH_2$—, —$CH_2CH_2$—, —$CH_2CH(CH_3)$—, —CH($CH_3$)—$CH_2$—, —$CH_2CH_2CH_2$—, —CH($CH_3$)$CH_2CH_2$—, —$CH_2CH(CH_3)$—$CH_2$—, —$CH_2CH_2CH(CH_3)$—, —CH—($CH_2CH_3$)$CH_2$— and —$CH_2CH_2$—$CH_2CH_2$—; but also —CH═CH—, —C≡C—, —$CH_2CH$═CH—, —CH═$CHCH_2$—, —$CH_2C$≡C— and —C≡$CCH_2$—. Preferred substituted monovalent aliphatics include —$CH_2F$, —$CHF_2$, —$CF_3$, —$CH_2CF_3$, —$CF_2CF_3$, —$CH_2OH$, —$CH_2CH_2OH$, —$CH_2CHOHCH_3$, —$CH_2OCH_3$ and $CH_2CH_2OCH_3$. Preferred substituted divalent aliphatics include —$CF_2$—, —$CF_2CF_2$—, —$CH_2CHOH$—, —$CHOHCH_2$— and —$CH_2CHOHCH_2$—.

Methyl, ethyl, n-propyl and n-butyl are particularly preferred aliphatics.

Preferably, cycloaliphatic is in each case a saturated or a mono- or polyunsaturated, unsubstituted or mono- or polysubstituted, aliphatic (i.e. non-aromatic), mono- or multicyclic hydrocarbon radical, The number of ring carbon atoms is preferably in the stated range (i.e. a "$C_{3-8}$-"cycloaliphatic preferably has 3, 4, 5, 6, 7 or 8 ring carbon atoms). For the purpose of the description, "$C_{3-8}$-cycloaliphatic" is preferably a cyclic hydrocarbon having 3, 4, 5, 6, 7 or 8 ring carbon atoms, saturated or unsaturated, but not aromatic, one or two carbon atoms independently of each other optionally being replaced by a hetero atom S, N or O. If cycloalkyl is mono- or polysubstituted, the substituents independently of each other are chosen from the group consisting of —F, —Cl, —Br, —I, —CN, —$NO_2$, —CHO, ═O, —$R_0$, —C(═O)$R_0$, —C(═O)OH, —C(═O)$OR_0$, —C(═O)$NH_2$, —C(═O)$NHR_0$, —C(═O)N($R_0$)$_2$, —OH, —$OR_0$, —OC(═O)H, —OC(═O)$R_0$, —OC(═O)$OR_0$, —OC(═O)$NHR_0$, —OC(═O)—N($R_0$)$_2$, —SH, —$SR_0$, —$SO_3H$, —S(═O)$_{1-2}$—$R_0$, —S(═O)$_{1-2}$$NH_2$, —$NH_2$, —$NHR_0$, —N($R_0$)$_2$, —$N^+$($R_0$)$_3$, —$N^+$($R_0$)$_2O^-$, —NHC(═O)$R_0$, —NHC(═O)$OR_0$, —NHC(═O)$NH_2$, —NHC(═O)$NHR_0$, —NHC(═O)N($R_0$)$_2$, NHS(═O)$_{1-2}$$R_0$, —Si $(R_0)_3$, —$PO(OR_0)_2$. $C_{3-8}$-Cycloaliphatic is advantageously chosen from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

Cyclopentyl and cyclohexyl are particularly preferred $C_{3-8}$-cycloaliphatics.

Preferably, in connection with "aliphatic" or "cycloaliphatic", "mono- or polysubstituted" is understood as meaning substitution once or several times, e.g. once, twice, three times or four times, of one or more hydrogen atoms by —F, —Cl, —Br, —I, —OH, —$OC_{1-6}$-alkyl, —$OC(=O)C_{1-6}$-alkyl, —SH, —$NH_2$, —$NHC_{1-6}$-alkyl, —$N(C_{1-6}$-alkyl$)_2$, —$O(=O)OC_{1-6}$-alkyl or —$O(=O)OH$. Compounds wherein "aliphatic substituted" or "cycloaliphatic substituted" means aliphatic or cycloaliphatic substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —$N(CH_3)_2$ are preferred. Particularly preferred substituents are —F, —Cl, —OH, —SH, —$NH_2$ and —$O(=O)OH$.

Polysubstituted radicals are to be understood as meaning those radicals which are polysubstituted, e.g. di- or trisubstituted, either on different or on the same atoms, for example trisubstituted on the same C atom, as in the case of —$CF_3$ or —$CH_2CF_3$, or at different places, as in the case of —$CH(OH)$—$CH=CH$—$CHCl_2$. Polysubstitution can be with the same or with various substituents. A substituent can optionally also be substituted in its turn; thus —Oaliphatic, inter alia, also includes —$OCH_2CH_2O$—$CH_2CH_2$—OH. It is preferable for aliphatic or cycloaliphatic to be substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —$N(CH_3)_2$. It is very particularly preferable for aliphatic or cycloaliphatic to be substituted by —OH, —$OCH_3$ or —$OC_2H_5$.

Preferably, "aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl. Preferred aryls are phenyl, naphthyl, anthracenyl, phenanthrenyl, fluoranthenyl, fluorenyl, indanyl and tetralinyl. Phenyl and naphthyl are particularly preferred. If aryl is mono- or polysubstituted, the substituents on aryl can be identical or different and can be in any desired and possible position of the aryl, and are independently of each other chosen from the group consisting of —F, —Cl, —Br, —I, —CN, —$NO_2$, —CHO, =O, —$R_0$, —$C(=O)R_0$, —$O(=O)OH$, —$O(=O)OR_0$, —$C(=O)$—$NH_2$, —$C(=O)$ $NHR_0$, —$C(=O)N(R_0)_2$, —OH, —$O(CH_2)_{1-2}O$—, —$OR_0$, —$OC(=O)H$, —$OC(=O)R_0$, —$OC(=O)OR_0$, —$OC(=O)$—$NHR_0$, —$OC(=O)N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —$NHC(=O)R_0$, —$NHC(=O)OR_0$, —$NHC(=O)NH_2$, —$NHC(=O)NHR_0$, —$NHC(=O)N(R_0)_2$, —$Si(R_0)_3$, —$PO(OR_0)_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxyphenyl, 3-methoxyphenyl, 4-methoxyphenyl, 2,3-dimethoxyphenyl, 2,4-dimethoxyphenyl, 3,4-dimethoxyphenyl, 2-methylphenyl, 3-methylphenyl, 4-methylphenyl, 2,3-dimethylphenyl, 2,4-dimethylphenyl and 3,4-dimethylphenyl.

Preferably, heteroaryl represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system. Preferably, "heteroaryl" is chosen from the group consisting of pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, where bonding can be via any desired and possible ring member of the heteroaryl radical. If heteroaryl is mono- or polysubstituted, the substituents on heteroaryl can be identical or different and can be in any desired and possible position of the heteroaryl, and are independently of each other chosen from the group consisting of —F, —Cl, —Br, —I, —CN, —$NO_2$, —CHO, =O, —$R_0$, —$O(=O)R_0$, —$O(=O)OH$, —$C(=O)OR_0$, —$C(=O)$—$NH_2$, —$C(=O)$ $NHR_0$, —$C(=O)N(R_0)_2$, —OH, —$O(CH_2)_{1-2}O$—, —$OR_0$, —$OC(=O)H$, —$OC(=O)R_0$, —$OC(=O)OR_0$, —$OC(=O)NHR_0$, —$OC(=O)$—$N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —$NH$—$C(=O)R_0$, —$NHC(=O)OR_0$, —$NHC(=O)NH_2$, —$NHC(=O)NHR_0$, —$NH$—$C(=O)N(R_0)_2$, —$Si(R_0)_3$, —$PO(OR_0)_2$; wherein N ring atoms optionally present can in each case be oxidised (N-oxide).

With respect to "aryl" or "heteroaryl", "mono- or polysubstituted" is understood as meaning substitution once or several times, e.g. twice, three times, four times or five times, of one or more hydrogen atoms of the ring system.

The substituents on aryl and heteroaryl are particularly preferably in each case independently of each other chosen from —F, —Cl, —Br, —I, —CN, —CHO, —$CO_2H$, —$NH_2$, —$NO_2$, —$NHR_0$, —$N(R_0)_2$, —$N^+(R_0)_3$, —$N^+(R_0)_2O^-$, —SH, —$SR_0$, —OH, —$OR_0$, —$O(=O)R_0$, —$CO_2R_0$, —$C(=O)NH_2$, —$C(=O)NHR_0$, —$C(=O)N(R_0)_2$, —$S(=O)_{1-2}R_0$, —$S(=O)_2NH_2$, —$SO_3H$, =O or —$R_0$. Preferred substituents are —F, —Cl, —Br, —I, —OH, —$OC_{1-6}$-alkyl, —O—$O(=O)$—$C_{1-6}$-alkyl, —SH, —$NH_2$, —$NHC_{1-6}$-alkyl, —$N(C_{1-6}$-alkyl$)_2$, —$O(=O)OC_{1-6}$-alkyl or —$O(=O)OH$. Compounds wherein "aryl substituted" or "heteroaryl substituted" means aryl or heteroaryl substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —$N(CH_3)_2$ are preferred. Particularly preferred substituents are —F, —Cl, —$CH_3$, —OH, —SH, —$NH_2$ and —$C(=O)$ OH.

The compounds according to the invention can be in the form of an individual stereoisomer or mixture thereof, the free compounds and/or their physiologically acceptable salts and/or solvates.

With respect to the spiro ring, the compounds according to the invention are isomers in which the substitution pattern on the spiro cyclohexane ring system can also be designated cis/trans, Z/E or syn/anti. "cis-trans isomers" are a subgroup of stereoisomers (configuration isomers).

The cis-trans isomers of the compound of the general formula (1) according to the invention have the general formula (1a) or (1b):

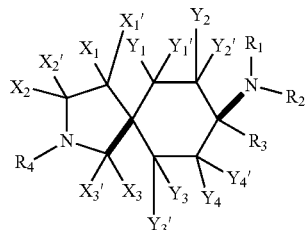

(1a)

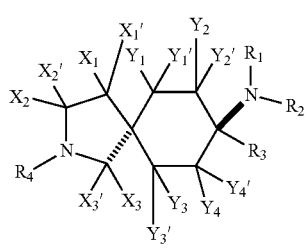

(1b)

The assignment of the two stereoisomers (1a) and (1b) according to the substitution pattern as the cis or trans isomer is known to the person skilled in the art.

In a preferred embodiment, the diastereomer excess of the cis isomer is at least 50% de, more preferably at least 75% de, still more preferably at least 90% de, most preferably at least 95% de and in particular at least 99% de. In another preferred embodiment, the diastereomer excess of the trans isomer is at least 50% de, more preferably at least 75% de, still more preferably at least 90% de, most preferably at least 95% de and in particular at least 99% de.

Suitable methods for separation of the isomers (diastereomers) are known to the person skilled in the art. Examples which may be mentioned are column chromatography, preparative HPLC and crystallization methods.

A person skilled in the art moreover recognises that the compounds according to the invention can be chiral or achiral, depending on the substitution pattern.

If the compounds according to the invention are chiral, they are preferably in the form of the racemate or in a concentrated form of one enantiomer. In a preferred embodiment the enantiomer excess (ee) of the S enantiomer is at least 50% ee, more preferably at least 75% ee, still more preferably at least 90% ee, most preferably at least 95% ee and in particular at least 99% ee. In another preferred embodiment the enantiomer excess (ee) of the R enantiomer is at least 50% ee, more preferably at least 75% ee, still more preferably at least 90% ee, most preferably at least 95% ee and in particular at least 99% de.

Suitable methods for separation of the enantiomers are known to the person skilled in the art. Examples which may be mentioned are preparative HPLC on chiral stationary phases and conversion into diastereomeric intermediates. The conversion into diastereomeric intermediates can be carried out, for example, as salt formation with the aid of chiral, enantiomerically pure acids. After the separation of the diastereomers formed in this way, the salt can then be converted back into the free base or another salt.

If not expressly specified, any reference to the compounds according to the invention includes all the isomers (e.g. stereoisomers, diastereomers, enantiomers) in any desired mixing ratio.

If not expressly specified, any reference to the compounds according to the invention includes the free compounds (i.e. the forms which are not in the form of a salt) and all physiologically acceptable salts.

For the purpose of the description, physiologically acceptable salts of the compounds according to the invention are in the form of salts with anions or acids of the particular compound with inorganic or organic acids which are physiologically acceptable—in particular when used in humans and/or mammals.

Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride, the citrate and the hemicitrate are particularly preferred.

Physiologically acceptable salts with cations or bases are salts of the particular compound—as the anion with at least one, preferably inorganic cation—which are physiologically acceptable—in particular when used in humans and/or mammals. The salts of alkali metals and alkaline earth metals but also ammonium salts are particularly preferred, but in particular (mono)- or (di)sodium, (mono)- or (di)potassium, magnesium or calcium salts.

The compounds according to the invention are defined by substituents, for example by $R_1$, $R_2$ and $R_3$ (substituents of the 1st generation), which in their turn are optionally substituted (substituents of the 2nd generation). Depending on the definition, these substituents of the substituents can in their turn be substituted again (substituents of the 3rd generation). For example, if $Y_1$=—$R_0$, wherein $R_0$= —$C_{1-8}$-aliphatic (substituent of the 1st generation), —$CO_{1-8}$-aliphatic can in its turn be substituted, e.g. by —$OR_0$, wherein $R_0$=-aryl (substituent of the 2nd generation). The functional group —$C_{1-8}$-aliphatic-Oaryl results from this. -Aryl can then in its turn be substituted again, e.g. by —Cl (substituent of the 3rd generation). The functional group —$C_{1-8}$-aliphatic-Oaryl-Cl overall then results from this.

In a preferred embodiment, however, the substituents of the 3rd generation cannot be substituted again, i.e. there are then no substituents of the 4th generation.

In another preferred embodiment, however, the substituents of the 2nd generation cannot be substituted again, i.e. there are then already no substituents of the 3rd generation. In other words, in this embodiment the functional groups for $R_0$ to $R_{10}$ can in each case be optionally substituted, but the particular substituents cannot then in their turn be substituted again.

In another preferred embodiment the substituents of the 1st generation already cannot be substituted again, i.e. there are then neither substituents of the 2nd nor substituents of the 3rd generation. In other words, in this embodiment the functional groups for $R_0$ to $R_{10}$ in each case cannot be substituted.

Preferred compounds are those wherein "aliphatic substituted" or "cycloaliphatic substituted" means aliphatic or cycloaliphatic substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —$N(CH_3)_2$; and "aryl substituted" or "heteroaryl substituted" means aryl or heteroaryl substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N(CH₃)₂ in the form of the racemate; the enantiomers, diastereomers, mixtures of the enantiomers or diastereomers or of an individual enantiomer or diastereomer; the bases and/or salts of physiologically acceptable acids or cations.

Very particularly preferred compounds are those according to the following structural formula (A), wherein the radicals have the meanings described in the following table and the compounds can be in the form of an individual stereoisomer or mixture thereof, the free compounds and/or their physiologically acceptable salts and/or solvates.

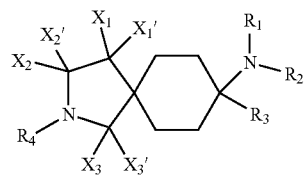

(A)

| Ex. | R₁ | R₂ | R₃ | X₁/X₁' | X₂/X₂' | X₃/X₃' | R₄ |
|---|---|---|---|---|---|---|---|
| 1; 2 | CH₃ | CH₃ | Benzyl | H/H | H/H | H/H | cinnamoyl (PhCH=CH-C(O)-) |
| 3 | CH₃ | CH₃ | Benzyl | H/H | H/H | H/H | Benzyl |
| 4; 5 | CH₃ | CH₃ | 2-Thienyl | H/H | H/H | H/H | cinnamoyl |
| 6 | CH₃ | CH₃ | 2-Thienyl | H/H | H/H | H/H | -C(CH₃)₂-C(O)-NH-CH₂CH₃ |
| 7 | CH₃ | CH₃ | 2-Thienyl | H/H | H/H | H/H | Benzyl |
| 8 | CH₃ | CH₃ | 2-Thienyl | H/H | H/H | H/H | 4-pyridylmethyl |
| 9 | CH₃ | CH₃ | Benzyl | H/H | H/H | H/H | -C(CH₃)₂-C(O)-NH-CH₂CH₃ |
| 10 | CH₃ | CH₃ | Benzyl | H/H | H/H | H/H | 4-pyridylmethyl |
| 11; 12 | CH₃ | CH₃ | Phenyl | H/H | H/H | H/H | cinnamoyl |
| 13 | CH₃ | CH₃ | 2-Thienyl | H/H | H/H | H/H | cinnamoyl |

-continued

| Ex. | R₁ | R₂ | R₃ | X₁/X₁' | X₂/X₂' | X₃/X₃' | R₄ |
|---|---|---|---|---|---|---|---|
| 14; 15 | CH₃ | CH₃ | 2-Thienyl | H/H | H/H | H/H | Benzyl |
| 16 | CH₃ | CH₃ | 5-(2-thienyl) | H/H | H/H | H/H | Benzyl |
| 17 | CH₃ | CH₃ | 5-(2-thienyl) | H/H | H/H | H/H | phenyl-C(O)-CH< |
| 18 | CH₃ | CH₃ | 5-(2-thienyl) | H/H | H/H | H/H | 3-pyridyl-C(O)-CH< |
| 19 | CH₃ | CH₃ | 5-(2-thienyl) | H/H | H/H | H/H | 4-pyridyl-C(O)-CH< |
| 20 | CH₃ | CH₃ | 5-(2-thienyl) | H/H | H/H | H/H | 2-pyridyl-C(O)-CH< |
| 21 | CH₃ | CH₃ | 5-(2-thienyl) | H/H | H/H | H/H | Phenyl |
| 22 | CH₃ | CH₃ | 5-(2-thienyl) | H/H | H/H | H/H | 3-pyridyl-CH₂- |
| 23 | CH₃ | CH₃ | 5-(2-thienyl) | H/H | H/H | H/H | 4-pyridyl-CH₂- |
| 24 | CH₃ | CH₃ | 2-Thienyl | H/H | H/H | H/H | phenyl-C(O)-CH< |
| 25 | CH₃ | CH₃ | 2-Thienyl | H/H | H/H | H/H | 4-pyridyl-C(O)-CH< |
| 26 | CH₃ | CH₃ | 2-Thienyl | H/H | H/H | H/H | 3-pyridyl-C(O)-CH< |

-continued

| Ex. | R$_1$ | R$_2$ | R$_3$ | X$_1$/X$_1$' | X$_2$/X$_2$' | X$_3$/X$_3$' | R$_4$ |
|---|---|---|---|---|---|---|---|
| 27 | CH$_3$ | CH$_3$ | 2-Thienyl | H/H | H/H | H/H | 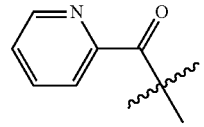 [SMILES: *C(=O)c1ccccn1] |
| 28; 29 | CH$_3$ | CH$_3$ | 2-Thienyl | H/H | H/H | H/H | 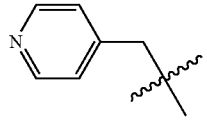 [SMILES: *Cc1ccncc1] |
| 30 | CH$_3$ | CH$_3$ | 2-Thienyl | H/H | H/H | H/H | 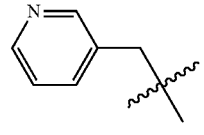 [SMILES: *Cc1cccnc1] |
| 31 | CH$_3$ | CH$_3$ | 2-Thienyl | H/H | H/H | H/H | Phenyl |
| 32 | CH$_3$ | CH$_3$ | 2-Thienyl | H/H | H/H | H/H | 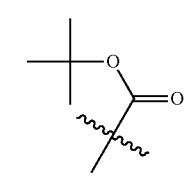 |
| 33 | CH$_3$ | CH$_3$ | 2-Thienyl | H/H | H/H | H/H | 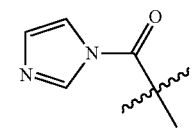 [SMILES: *C(=O)n1ccnc1] |
| 34 | CH$_3$ | CH$_3$ | 2-Thienyl | H/H | H/H | H/H | 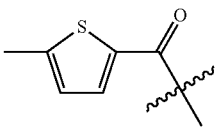 [SMILES: *C(=O)c1ccc(C)s1] |
| 35 | CH$_3$ | CH$_3$ | 2-Thienyl | H/H | H/H | H/H | 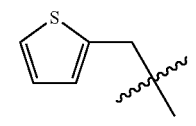 [SMILES: *Cc1cccs1] |
| 36 | CH$_3$ | CH$_3$ | 2-Thienyl | H/H | H/H | H/H | 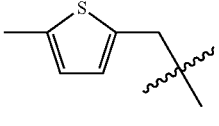 [SMILES: *Cc1ccc(C)s1] |
| 37 | CH$_3$ | CH$_3$ | 2-Thienyl | H/H | H/H | H/H | 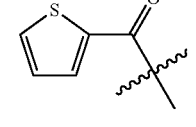 |
| 38 | CH$_3$ | CH$_3$ | 2-Thienyl | H/H | H/H | H/H | 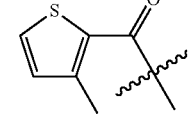 |
| 39 | CH$_3$ | CH$_3$ | 2-Thienyl | H/H | H/H | H/H | 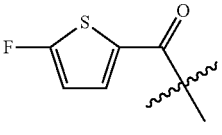 [SMILES: *C(=O)c1ccc(F)s1] |

-continued
| Ex. | R₁ | R₂ | R₃ | X₁/X₁' | X₂/X₂' | X₃/X₃' | R₄ |
|---|---|---|---|---|---|---|---|
| 40 | CH₃ | CH₃ | 2-Thienyl | H/H | H/H | H/H | 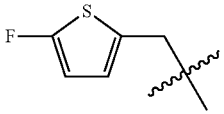 |
| 41 | CH₃ | CH₃ | 2-Thienyl | H/H | H/H | H/H | 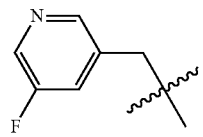 [SMILES: *Cc1cncc(F)c1] |
| 42 | CH₃ | CH₃ | 2-Thienyl | H/H | H/H | H/H | 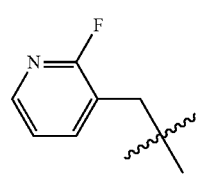 [SMILES: *Cc1cccnc1F] |
| 43 | CH₃ | CH₃ | 2-Thienyl | H/H | H/H | H/H | 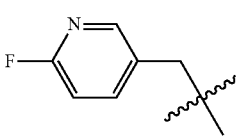 |
| 44 | CH₃ | CH₃ | 2-Thienyl | H/H | H/H | H/H | 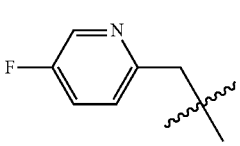 |
| 45 | CH₃ | CH₃ | 2-Thienyl | H/H | H/H | H/H | 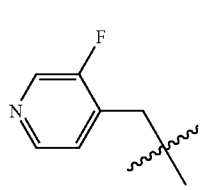 [SMILES: *Cc1ccncc1F] |
| 46 | CH₃ | CH₃ | 2-Thienyl | H/H | H/H | H/H | Benzyl |
| 47 | CH₃ | CH₃ | 2-Thienyl | H/H | H/H | H/H | 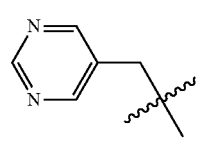 |
| 48 | CH₃ | CH₃ | 2-Thienyl | H/H | H/H | H/H | 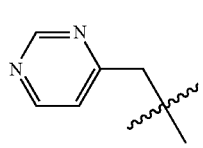 [SMILES: *Cc1ccncn1] |
| 49 | CH₃ | CH₃ | Phenyl | H/H | H/H | H/H | 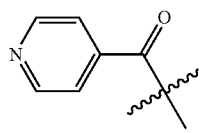 |
| 50 | CH₃ | CH₃ | Phenyl | H/H | H/H | H/H | 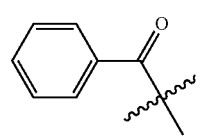 |

-continued
| Ex. | R₁ | R₂ | R₃ | X₁/X₁' | X₂/X₂' | X₃/X₃' | R₄ |
|---|---|---|---|---|---|---|---|
| 51 | CH₃ | CH₃ | Phenyl | H/H | H/H | H/H | Benzyl |
| 52 | CH₃ | CH₃ | Phenyl | H/H | H/H | H/H | 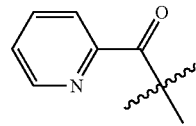 [SMILES: *C(=O)c1ccccn1] |
| 53 | CH₃ | CH₃ | Phenyl | H/H | H/H | H/H | 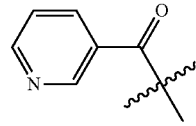 |
| 54 | CH₃ | CH₃ | Phenyl | H/H | H/H | H/H | 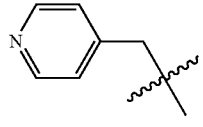 |
| 55 | CH₃ | CH₃ | Phenyl | H/H | H/H | H/H | 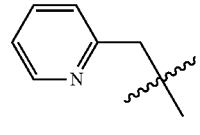 [SMILES: *Cc1ccccn1] |
| 56 | CH₃ | CH₃ | Phenyl | H/H | H/H | H/H | 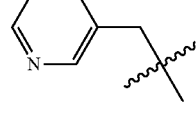 |
| 57 | CH₃ | CH₃ | Phenyl | H/H | H/H | H/H | 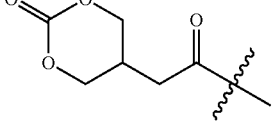 |
| 58 | CH₃ | CH₃ | 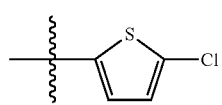 [SMILES: *c1ccc(Cl)s1] | H/H | H/H | H/H | 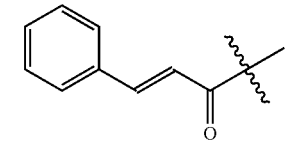 [SMILES: *C(=O)/C=C/c1ccccc1] |
| 59 | CH₃ | CH₃ | 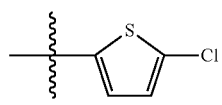 [SMILES: *c1ccc(Cl)s1] | H/H | H/H | H/H | Benzyl |
| 60 | CH₃ | CH₃ | 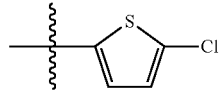 | H/H | H/H | H/H | 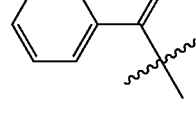 |
| 61 | CH₃ | CH₃ | 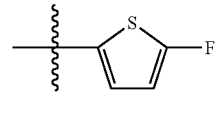 [SMILES: *c1ccc(F)s1] | H/H | H/H | H/H | 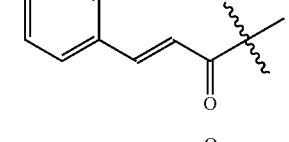 |
| 62 | CH₃ | CH₃ | 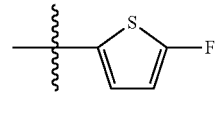 | H/H | H/H | H/H | 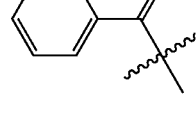 |

-continued
| Ex. | R₁ | R₂ | R₃ | X₁/X₁' | X₂/X₂' | X₃/X₃' | R₄ |
|---|---|---|---|---|---|---|---|
| 63 | CH₃ | CH₃ | 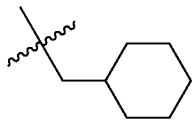 [SMILES: *CC1CCCCC1] | H/H | H/H | H/H | 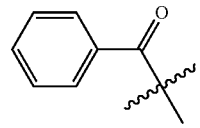 [SMILES: *C(=O)c1ccccc1] |
| 64 | CH₃ | CH₃ | 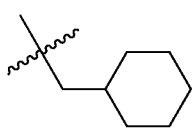 | H/H | H/H | H/H | Benzyl |
| 65 | CH₃ | CH₃ | 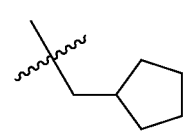 [SMILES: *CC1CCCC1] | H/H | H/H | H/H | 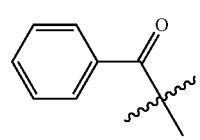 |
| 66 | CH₃ | CH₃ | 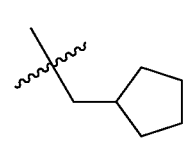 [SMILES: *CC1CCCC1] | H/H | H/H | H/H | Benzyl |
| 67 | CH₃ | CH₃ | 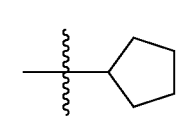 [SMILES: *C1CCCC1] | H/H | H/H | H/H | 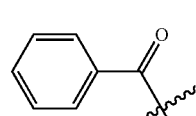 |
| 68 | CH₃ | CH₃ | 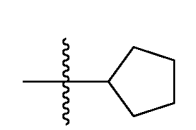 | H/H | H/H | H/H | Benzyl |
| 69; 70 | CH₃ | CH₃ | 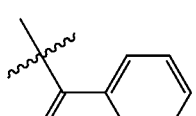 | H/H | H/H | H/H | Benzyl |
| 71; 72 | CH₃ | CH₃ | 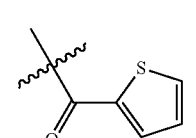 | H/H | H/H | H/H | Benzyl |
| 73; 74 | —CH₂CH₂CH₂— | | 2-Thienyl | H/H | H/H | H/H | 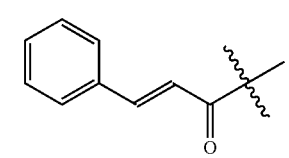 [SMILES: *C(=O)/C=C/c1ccccc1] |
| 75; 76 | —CH₂CH₂CH₂— | | 2-Thienyl | H/H | H/H | H/H | 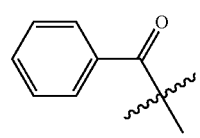 [SMILES: *C(=O)c1ccccc1] |
| 77 | —CH₂CH₂CH₂— | | 2-Thienyl | H/H | H/H | H/H | Benzyl |
| 78; 79 | —CH₂CH₂CH₂— | | Phenyl | H/H | H/H | H/H | 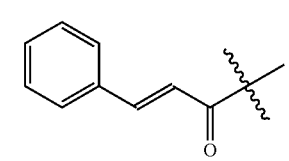 [SMILES: *C(=O)/C=C/c1ccccc1] |

-continued

| Ex. | R₁ | R₂ | R₃ | X₁/X₁' | X₂/X₂' | X₃/X₃' | R₄ |
|---|---|---|---|---|---|---|---|
| 80, 81 | —CH₂CH₂CH₂— | | Phenyl | H/H | H/H | H/H | 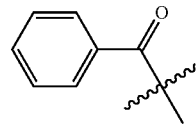 [SMILES: *C(=O)c1ccccc1] |
| 82, 83 | —CH₂CH₂CH₂— | | Phenyl | H/H | H/H | H/H | Benzyl |
| 84 | CH₃ | CH₃ | H/H | H/H | H/H | =O | Benzyl |
| 85 | CH₃ | CH₃ | H/H | H/H | H/H | =O | 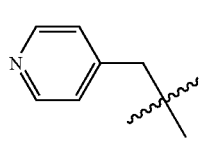 |
| 86; 87 | CH₃ | CH₃ | Benzyl | H/H | H/H | =O | Benzyl |
| 88; 89 | CH₃ | CH₃ | 2-Thienyl | H/H | =O | H/H | 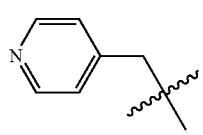 [SMILES: *Cc1ccncc1] |
| 90; 91 | CH₃ | CH₃ | 2-Thienyl | H/H | =O | H/H | 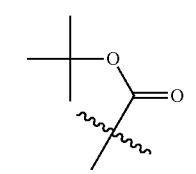 [SMILES: *C(=O)OC(C)(C)C] |
| 92; 93 | CH₃ | CH₃ | 2-Thienyl | H/H | =O | H/H | 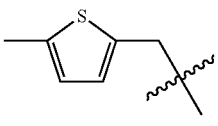 [SMILES: *Cc1ccc(C)s1] |
| 94; 95 | CH₃ | CH₃ | 2-Thienyl | H/H | =O | H/H | 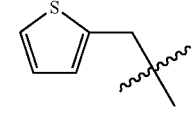 [SMILES: *Cc1cccs1] |
| 96; 97 | CH₃ | CH₃ | 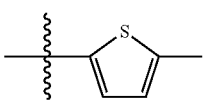 | H/H | =O | H/H | 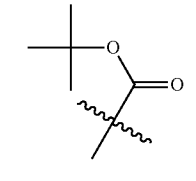 |
| 98; 99 | CH₃ | CH₃ | 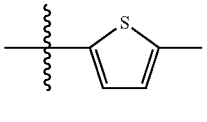 | H/H | =O | H/H | Benzyl |
| 100; | CH₃ | CH₃ | 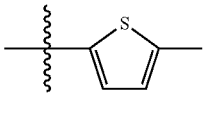 | H/H | =O | H/H | 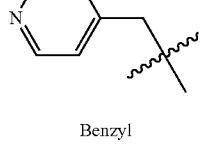 |
| 101; 102 | CH₃ | CH₃ | Phenyl | H/H | =O | H/H | Benzyl |
| 103; 104 | CH₃ | CH₃ | Phenyl | H/H | =O | H/H | 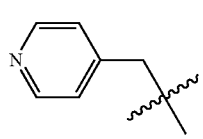 [SMILES: *Cc1ccncc1] |

-continued

| Ex. | R₁ | R₂ | R₃ | X₁/X₁' | X₂/X₂' | X₃/X₃' | R₄ |
|---|---|---|---|---|---|---|---|
| 105; 106 | CH₃ | CH₃ | Phenyl | H/H | =O | H/H | 2-thienylmethyl (thiophen-2-yl-CH₂-) |
| 107; 108 | CH₃ | CH₃ | Phenyl | H/H | =O | H/H | (5-methylthiophen-2-yl)methyl |
| 109 | CH₃ | CH₃ | Phenyl | H/H | =O | H/H | (5-fluorothiophen-2-yl)methyl |
| 110 | CH₃ | CH₃ | 2-Thienyl | H/H | H/H | H/H | 3-(dimethylamino)-3-oxopropyl |
| 111 | CH₃ | CH₃ | 2-Thienyl | H/H | H/H | H/H | 2-(dimethylamino)-2-oxoethyl |
| 112 | CH₃ | CH₃ | 2-Thienyl | H/H | H/H | H/H | 2-(azetidin-1-yl)-2-oxoethyl |
| 113 | CH₃ | CH₃ | 2-Thienyl | H/H | H/H | H/H | 3-(azetidin-1-yl)-3-oxopropyl |
| 114 | CH₃ | CH₃ | cyclopentyl | H/H | =O | H/H | Benzyl |
| 115 | CH₃ | CH₃ | 2-Thienyl | H/H | =O | H/H | 2-(1-methylpiperidin-4-yl)ethyl |
| 116 | CH₃ | CH₃ | 2-Thienyl | H/H | =O | H/H | (1-methylpiperidin-4-yl)methyl |
| 117 | CH₃ | CH₃ | 2-Thienyl | H/H | =O | H/H | 2-(1-methylazetidin-3-yl)ethyl |
| 118 | CH₃ | CH₃ | 2-Thienyl | H/H | =O | H/H | (1-methylazetidin-3-yl)methyl |

-continued
| Ex. | R₁ | R₂ | R₃ | X₁/X₁' | X₂/X₂' | X₃/X₃' | R₄ |
|---|---|---|---|---|---|---|---|
| 119 | CH₃ | CH₃ | Phenyl | H/H | =O | H/H | 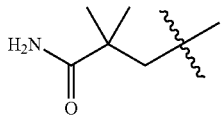 [SMILES: *CC(C)(C)C(N)=O] |
| 120 | CH₃ | CH₃ | Phenyl | H/H | H/H | H/H | 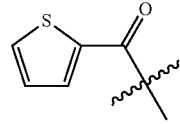 [SMILES: *C(=O)c1cccs1] |
| 121 | CH₃ | CH₃ | Phenyl | H/H | H/H | H/H | 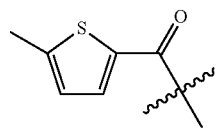 [SMILES: *C(=O)c1ccc(C)s1] |
| 122 | CH₃ | CH₃ | Phenyl | H/H | H/H | H/H | 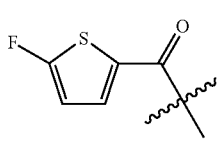 [SMILES: *C(=O)c1ccc(F)s1] |
| 123 | CH₃ | CH₃ | n-Butyl | H/H | H/H | H/H | 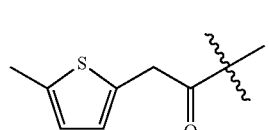 |
| 124; 128 | CH₃ | CH₃ | n-Butyl | H/H | =O | H/H | Benzyl |
| 125 | CH₃ | CH₃ | Phenyl | H/H | H/H | H/H | 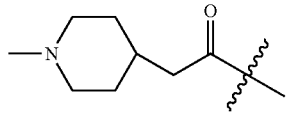 [SMILES: *C(=O)CC1CCN(C)CC1] |
| 126 | CH₃ | CH₃ | 2-Thienyl | H/H | H/H | H/H | 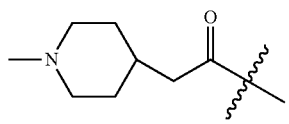 [SMILES: *C(=O)CC1CCN(C)CC1] |
| 127 | CH₃ | CH₃ | Phenyl | H/H | H/H | H/H | 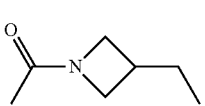 |
| 129 | CH₃ | CH₃ | 2-Thienyl | H/H | H/H | H/H | 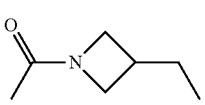 |
| SC-1001 | CH₃ | CH₃ | Phenyl | H/H | =O | H/H | 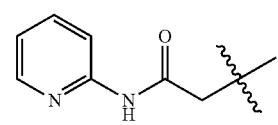 [SMILES: *CC(=O)Nc1ccccn1] |
| SC-1002 | CH₃ | CH₃ | Phenyl | H/H | =O | H/H | 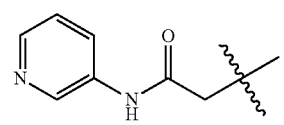 [SMILES: *CC(=O)Nc1cccnc1] |

-continued

| Ex. | R₁ | R₂ | R₃ | X₁/X₁' | X₂/X₂' | X₃/X₃' | R₄ |
|---|---|---|---|---|---|---|---|
| SC-1003 | CH₃ | CH₃ | Phenyl | H/H | =O | H/H | (1,1-dioxo-tetrahydrothiopyran-4-yl)methyl-NH-C(=O)-CH₂CH₂CH₂-C(CH₃)- |
| SC-1004 | CH₃ | CH₃ | Phenyl | H/H | =O | H/H | pyrimidin-5-yl-NH-C(=O)-C(CH₃)₂-CH₂- |
| SC-1005 | CH₃ | CH₃ | Phenyl | H/H | =O | H/H | pyrimidin-4-yl-NH-C(=O)-C(CH₃)₂-CH₂- |
| SC-1006 | CH₃ | CH₃ | CH₃O-CH₂CH₂CH₂CH₂- | H/H | =O | H/H | H₂N-C(=O)-CH₂-C(CH₃)- |
| SC-1007 | CH₃ | CH₃ | CH₃O-CH₂CH₂CH₂CH₂- | H/H | =O | H/H | H₂N-C(=O)-CH₂CH₂-C(CH₃)- |
| SC-1008 | CH₃ | CH₃ | pyrazin-2-yl | H/H | =O | H/H | H₂N-C(=O)-CH₂-C(CH₃)- |
| SC-1009 | CH₃ | CH₃ | pyrazin-2-yl | H/H | =O | H/H | H₂N-C(=O)-CH₂CH₂-C(CH₃)- |
| SC-1010 | CH₃ | CH₃ | pyrazin-2-yl | H/H | =O | H/H | H₂N-C(=O)-CH₂CH₂CH₂-C(CH₃)- |
| SC-1011 | CH₃ | CH₃ | pyridin-2-yl | H/H | =O | H/H | H₂N-C(=O)-CH₂-C(CH₃)- |
| SC-1012 | CH₃ | CH₃ | pyridin-2-yl | H/H | =O | H/H | H₂N-C(=O)-CH₂CH₂-C(CH₃)- |
| SC-1013 | CH₃ | CH₃ | pyridin-2-yl | H/H | =O | H/H | H₂N-C(=O)-CH₂CH₂CH₂-C(CH₃)- |
| SC-1014 | CH₃ | CH₃ | Phenyl | H/H | =O | H/H | benzyl-NH-C(=O)-CH₂CH₂-C(CH₃)- |

-continued

| Ex. | R₁ | R₂ | R₃ | X₁/X₁' | X₂/X₂' | X₃/X₃' | R₄ |
|---|---|---|---|---|---|---|---|
| SC-1015 | CH₃ | CH₃ | Phenyl | H/H | =O | H/H | methoxyethyl-NH-C(=O)-CH₂-$\xi$ |
| SC-1016 | CH₃ | CH₃ | Phenyl | H/H | =O | H/H | N≡C-CH₂CH₂-NH-C(=O)-CH₂-$\xi$ |
| SC-1017 | CH₃ | CH₃ | Phenyl | H/H | =O | H/H | methoxypropyl-NH-C(=O)-CH₂CH₂-$\xi$ |
| SC-1018 | CH₃ | CH₃ | Phenyl | H/H | =O | H/H | N≡C-CH₂-NH-C(=O)-CH₂CH₂-$\xi$ |
| SC-1019 | CH₃ | CH₃ | Phenyl | H/H | =O | H/H | N≡C-CH₂CH₂-NH-C(=O)-CH₂CH₂-$\xi$ |
| SC-1020 | CH₃ | CH₃ | Phenyl | H/H | =O | H/H | N≡C-CH₂-NH-C(=O)-CH₂CH₂-$\xi$ (gem-dimethyl) |
| SC-1021 | CH₃ | CH₃ | Phenyl | H/H | =O | H/H | N≡C-CH₂CH₂-NH-C(=O)-CH₂CH₂-$\xi$ (gem-dimethyl) |
| SC-1022 | CH₃ | CH₃ | Phenyl | H/H | =O | H/H | 2-pyridyl-NH-C(=O)-CH₂CH₂-$\xi$ |
| SC-1023 | CH₃ | CH₃ | Phenyl | H/H | =O | H/H | PhCH₂CH₂-NH-C(=O)-CH₂CH₂-$\xi$ |
| SC-1024 | CH₃ | CH₃ | Phenyl | H/H | =O | H/H | methoxyethyl-NH-C(=O)-CH₂CH₂-$\xi$ (gem-dimethyl) |
| SC-1025 | CH₃ | CH₃ | Phenyl | H/H | =O | H/H | PhCH₂-NH-C(=O)-CH₂CH₂-$\xi$ (gem-dimethyl) |
| SC-1026 | CH₃ | CH₃ | Phenyl | H/H | =O | H/H | methoxypropyl-NH-C(=O)-CH₂-$\xi$ |

-continued
| Ex. | R₁ | R₂ | R₃ | X₁/X₁' | X₂/X₂' | X₃/X₃' | R₄ |
|---|---|---|---|---|---|---|---|
| SC-1027 | CH₃ | CH₃ | Phenyl | H/H | =O | H/H | 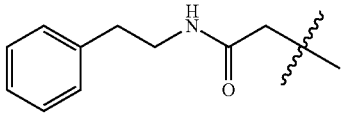 [SMILES: *CC(=O)NCCc1ccccc1] |
| SC-1028 | CH₃ | CH₃ | Phenyl | H/H | =O | H/H | 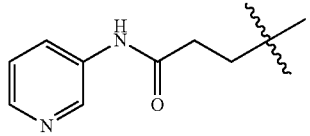 [SMILES: *CCC(=O)Nc1cccnc1] |
| SC-1029 | CH₃ | CH₃ | Phenyl | H/H | =O | H/H | 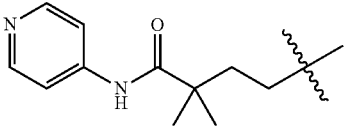 [SMILES: *CCC(C)(C)C(=O)Nc1ccncc1] |
| SC-1030 | CH₃ | CH₃ | Phenyl | H/H | =O | H/H | 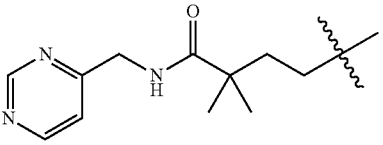 [SMILES: *CCC(C)(C)C(=O)NCc1ccncn1] |
| SC-1031 | CH₃ | CH₃ | Phenyl | H/H | =O | H/H | 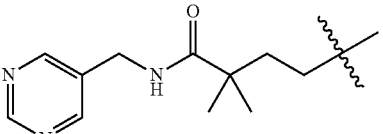 |
| SC-1032 | CH₃ | CH₃ | Phenyl | H/H | =O | H/H | 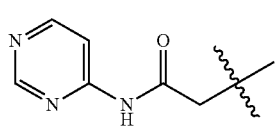 [SMILES: *CC(=O)Nc1ccncn1] |
| SC-1033 | CH₃ | CH₃ | Phenyl | H/H | H/H | H/H | 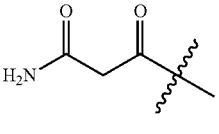 |
| SC-1034 | CH₃ | CH₃ | Phenyl | H/H | H/H | H/H | 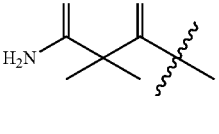 |
| SC-1035 | CH₃ | CH₃ | Phenyl | H/H | =O | H/H | 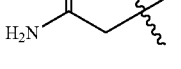 |
| SC-1036 | CH₃ | CH₃ | Phenyl | H/H | =O | H/H | 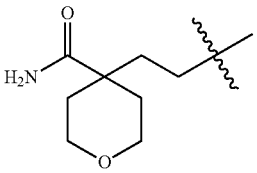 [SMILES: *CCC1(C(N)=O)CCOCC1] |

-continued

| Ex. | R₁ | R₂ | R₃ | X₁/X₁' | X₂/X₂' | X₃/X₃' | R₄ |
|---|---|---|---|---|---|---|---|
| SC-1037 | CH₃ | CH₃ | Phenyl | H/H | =O | H/H | 4-carbamoyl-1,1-dioxo-tetrahydrothiopyran with ethyl linker |
| SC-1038 | CH₃ | CH₃ | Phenyl | H/H | =O | H/H | 1-cyanocyclopropyl amide of 2,2-dimethylbutanoyl |
| SC-1039 | CH₃ | CH₃ | Phenyl | H/H | =O | H/H | N-(1,1-dioxo-tetrahydrothiopyran-4-yl) 2,2-dimethylbutanamide |
| SC-1040 | CH₃ | CH₃ | Phenyl | H/H | =O | H/H | 2-(hydroxymethyl)morpholine N-acyl 2,2-dimethylbutanoyl |
| SC-1041 | CH₃ | CH₃ | Phenyl | H/H | =O | H/H | H₂N-C(=O)-CH₂CH₂-C(CH₃)₂- |
| SC-1042 | CH₃ | CH₃ | 2-pyridyl | H/H | =O | H/H | HOOC-CH₂CH₂CH₂-C(CH₃)₂- |
| SC-1043 | CH₃ | CH₃ | 2-pyridyl | H/H | =O | H/H | HOOC-C(CH₃)₂-CH₂CH₂- |
| SC-1044 | CH₃ | CH₃ | Phenyl | H/H | =O | H/H | HOOC-C(CH₃)₂-CH₂CH₂CH₂- |
| SC-1045 | CH₃ | CH₃ | Phenyl | H/H | =O | H/H | HOOC-C(CH₃)₂-CH₂CH₂- |
| SC-1046 | CH₃ | CH₃ | 2-pyridyl | H/H | =O | H/H | HOOC-CH₂-C(CH₃)₂- |
| SC-1047 | CH₃ | CH₃ | 2-pyridyl | H/H | =O | H/H | HOOC-CH₂CH₂-C(CH₃)₂- |

-continued

| Ex. | R₁ | R₂ | R₃ | X₁/X₁' | X₂/X₂' | X₃/X₃' | R₄ |
|---|---|---|---|---|---|---|---|
| SC-1048 | CH₃ | CH₃ | Phenyl | H/H | =O | H/H | HOOC-CH₂-* |
| SC-1049 | CH₃ | CH₃ | Phenyl | H/H | =O | H/H | Boc-NH-(CH₂)₄-* |
| SC-1050 | CH₃ | CH₃ | Phenyl | H/H | =O | H/H | MeO₂C-CH₂-* |
| SC-1051 | CH₃ | CH₃ | Phenyl | H/H | =O | H/H | 4-(tBuO₂C)-tetrahydropyran-4-yl-(CH₂)₂-* |
| SC-1052 | CH₃ | CH₃ | Phenyl | H/H | =O | H/H | 4-(tBuO₂C)-1,1-dioxo-tetrahydrothiopyran-4-yl-(CH₂)₂-* |
| SC-1053 | CH₃ | CH₃ | Phenyl | H/H | =O | H/H | MeO₂C-C(CH₃)₂-(CH₂)₂-* |
| SC-1054 | CH₃ | CH₃ | Phenyl | H/H | =O | H/H | pyridin-2-yl-CH₂-* |
| SC-1055 | CH₃ | CH₃ | Phenyl | H/H | =O | H/H | pyridin-3-yl-CH₂-* |
| SC-1056 | CH₃ | CH₃ | Phenyl | H/H | =O | H/H | 6-methoxypyridin-3-yl-* |
| SC-1057 | CH₃ | CH₃ | Phenyl | H/H | =O | H/H | 2-methoxypyrimidin-5-yl-* |
| SC-1058 | CH₃ | CH₃ | Phenyl | H/H | =O | H/H | 5-methoxypyrimidin-2-yl-* |
| SC-1059 | CH₃ | CH₃ | Phenyl | H/H | =O | H/H | 3-methoxypyridin-2-yl-* |

-continued

| Ex. | R₁ | R₂ | R₃ | X₁/X₁' | X₂/X₂' | X₃/X₃' | R₄ |
|---|---|---|---|---|---|---|---|
| SC-1060 | CH₃ | CH₃ | Phenyl | H/H | =O | H/H | 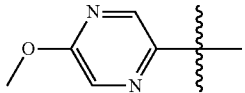 |
| SC-1061 | CH₃ | CH₃ | Phenyl | H/H | =O | H/H | 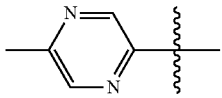 [SMILES: *c1cnc(C)cn1] |
| SC-1062 | CH₃ | CH₃ | Phenyl | H/H | =O | H/H | 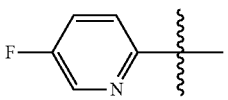 [SMILES: *c1ccc(F)cn1] |
| SC-1063 | CH₃ | CH₃ | Phenyl | H/H | =O | H/H | 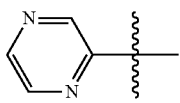 |
| SC-1064 | CH₃ | CH₃ | Phenyl | H/H | =O | H/H | 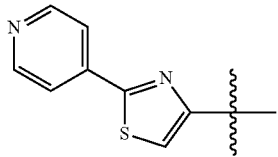 [SMILES: *c1csc(-c2ccncc2)n1] |
| SC-1065 | CH₃ | CH₃ | Phenyl | H/H | =O | H/H | 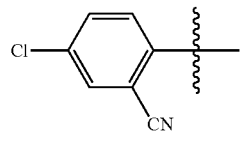 [SMILES: *c1ccc(Cl)cc1C#N] |
| SC-1066 | CH₃ | CH₃ | Phenyl | H/H | =O | H/H | 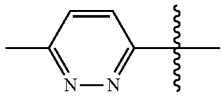 [SMILES: *c1ccc(C)nn1] |
| SC-1067 | CH₃ | CH₃ | Phenyl | H/H | =O | H/H | 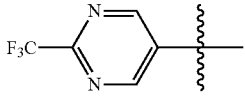 [SMILES: *c1cnc(C(F)(F)F)nc1] |
| SC-1068 | CH₃ | CH₃ | Phenyl | H/H | =O | H/H | 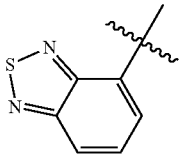 |
| SC-1069; SC-1070 | CH₃ | CH₃ | Phenyl | H/H | =O | H/H | Phenyl |
| SC-1071 | CH₃ | CH₃ | Phenyl | H/H | =O | H/H | 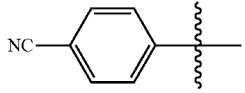 [SMILES: *c1ccc(C#N)cc1] |
| SC-1072 | CH₃ | CH₃ | Phenyl | H/H | =O | H/H | 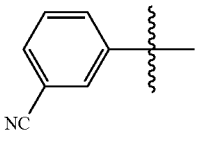 |

-continued
| Ex. | R₁ | R₂ | R₃ | X₁/X₁' | X₂/X₂' | X₃/X₃' | R₄ |
|---|---|---|---|---|---|---|---|
| SC-1073 | CH₃ | CH₃ | Phenyl | H/H | =O | H/H | 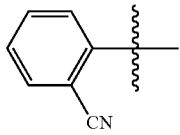 [SMILES: *c1ccccc1C#N] |
| SC-1074 | CH₃ | CH₃ | Phenyl | H/H | =O | H/H | 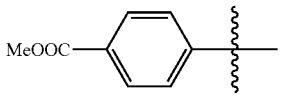 [SMILES: *c1ccc(C(=O)OC)cc1] |
| SC-1075 | CH₃ | CH₃ | Phenyl | H/H | =O | H/H | 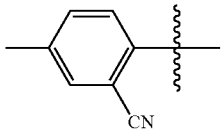 [SMILES: *c1ccc(C)cc1C#N] |
| SC-1076 | CH₃ | CH₃ | Phenyl | H/H | =O | H/H | 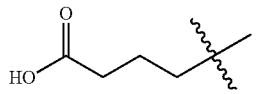 [SMILES: *CCCC(=O)O] |
| SC-1077 | CH₃ | CH₃ | Phenyl | H/H | =O | H/H | 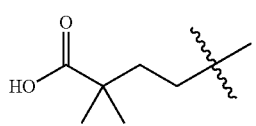 [SMILES: *CCC(C)(C)C(=O)O] |
| SC-1078 | CH₃ | CH₃ | 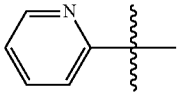 | H/H | =O | H/H | 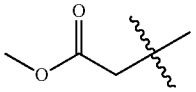 [SMILES: *CC(=O)OC] |
| SC-1079 | CH₃ | CH₃ | 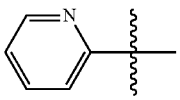 | H/H | =O | H/H | 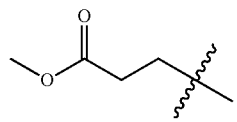 [SMILES: *CCC(=O)OC] |
| SC-1080 | CH₃ | CH₃ | 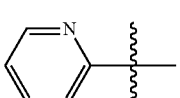 | H/H | =O | H/H | 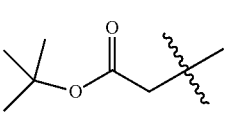 [SMILES: *CC(=O)OC(C)(C)C] |
| SC-1081 | CH₃ | CH₃ | 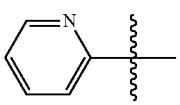 | H/H | =O | H/H | 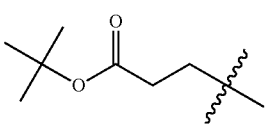 [SMILES: *CCC(=O)OC(C)(C)C] |
| SC-1082 | H | CH₃ | Phenyl | H/H | =O | H/H | 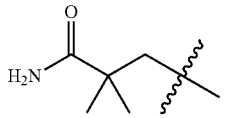 [SMILES: *CC(C)(C)C(N)=O] |
| SC-1083 | H | CH₃ | 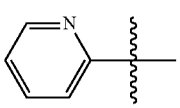 | H/H | =O | H/H | 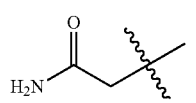 [SMILES: *CC(N)=O] |
| SC-1084 | H | CH₃ | 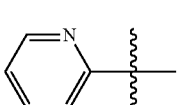 | H/H | =O | H/H | 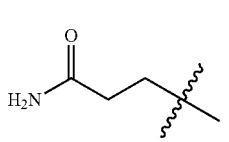 [SMILES: *CCC(N)=O] |

-continued
| Ex. | R₁ | R₂ | R₃ | X₁/X₁' | X₂/X₂' | X₃/X₃' | R₄ |
|---|---|---|---|---|---|---|---|
| SC-1085 | H | CH₃ | 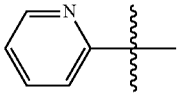 [SMILES: *c1ccccn1] | H/H | =O | H/H | 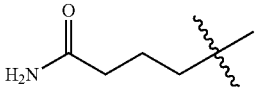 [SMILES: *CCCC(N)=O] |
| SC-1086 SC-1088 | H | CH₃ | 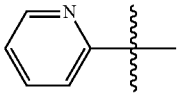 [SMILES: *c1ccccn1] | H/H | =O | H/H | 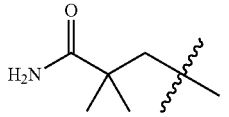 |
| SC-1087 | H | CH₃ | 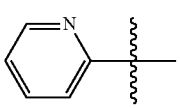 | H/H | =O | H/H | 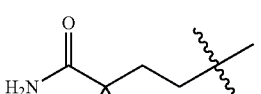 |
| SC-1089 | CH₃ | CH₃ | 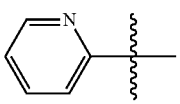 [SMILES: *c1ccccn1] | H/H | =O | H/H | 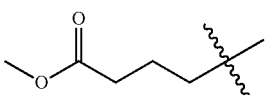 [SMILES: *CCCC(=O)OC] |
| SC-1090 | CH₃ | CH₃ | 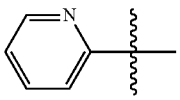 | H/H | =O | H/H | 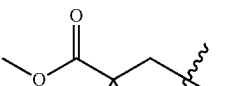 |
| SC-1091 | CH₃ | CH₃ | Phenyl | H/H | =O | H/H | 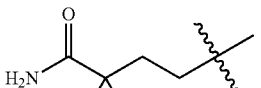 |
| SC-1092 | CH₃ | CH₃ | Phenyl | H/H | =O | H/H | 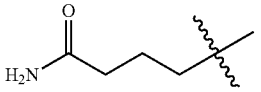 [SMILES: *CCCC(N)=O] |
| SC-1093 | CH₃ | CH₃ | Phenyl | H/H | =O | H/H | 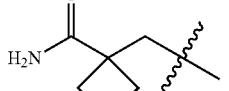 |
| SC-1094 | CH₃ | CH₃ | 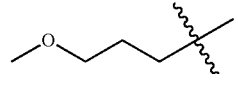 | H/H | =O | H/H | 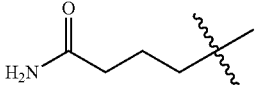 |
| SC-1095 | CH₃ | CH₃ | 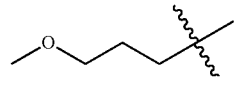 [SMILES: *CCCOC] | H/H | =O | H/H | 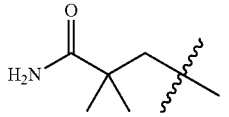 [SMILES: *CC(C)(C)C(N)=O] |
| SC-1096 | CH₃ | CH₃ | 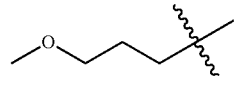 [SMILES: *CCCOC] | H/H | =O | H/H | 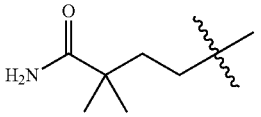 [SMILES: *CCC(C)(C)C(N)=O] |
| SC-1097 | CH₃ | CH₃ | 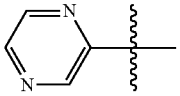 | H/H | =O | H/H | !! EMBED |

-continued
| Ex. | R₁ | R₂ | R₃ | X₁/X₁' | X₂/X₂' | X₃/X₃' | R₄ |
|---|---|---|---|---|---|---|---|
| SC-1098 | CH₃ | CH₃ | 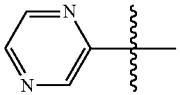 | H/H | =O | H/H | 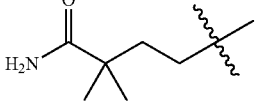 |
| SC-1099 SC-1101 | CH₃ | CH₃ | 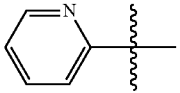 | H/H | =O | H/H | 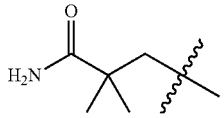 [SMILES: *CC(C)(C)C(N)=O] |
| SC-1100 | CH₃ | CH₃ | 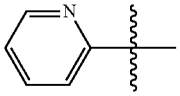 | H/H | =O | H/H | 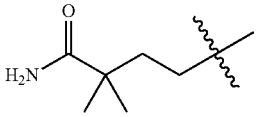 [SMILES: *CCC(C)(C)C(N)=O] |
| SC-1102 | CH₃ | CH₃ | Phenyl | H/H | =O | H/H | 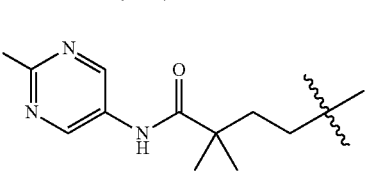 |
| SC-1103 | CH₃ | CH₃ | Phenyl | H/H | =O | H/H | 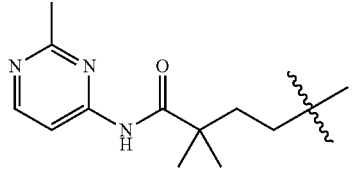 [SMILES: *CCC(C)(C)C(=O)Nc1ccnc(C)n1] |
| SC-1104 | CH₃ | CH₃ | Phenyl | Benzyl/H | =O | H/H | 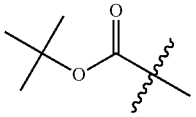 [SMILES: *C(=O)OC(C)(C)C] |
| SC-1107 SC-1108 | CH₃ | CH₃ | Phenyl | H/H | =O | H/H | 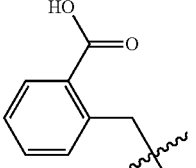 |
| SC-1109 | CH₃ | CH₃ | Phenyl | H/H | =O | H/H | 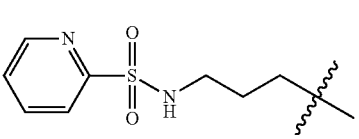 [SMILES: *CCCNS(=O)(=O)c1ccccn1] |
| SC-1110 | CH₃ | CH₃ | Phenyl | H/H | =O | H/H | 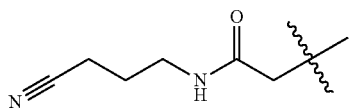 [SMILES: *CC(=O)NCCCC#N] |
| SC-1111 | CH₃ | CH₃ | Phenyl | H/H | =O | H/H | 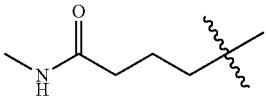 [SMILES: *CCCC(=O)NC] |

| Ex. | R₁ | R₂ | R₃ | X₁/X₁' | X₂/X₂' | X₃/X₃' | R₄ |
|---|---|---|---|---|---|---|---|
| SC-1112 | CH₃ | CH₃ | Phenyl | H/H | =O | H/H | 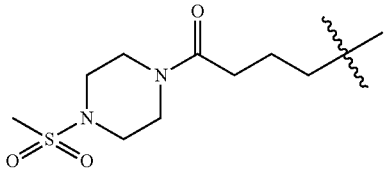 [SMILES: *CCCC(=O)N1CCN(S(C)(=O)=O)CC1] |
| SC-1113 | CH₃ | CH₃ | Phenyl | H/H | =O | H/H | 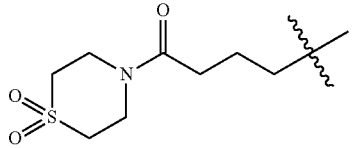 [SMILES: *CCCC(=O)N1CCS(=O)(=O)CC1] |
| SC-1114 | CH₃ | CH₃ | Phenyl | H/H | =O | H/H | 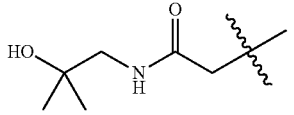 |
| SC-1115 | CH₃ | CH₃ | Phenyl | H/H | =O | H/H | 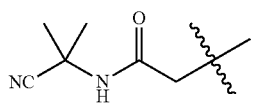 [SMILES: *CC(=O)NC(C)(C)C#N] |
| SC-1116 | CH₃ | CH₃ | Phenyl | H/H | =O | H/H | 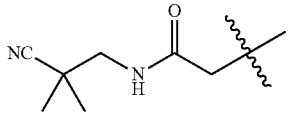 [SMILES: *CC(=O)NCC(C)(C)C#N] |
| SC-1117 | CH₃ | CH₃ | Phenyl | H/H | =O | H/H | 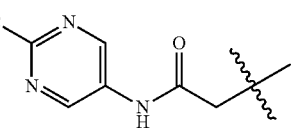 |
| SC-1118 | CH₃ | CH₃ | Phenyl | H/H | =O | H/H | 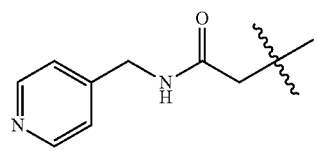 [SMILES: *CC(=O)NCc1ccncc1] |
| SC-1119 | CH₃ | CH₃ | Phenyl | H/H | =O | H/H | 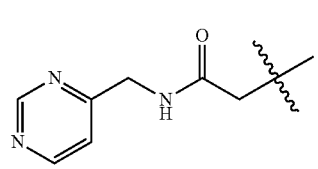 [SMILES: *CC(=O)NCc1ccncn1] |
| SC-1120 | CH₃ | CH₃ | Phenyl | H/H | =O | H/H | 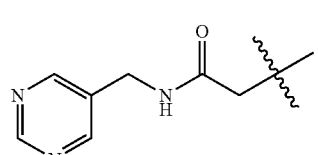 |
| SC-1123 | CH₃ | CH₃ | Phenyl | H/H | =O | H/H | 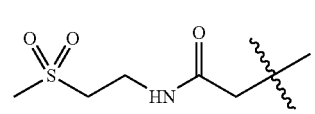 [SMILES: *CC(=O)NCCS(C)(=O)=O] |
| SC-1124 | CH₃ | CH₃ | Phenyl | H/H | =O | H/H | 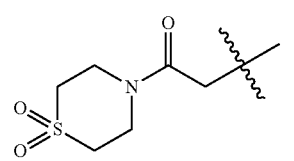 [SMILES: *CC(=O)N1CCS(=O)(=O)CC1] |

-continued

| Ex. | R₁ | R₂ | R₃ | X₁/X₁' | X₂/X₂' | X₃/X₃' | R₄ |
|---|---|---|---|---|---|---|---|
| SC-1125 | CH₃ | CH₃ | Phenyl | H/H | =O | H/H | (CH₃)₂N-C(=O)-CH₂-NH-C(=O)-C(CH₃)₂-~ |
| SC-1126 | CH₃ | CH₃ | Phenyl | H/H | =O | H/H | H₂N-C(=O)-CH₂-NH-C(=O)-C(CH₃)₂-~ |
| SC-1127 | CH₃ | CH₃ | Phenyl | H/H | =O | H/H | CH₃NH-C(=O)-CH₂-NH-C(=O)-C(CH₃)₂-~ |
| SC-1128 | CH₃ | CH₃ | Phenyl | H/H | =O | H/H | CH₃NH-C(=O)-C(CH₃)₂-NH-C(=O)-C(CH₃)₂-~ |
| SC-1129 | CH₃ | CH₃ | Phenyl | H/H | =O | H/H | (CH₃)₂N-C(=O)-CH₂-N(CH₃)-C(=O)-C(CH₃)₂-~ |
| SC-1130 | CH₃ | CH₃ | Phenyl | H/H | =O | H/H | H₂N-C(=O)-CH₂-N(CH₃)-C(=O)-C(CH₃)₂-~ |
| SC-1131 | CH₃ | CH₃ | Phenyl | H/H | =O | H/H | CH₃NH-C(=O)-CH₂-N(CH₃)-C(=O)-C(CH₃)₂-~ |
| SC-1132 | CH₃ | CH₃ | Phenyl | H/H | =O | H/H | CH₃NH-C(=O)-C(CH₃)₂-N(CH₃)-C(=O)-C(CH₃)₂-~ |
| SC-1133 | CH₃ | CH₃ | Phenyl | H/H | =O | H/H | HO-CH₂CH₂-NH-C(=O)-CH₂-C(CH₃)₂-~ |
| SC-1134 | CH₃ | CH₃ | Phenyl | H/H | =O | H/H | CH₃O-CH₂CH₂-NH-C(=O)-CH₂-C(CH₃)₂-~ |
| SC-1135 | CH₃ | CH₃ | Phenyl | H/H | =O | H/H | 1,1-dioxo-thiomorpholin-4-yl-C(=O)-C(CH₃)₂-CH₂-~ |

-continued
| Ex. | R₁ | R₂ | R₃ | X₁/X₁' | X₂/X₂' | X₃/X₃' | R₄ |
|---|---|---|---|---|---|---|---|
| SC-1136 | CH₃ | CH₃ | Phenyl | H/H | =O | H/H | 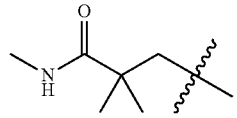 |
| SC-1137 | CH₃ | CH₃ | Phenyl | H/H | =O | H/H | 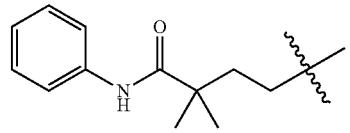 [SMILES: *CCC(C)(C)C(=O)Nc1ccccc1] |
| SC-1138 | CH₃ | CH₃ | Phenyl | H/H | =O | H/H | 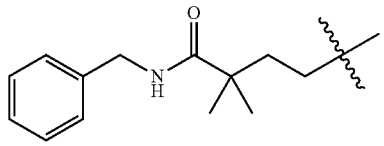 [SMILES: *CCC(C)(C)C(=O)NCc1ccccc1] |
| SC-1139 | CH₃ | CH₃ | Phenyl | H/H | =O | H/H | 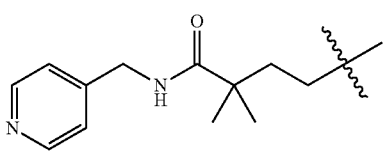 [SMILES: *CCC(C)(C)C(=O)NCc1ccncc1] |
| SC-1140 | CH₃ | CH₃ | Phenyl | H/H | =O | H/H | 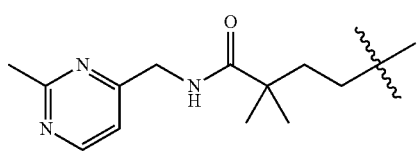 [SMILES: *CCC(C)(C)C(=O)NCc1ccnc(C)n1] |
| SC-1141 | CH₃ | CH₃ | Phenyl | H/H | =O | H/H | 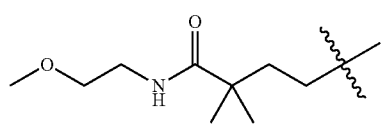 [SMILES: *CCC(C)(C)C(=O)NCCOC] |
| SC-1142 | CH₃ | CH₃ | Phenyl | H/H | =O | H/H | 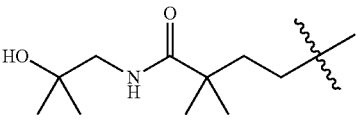 [SMILES: *CCC(C)(C)C(=O)NCC(C)(C)O] |
| SC-1145 | CH₃ | CH₃ | Phenyl | H/H | =O | H/H | 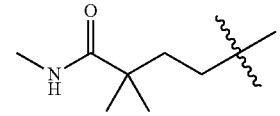 [SMILES: *CCC(C)(C)C(=O)NC] |
| SC-1146 | CH₃ | CH₃ | Phenyl | H/H | =O | H/H | 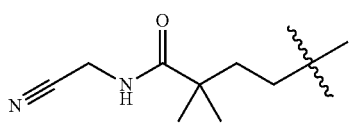 [SMILES: *CCC(C)(C)C(=O)NCC#N] |
| SC-1147 | CH₃ | CH₃ | Phenyl | H/H | =O | H/H | 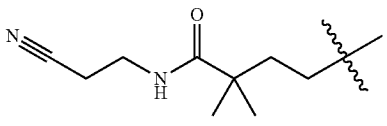 [SMILES: *CCC(C)(C)C(=O)NCCC#N] |
| SC-1148 | CH₃ | CH₃ | Phenyl | H/H | =O | H/H | 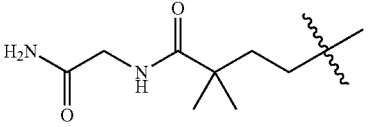 [SMILES: *CCC(C)(C)C(=O)NCC(N)=O] |

-continued
| Ex. | R₁ | R₂ | R₃ | X₁/X₁' | X₂/X₂' | X₃/X₃' | R₄ |
|---|---|---|---|---|---|---|---|
| SC-1149 | CH₃ | CH₃ | Phenyl | H/H | =O | H/H | 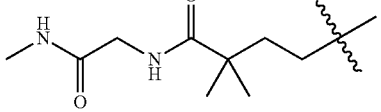 |
| SC-1150 | CH₃ | CH₃ | Phenyl | H/H | =O | H/H | 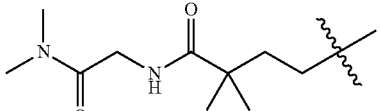 |
| SC-1151 | CH₃ | CH₃ | Phenyl | H/H | =O | H/H | 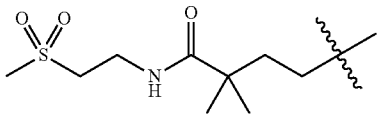 [SMILES: *CCC(C)(C)C(=O)NCCS(C)(=O)=O] |
| SC-1152 | CH₃ | CH₃ | Phenyl | H/H | =O | H/H | 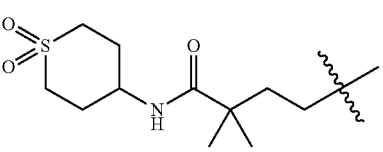 [SMILES: *CCC(C)(C)C(=O)NC1CCS(=O)(=O)CC1] |
| SC-1153 | CH₃ | CH₃ | Phenyl | H/H | =O | H/H | 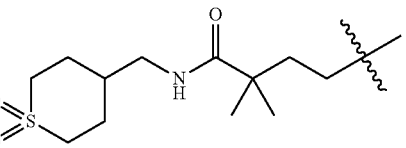 |
| SC-1154 | CH₃ | CH₃ | Phenyl | H/H | =O | H/H | 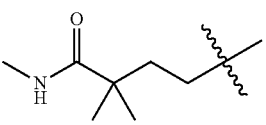 [SMILES: *CCC(C)(C)C(=O)NC] |
| SC-1155 | CH₃ | CH₃ | Phenyl | H/H | H/H | H/H | 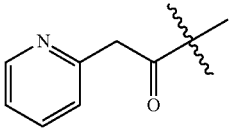 [SMILES: *C(=O)Cc1ccccn1] |
| SC-1156 | CH₃ | CH₃ | Phenyl | H/H | H/H | H/H | 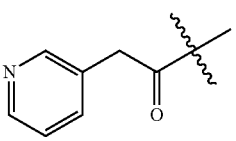 [SMILES: *C(=O)Cc1cccnc1] |
| SC-1157 | CH₃ | CH₃ | Phenyl | H/H | H/H | H/H | 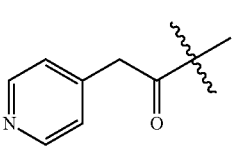 [SMILES: *C(=O)Cc1ccncc1] |
| SC-1158 | CH₃ | CH₃ | Phenyl | H/H | H/H | H/H | 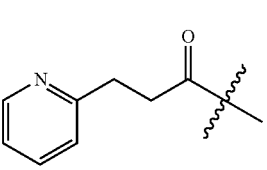 [SMILES: *C(=O)CCc1ccccn1] |

-continued
| Ex. | R₁ | R₂ | R₃ | X₁/X₁' | X₂/X₂' | X₃/X₃' | R₄ |
|---|---|---|---|---|---|---|---|
| SC-1159 | CH₃ | CH₃ | Phenyl | H/H | H/H | H/H | 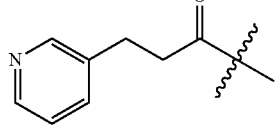 |
| SC-1160 | CH₃ | CH₃ | Phenyl | H/H | H/H | H/H | 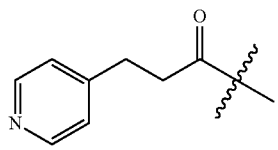 [SMILES: *C(=O)CCc1ccncc1] |
| SC-1161 | CH₃ | CH₃ | Phenyl | H/H | H/H | H/H | 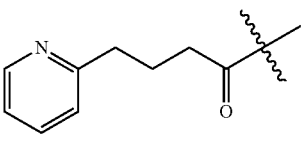 [SMILES: *C(=O)CCCc1ccccn1] |
| SC-1162 | CH₃ | CH₃ | Phenyl | H/H | H/H | H/H | 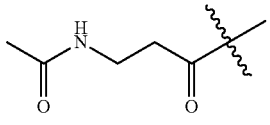 [SMILES: *C(=O)CCNC(C)=O] |
| SC-1163 | CH₃ | CH₃ | Phenyl | H/H | H/H | H/H | 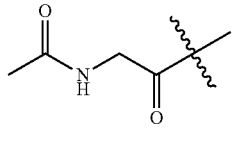 [SMILES: *C(=O)CNC(C)=O] |
| SC-1164 | CH₃ | CH₃ | Phenyl | H/H | H/H | H/H | 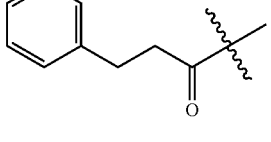 |
| SC-1165 | CH₃ | CH₃ | Phenyl | H/H | H/H | H/H | 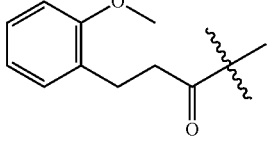 [SMILES: *C(=O)CCc1ccccc1] |
| SC-1166 | CH₃ | CH₃ | Phenyl | H/H | H/H | H/H | 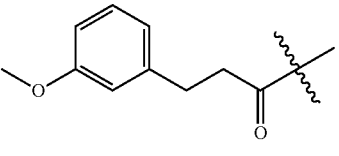 [SMILES: *C(=O)CCc1cccc(OC)c1] |
| SC-1167 | CH₃ | CH₃ | Phenyl | H/H | H/H | H/H | 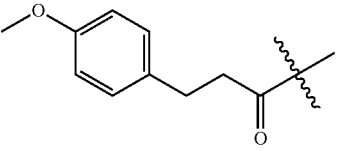 [SMILES: *C(=O)CCc1ccc(OC)cc1] |
| SC-1168 | CH₃ | CH₃ | Phenyl | H/H | H/H | H/H | 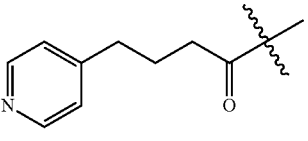 [SMILES: *C(=O)CCCc1ccncc1] |

-continued
| Ex. | R₁ | R₂ | R₃ | X₁/X₁' | X₂/X₂' | X₃/X₃' | R₄ |
|---|---|---|---|---|---|---|---|
| SC-1169 | CH₃ | CH₃ | Phenyl | H/H | H/H | H/H | 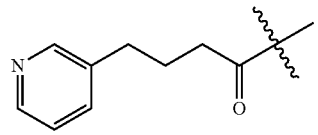 [SMILES: *C(=O)CCCc1cccnc1] |
| SC-1170 | CH₃ | CH₃ | Phenyl | H/H | =O | H/H | 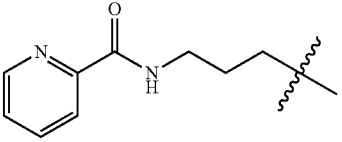 [SMILES: *CCCNC(=O)c1ccccn1] |
| SC-1171 | CH₃ | CH₃ | Phenyl | H/H | =O | H/H | 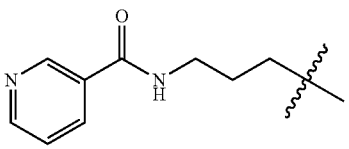 [SMILES: *CCCNC(=O)c1cccnc1] |
| SC-1172 | CH₃ | CH₃ | Phenyl | H/H | =O | H/H | 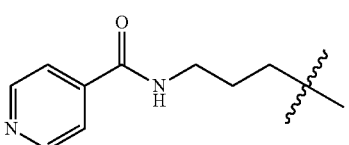 |
| SC-1173 | CH₃ | CH₃ | Phenyl | H/H | =O | H/H | 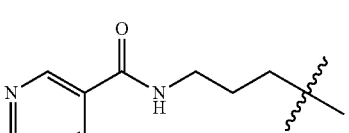 |
| SC-1174 | CH₃ | CH₃ | Phenyl | H/H | =O | H/H | 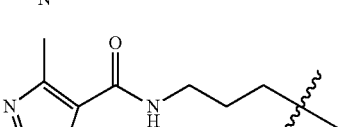 |
| SC-1175 | CH₃ | CH₃ | Phenyl | H/H | =O | H/H | 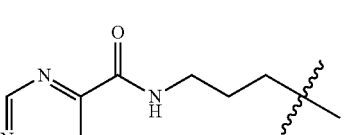 |
| SC1176 | CH₃ | CH₃ | Phenyl | H/H | =O | H/H | 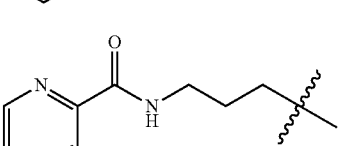 |
| SC-1177 | CH₃ | CH₃ | Phenyl | H/H | =O | H/H | 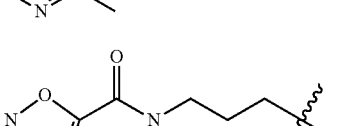 |
| SC-1178 | CH₃ | CH₃ | Phenyl | H/H | =O | H/H | 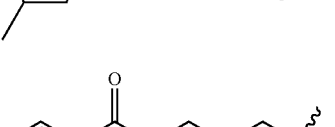 |

-continued
| Ex. | R₁ | R₂ | R₃ | X₁/X₁' | X₂/X₂' | X₃/X₃' | R₄ |
|---|---|---|---|---|---|---|---|
| SC-1179 | CH₃ | CH₃ | Phenyl | H/H | =O | H/H | 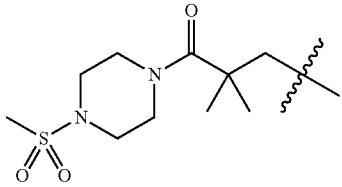 [SMILES: *CC(C)(C)C(=O)N1CCN(S(C)(=O)=O)CC1] |
| SC-1180 | CH₃ | CH₃ | Phenyl | H/H | =O | H/H | 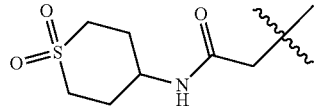 [SMILES: *CC(=O)NC1CCS(=O)(=O)CC1] |
| SC-1181 | CH₃ | CH₃ | Phenyl | H/H | =O | H/H | 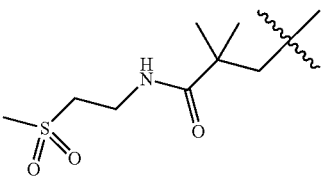 [SMILES: *CC(C)(C)C(=O)NCCS(C)(=O)=O] |
| SC-1182 | CH₃ | CH₃ | Phenyl | H/H | =O | H/H | 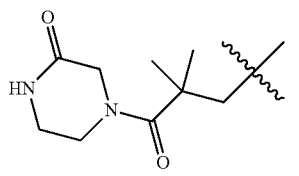 [SMILES: *CC(C)(C)C(=O)N1CCNC(=O)C1] |
| SC-1183 | CH₃ | CH₃ | Phenyl | H/H | =O | H/H | 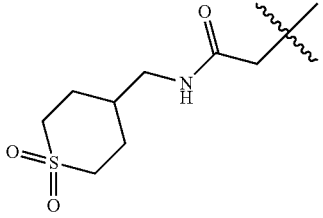 [SMILES: *CC(=O)NCC1CCS(=O)(=O)CC1] |
| SC-1184 | CH₃ | CH₃ | Phenyl | H/H | =O | H/H | 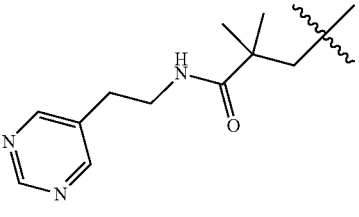 [SMILES: *CC(C)(C)C(=O)NCCc1cncnc1] |
| SC-1185 | CH₃ | CH₃ | Phenyl | H/H | =O | H/H | 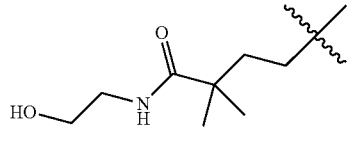 [SMILES: *CCC(C)(C)C(=O)NCCO] |
| SC-1186 | CH₃ | CH₃ | Phenyl | H/H | =O | H/H | 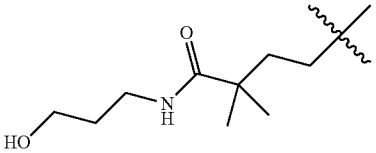 [SMILES: *CCC(C)(C)C(=O)NCCCO] |

-continued
| Ex. | R₁ | R₂ | R₃ | X₁/X₁' | X₂/X₂' | X₃/X₃' | R₄ |
|---|---|---|---|---|---|---|---|
| SC-1187 | CH₃ | CH₃ | Phenyl | H/H | =O | H/H | 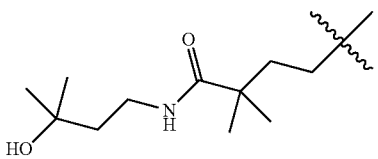 [SMILES: *CCC(C)(C)C(=O)NCCC(C)(C)O] |
| SC-1189 | CH₃ | CH₃ | Phenyl | H/H | =O | H/H | 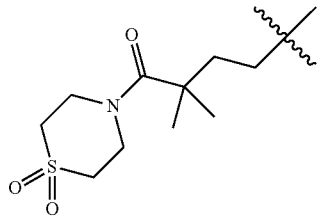 [SMILES: *CCC(C)(C)C(=O)N1CCS(=O)(=O)CC1] |
| SC-1190 | CH₃ | CH₃ | Phenyl | H/H | =O | H/H | 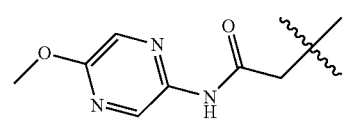 [SMILES: *CC(=O)Nc1cnc(OC)cn1] |
| SC-1191 | CH₃ | CH₃ | Phenyl | H/H | =O | H/H | 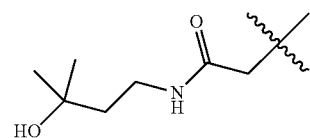 [SMILES: *CC(=O)NCCC(C)(C)O] |
| SC-1192 | CH₃ | CH₃ | Phenyl | H/H | =O | H/H | 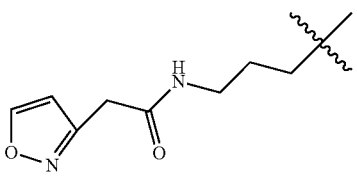 [SMILES: *CCCNC(=O)Cc1ccon1] |
| SC-1193 | CH₃ | CH₃ | Phenyl | H/H | =O | H/H | 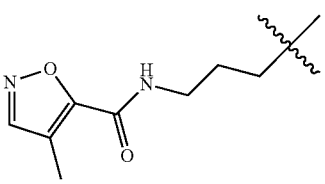 [SMILES: *CCCNC(=O)c1oncc1C] |
| SC-1194 | CH₃ | CH₃ | Phenyl | H/H | =O | H/H | 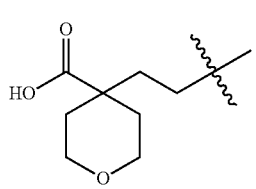 [SMILES: *CCC1(C(=O)O)CCOCC1] |
| SC-1195 | CH₃ | CH₃ | Phenyl | H/H | =O | H/H | 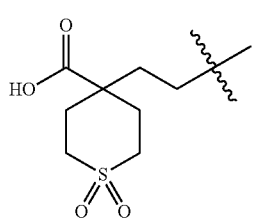 [SMILES: *CCC1(C(=O)O)CCS(=O)(=O)CC1] |
| SC-1198 | CH₃ | CH₃ | Phenyl | H/H | =O | H/H | 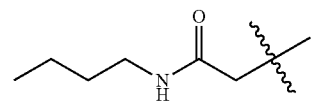 [SMILES: *CC(=O)NCCCC] |

| Ex. | R$_1$ | R$_2$ | R$_3$ | X$_1$/X$_1$' | X$_2$/X$_2$' | X$_3$/X$_3$' | R$_4$ |
|---|---|---|---|---|---|---|---|
| SC-1199 | CH$_3$ | CH$_3$ | Phenyl | H/H | =O | H/H | 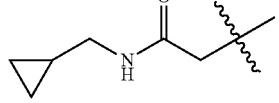 |
| SC-1200 | CH$_3$ | CH$_3$ | Phenyl | H/H | =O | H/H | 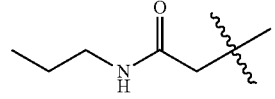 [SMILES: *CC(=O)NCCC] |
| SC-1201 | CH$_3$ | CH$_3$ | Phenyl | H/H | =O | H/H | 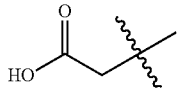 [SMILES: *CC(=O)O] | in the form of an individual stereoisomer or mixture thereof, the free compounds and/or their physiologically acceptable salts and/or solvates.

The compounds according to the invention act, for example, on the ORL1 receptor relevant in connection with various diseases, so that they are suitable as a pharmaceutical active compound in a medicament.

The invention therefore also provides medicaments which contain at least one compound according to the invention and optionally suitable additives and/or auxiliary substances and/or optionally further active compounds.

The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, solutions, suspensions, easily reconstitutable dry formulations and sprays are suitable for parenteral, topical and inhalatory administration. Compounds according to the invention in a depot, in dissolved form or in a plaster, optionally with the addition of agents which promote penetration through the skin, are suitable formulations for percutaneous administration. Formulation forms which can be used orally or percutaneously can release the compounds according to the invention in a delayed manner. The compounds according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, preferably 0.001 to 0.5 mg/kg of at least one compound according to the invention are conventionally administered.

For all the above forms of the medicaments according to the invention, it is particularly preferable if the medicament also contains, in addition to at least one compound according to the invention, a further active compound, in particular an opioid, preferably a potent opioid, in particular morphine, or an anaesthetic, preferably hexobarbital or halothane.

In a preferred form of the medicament, a compound according to the invention contained therein is in the form of a pure diastereomer and/or enantiomer.

The ORL1 receptor has been identified in particular in the pain event. Compounds according to the invention can accordingly be used for the preparation of a medicament for treatment of pain, in particular acute, visceral, neuropathic or chronic pain.

The invention therefore also provides the use of a compound according to the invention for the preparation of a medicament for treatment of pain, in particular acute, visceral, neuropathic or chronic pain.

The invention also provides the use of a compound according to the invention for the preparation of a medicament for treatment of anxiety states, of stress and syndromes associated with stress, depression, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids.

In this context, in one of the above uses it may be preferable for a compound which is used to be in the form of a pure diastereomer and/or enantiomer, a racemate or a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a compound according to the invention, or of a medicament according to the invention.

The invention also provides a process for the preparation of the compounds according to the invention as described in the following description and examples.

General Synthesis Equations:

In a preferred embodiment the synthesis of the compounds according to the invention follows the following general synthesis equation:

hydride (Wang, Jun et al., J. Am. Chem. Soc., 131(23), 8066-8076; 2009; Bhandari, Kalpana et al., Chemistry & Industry (London, United Kingdom), (17), 547-8; 1990). By methods known from the literature, the compounds of the general formula H are alkylated (Hutchins, Robert O., Markowitz, Morris J. Org. Chem. 46(17), 3571-4; 1981; Setaki, Despina et al., Bioorg. Chem., 34(5), 248-273; 2006; Stamatiou, G. et al.; Bioorg. & Med. Chem. Lett. 11(16), 2137-2142; 2001), arylated (WO2007070826, U.S. Pat. No. 7,157,456, WO2002085838) and acylated

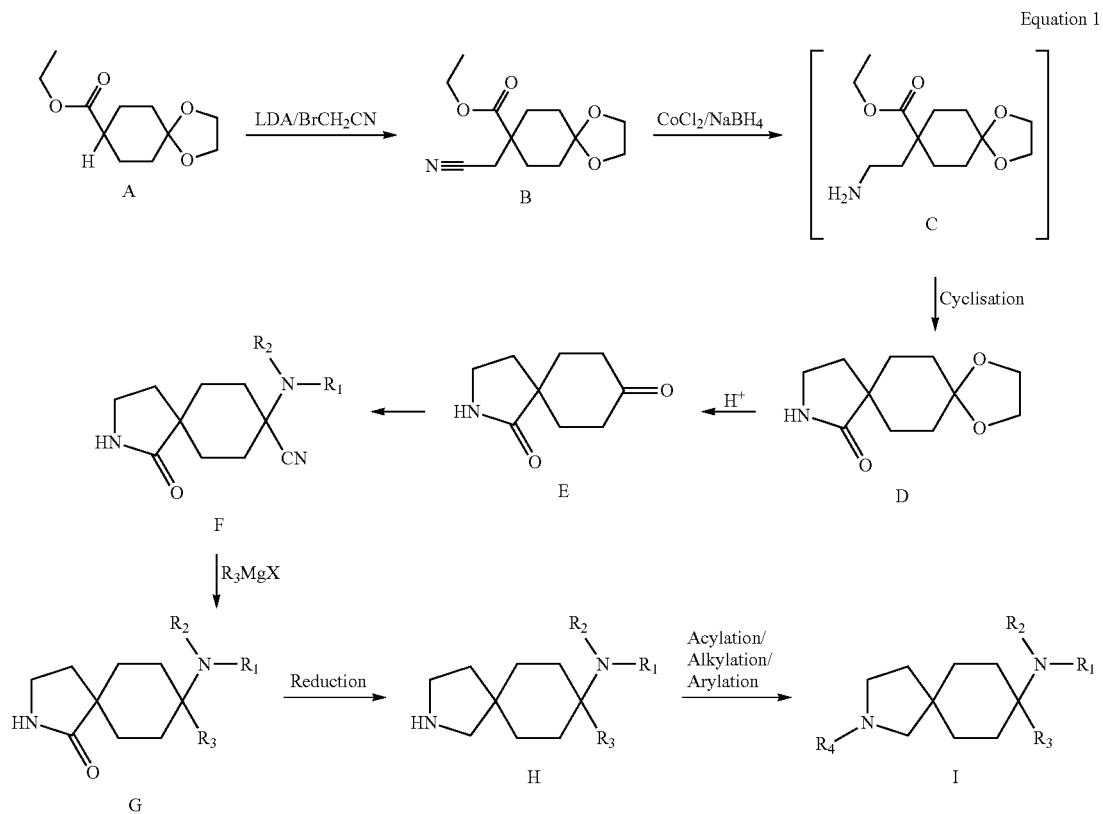

Equation 1

In step 1 compound A (WO2007079930) is converted into the nitrile B under basic conditions (WO2007127763; Reimann, Eberhard et al., Archiv der Pharmazie (Weinheim, Germany) (1988), 321(12), 935-41). The reduction of the nitrile B is carried out e.g. with cobalt boride (WO2007127763), the intermediate C cyclising spontaneously to the lactam D. The lactam D is deprotected under acid conditions (cerium ammonium nitrate/acetonitrile/water (I. Marko et al., Angew. Chem. 1999, 111, 3411-3413; Tetrahedron 2003, 59, 8989-8999), palladium chloride-bis-acetonitrile complex/acetone (B. H. Lipshutz et al., Tetrahedron Lett. 1985, 26, 705-708), sodium iodide/cerium(III) chloride/acetonitrile (E. Marcantoni et al., J. Org. Chem. 1997, 62, 4183-4184) and thiourea/ethanol/water (S. Majumdar, A. Bhattacharjya, J. Org. Chem. 1999, 64, 5682-5685) and then it is converted into the nitrile F in a Strecker reaction (WO2008101660, WO2008009415). The nitrile F reacts in a Bruylants reaction (D. Alberti et al., Bioorg. Med. Chem. Lett. 2006, 16, 4321-4325) with a Grignard reagent to give the compound of the general formula G. The compounds of the general formula G are reduced by methods known from the literature, e.g. with lithium aluminium (WO2008034731, WO2008036755, US20070117824, WO2007030061) on the nitrogen. Alternatively, the compound G can also first be alkylated or arylated and thereafter reduced. A polar and a non-polar diastereomer of the general formula G, but preferably the polar diastereomer G, are formed by this synthesis route.

In another preferred embodiment the synthesis of the compounds according to the invention follows the following general synthesis equation:

Equation 2

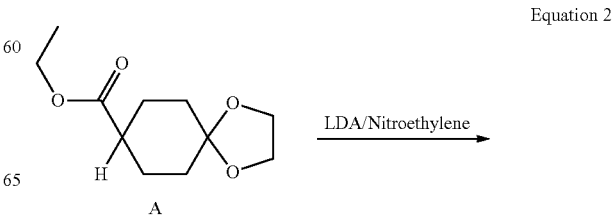

-continued

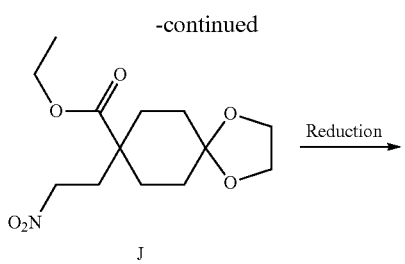

J

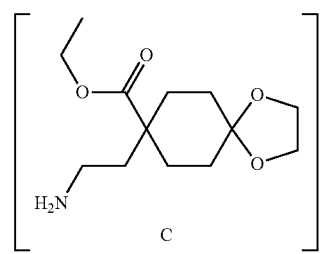

C

|Cyclisation

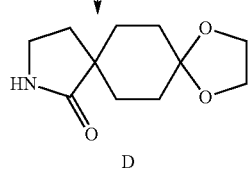

D

In step 1 compound A (WO2007079930) is converted into the nitro compound J under basic conditions and then reduced (G. H. Posner, D. R. Crouch, Tetrahedron 1990, 46, 7509-7530; R. J. Flintoft et al., Tetrahedron Lett. 1999, 44, 4485-4488; E. A. Krafft et al., Synthesis 2005, 3245-3252). Further reaction of the compound D is carried out as described in equation 1.

In another preferred embodiment the synthesis of the compounds according to the invention follows the following general synthesis equation:

In step 1 ketones of the general formula K (synthesised analogously to WO2006/031610 and U.S. Pat. No. 6,573,386) are converted into nitriles of the general formula L with TosMIC (Van Leusen, Daan et al., Organic Reactions (Hoboken, N.J., United States), 57, 2001). The nitrile L is converted into the imido-ester M in a Pinner reaction (Whitlock, Gavin A. et al., Bioorg. & Med. Chem. Lett. 18(9), 2930-2934, 2008; Geffken, Detlef et al., Archiv der Pharmazie (Weinheim, Germany), 321(1), 45-9; 1988) and then hydrolysed (US2002/58687). The ester N is converted into the nitrile O under basic conditions, like the ester A in equation 1. The nitrile O is reduced under conditions known from the literature and cyclised to the lactam G (WO2007127763). A polar and a non-polar diastereomer of the general formula G are formed by this synthesis route. Further reaction of compound G is carried out as described in equation 1.

In another preferred embodiment the synthesis of the compounds according to the invention follows the following general synthesis equation:

Equation 4

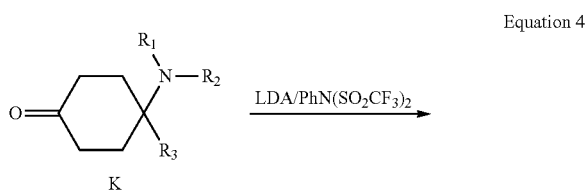

Equation 3

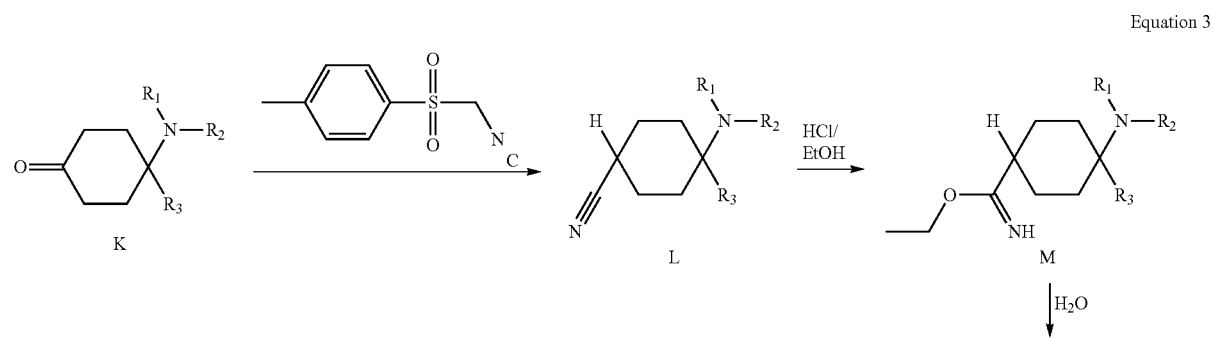

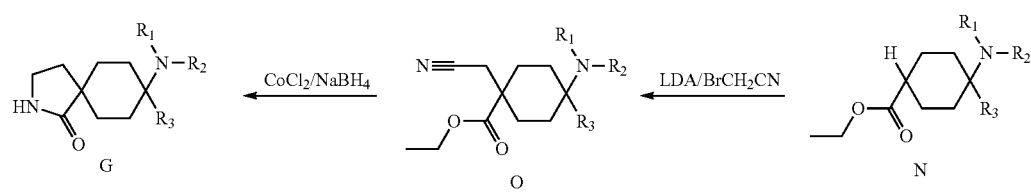

-continued

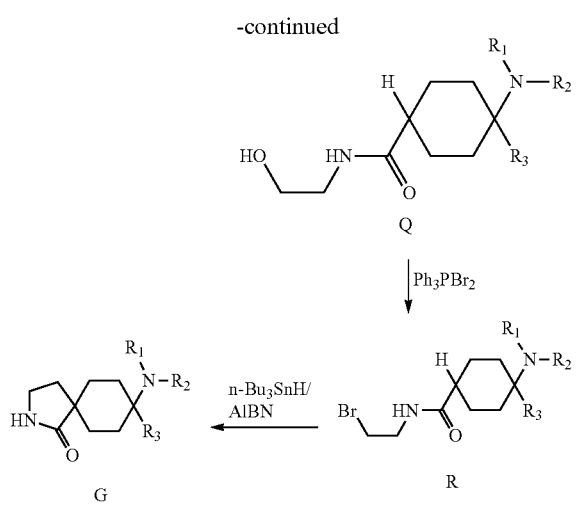

In step 1 ketones of the general formula K (synthesised analogously to WO2006/031610 and U.S. Pat. No. 6,573, 386) are converted into enol triflates (P) (WO2009111056). The aminocarbonylation with ethanolamine proceeds under extremely mild conditions (O. Lagerlund et al., Tetrahedron 2009, 65, 7646-7652; A. I. Meyers et al., Tetrahedron Lett. 1991, 33, 1181-1184). The alcohol Q is converted into a bromine derivative of the general formula R under conditions known from the literature (Van der Mey, Margaretha et al., J. Med. Chem. 45(12), 2520-2525; 2002). An exo-trig cyclisation between a primary radical and an α,β-unsaturated carboxylic acid derivative is then carried out to give the compound G (T. J. Murray et al. Tetrahedron 1995, 51, 635-640). A polar and a non-polar diastereomer of the general formula G are formed by this synthesis route. Further reaction of the compound G is carried out as described in equation 1.

In another preferred embodiment the synthesis of the compounds according to the invention follows the following general synthesis equation:

Equation 5

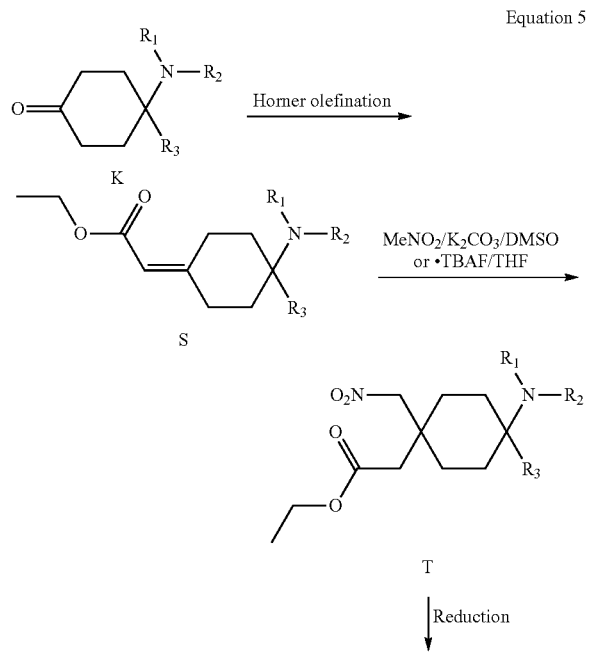

In step 1 ketones of the general formula K (synthesised analogously to WO2006/031610 and U.S. Pat. No. 6,573, 386) are converted into the compounds S in a Horner olefination known from the literature (Wadsworth, W. S., Jr. Et al., Organic Syntheses, 45, 1965). The compounds of the general formula S are reacted with nitromethane in a Michael addition to give the compound T (U.S. Pat. No. 5,091,567; WO2008/129007; J. S. Bryans et al., J. Med. Chem. 1998, 41, 1838-1845). The nitro compound T is reduced under conditions known from the literature and cyclised in situ to give the lactam U (G. H. Posner, D. R. Crouch, Tetrahedron 1990, 46, 7509-7530; R. J. Flintoft et al., Tetrahedron Lett. 1999, 44, 4485-4488; E. A. Krafft et al., Synthesis 2005, 3245-3252). By reduction of U the target compounds of the general formula H are obtained (Wang, Jun et al., J. Am. Chem. Soc., 131(23), 8066-8076; 2009; Bhandari, Kalpana et al., Chemistry & Industry (London, United Kingdom), (17), 547-8; 1990). A polar and a non-polar diastereomer of the general formula U are formed by this synthesis route. By methods known from the literature, the compounds of the general formula H are alkylated (Hutchins, Robert O., Markowitz, Morris J. Org. Chem. 46(17), 3571-4; 1981; Setaki, Despina et al., Bioorg. Chem., 34(5), 248-273; 2006; Stamatiou, G. et al.; Bioorg. & Med. Chem. Lett. 11(16), 2137-2142; 2001), arylated (WO2007070826, U.S. Pat. No. 7,157,456, WO2002085838) and acylated (WO2008034731, WO2008036755, US20070117824, WO2007030061) on the nitrogen. Alternatively, the compound U can also first be alkylated or arylated and thereafter reduced.

With respect to further details of the synthesis of the compounds according to the invention, in particular with respect to the synthesis of suitable educts, reference is furthermore made to the full scope of WO2004/043967, WO2005/063769, WO2005/066183, WO2006/018184, WO2006/108565, WO2007/124903, WO2008/004915 and WO2008/009416. A person skilled in the art recognises that suitable educt units for the synthesis of the compounds according to the invention can be prepared analogously to the synthesis equations and embodiment examples disclosed in these publications.

EXAMPLES

The following examples serve to illustrate the invention in more detail, but are not to be interpreted as limiting.

The yields of the compounds prepared are not optimized. All the temperatures are uncorrected. The term "MC" means methylene chloride. The term "equivalent" means equivalent substance amount, "m.p." melting point or melting range, "decomp." decomposition, "RT" room temperature (23±7° C.), "abs." absolute (anhydrous), "rac." racemic, "conc." concentrated, "min" minutes, "h" hours, "d" days, "vol. %" percent by volume, "wt. %" percent by weight, and "M" is a concentration stated in mold.

Silica gel 60 (0.040-0.063 mm) from E. Merck, Darmstadt was employed as the stationary phase for the column chromatography. The thin layer chromatography investigations were carried out with HPTLC precoated plates, silica gel 60

F 254 from E. Merck, Darmstadt. The mixing ratios of mobile phases for chromatography investigations are always stated in volume/volume.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by means of ¹H-NMR spectroscopy. In addition, mass spectrometry tests (MS, m/z for [M+H]⁺) were carried out for all the exemplary compounds and selected intermediate products.

Further Abbreviations aq. aqueous
brine saturated aqueous sodium chloride solution
CC column chromatography
DCM dichloromethane
DIPEA N,N-diisopropylethylamine
DMF N,N-dimethylformamide
Et Ethyl
ether diethyl ether
EtOAc, EA ethyl acetate
EtOH ethanol
H₂O water
HATU O-(7-aza-benzotriazol-1-yl)-N,N,N',N'-tetramethyluroniumhexafluorophosphate
Me Methyl
m/z mass-to-charge ratio
MeOH methanol
MeCN acetonitrile
min minutes
MS mass spectrometry
NIS N-iodo-succinimide
NEt₃ triethylamine
PE Petrol Ether (60-80° C.)
RM reaction mixture
RT room temperature
sat. saturated
sol. solution
THF tetrahydrofuran
v/v volume to volume
Synthesis Instructions
Building Blocks Synthesis of 8-(dimethylamino)-8-(phenyl)-2-azaspiro[4.5]decan-3-one

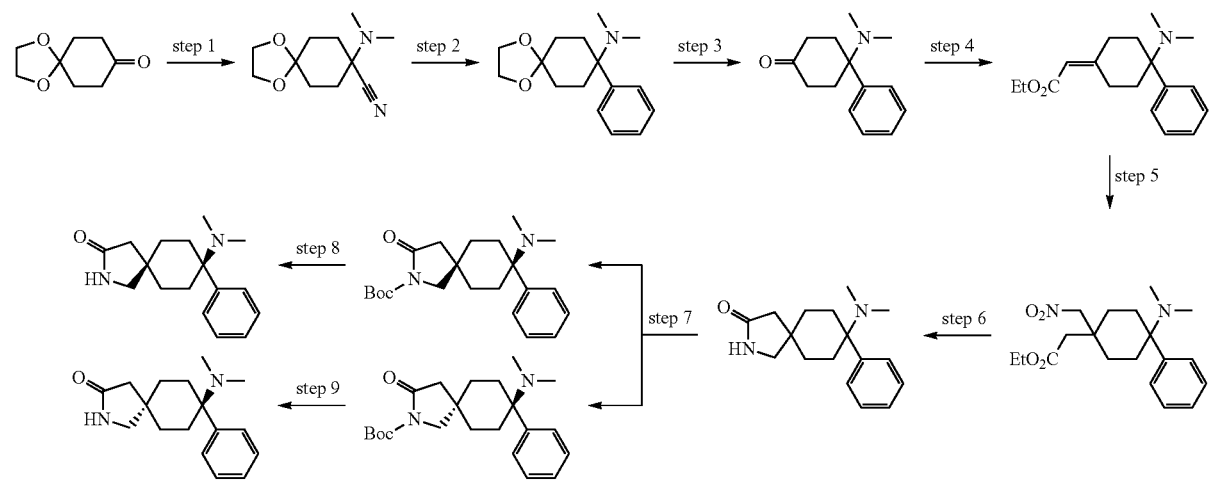

Step 1: 8-Dimethylamino-1,4-dioxaspiro[4.5]decane-8-carbonitrile

To a stirred solution of compound 1,4-Dioxaspiro[4.5]decan-8-one (50 g, 320 mmol) in MeOH (500 mL) was added N, N'-dimethylamine hydrochloride (155 g, 1920 mmol), KCN (52 g, 801 mmol) at 0° C. then allowed to RT stirred for 24 h. The RM was quenched with ice-water (200 mL) and extracted with EtOAc (2×100 mL). The combined organic layer was washed with water (100 mL), brine (100 mL), dried (Na₂SO₄) and evaporated under reduced pressure. The crude obtained was purified by column chromatography (silica gel 100-200 mesh) using 20% EtOAc in pet ether to get compound 8-Dimethylamino-1,4-dioxaspiro[4.5]decane-8-carbonitrile (60 g, ~89%) as off-white solid.

Step 2: Dimethyl-(8-phenyl-1,4-dioxaspiro[4.5]decan-8-yl)-amine

To a stirred solution of compound 8-Dimethylamino-1,4-dioxaspiro[4.5]decane-8-carbonitrile (60 g, 285 mmol) in THF (600 mL) under argon at 0° C. was added PhMgCl (514 mL, 1028 mmol) then allowed to RT stirred for 16 h. The RM was quenched with sat. NH₄Cl (50 mL) and extracted with EtOAc (2×100 mL). The combined organic layer was washed with water (50 mL), brine (50 mL), dried (Na₂SO₄) and evaporated under reduced pressure to get crude was purified by column chromatography (silica gel 100-200 mesh) using 3% MeOH in DCM to get compound Dimethyl-(8-phenyl-1,4-dioxaspiro[4.5]decan-8-yl)-amine (36 g, crude) as an thick liquid.

Step 3: 4-Dimethylamino-4-phenyl-cyclohexan-1-one

To a stirred solution of compound Dimethyl-(8-phenyl-1,4-dioxaspiro[4.5]decan-8-yl)-amine (36 g, 261 mmol) in 5% $H_2SO_4$ (500 mL) at RT then stirred at RT for 16 h. The RM was basified with 2N NaOH (pH~9) and extracted with DCM (2×50 mL), dried ($Na_2SO_4$) and evaporated under reduced pressure to get compound 4-Dimethylamino-4-phenyl-cyclohexan-1-one (20 g, ~32% over 2 steps) as off white solid. The compound used for next step.

Step 4: Ethyl 2-(4-(dimethylamino)-4-phenylcyclohexylidene)acetate

To a stirred solution of $^t$BuOK (23 g, 207 mmol) in DMF (150 mL) at RT under inert condition was added compound ethyl 2-(diethoxyphosphoryl)acetate (41.1 mL, 207 mmol) drop wise, stirred for 30 min then added compound 4-Dimethylamino-4-phenyl-cyclohexan-1-one (30 g, 217 mmol) in DMF (150 mL) drop wise stirred for 16 h at 60° C. The RM was cool to RT diluted with water (50 mL), extract with EtOAc (2×50 mL), wash with brine (2×50 mL), dried ($Na_2SO_4$) and evaporated under reduced pressure to get crude compound. The crude compound was purified by column chromatography (silica gel 100-200 mesh) using 20% EtOAc in PE to get compound Ethyl 2-(4-(dimethylamino)-4-phenylcyclohexylidene)acetate (25 g, ~63%) as a thick liquid.

Step 5: Ethyl 2-(4-(dimethylamino)-1-(nitromethyl)-4-phenylcyclohexyl)acetate To a stirred solution of compound Ethyl 2-(4-(dimethylamino)-4-phenylcyclohexylidene)acetate (22 g, 76.65 mmol) in THF (200 mL) at RT under nitrogen condition was added nitromethane (6.1 mL, 114 mmol), $Bu_4N^+F^-.3H_2O$ (36 g, 114 mmol) then the reactions mixture was warmed to 60° C., stirred for 16 h. The mixture was cool to RT, quenched with ice water (70 mL), extracted with Ethyl acetate (2×70 mL), combined organic layers was washed with water (50 mL), brine (50 mL), dried ($Na_2SO_4$) and evaporated under reduced pressure to get crude compound. The crude compound was purified by column chromatography (silica gel 100-200 mesh) using 5% MeOH in DCM to get compound Ethyl 2-(4-(dimethylamino)-1-(nitromethyl)-4-phenylcyclohexyl)acetate (20 g, ~77%) as thick liquid.

Step 6: 8-(dimethylamino)-8-phenyl-2-azaspiro[4.5]decan-3-one

To a stirred degassed solution of compound Ethyl 2-(4-(dimethylamino)-1-(nitromethyl)-4-phenylcyclohexyl)acetate (20 g, 57.47 mmol) in $EtOH/H_2O$ (2:1, 200 mL) at RT was added Fe powder (16 g, 287 mmol), $NH_4Cl$ (50 g, 574 mmol) then stirred at the 80° C. for 16 h. The RM was cooled to RT and filtered through celite pad, filtrate extracted with EtOAc (2×50 mL). The combined organic was washed with brine (50 mL) dried ($Na_2SO_4$) and evaporated and residue washed with pentane to get compound 8-(dimethylamino)-8-phenyl-2-azaspiro[4.5]decan-3-one (12.5 g, ~80%) as off white solid.

Step 7: 8-Dimethylamino-3-oxo-8-phenyl-2-azaspiro[4.5]decane-2-carboxylic acid tert-butyl ester To a stirred solution of compound 8-(dimethylamino)-8-phenyl-2-azaspiro[4.5]decan-3-one (12 g, 45.95 mmol) in ACN (100 mL) at RT under nitrogen condition was added DMAP (588 mg, 4.59 mmol), stirred for 30 min then added $(Boc)_2O$ (20 mL, 91.90 mmol) then stirred for 16 h. The RM was evaporated, residue diluted with DCM (50 mL), washed with water (50 mL), brine (50 mL), dried ($Na_2SO_4$) and evaporated under reduced pressure. The residue was purified by column chromatography (Neutral alumina) using 1% MeOH in DCM to get compound cis-8-Dimethylamino-3-oxo-8-phenyl-2-azaspiro[4.5]decane-2-carboxylic acid tert-butyl ester (8.0 g, ~47%) and trans-8-Dimethylamino-3-oxo-8-phenyl-2-azaspiro[4.5]decane-2-carboxylic acid tert-butyl ester (6.0 g, ~35%) as off white solid.

Step 8: Cis-8-(dimethylamino)-8-phenyl-2-azaspiro[4.5]decan-3-one

Cis-8-Dimethylamino-3-oxo-8-phenyl-2-azaspiro[4.5]decane-2-carboxylic acid tert-butyl ester (12 g, 32 mmol) was dissolved in DCM and trifluoroacetic acid (35 mL, 451 mmol) is added at 0° C. and stirred for 2 h at RT. After removal of all volatiles in vacuo, the crude reaction product is dissolved in DCM (200 mL) and extracted with Na2CO3 (150 mL). The organic layer is subsequently washed with NaHCO3 (4×150 mL) and kept for later use. The combined aqueous layers were extracted with DCM and all organic layers were combined. The combined organic layers were dried over MgSO4 and concentrated in vacuo. The crude product was dissolved in DCM (30 mL) and diisopropyl ether was added (120 mL). A white precipitate formed and was collected by filtration to yield Cis-8-(dimethylamino)-8-phenyl-2-azaspiro[4.5]decan-3-one (8.5 g) as a white solid.

Step 9: Trans-8-(dimethylamino)-8-phenyl-2-azaspiro[4.5]decan-3-one

Prepared in analogy to Cis-8-(dimethylamino)-8-phenyl-2-azaspiro[4.5]decan-3-one.

Analogue Synthesis

The following compounds were prepared in analogy to 8-(dimethylamino)-8-(phenyl)-2-azaspiro[4, 5] decan-3-one, starting from intermediates, described herein.

cis-8-(dimethylamino)-8-(pyrazin-2-yl)-2-azaspiro[4,5]decan-3-one cis-8-(dimethylamino)-8-(pyridin-2-yl)-2-azaspiro[4,5]decan-3-one trans-8-(dimethylamino)-8-(pyrazin-2-yl)-2-azaspiro[4,5]decan-3-one trans-8-(dimethylamino)-8-(pyridin-2-yl)-2-azaspiro[4,5]decan-3-one Synthesis of cis-N,N-dimethyl-8-phenyl-2-azaspiro-[4.5]-decan-8-amine

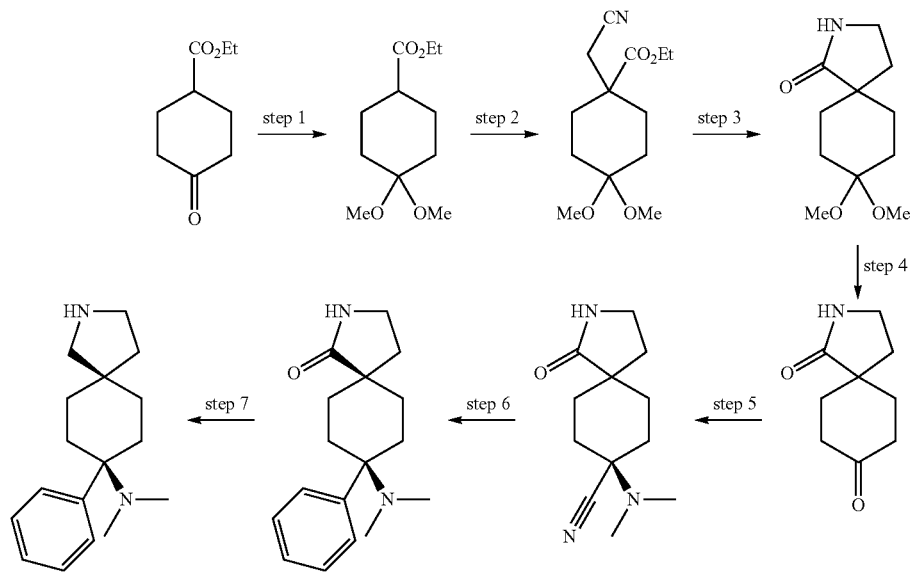

Step 1: Ethyl-4,4-dimethoxy-cyclohexane-carboxylate

To a solution of Methyl-4-oxocyclohexancarboxylat (10 g, 59.81 mmol) in MeOH (97 mL) trimethyl-orthoformiate (7.85 mL, 71.8 mmol) and campher sulphonic acid (0.69 g, 2.99 mmol) were added at RT. After stirring for 30 minutes, triethylamine (0.41 mL, 2.99 mmol) was added and the solvent was distilled of in vacuo. The crude reaction mixture was dissolved in diethyl ether (200 mL) and was extracted with water (3×100 mL). The organic layer was dried over Na2SO4 and the solvent was removed in vacuo to yield ethyl-4,4-dimethoxy-cyclohexane-carboxylate (11 g, 54.44 mmol, 91%) as a yellow oil.

Step 2: Ethyl-1-(cyanomethyl)-4,4-dimethoxycyclohexane-carboxylate

Under a nitrogen atmosphere, diisopropylamine (10.5 mL, 75 mmol) was dissolved in THF 75 mL) and n-butyl lithium (15% in hexanes, 44 mL, 70 mmol) was slowly added at −30° C. After stirring for 15 min, the reaction mixture was warmed to 0° C. and a suspension of ethyl-4,4-dimethoxy-cyclohexane-carboxylate (10 g, 46 mmol) in THF (80 mL) was added dropwise. The reaction was stirred for 90 min and then cooled to −78° C. and a solution of bromoacetontrile (3.02 mL, 75 mmol), DMPU (2.7 mL, 22.5 mmol) in THF (40 mL) was added via a dropping funnel. The reaction mixture is slowly warmed to RT and stirred for 24 h. Water (100 mL) is then added and the organic layer is separated. The aqueous layer is extracted either diethyl ether (3×50 mL) and the combined organic layers are washed with sat. NaHCO3 (2×50 mL), brine (4×50 mL), dried over Na2SO4 and concentrated in vacuo. Ethyl-1-(cyanomethyl)-4,4-dimethoxycyclohexane-carboxylate (6.5 g, 25 mmol) can be isolated after purification by column chromatography.

Step 3: 8,8-Dimethoxy-2-azaspiro-[4.5]-decan-1-one

Ethyl-1-(cyanomethyl)-4,4-dimethoxycyclohexane-carboxylate (40 g, 157 mmol) and CoCl2 (10.2 g, 78.3 mmol) are dissolved in a mixture of THF (451 mL) and water (254 mL). Sodium borohydride (30 g, 783 mmol) is added portionswise at 0° C. The reaction is stirred for 24 h and then treated with aq. ammonia (25%, 28 mL). The reaction mixture is filtered over a pad of celite and then extracted with DCM (3×300 mL). The combined organic layers are washed with brine (300 mL) and dried over MgSO4 and concentrated in vacuo. Trituration of the viscous residue yields 8,8-Dimethoxy-2-azaspiro-[4.5]-decan-1-one (20 g, 93 mmol, 60%) as a colorless solid.

Step 4: 2-Azaspiro-[4.5]-decan-1,8-dione 8,8-Dimethoxy-2-azaspiro-[4.5]-decan-1-one (8.2 g, 38 mmol) is suspended in THF (31 mL) and aq. HCl (32%, 0.38 mL) and water (0.76 mL) are added. After stirring for 2 h, solvents are removed in vacuo and the crude reaction product is triturated with diisoproyl ether (100 mL) to yield 2-Azaspiro-[4.5]-decan-1,8-dione (5.9 g, 35 mmol, 92%) as a colorless solid.

Step 5: 8-(Dimethylamino)-1-oxo-2-azaspiro-[4.5]-decan-8-carbonitrile

To an aqueous solution of dimethyl amine (40%, 32 mL, 178 mmol) is added methanol (103 mL), 4 M hydrochloric acid (16 mL, 64 mmol) at 0° C. Then, solid potassium cyanide (6.8 g, 104 mmol) and a suspension of 2-Azaspiro-[4.5]-decan-1,8-dione (8.5 g, 51 mmol) in methanol (98 mL) are added. The reaction mixture is stirred for 24 h at RT, then water (250 mL) is added at 0° C. and the aqueous layer is extracted with DCM (3×200 mL). The combined organic layers are dried over Na2SO4 and then concentrated in vacuo. Recrystallization from THF (150 mL) yields 8-(Dimethylamino)-1-oxo-2-azaspiro-[4.5]-decan-8-carbonitrile (7.3 g, 33 mmol) as a colorless solid.

Step 6: cis-8-(Dimethylamino)-8-phenyl-2-azaspiro-[4.5]-decan-1-one

A suspension of 8-(Dimethylamino)-1-oxo-2-azaspiro-[4.5]-decan-8-carbonitrile (7.0 g, 32 mmol) in THF (217 mL) is slowly added to PhMgBr (2M solution in THF, 57 mL, 114 mmol) in THF (40 mL) and stirred at RT for 18 h. Sat. NH4Cl (272 mL) is added and the aqueous layer is extracted with DCM (3×300 mL). The organic layer is extracted with 1M NaOH (200 mL) and then dried over Na2SO4 and concentrated in vacuo. The residue is dissolved in DCM (50 mL) and treated with diisopropyl ether (150 mL) to yield cis-8-(Dimethylamino)-8-phenyl-2-azaspiro-[4.5]-decan-1-one (5.5 g, 20 mmol) as a colorless solid.

Step 7: cis-8-(Dimethylamino)-8-phenyl-2-azaspiro-[4.5]-decan-1-one

A solution of cis-8-(Dimethylamino)-8-phenyl-2-azaspiro-[4.5]-decan-1-one (5.5 g, 20 mmol) in THF (100 mL) is added at 0° C. to a suspension of LiAlH4 (3.8 g, 101 mmol) in THF (163 mL). After complete addition, the reaction mixture is heated for 4 h to 60° C., then cooled to RT and a sat. aq. Na2SO4 solution (20 mL) is slowly added under the formation of a fine precipitate. The mother liquor is filtered off, the precipitate extracted with diethyl ether (3×250 mL) and the combined organic layers are concentrated in vacuo to yield cis-8-(Dimethylamino)-8-phenyl-2-azaspiro-[4.5]-decan-1-one (4.5 g, 17 mmol) as a colorless oil Synthesis of 4-(dimethyl amino)-4-(pyrazin-2-yl) cyclohexanone Step 2: 2-(pyrazin-2-yl) acetonitrile Lithium bromide (79.2 g, 0.9122 mol) was added to tert-butyl 2-cyano-2-(pyrazin-2-yl) acetate (400 g, 1.8244 mol) in 4% aqueous DMSO (800 mL). The solution was heated to 130° C. and stirred the reaction mass at reflux for 4 h. The reaction completion was monitored by TLC. The mixture was cooled to RT; quenched with ice cold water (1 L) and extracted with 10% MeOH:DCM (1 L×3). The combined organic layer was dried ($Na_2SO_4$) and concentrated in vacuo. The crude product was purified by column chromatography (using 100-200 mesh silica gel and 0-100% EtOAc in hexane as eluent) to afford 134 g of 2-(pyrazin-2-yl) acetonitrile (61%) as reddish brown liquid.

Step 3: Ethyl 5-cyano-2-hydroxy-5-(pyrazin-2-yl) cyclohex-1-enecarboxylate

Solid potassium tertiary butoxide (189.3 g, 16.3873 mol) was added to a solution of ethyl acrylate (239.6 mL, 2.2498 mol) and 2-(pyrazin-2-yl) acetonitrile (134 g, 1.1249 mol) in THF (2.6 L) at 10° C. and allowed to RT and stirred the reaction mass at RT under argon atmosphere for 2 h. The reaction completion was monitored by TLC. The reaction mass was directly moved to the next step.

Step 4: 4-oxo-1-(pyrazin-2-yl) cyclohexanecarbonitrile

Water (9.1 L) was added to the reaction mass of ethyl 5-cyano-2-hydroxy-5-(pyrazin-2-yl) cyclohex-1-enecar-

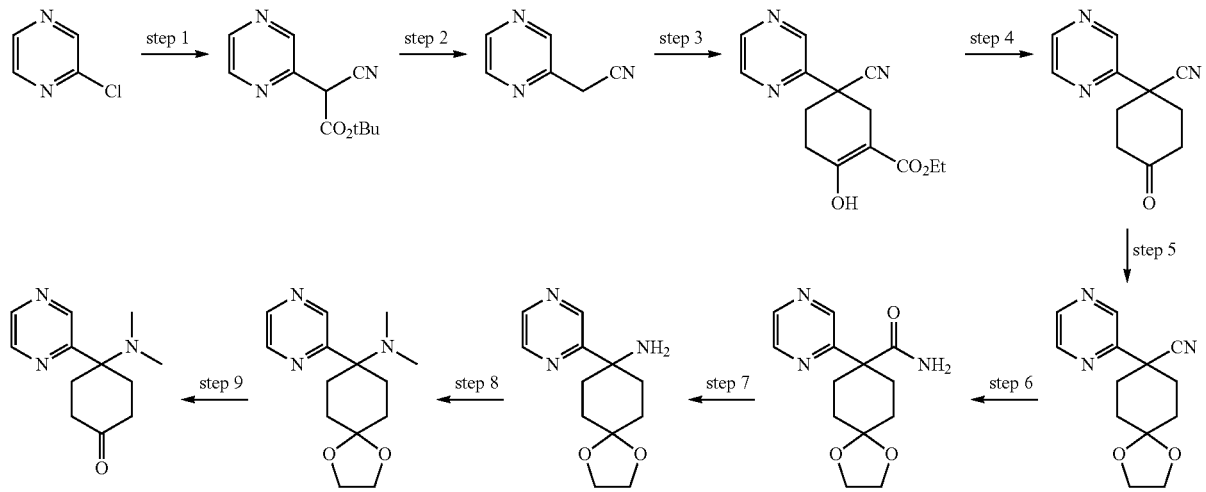

Step 1: tert-butyl 2-cyano-2-(pyrazin-2-yl) acetate

2-Chloropyrazine (400.0 g, 3.4925 mol) was added to a solution of t-Butylcyanoacetate (1 kg, 6.9850 mol), KOBu-t (980 g, 8.7313 mol) in THF (10 L) at RT under argon atmosphere. The solution was heated to reflux temperature and stirred for the reaction mass at reflux under argon atmosphere for 16 h while being monitored by TLC. The reaction mixture was concentrated in vacuo, the residue was diluted with water (8 L) and adjusted the pH to 3-4 with acetic acid and extracted with DCM (10 L×2). The combined organic layer was dried ($Na_2SO_4$) and concentrated in vacuo and washed with n-Pentane to afford 400 g of tert-butyl 2-cyano-2-(pyrazin-2-yl) acetate (52%) as brown amorphous solid.

boxylate, and heated the reaction mass to 85° C. and stirred the reaction mass at reflux temperature for 16 h. The reaction completion was monitored by TLC. Cooled the reaction mass to RT and extracted with 10% MeOH:DCM (10 L×3). The combined organic layer was dried (Na2SO4) and concentrated in vacuo to afford 96.1 g of 4-oxo-1-(pyrazin-2-yl) cyclohexane carbonitrile (42%) as off white solid.

Step 5: 8-(pyrazin-2-yl)-1,4-dioxaspiro[4,5]decane-8-carbonitrile p-Toluene sulphonic acid (9.0 g, 0.0477 mol) and ethylene glycol (26.6 g, 0.4770 mol) was added to 4-oxo-1-(pyrazin-2-yl) cyclohexane carbonitrile (96 g, 0.4770 mol) in toluene (2.8 L). Stirred the contents at 120° C. for 16 h. The product formation was monitored by TLC. The reaction mixture was cooled, and washed with saturated NaHCO₃ (2 L) and separated the layers and aqueous layer was extracted with ethyl acetate (2 L). The combined organic layer was dried (Na₂SO₄) and concentrated in vacuo to afford 96 g of 8-(pyrazin-2-yl)-1,4-dioxaspiro[4,5]decane-8-carbonitrile (82%) as off white solid.

Step 6: 8-(pyrazin-2-yl)-1,4-dioxaspiro[4,5]decane-8-carboxamide

30% H₂O₂ solution (133 mL, 1.1741 mol) was added to K₂CO₃ (81.0 g, 0.5870 mol) and 8-(pyrazin-2-yl)-1,4-dioxaspiro[4,5]decane-8-carbonitrile (96.0 g, 0.3913 mol) in DMSO (800 mL) at 10° C. and allowed the reaction mass to RT. Stirred the reaction mass at RT for 16 h. The reaction completion was monitored by TLC. Quenched the reaction mass with ice cold water (2 L) and extracted with 10% MeOH:DCM (2 L×3). The combined organic layer was dried (Na₂SO₄) and concentrated in vacuo to afford 63 g of 8-(pyrazin-2-yl)-1,4-dioxaspiro[4,5]decane-8-carboxamide (61%) as off white solid.

Step 7: 8-(pyrazin-2-yl)-1,4-dioxaspiro[4,5]decan-8-amine 9-12% NaOCl solution (495 mL, 0.5985 mol) was added slowly to a solution of 8-(pyrazin-2-yl)-1,4-dioxaspiro[4,5]decane-8-carboxamide (63.0 g, 0.2394 mol) in 1,4-Dioxane (630 mL) at RT. Stirred the reaction mass at RT for 16 h. The reaction completion was monitored by TLC. Concentrated the reaction mass in vacuo and extracted with 10% MeOH:DCM (1 L×3). The combined organic layer was dried (Na₂SO₄) and concentrated in vacuo to afford 26 g of 8-(pyrazin-2-yl)-1,4-dioxaspiro[4,5]decane-8-amine (46%) as yellow semi solid.

Step 8: N,N-dimethyl-8-(pyrazin-2-yl)-1,4-dioxaspiro[4,5]decan-8-amine

37% HCHO solution (89.6 mL, 1.1050 mol) was added to a solution of 8-(pyrazin-2-yl)-1,4-dioxaspiro[4,5]decane-8-amine (26.0 g, 0.1105 mol) in CAN (260 mL) and stirred the reaction mass under nitrogen atmosphere for 2 h. Then cooled the reaction mass to 10° C. and added NaCNBH₃ (27.7 g, 0.4420 mol) and allowed to RT and stirred the reaction mass at RT under nitrogen atmosphere for 8 h. The reaction completion was monitored by TLC. Concentrated the reaction mass in vacuo and extracted with 10% MeOH:DCM (1 L×3). The combined organic layer was dried (Na₂SO₄) and concentrated in vacuo. The crude product was purified by column chromatography (using 100-200 mesh silica gel and 0-10% MeOH in DCM as eluent) to afford 12 g of N,N-dimethyl-8-(pyrazin-2-yl)-1,4-dioxaspiro[4,5]decane-8-amine (41%) as yellow semi solid.

Step 9: 4-(dimethyl amino)-4-(pyrazin-2-yl)cyclohexanone

5N HCl solution (60 mL) was added to a solution of N,N-dimethyl-8-(pyrazin-2-yl)-1,4-dioxaspiro[4,5]decane-8-amine (12 g, 0.0455 mol) in THF (35 mL) at 10° C. and allowed to RT. Stirred the reaction mass at RT for 16 h. The reaction completion was monitored by TLC. Adjusted the reaction mass pH to 8.0 with solid NaHCO₃ and extracted with 10% MeOH:DCM (250×3). The combined organic layer was dried (Na₂SO₄) and concentrated in vacuo. The crude product was purified by column chromatography (using 100-200 mesh silica gel and 0-3% MeOH in DCM as eluent) to afford 8.0 g of 4-(dimethyl amino)-4-(pyrazin-2-yl) cyclohexanone (80%) as off white solid.

Synthesis of 4-(dimethylamino)-4-(pyridin-2-yl)cyclohexanone

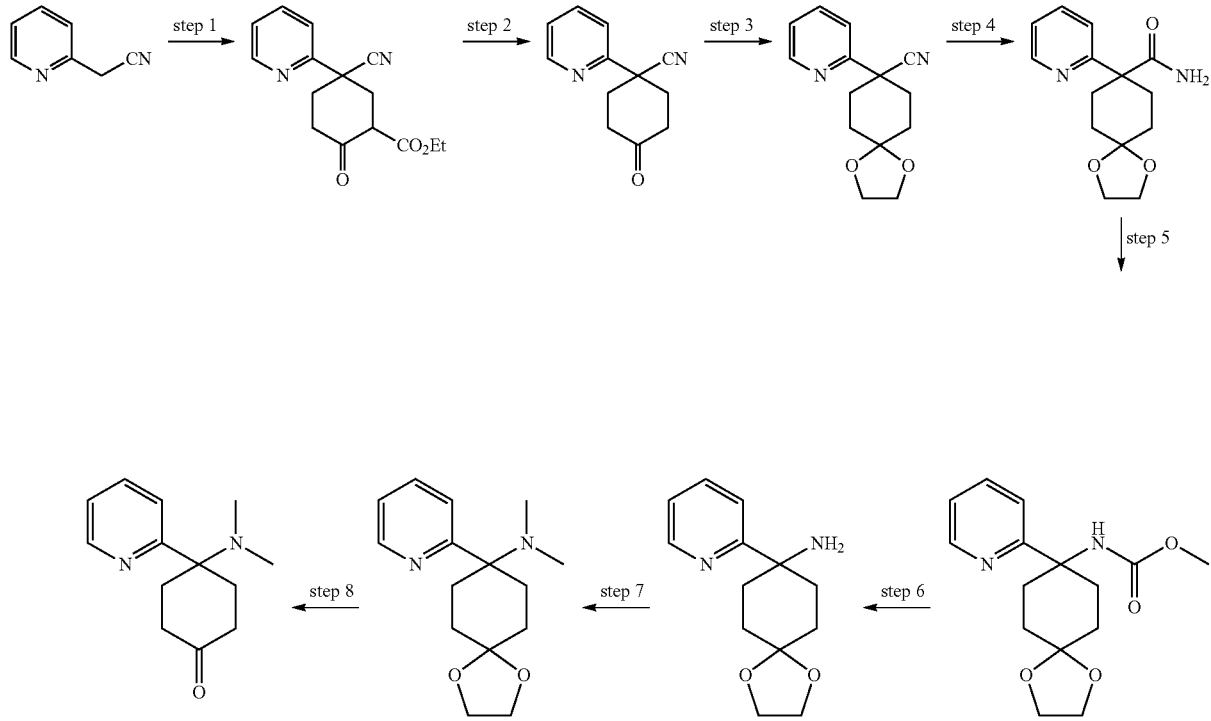

Step 1: Ethyl 5-cyano-2-oxo-5-(pyridin-2-yl)cyclohexanecarboxylate

KOBu$^t$ (57.0 g, 508.4 mmol) was added to a solution 2-Pyridine acetonitrile (50.0 g, 423.72 mmol) and ethyl acrylate (89.0 g, 889.8 mmol) in THF (500 mL) at 0° C. and stirred for 16 h at RT. The reaction mixture was quenched with sat NH$_4$Cl solution and extracted with ethyl acetate (2×500 mL). The combined organic layer was washed with brine, dried over Na$_2$SO$_4$ and distilled under reduced pressure to afford 68.0 g (60%; crude) of Ethyl 5-cyano-2-oxo-5-(pyridin-2-yl)cyclohexanecarboxylate as brown color liquid

Step 2: 4-oxo-1-(pyridin-2-yl)cyclohexanecarbonitrile

A solution of Ethyl 5-cyano-2-oxo-5-(pyridin-2-yl)cyclohexanecarboxylate (68.0 g, 250.0 mmol) was added to a mixture of Conc HCl and glacial acetic acid (170 mL:510 mL) at 0° C. The reaction mixture was heated at 100° C. for 16 h. Volatiles was evaporated, residue was diluted with sat NaHCO3 solution and extracted with ethyl acetate (3×300 mL). The combined organic layer was washed with brine, dried over Na2SO4 and distilled under reduced pressure to afford 44.0 g (88%) of 4-oxo-1-(pyridin-2-yl) cyclohexanecarbonitrile as brown color solid

Step 3: 8-(pyridin-2-yl)-1,4-dioxaspiro[4.5]decane-8-carbonitrile

A solution of 4-oxo-1-(pyridin-2-yl)cyclohexanecarbonitrile (44.0 g, 220.00 mmol), ethylene glycol (27.0 g, 440.00 mmol) and PTSA (4.2 g, 22.00 mmol) in toluene (450 mL) was heated at 120° C. for 16 h using Dean Stark apparatus. Volatiles was evaporated, residue was diluted with sat NaHCO$_3$ solution and extracted with ethyl acetate (3×300 mL). The combined organic layer washed with brine, dried over Na$_2$SO$_4$ and distilled under reduced pressure to afford 45.0 g (85%) of 8-(pyridin-2-yl)-1,4-dioxaspiro[4.5]decane-8-carbonitrile as light brown color solid

Step 4: 8-(pyridin-2-yl)-1,4-dioxaspiro[4.5]decane-8-carboxamide

Potassium carbonate (50.0 g, 368.84 mmol) and 30% aq. H$_2$O$_2$ (210.0 mL, 1844.2 mmol) were added to a solution of 8-(pyridin-2-yl)-1,4-dioxaspiro[4.5]decane-8-carbonitrile (45.0 g, 184.42 mmol) in DMSO (450 mL) at 0° C. and stirred at RT for 14 h. Diluted with excess water (1.5 L) and stirred for 1 h. The resulting solid was collected by filtration, washed with water, pet ether and dried to get 32.0 g (66%) of 8-(pyridin-2-yl)-1,4-dioxaspiro[4.5]decane-8-carboxamide as white solid.

Step 5: Methyl 8-(pyridin-2-yl)-1,4-dioxaspiro[4.5]decan-8-ylcarbamate

A mixture of 8-(pyridin-2-yl)-1,4-dioxaspiro[4.5]decane-8-carboxamide (25.0 g, 95.41 mmol), Sodium hypochlorite (5%, 700 mL, 477.09 mmol) and KF—Al2O3 (125.0 g) in methanol (500 mL) was heated at 80° C. for 16 h. The reaction mixture was filtered over celite and washed with methanol. Volatiles was evaporated, the residue was diluted with water and extracted with ethyl acetate (3×500 mL). The combined organic layer washed with brine, dried over Na2SO4 and distilled under reduced pressure to afford 18.0 g (66%) of methyl 8-(pyridin-2-yl)-1,4-dioxaspiro[4.5]decan-8-ylcarbamate as light brown color solid.

Step 6: 8-(pyridin-2-yl)-1,4-dioxaspiro[4.5]decan-8-amine

A mixture of methyl 8-(pyridin-2-yl)-1,4-dioxaspiro[4.5]decan-8-ylcarbamate (18.0 g, 61.64 mmol) in 10% Sodium hydroxide (200 mL) was heated at 100° C. for 24 h. The reaction mixture was filtered over celite, washed with water and filtrate was extracted with ethyl acetate (4×200 mL). The combined organic layer washed with brine, dried over Na$_2$SO$_4$ and distilled under reduced pressure to afford 12.5 g (88%) of 8-(pyridin-2-yl)-1,4-dioxaspiro[4.5]decan-8-amine as light brown color semi solid.

Step 7: N,N-dimethyl-8-(pyridin-2-yl)-1,4-dioxaspiro[4.5]decan-8-amin

Sodium cyanoborohydride (13.7 g, 0.213 mol) was added lot-wise to a solution of 8-(pyridin-2-yl)-1,4-dioxaspiro[4.5]decan-8-amine (12.5 g, 53.418 mmol) and 35% formaldehyde (45 mL, 0.534 mol) in acetonitrile (130 mL) at 0° C. The reaction mixture was warmed to room temperature and stirred for 16 h. The reaction mixture was quenched with sat NH$_4$Cl solution, volatiles was evaporated; the residue was dissolved in water and extracted with ethyl acetate (3×200 mL). The combined organic layer was washed with brine, dried over Na$_2$SO$_4$ and distilled under reduced pressure to afford 10.5 g (72%) of N,N-dimethyl-8-(pyridin-2-yl)-1,4-dioxaspiro[4.5]decan-8-amin as light brown color solid.

Step 8: 4-(dimethylamino)-4-(pyridin-2-yl)cyclohexanone

A solution of N,N-dimethyl-8-(pyridin-2-yl)-1,4-dioxaspiro[4.5]decan-8-amin (10.5 g, 40.076 mmol) in 5% Sulfuric acid (300 mL) was stirred at RT for 24 h. The reaction mixture was basified with solid NaHCO$_3$ and extracted with ethyl acetate (3×200 mL). The combined organic layer was washed with brine, dried over Na$_2$SO$_4$ and distilled under reduced pressure to get crude, which was purified by flash column chromatography (silica gel; 100-200 mesh); the product eluted with 2-6% MeOH in DCM to yield 7.0 g (80%) of 4-(dimethylamino)-4-(pyridin-2-yl)cyclohexanone as light yellow semi solid.

105

Synthesis of cis-8-(dimethylamino)-8-(3-methoxy-propyl)-2-azaspiro-[4.5]-decan-3-one

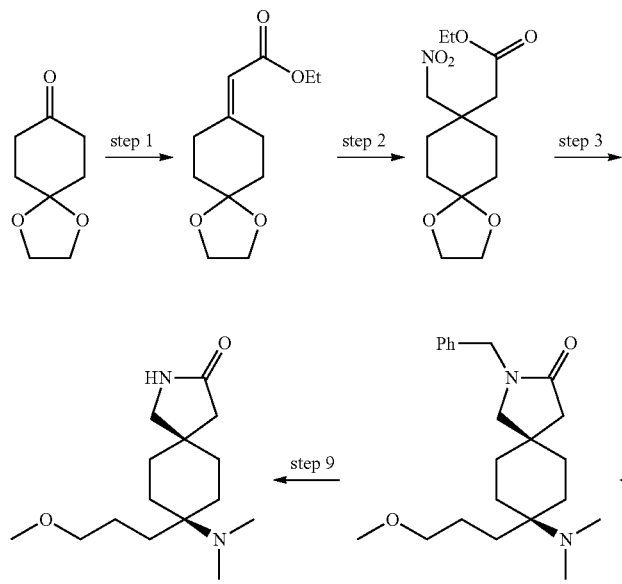

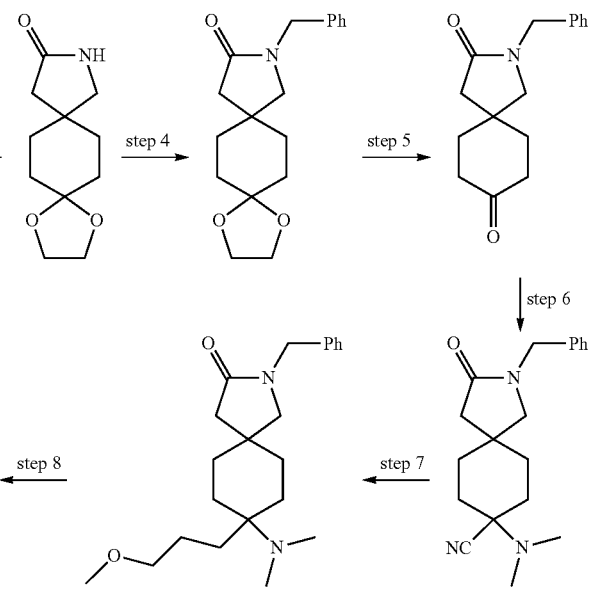

Step 1: Ethyl-2-(1,4-dioxaspiro-[4.5]-decan-8-ylidene)-acetate

Triethylphosphono acetate (61 mL, 0.30 mol) was added to a suspension KOBu-t (33 g, 0.30 mol) in DMF (200 mL) at 0° C., stirred for 1 h at RT. A solution of 1,4-dioxaspiro [4.5]decan-8-one (40 g, 0.25 mol) in DMF (200 mL) was added at 0° C. and the whole then stirred for 16 h at RT. The reaction mixture was quenched with sat $NH_4Cl$ solution and extracted with ethyl acetate (2×500 mL). The combined organic layer was washed with water, brine, dried over $Na_2SO_4$ and distilled under reduced pressure to afford crude, which was purified by column chromatography (silica gel; 60-120 mesh); the product eluted with 10-15% ethyl acetate in hexane to yield 50.0 g (86%) of Ethyl-2-(1,4-dioxaspiro-[4.5]-decan-8-ylidene)-acetate as liquid.

Step 2: Ethyl 2-(8-(nitromethyl)-1,4-dioxaspiro-[4.5]-decan-8-yl-acetate

A solution ethyl Ethyl-2-(1,4-dioxaspiro-[4.5]-decan-8-ylidene)-acetate (50.0 g, 0.22 mol), nitro methane (16.6 g, 0.26 mol) and tetra butylammoniumfluoride trihydrate (83 g, 0.26 mol) in THF (500 mL) was stirred for 16 h at 80° C. Volatiles were evaporated, Residue was dissolved in water and extracted with ethyl acetate (3×200 mL). The combined organic layer washed with water, brine, dried over $Na_2SO_4$ and distilled under reduced pressure to afford 50 g (73%) of Ethyl 2-(8-(nitromethyl)-1,4-dioxaspiro-[4.5]-decan-8-yl-acetate as liquid.

Step 3: 1,4-Dioxa-10-aza-dispiro[4.2.4.2]tetradecan-11-one

60% NaH (8.52 g, 0.213 mol) was added to a suspension of 1,4-Dioxa-10-aza-dispiro [4.2.4.2] tetradecan-11-one (30 g, 0.142 mol) in THF (250 mL) at 0° C., stirred for 30 min at RT. A solution of benzyl bromide (17.85 mL, 0.142 mol) in THF (50 mL) was added at 0° C. over a period of 1 h. The

106 resultant mixture was stirred for 16 h at 80° C. The reaction mixture was quenched with saturated $NH_4Cl$ solution and extracted with ethyl acetate (3×200 mL). The combined organic layer was washed with water, brine, dried over anhydrous $Na_2SO_4$ and distilled under reduced pressure to afford crude, which was purified by column chromatography over silica gel (60-120) by using 50-60% ethyl acetate in hexane as eluent to give 30 g (70%) of 10-Benzyl-1,4-dioxa-10-aza-dispiro[4.2.4.2]tetradecan-11-one as a solid.

Step 4: 10-Benzyl-1,4-dioxa-10-aza-dispiro[4.2.4.2]tetradecan-11-one

A solution of Ethyl 2-(8-(nitromethyl)-1,4-dioxaspiro-[4.5]-decan-8-yl-acetate (50 g, 0.17 mol) was hydrogenated over Raney Ni (10 g) in methanol (800 mL) at 60 psi and 60° C. for 16 h. Reaction mixture was filtered through celite bed, washed with methanol. Volatiles was evaporated under reduced pressure to afford 35.0 g (95%) of 1,4-Dioxa-10-aza-dispiro[4.2.4.2] tetradecan-11-one as solid Step 5: 10-Benzyl-1,4-dioxa-10-aza-dispiro[4.2.4.2]tetradecan-11-one

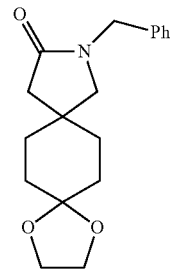 [SMILES: O=C1CC2(CCC3(CC2)OCCO3)CN1Cc1ccccc1]

60% NaH (8.52 g, 0.213 mol) was added to a suspension of 1,4-Dioxa-10-aza-dispiro [4.2.4.2] tetradecan-11-one (30 g, 0.142 mol) in THF (250 mL) at 0° C., stirred for 30 min at RT. A solution of benzyl bromide (17.85 mL, 0.142 mol)

in THF (50 mL) was added at 0° C. over a period of 1 h. The resultant mixture was stirred for 16 h at 80° C. The reaction mixture was quenched with saturated NH₄Cl solution and extracted with ethyl acetate (3×200 mL). The combined organic layer was washed with water, brine, dried over anhydrous Na₂SO₄ and distilled under reduced pressure to afford crude, which was purified by column chromatography over silica gel (60-120) by using 50-60% ethyl acetate in hexane as eluent to give 30 g (70%) of 10-Benzyl-1,4-dioxa-10-aza-dispiro[4.2.4.2]tetradecan-11-one as a solid.

Step 6: 2-Benzyl-2-azaspiro-[4.5]-decane-3,8-dione

A solution of 3-Benzyl-9,12-dioxa-3-azadispiro[4.2.4.2] tetradecan-2-one (30 g, 99.66 mol) in 5% sulfuric acid (300 mL) was stirred at RT for 24 h. The reaction mixture was basified with solid NaHCO3—and extracted with ethyl acetate (3×200 mL). The combined organic layer was washed with brine, dried over Na2SO4 and distilled under reduced pressure to yield 22 g (85%) of 2-Benzyl-2-azaspiro-[4.5]-decane-3,8-dione as light yellow semi solid.

Step 7: 2-Benzyl-8-(dimethylamino)-3-oxo-2-azaspiro-[4.5]-decane-8-carbonitrile

A mixture of 2-Benzyl-2-azaspiro-[4.5]-decane-3,8-dione (20.0 g, 77.80 mmol), potassium cyanide (12.64 g, 0.19 mol) and dimethyl amine hydrochloride (15.75 g, 0.19 mol) in methanol (200 mL) was stirred for 24 h at rt. The reaction mixture was quenched with water & extracted with 10% MeOH in DCM (4×200 mL). The combined organic layer dried over Na₂SO₄ and distilled under reduced pressure to afford 20.0 g (82%) of 2-benzyl-8-(dimethylamino)-3-oxo-2-azaspiro-[4.5]-decane-8-carbonitrile as semi solid.

Step 8: 2-Benzyl-8-(dimethylamino)-8-(3-methoxypropyl)-2-azaspiro-[4.5]-decan-3-one A freshly prepared Grignard reagent [using 1-bromo-3-methoxy propane (16 mL, 0.12 mol) and activated magnesium (3.08 g, 0.12 mol)] in THF (100 mL) was added to a solution of 2-Benzyl-8-(dimethylamino)-3-oxo-2-azaspiro-[4.5]-decane-8-carbonitrile (10 g, 32.15 mmol) in THF (100 mL) at 0° C.; warmed to room temperature and stirred for 2 h. The reaction mixture was quenched with sat NH₄Cl solution, extracted with ethyl acetate (3×200 mL). The combined organic layer was washed with brine, dried over Na₂SO₄ and distilled under reduced pressure to give crude which was purified by column chromatography over silica gel (60-120) by using 50-60% ethyl acetate in hexane as eluent to give the 0007C4 mixture (4 g). This was further purified by preparative HPLC to afford 750 mg of (6.5%) of cis-2-Benzyl-8-(dimethylamino)-8-(3-methoxypropyl)-2-azaspiro-[4.5]-decan-3-one and 1.10 g (9.5%) of trans-2-Benzyl-8-(dimethylamino)-8-(3-methoxypropyl)-2-azaspiro-[4.5]-decan-3-one as semi solids.

Step 9: cis-8-(dimethylamino)-8-(3-methoxypropyl)-2-azaspiro[4.5]-decan-3-one

Sodium metal (481 mg, 20.94 mmol) was added to liquid ammonia (~20 mL) at −78° C. The resultant mixture was stirred for 10 min at −78° C. A solution of cis-2-Benzyl-8-(dimethylamino)-8-(3-methoxypropyl)-2-azaspiro-[4.5]-decan-3-one (750 mg, 2.09 mmol) in THF (10 mL) was added to the reaction mixture at −78° C. and stirred for 15 min. The reaction mixture was quenched with sat NH₄Cl solution, warmed to room temperature & stirred for 1 h. Extracted with 10% methanol in DCM (50 mL×3) and the combined organic layer was washed with water; distilled under reduced pressure to afford 350 mg (62%) of cis-8-(dimethylamino)-8-(3-methoxypropyl)-2-azaspiro-[4.5]-decan-3-one as off-white solid.

Syntheses of Additional Building Blocks:
Building Block No. 1:

Dimethyl-[8-(5-methylthiophen-2-yl)-3-azaspiro [4.5]decan-8-yl]-amine (Building Block No. 1, Polar Diastereomer)

A solution of 8-(dimethylamino)-8-(5-methylthiophen-2-yl)-3-azaspiro[4.5]decan-4-one (polar diastereomer) (1.40 g, 4.8 mmol) in anhydrous tetrahydrofuran (100 ml) was added to a suspension of lithium aluminium hydride (456 mg, 12 mmol) in anhydrous tetrahydrofuran (20 ml) in a thoroughly heated apparatus, while cooling with ice, and the mixture was then stirred at 60° C. overnight. Water (857 µl), 1 N sodium hydroxide solution (2.1 ml) and again water (2.1 ml) were added to the reaction solution, while cooling with ice, and the mixture was stirred for 1 h at room temperature. The mixture was filtered through sea sand and the residue was washed with tetrahydrofuran. The filtrate was dried with sodium sulfate and concentrated i. vac. 160 mg of the crude product (1.18 g) were purified, for the purpose of release, by means of flash chromatography (10 g, 20×1.5 cm) with ethyl acetate/methanol (4:1)→methanol+1% ammonia (25% in water), as a result of which 80 mg of the target compound were obtained, which still contained minimal impurities.

Building Block No. 1 (Polar Diastereoisomer)
Yield: 1.18 g (crude product), yellow viscous oil
¹H-NMR (CDCl₃): 1.37-1.41 (m, 2H); 1.47 (t, J=7.1 Hz, 2H); 1.57-1.65 (m, 2H); 1.85-1.91 (m, 2H); 2.00-2.16 (m, 2H, overlapped); 2.11 (s, 6H); 2.47 (s, 3H); 2.75 (s, 2H); 2.91 (t, J=7.1 Hz, 2H); 6.62 (d, J=3.5 Hz, 1H); 6.67-6.68 (m, 1H). The NH proton could not be identified.
¹³C-NMR (CDCl₃): 15.3; 32.9; 33.6; 38.2; 42.4; 46.1; 57.9; 59.9; 64.2; 124.3; 124.9; 137.6; 140.8.
LC-MS: m/z: [MH-HNMe₂]⁺=234.2, R$_f$=0.7 min.
Building Block No. 2:

Dimethyl-(8-thiophen-2-yl-3-azaspiro[4.5]decan-8-yl)-amine (Building Block no. 2, Polar Diastereomer)

A solution of 8-(dimethylamino)-8-thiophen-2-yl-3-azaspiro[4.5]decan-4-one (polar diastereomer) (714 mg, 2.56 mmol) in tetrahydrofuran (20 ml) was added to a suspension of lithium aluminium hydride (490 mg, 12.9 mmol) in tetrahydrofuran (4 ml) at room temperature and the mixture was stirred for 18 h at 60° C. The reaction mixture was cooled to 0° C., water (0.5 ml), 1 N sodium hydroxide solution (1 ml) and again water (1 ml) were added and the mixture was then stirred for 1 h at room temperature. The precipitate was filtered off, ethyl acetate (20 ml) was added to the filtrate and the phases were separated. The organic phase was dried with sodium sulfate and the solvent was removed i. vac. The residue (570 mg) was purified by flash chromatography (30 g, 19×2.5 cm) with methylene chloride/methanol (4:1) and 1% ammonia (25% in H₂O).
Building Block No. 2 (Polar Diastereomer)
Yield: 280 mg (41%), white oily solid.
Melting point: 80-84° C.
¹H-NMR (CDCl₃): 1.38 (ddd, 2H, J=3.6, 13.3 Hz); 1.43-1.50 (m, 1H); 1.58-1.70 (m, 2H); 1.86-2.01 (m, 2H); 2.09

(m, 9H); 2.75 (s, 2H); 2.90 (t, 2H, J=7.1 Hz); 6.84 (dd, 1H, J=1.1 and 3.6 Hz); 7.03 (dd, 1H, J=3.6 and 5.1 Hz); 7.23 (dd, 1H, J=1.1 and 5.1 Hz). The NH proton could not be identified.

$^{13}$C-NMR (CDCl$_3$): 32.8 (2C); 33.7 (2C); 38.1; 39.0; 42.3; 57.8; 59.8; 123.2; 124.9; 126.1; 143.2.

LC-MS: m/z: [M+H]$^+$=265.2, R$_t$=0.5 min.

Building Block No. 3:

Dimethyl-(8-phenyl-3-azaspiro[4.5]decan-8-yl)amine

A solution of the non-polar diastereoisomer of 8-(dimethylamino)-8-phenyl-2-azaspiro[4.5]decan-2-one (345 mg, 1.28 mmol) in anhydrous tetrahydrofuran (50 ml) was added to a suspension of lithium aluminium hydride (245 mg, 6.4 mmol) in anhydrous tetrahydrofuran (10 ml), while cooling with ice, and the mixture was then stirred overnight at 60° C. Water (200 µl), 1 N sodium hydroxide solution (500 µl) and again water (500 µl) were added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Yield: 329 mg (99%), oil $^1$H-NMR (CDCl$_3$): 1.23-1.32 (m, 2H); 1.53-1.62 (m, 2H), 1.65 (t, 2H, J=7.0 Hz); 1.77 (br s, 2H); 1.87-1.96 (m, 2H); 2.04 (s, 6H); 2.23-2.35 (m, 1H); 2.52 (s, 2H); 2.94 (t, 2H, J=7.0 Hz); 7.27-7.33 (m, 3H); 7.34-7.40 (m, 2H).

LC-MS: m/z: [M+H]$^+$=259.2, R$_t$ 0.6

Building Block 3a:

The reaction of the polar diastereoisomer of 8-(dimethylamino)-8-phenyl-2-azaspiro[4.5]decan-3-one was carried out analogously to the synthesis of Building Block 3 described above.

Yield: 374 mg (96%), oil $^1$H-NMR (CDCl$_3$): 1.23-1.35 (m, 2H); 1.39 (t, 2H, J=7.1 Hz); 1.56-1.67 (m, 2H); 1.78-1.95 (m, 4H); 2.03 (s, 6H); 2.17-2.33 (m, 1H); 2.79 (s, 2H); 2.88 (t, 2H, J=7.1 Hz); 7.24-7.33 (m, 3H); 7.34-7.40 (m, 2H).

LC-MS: m/z: [M+H]$^+$=259.2

Building Block No. 4:

Step 1: 8-(Cyclohexylmethyl)-8-dimethylamino-3-azaspiro[4.5]decan-4-one

A 0.5 M solution of cyclohexylmethylmagnesium bromide in tetrahydrofuran (63.2 ml, 31.6 mmol) was added dropwise to a solution of 8-(dimethylamino)-1-oxo-2-azaspiro[4.5]decane-8-carbonitrile (2 g, 9.03 mmol) in anhydrous tetrahydrofuran (75 ml) at 0° C. and the mixture was stirred for 18 h at room temperature. Saturated ammonium chloride solution (90 ml) was then added to the mixture, while cooling with ice. The phases were separated and the aqueous phase was extracted with ethyl acetate (2×25 ml). The combined organic phases were dried with sodium sulfate and concentrated i. vac. The residue (2.4 g) was purified by flash chromatography (200 g, 20×5.7 cm) with methylene chloride/methanol (98:2) and 1% ammonia (25% in water).

Step 1: (a Diastereoisomer)

Yield: 1.20 g (46%), white solid

Melting point: 190-193° C.

$^1$H-NMR (CDCl$_3$): 0.88-1.00 (2H, m); 1.06-1.27 (8H, m); 1.32 (2H, dt, J=14.1 and 3.4 Hz); 1.54-1.74 (7H, m); 2.03 (2H, t, J=7.0 Hz); 2.08 (2H, dt, J=13.2 and 3.2 Hz); 2.16 (6H, s); 3.26-3.31 (2H, m); 6.04 (1H, br s).

$^{13}$C-NMR (CDCl$_3$): 26.2; 26.7; 27.0; 28.9; 32.0; 32.9; 33.5; 36.0; 36.9; 37.7; 38.1; 38.8; 43.8; 56.4; 183.5.

Only one diastereoisomer was isolated.

LC-MS: m/z: [M+H]$^+$=293.2, low UV activity.

Step 2: (8-Cyclohexylmethyl-2-azaspiro[4.5]dec-8-yl)dimethylamine

A solution of 8-(cyclohexylmethyl)-8-dimethylamino-3-azaspiro[4.5]decan-4-one (Example no. 158, a diastereoisomer) (1.05 g, 3.59 mmol) in anhydrous tetrahydrofuran (40 ml) was added dropwise to a suspension of lithium aluminium hydride (683 mg, 18 mmol) in anhydrous tetrahydrofuran (20 ml), while cooling with ice. The mixture was stirred for 18 h at 50° C. and water (700 µl), 1 N sodium hydroxide solution (1.4 ml) and again water (1.4 ml) were then added dropwise, while cooling with ice. The suspension was stirred for 1 h at room temperature and thereafter filtered through sodium sulfate. The residue on the filter was washed with tetrahydrofuran and the filtrate was concentrated i. vac.

Yield: 884 mg (99%), colourless oil $^1$H-NMR (CDCl$_3$): 0.89-1.01 (2H, m); 1.06-1.45 (9H, m); 1.50-1.74 (10H, m); 1.80-1.90 (2H, m); 2.17 (6H, s); 2.64 (2H, s); 2.94 (2H, t, J=7.1 Hz). The NH proton could not be identified.

Building Block No. 5:

8-Dimethylamino-8-thiophen-2-yl-3-azaspiro[4.5]decan-4-one (Building Block No. 5, a Diastereomer)

A solution of dimethylamino-1-oxo-2-azaspiro[4.5]decane-8-carbonitrile (800 mg, 3.6 mmol) in tetrahydrofuran (15 ml) was added dropwise to a 1 M solution of 2-thienylmagnesium bromide in tetrahydrofuran (11.5 ml, 11.5 mmol) at 0° C. and under argon and thereafter the mixture was stirred overnight at room temperature. 20% strength ammonium chloride solution (35 ml) was then added to the reaction solution. The phases were separated and the aqueous phase was extracted with ethyl acetate (2×30 ml). The combined organic phases were dried with sodium sulfate and concentrated. The crude product (950 mg) was purified by flash chromatography (80 g, 17×3.7 cm) with methylene chloride/methanol [9:1+2% ammonia (33% in H$_2$O)].

Building Block No. 5 (a Diastereomer)

Yield: 840 mg (84%), yellowish solid

Melting point: 168-174° C.

$^1$H-NMR (CDCl$_3$): 1.26-1.36 (m, 2H); 1.69 (dt, 2H, J=3.2 and 13.8 Hz); 1.99 (t, 2H, J=6.9 Hz); 2.10 (s, 6H); 2.20 (dt, 2H, J=3.2 and 13.1 Hz); 2.45 (br d, 2H, J=13.6 Hz); 3.25-3.34 (m, 2H); 6.76 (br s, 1H); 6.85 (dd, 1H, J=1.1 and 3.6 Hz); 7.03 (dd, 1H, J=3.6 and 5.1 Hz); 7.21 (dd, 1H, J=1.1 and 5.1 Hz).

$^{13}$C-NMR (CDCl$_3$): 27.9 (2C); 31.9 (2C); 32.5; 38.0 (2C); 38.9; 43.4; 58.4; 122.8; 123.6; 126.0; 145.4; 183.0.

LC-MS: m/z: [M+H]$^+$=279.2, R$_t$=1.3 min.

Building Block No. 6 and 7:

Step 1: 8-Cyanomethyl-1,4-dioxaspiro[4.5]decane-8-carboxylic acid ethyl ester

A 2.5 M solution of n-butyllithium in n-hexane (22 ml, 55 mmol) was added dropwise to a solution of diisopropylamine (5.56 g, 55 mmol) in anhydrous tetrahydrofuran (80 ml) under argon at −78° C. and the mixture was then stirred for 15 min at 0° C. A solution of ethyl 1,4-dioxaspiro[4.5] decane-8-carboxylate (10.7 g, 50 mmol) in tetrahydrofuran (15 ml) was added dropwise to this lemon-yellow solution at −78° C. in the course of 20 min. The dark yellow mixture was stirred for 1.5 h at −78° C. and a solution of bromoacetonitrile (7.16 g, 3.98 ml, 60 mmol) and 1,3-dimethyl-3,4,5,6-tetrahydro-2-(1H)pyrimidone (DMPU, 3.20 g, 3.0 ml, 25 mmol) in tetrahydrofuran (15 ml) was then added dropwise. Thereafter, the orange-coloured solution was warmed slowly to room temperature and stirred overnight. 0.5 N hydrochloric acid (38 ml) was added to the now red-brown solution and the phases were separated. The aqueous phase was extracted with diethyl ether (3×50 ml). The combined organic phases were washed with saturated sodium bicarbonate solution (2×100 ml) and with saturated sodium chloride solution (4×100 ml), dried with sodium sulfate and concentrated i. vac. The crude product (12.1 g) was purified by flash chromatography (400 g, 20×7.5 cm) with ethyl acetate/cyclohexane (1:2).

Yield: 6.50 g (51%), yellowish oil.

$^1$H-NMR (CDCl$_3$): 1.29 (t, 3H, J=7.1 Hz); 1.62-1.76 (m, 6H); 2.17-2.29 (m, 2H); 2.57 (s, 2H); 3.93 (t, 4H, J=2.2 Hz); 4.23 (q, 2H, J=7.1 Hz).

Step 2: 1,4-Dioxa-10-azadispiro[4.2.4.2]tetradecan-9-one

Sodium borohydride (4.84 g, 128 mmol) was added in portions to a raspberry-coloured mixture of 8-cyanomethyl-1,4-dioxaspiro[4.5]decane-8-carboxylic acid ethyl ester (6.50 g, 25.6 mmol) and anhydrous cobalt(II) chloride (1.66 g, 12.8 mmol) in tetrahydrofuran (100 ml) and water (50 ml) under argon at 0° C. and the mixture was then stirred overnight at room temperature. During this operation the solution became black in colour. Since the reaction was not yet complete, cobalt(II) chloride (830 mg, 6.4 mmol) and sodium borohydride (2.42 g, 64 mmol) were again added and the mixture was stirred for a further 24 h. 25% strength aqueous ammonia solution (5 ml) was added to the reaction mixture and the mixture was filtered. The residue on the filter was washed with tetrahydrofuran/water (2:1). The filtrate was concentrated i. vac. and the aqueous solution was extracted with methylene chloride (3×50 ml). The combined organic extracts were dried with sodium sulfate and concentrated i. vac.

Yield: 4.64 g (86%), white solid which still contained approx. 30% of educt.

Step 3: 2-Azaspiro[4.5]decane-1,8-dione p-Toluenesulfonic acid (5.00 g, 26.3 mmol) was added to a solution of 1,4-dioxa-10-azadispiro[4.2.4.2]tetradecan-9-one (4.64 g, 21.9 mmol) in methanol (75 ml) and water (25 ml) and the mixture was stirred for 24 h at room temperature and 24 h at 50° C. The reaction mixture was then rendered alkaline with 5 N sodium hydroxide solution and concentrated. The residue was diluted with water (50 ml) and the mixture was extracted with methylene chloride (6×30 ml). The organic phase was dried with sodium sulfate and concentrated i. vac. The crude product (2.09 g) was purified by flash chromatography (200 g, 20×5.7 cm) with ethyl acetate/methylene chloride (4:1) and ethyl acetate/methylene chloride/methanol (3:1:1). The mixed fractions (850 mg) were purified again by flash chromatography (100 g, 20×4.0 cm) with tert-butyl methyl ether/methanol (14:1).

Yield: 1.20 g (33%), white solid

Melting point: 128-130° C.

$^1$H-NMR (CDCl$_3$): 1.73-1.89 (m, 2H); 2.08-2.21 (m, 4H); 2.33 (ddd, 2H, J=5.8, 10.2 and 15.0 Hz); 2.70 (td, 2H, J=6.3 and 14.8 Hz); 3.41 (dt, 2H, J=0.8 and 7.1 Hz); 3.72 (s, 1H).

Step 4: Dimethylamino-1-oxo-2-azaspiro[4.5]decane-8-carbonitrile

4 N hydrochloric acid (2.15 ml, 8.56 mmol) and 2-azaspiro[4.5]decane-1,8-dione (1.20 g, 7.17 mmol) in methanol (16 ml) were added to a 40% strength aqueous dimethylamine solution (3.6 ml, 28.7 mmol), cooled to 0° C., in methanol (1.6 ml). Potassium cyanide (931 mg, 14.3 mmol) was added to this mixture and the mixture was stirred over the weekend at room temperature. After addition of water (30 ml) the solution was extracted with diethyl ether and methylene chloride (3×30 ml of each). The combined organic phases were dried with sodium sulfate and concentrated i. vac.

Yield: 1.40 g (88%), white solid $^1$H-NMR (CDCl$_3$): 1.35-1.67 (m, 3H); 1.76-2.09 (m, 5H); 2.18-2.31 (m, 2H); 2.33 and 2.35 (2s, 6H); 3.28-3.35 (m, 2H); 6.50 and 6.60 (2s, 1H). This is a diastereoisomer mixture in the ratio of approx. 2:1.

Step 5: 8-Benzyl-8-(dimethylamino)-3-azaspiro[4.5] decan-4-one (Building Block No. 6, Polar Diastereomer, Building Block No. 7, Non-Polar Diastereomer)

A solution of dimethylamino-1-oxo-2-azaspiro[4.5]decane-8-carbonitrile (1.40 g, 6.3 mmol) in anhydrous tetrahydrofuran (60 ml) was added dropwise to a 2 M solution of benzylmagnesium chloride in tetrahydrofuran (9.5 ml, 19 mmol) at 0° C. under argon and thereafter the mixture was stirred at room temperature overnight. 20% strength ammonium chloride solution (25 ml) was then added to the reaction solution. The phases were separated and the aqueous phase was extracted with ethyl acetate (3×30 ml). The combined organic phases were dried with sodium sulfate and concentrated i. vac. The crude product (2.00 g) was purified by flash chromatography (100 g, 20×4.0 cm) with methylene chloride/methanol (48:1) and 0.25% ammonia (25% in water). The mixed fractions (560 mg) were purified again by flash chromatography (38 g, 20×2.5 cm) with methylene chloride/isopropanol (95:5) and 1% ammonia (25% in water).

Building Block No. 6 (Polar Diastereoisomer)

Yield: 511 mg (28%), colourless oil which also contains approx. 20% of the non-polar diastereoisomer.

$^1$H-NMR (CDCl$_3$): 1.53-1.63 (m, 4H); 1.67-1.75 (m, 2H); 1.85-1.92 (m, 2H); 1.95 (t, 2H, J=6.8 Hz); 2.28 (s, 6H); 2.77 (s, 2H); 3.21-3.26 (m, 2H); 5.71 (br s, 1H); 7.13-7.26 (m, 5H).

$^{13}$C-NMR (CDCl$_3$): 28.2; 29.0; 35.3; 36.7; 37.4; 38.6; 41.5; 57.6; 125.7; 127.7; 130.8; 139.2; 182.6.

LC-MS: m/z: [M+H]$^+$=287.3, R$_f$=1.0 min.

Building Block No. 7 (Non-Polar Diastereoisomer)

Yield: 970 mg (54%), white solid

Melting point: 202-204° C.

$^1$H-NMR (CDCl$_3$): 1.05-1.19 (m, 4H); 1.67-1.80 (m, 4H); 2.00-2.14 (m, 2H); 2.30 (s, 6H); 2.62 (s, 2H); 3.15 (t, 2H, J=7.2 Hz); 5.90 (br s, 1H); 7.00-7.13 (m, 2H); 7.15-7.28 (m, 3H).

$^{13}$C-NMR (CDCl$_3$): 26.9; 28.6; 31.6; 37.0; 38.8; 43.6; 57.1; 125.6; 127.7; 130.6; 139.3; 183.3.

LC-MS: m/z: [M+H]$^+$=287.3, R$_f$=2.3 min.

Building Block No. 8 and 9

Step 1: (4-Dimethylamino-4-thiophen-2-ylcyclohexylidene)-acetic acid ethyl ester Potassium tert-butylate (3.01 g, 26.9 mmol) was added to a solution of triethyl phosphonoacetate (6.02 g, 5.33 ml, 26.9 mmol) in absolute N,N-dimethylformamide (30 ml) under argon. The mixture was stirred for 10 min at room temperature, before a solution of 4-(dimethylamino)-4-(thiophen-2-yl)cyclohexanone (4.0 g, 17.9 mmol) in absolute N,N-dimethylformamide (60 ml) was added, and the mixture was then stirred for 1 h at room temperature. The reaction mixture was then poured into ice-water (75 g) and the aqueous suspension was extracted with diethyl ether (4×50 ml). The combined organic phases were dried with sodium sulfate and concentrated i. vac.

Yield: 5.20 g (99%), yellow oil $^1$H-NMR (CDCl$_3$): 1.26 (t, 3H, J=7.1 Hz); 2.03-2.12 (m, 2H); 2.13 (s, 6H); 2.15-2.27 (m, 2H); 2.90-3.09 (m, 4H); 4.13 (q, 2H, J=7.1 Hz); 5.61 (s, 1H); 6.87 (dd, 1H, J=1.1, 3.6 Hz); 7.03 (dd, 1H, J=3.6, 5.1 Hz); 7.23 (dd, 1H, J=1.1, 5.1 Hz).

LC-MS: m/z: [MH-HNMe$_2$]$^+$=249.2 (90%), R$_t$=2.8 min.

Step 2: (4-Dimethylamino-1-nitromethyl-4-thiophen-2-yl-cyclohexyl)-acetic acid ethyl ester Tetra-n-butylammonium fluoride trihydrate (5.10 g, 19.5 mmol) and nitromethane (5.40 g, 4.79 ml, 88.5 mmol) were added to a solution of the crude product of (4-dimethylamino-4-thiophen-2-ylcyclohexylidene)-acetic acid ethyl ester (5.20 g, 17.7 mmol) in tetrahydrofuran (120 ml) and the mixture was stirred for 3 h at 70° C. and then 18 h at 45° C. The reaction mixture was then concentrated i. vac. The residue was purified by means of flash chromatography (200 g, 20×4.0 cm) with cyclohexane/ethyl acetate (1:9).

Yield: 4.9 g (78%), orange-coloured oil $^1$H-NMR (CDCl$_3$): 1.20-1.28 (m, 3H); 1.44-1.53 (m, 4H); 1.77-1.88 (m, 4H); 2.09 (s, 6H); 2.46 and 2.61 (2 s, 2H); 4.04-4.22 (m, 2H); 4.62 and 4.77 (s, 2H); 6.82-6.85 (m, 1H); 7.02-7.06 (m, 1H); 7.22-7.25 (m, 1H).

LC-MS: m/z: [M+H]$^+$=355.2, R$_t$=2.5 min.

This is a diastereoisomer mixture in the ratio of approx. 1:1 which is still contaminated with approx. 15% of educt.

Step 3: 8-(Dimethylamino)-8-thiophenyl-2-yl-3-azaspiro[4.5]decan-3-one (Building Block No. 8, Polar Diastereomer, Building Block No. 9, Non-Polar Diastereomer)

A solution of the diastereoisomer mixture of (4-dimethylamino-1-nitromethyl-4-thiophen-2-ylcyclohexyl)-acetic acid ethyl ester (4.90 g, 13.8 mmol) in ethanol (138 ml) was added to a mixture of iron powder (3.85 g, 69 mmol) and ammonium chloride (18.5 g, 345 mmol) in water (14 ml) and the mixture was heated for 5 h under reflux. The reaction mixture was then filtered, saturated sodium bicarbonate solution (4 ml) was added to the filtrate and the mixture was concentrated i. vac. The residue was separated by flash chromatography (200 g, 20×5.7 cm) with methylene chloride/methanol (10:1) and 1% ammonia (32% in water).

Yield: 2.33 g (61%), diastereoisomer mixture in the ratio of approx. 1:1

The diastereoisomer mixture was separated by repeated medium pressure chromatography (230 g, 3.6×46 cm) or flash chromatography (100 g, 20×4.0 cm), the column material used being spherical silica gel (PharmPrep 60 CC (40-63 μm) and the eluent used being methylene chloride/methanol 95:5 and 1% ammonia (32% in H$_2$O). The ratio of sample to silica gel weight was in each case approx. 1:200.

Building Block No. 8 (Polar Diastereomer)
Melting point: 215° C., white solid $^1$H-NMR (CDCl$_3$): 1.47-1.55 (m, 2H); 1.78-1.86 (m, 2H); 1.97-2.09 (m, 4H); 2.10 (s, 6H); 2.12 (s, 2H); 3.23 (s, 2H); 5.69 (br s, 1H); 6.85 (dd, 1H, J=1.1, 3.6 Hz); 7.05 (dd, 1H, J=3.6, 5.1 Hz); 7.25 (dd, 1H, J=1.2, 5.1 Hz).

$^{13}$C-NMR (CDCl$_3$): 32.6; 32.7; 38.1; 38.8; 43.1; 53.0; 59.3; 123.4; 124.9; 126.3; 142.6; 177.5.

LC-MS: m/z: [MH-HNMe$_2$]$^+$=234.2 (100%) and [M+H]$^+$=279.2 (16%), R$_t$=1.3 min.

Building Block No. 9 (Non-Polar Diastereoisomer)
Melting point: 213-222° C., white solid $^1$H-NMR (CDCl$_3$): 1.46-1.54 (m, 2H); 1.76-1.84 (m, 2H); 1.93-2.12 (m, 4H); 2.09 (s, 6H); 2.26 (s, 2H); 3.08 (s, 2H); 5.78 (br s, 1H); 6.85 (dd, 1H, J=1.1, 3.6 Hz); 7.04 (dd, 1H, J=3.6, 5.1 Hz); 7.24 (dd, 1H, J=1.1, 5.1 Hz).

$^{13}$C-NMR (CDCl$_3$): 32.7; 32.8; 38.1; 38.9; 42.5; 53.6; 59.5; 123.4; 124.8; 124.9; 126.3; 142.7; 177.5.

LC-MS: m/z: [MH-HNMe$_2$]$^+$=234.2 (100%) and [M+H]$^+$=279.2 (22%), R$_t$=1.4 min.

Building Block No. 10:

Step 1: Cyclopent-1-enemagnesium bromide

Magnesium (1.70 g, 70 mmol) and an iodine crystal were heated in a secure apparatus such that iodine gas was formed. The mixture was cooled to room temperature and anhydrous tetrahydrofuran (17 ml) and a further iodine crystal were then added. A solution of 1-bromocyclopentene (10.3 g, 70 mmol) in anhydrous tetrahydrofuran (23 ml) was then added dropwise such that the reaction mixture started to boil. The mixture was stirred for a further 1 h under reflux and then cooled to room temperature. The solution obtained in this way was employed in the next step.

Step 2: (8-Cyclopent-1-enyl-1,4-dioxaspiro[4.5]dec-8-yl)-dimethylamine

A solution of 8-(dimethylamino)-1,4-dioxaspiro[4.5]decane-8-carbonitrile (6.05 g, 28.7 mmol) in anhydrous tetrahydrofuran (40 ml) was added dropwise to the solution from step 1 (max. 70 mmol). The mixture was stirred overnight at room temperature and then for 2 h at 60° C. and thereafter saturated ammonium chloride solution (50 ml) and water (50 ml) were added, while cooling with ice. The pH of the mixture was adjusted to 9 with 4 N sodium hydroxide solution. The phases were separated and the aqueous phase was extracted with ethyl acetate (3×50 ml). The combined organic phases were dried with sodium sulfate and concentrated i. vac. The crude product was purified by flash chromatography (400 g, 20×7.5 cm) with methylene chloride/methanol (95:5) and 1% ammonia (25% in water).

Yield: 2.54 g (35%), yellow oil $^1$H-NMR (CDCl$_3$): 1.50-1.60 (2H, m); 1.70-1.94 (8H, m); 2.20 (6H, s); 2.24-2.30 (2H, m); 2.31-2.39 (2H, m); 3.88-3.96 (4H, m); 5.53 (1H, m).

$^{13}$C-NMR (CDCl$_3$): 23.6; 29.0; 31.4; 32.2; 33.1; 38.5; 58.4; 64.1; 109.0; 128.2; 143.8.

LC-MS: [M+H]$^+$: m/z=252.3, R$_t$=1.9 min.

Step 3: (8-Cyclopentyl-1,4-dioxaspiro[4.5]dec-8-yl)-dimethylamine

5% rhodium on activated aluminium oxide (2.05 g, 1 mmol) was added to a solution of (8-cyclopent-1-enyl-1,4- dioxaspiro[4.5]dec-8-yl)-dimethylamine (2.53 g, 10 mmol) in anhydrous methanol (220 ml). The suspension was stirred for 18 h at 50° C. and under a hydrogen pressure of 4 bar and then filtered through Celite which had been washed with methanol beforehand. The filtrate was concentrated i. vac.

Yield: 2.51 g (100%), yellow oil $^1$H-NMR (CDCl$_3$): 1.20-1.34 (2H, m); 1.38-1.64 (10H, m); 1.68-1.78 (2H, m); 1.82-1.94 (2H, m); 2.07 (1H, m); 2.27 (6H, s); 3.91-3.94 (4H, m).

$^{13}$C-NMR (CDCl$_3$): 25.0; 28.0; 28.5; 30.0; 37.8; 43.8; 57.5; 64.1; 109.6.

Step 4:
4-Cyclopentyl-4-dimethylaminocyclohexanone

A solution of (8-cyclopentyl-1,4-dioxaspiro[4.5]dec-8-yl)-dimethylamine (5.21 g, 20.5 mmol) in 1 M aqueous sulfuric acid (150 ml) was stirred for 48 h at room temperature. The mixture was washed with methylene chloride (2×70 ml). The aqueous phase was rendered alkaline with 4 N sodium hydroxide solution and extracted with methylene chloride (4×50 ml). The combined organic phases were dried with sodium sulfate and concentrated i. vac.

Yield: 3.52 g (82%), yellow oil $^1$H-NMR (CDCl$_3$): 1.18-1.34 (2H, m); 1.40-1.80 (8H, m); 1.96-2.08 (2H, m); 2.10-2.22 (3H, m); 2.34 (6H, s); 2.51-2.63 (2H, m).

$^{13}$C-NMR (CDCl$_3$): 24.9; 28.6; 30.1; 36.6; 37.2; 38.0; 43.4; 57.5.

The carbonyl carbon was detected by a gHMBC spectrum at 212 ppm.

LC-MS: [M+H]$^+$: m/z=210.3, R$_t$=0.8 min.

Step 5: (4-Cyclopentyl-4-dimethylaminocyclohex-ylidene)-acetic acid ethyl ester

Potassium tert-butanolate (2.99 g, 26.7 mmol) was added to a solution of phosphonoacetic acid triethyl ester (6.74 g, 5.98 ml, 30.1 mmol) in anhydrous N,N-dimethylformamide (30 ml) and the mixture was stirred for 1 h at 50° C. The solution was cooled to room temperature and a solution of 4-cyclopentyl-4-dimethylaminocyclohexanone (3.96 g, 18.9 mmol) in anhydrous N,N-dimethylformamide (50 ml) was then added. The reaction mixture was stirred for 20 h at room temperature and then poured into ice-water (75 g). The suspension was extracted with diethyl ether (4×40 ml). The combined organic phases were dried with sodium sulfate and concentrated i. vac. Toluene was first repeatedly added to the residue and the mixture concentrated i. vac. again each time and thereafter the procedure was repeated with cyclohexane. This residue (5.49 g) was taken up in ethyl acetate (30 ml) and the solution was extracted with 10% strength formic acid (5×30 ml). The combined acid, aqueous phases were rendered alkaline with 4 N sodium hydroxide solution and extracted with methylene chloride (5×30 ml). The combined organic phases were dried with sodium sulfate and concentrated i. vac.

Yield: 4.36 g (77%), colourless oil $^1$H-NMR (CDCl$_3$): 1.14-1.70 (13H, m); 1.78-2.40 (5H, m); 2.32 (6H, s); 2.57 (1H, br t, J=13.9 Hz); 3.55 (1H, br d, J=12.6 Hz); 4.13 (2H, q, J=7.0 Hz); 5.58 (1H, s).

Step 6: (4-Cyclopentyl-4-dimethylamino-1-nitromethylcyclohexyl)-acetic acid ethyl ester Nitromethane (1.22 ml, 1.07 ml, 20 mmol) was added to a mixture of (4-cyclopentyl-4-dimethylaminocyclohex-ylidene)-acetic acid ethyl ester (4.35 g, 15.6 mmol) and tetra-n-butylammonium fluoride trihydrate (5.36 g, 17 mmol) in anhydrous tetrahydrofuran (37 ml). The solution was stirred for 7.5 h at 70° C. and then 18 h at 45° C. The mixture was concentrated i. vac. The residue (9.9 g) was purified by flash chromatography (400 g, 20×7.5 cm) with cyclohexane/ethyl acetate (1:4).

Yield: 3.04 g (57%), yellowish oil.

$^1$H-NMR (CDCl$_3$): 1.26 (0.3H, t, J=7.0 Hz); 1.27 (2.7H, t, J=7.1 Hz); 1.30-1.75 (16H, m); 2.06 (1H, m); 2.24 (6H, s); 2.46 (0.2H, s); 2.59 (1.8H, s); 4.15 (2H, q, J=7.1 Hz); 4.58 (1.8H, s); 4.81 (0.2H, s)

$^{13}$C-NMR (CDCl$_3$): 14.2; 25.05; 24.14; 25.4; 28.1; 28.45; 28.50; 35.0; 36.8; 37.7; 43.6; 44.0; 44.1; 57.4; 60.1; 60.2; 84.3; 171.3.

This is a diastereoisomer mixture.

Step 7: 8-Cyclopentyl-8-dimethylamino-2-azaspiro[4.5]decan-3-one

A 50% strength aqueous Raney nickel suspension (1.15 ml) was added to a solution of (4-cyclopentyl-4-dimethyl-amino-1-nitromethylcyclohexyl)-acetic acid ethyl ester (3.04 g) in methanol (50 ml). The suspension was stirred for 5 h at 60° C. and under a hydrogen pressure of 5 bar. The suspension was filtered through Celite, the residue on the filter was washed with methanol (2×10 ml) and the filtrate was concentrated i. vac.

Yield: 2.36 g (100%), white solid $^1$H-NMR (CDCl$_3$): 1.16-1.80 (16H, m); 2.05 (1H, m); 2.12 (0.3H, s); 2.20 (1.7H, s); 2.26 (6H, s); 3.09 (1.7H, s); 3.18 (0.3H, s); 6.04 (1H, br s).

This is a diastereoisomer mixture in the ratio of approx. 7:1.

Step 8: 8-Cyclopentyl-8-dimethylamino-3-oxo-2-azaspiro[4.5]decane-2-carboxylic acid tert-butyl ester A solution of di-tert-butyl dicarbonate (2.14 g, 9.83 mmol) in anhydrous acetonitrile (20 ml) and 4-dimethylaminopyridine (69 mg, 0.87 mmol) was added to a solution of 8-cyclopentyl-8-dimethylamino-2-azaspiro[4.5]decan-3-one (2.36 g, 8.92 mmol) in anhydrous acetonitrile (60 ml) and the mixture was then stirred overnight at 50° C. Since the conversion ($^1$H-NMR) was not complete, further di-tert-butyl carbonate (2.14 g, 9.83 mmol) was added and the mixture was stirred for a further 18 h at 50° C. The mixture was concentrated I. vac. and the residue was taken up in methylene chloride (100 ml). The solution was washed with water (3×80 ml) and saturated sodium chloride solution (2×50 ml). The organic phase was dried with sodium sulfate and concentrated i. vac. The crude product (3.54 g) was purified by flash chromatography (200 g, 20×5.7 cm) with methylene chloride/methanol (98:2-95:5).

Nonpolar Diastereoisomer

Yield: 1.74 g (53%), yellowish solid $^1$H-NMR (CDCl$_3$): 1.16-1.36 (6H, m); 1.38-1.63 (6H, m); 1.51 (9H, s); 1.64-1.80 (4H, m); 2.05 (1H, m); 2.26 (6H, s); 2.40 (2H, s); 3.44 (2H, s).

Polar Diastereoisomer

Yield: 408 mg (12%), yellow oil $^1$H-NMR (CDCl$_3$): 1.10-1.85 (25H, m); 2.06 (1H, m); 2.25 (6H, s); 2.32 (2H, s); 3.54 (2H, s).

Step 9: 8-Cyclopentyl-8-dimethylamino-2-azaspiro[4.5]decan-3-one (Building Block No. 10, Non-Polar Diastereoisomer)

Trifluoroacetic acid (10 ml) was added to a solution of 8-cyclopentyl-8-dimethylamino-3-oxo-2-azaspiro[4.5]decane-2-carboxylic acid tert-butyl ester—non-polar diastereoisomer (1.74 g, 4.77 mmol) in anhydrous methylene chloride (75 ml) and the mixture was stirred overnight at room temperature. The mixture was concentrated i. vac., the residue was taken up in methylene chloride (150 ml) and the solution was washed with saturated sodium bicarbonate solution (3×50 ml). The aqueous phase was extracted with a methylene chloride/isopropanol mixture (4:1, 3×50 ml). The combined organic phases were dried with sodium sulfate and concentrated i. vac.

Building Block No. 10:

Yield: 1.08 g (86%), white solid $^1$H-NMR (CDCl$_3$): 1.16-1.82 (16H, m); 2.06 (1H, m); 2.21 (2H, s); 2.26 (6H, s); 3.10 (2H, s); 5.86 (1H, br s).

Building Block No. 11

(8-Butyl-2-azaspiro[4.5]dec-8-yl)-dimethylamine

A solution of Example no. 19 (5.00 g, 19.8 mmol) in anhydrous tetrahydrofuran (50 ml) was added to a suspension of lithium aluminium hydride (3.01 g, 79.2 mmol) in anhydrous tetrahydrofuran (50 ml) in a thoroughly heated apparatus, while cooling with ice, and the mixture was stirred for 18 h at 50° C. and then 72 h at room temperature. Water (3 ml), 15% strength sodium hydroxide solution (3 ml) and again water (9 ml) were added dropwise to the reaction mixture, while cooling with ice, and the mixture was stirred for 2 h at room temperature. The suspension was then filtered through sea sand, the residue was washed with tetrahydrofuran and the filtrate was dried with sodium sulfate and concentrated i. vac. The residue was taken up several times in methylene chloride (3×25 ml) and the solution was in each case concentrated i. vac. again.

Building Block No. 11:

Yield: 4.71 g (100%), yellow oil $^1$H-NMR (CDCl$_3$): 0.87 (3H, t, J=7.1 Hz); 1.14-1.33 (10H, m); 1.44-1.57 (8H, m); 2.13 (6H, s); 2.80 (2H, t, J=7.1 Hz); 3.65 (1H, br s).

Building Block No. 12

Step 1: 8-Cyclopentylmethyl-8-dimethylamino-2-azaspiro[4.5]decan-1-one

A solution of 8-(dimethylamino)-1-oxo-2-azaspiro[4.5]decane-8-carbonitrile (1.96 g, 8.8 mmol) in anhydrous tetrahydrofuran (40 ml) was added dropwise to a solution of cyclopentylmethylmagnesium iodide (approx. 32 mmol) under an argon atmosphere at 0° C. The reaction mixture was stirred for 18 h at room temperature and saturated ammonium chloride solution (80 ml) was then added, while cooling with ice. The phases were separated and the aqueous phase was extracted with ethyl acetate (2×30 ml). The combined organic phases were dried with sodium sulfate and concentrated i. vac. The residue (1.88 g) was purified by flash chromatography (100 g, 20×4.0 cm) with methylene chloride/methanol (95:5) and 1% ammonia (25% in water).

Yield: 519 mg (21%), white solid $^1$H-NMR (CDCl$_3$): 0.98-1.10 (2H, m); 1.10-1.17 (2H, m); 1.30-1.40 (4H, m); 1.42-1.84 (9H, m); 2.01 (2H, t, J=6.9 Hz); 2.17 (6H, s); 3.28 (2H, dd, J=13.9 and 0.8 Hz); 6.51 (1H, 5).

$^{13}$C-NMR (CDCl$_3$): 25.2; 27.2; 29.1; 32.2; 35.3; 36.1; 36.9; 38.9; 43.8; 56.2; 183.3.

Step 2: (8-Cyclopentylmethyl-2-azaspiro[4.5]dec-8-yl)dimethylamine (Building Block No. 12)

A solution of 8-cyclopentylmethyl-8-dimethylamino-2-azaspiro[4.5]decan-1-one (539 mg, 1.93 mmol) in anhydrous tetrahydrofuran (20 ml) was added dropwise to a suspension of lithium aluminium hydride (368 mg, 9.7 mmol) in anhydrous tetrahydrofuran (10 ml), while cooling with ice. The mixture was stirred for 18 h at 50° C. and thereafter water (377 µl), 1 N sodium hydroxide solution (754 µl) and again water (754 µl) were added dropwise, while cooling with ice. The suspension was stirred for 1 h at room temperature and then filtered through sodium sulfate, the residue on the filter was washed with tetrahydrofuran and the filtrate was concentrated i. vac.

Yield: 463 mg (90%), colourless oil $^1$H-NMR (CDCl$_3$): 1.00-1.12 (2H, m); 1.17-1.27 (2H, m); 1.31-1.95 (17H, m); 2.18 (6H, s); 2.64 (2H, s); 2.93 (2H, t, J=7.0 Hz). The NH signal could not be identified.

$^{13}$C-NMR (CDCl$_3$): 25.0; 29.8; 31.8; 35.1; 36.0; 36.7; 37.2; 37.4; 42.6; 46.6; 56.9; 60.7.

Building Block No. 13

8-(Dimethylamino)-8-(5-methylthiophen-2-yl)-3-azaspiro[4.5]decan-2-one (Building Block No. 13, Polar Diastereomer)

Trifluoroacetic acid (5 ml) was added to a solution of 8-(dimethylamino)-8-(5-methylthiophen-2-yl)-2-oxo-3-azaspiro[4.5]decane-3-carboxylic acid tert-butyl ester (Example no. 252, polar diastereoisomer) (900 mg, 2.3 mmol) in anhydrous methylene chloride (50 ml) and the mixture was stirred for 3 h at room temperature. The reaction mixture was concentrated i. vac., methylene chloride (30 ml) was added to the residue and the mixture was washed with saturated sodium bicarbonate solution (3×20 ml). The organic phase was dried with sodium sulfate and concentrated i. vac. The crude product (622 mg) was purified by flash chromatography (18 g, 20×2.0 cm) with methylene chloride/methanol (14:1) and 0.5% ammonia (25% in water).

Building Block No. 13 (Polar Diastereoisomer)

Yield: 502 mg (75%), white solid

Melting point: 198-201° C.

$^1$H-NMR (CDCl$_3$): 1.46-1.54 (2H, m); 1.72-1.80 (2H, m); 1.85-2.10 (4H, m); 2.11 (6H, s); 2.25 (2H, s); 2.45 (3H, d, J=1.0 Hz); 3.07 (2H, s); 5.72 (1H, br s); 6.61 (1H, d, J=3.5 Hz); 6.66-6.69 (1H, m).

$^{13}$C-NMR (CDCl$_3$): 15.2; 32.6; 32.8; 38.2; 38.9; 42.3; 53.7; 59.7; 124.5; 125.0; 137.9; 177.4.

LC-MS: m/z: [MH-HNMe$_2$]$^+$=248.3 (100%) and [M+H]$^+$=293.3 (10%), R$_t$=2.2 min.

Building Block No. 14

8-(Dimethylamino)-8-(5-methylthiophen-2-yl)-3-azaspiro[4.5]decan-2-one (Example No. 14, Non-Polar Diastereomer)

Trifluoroacetic acid (5 ml) was added to a solution of 8-(dimethylamino)-8-(5-methylthiophen-2-yl)-2-oxo-3- azaspiro[4.5]decane-3-carboxylic acid tert-butyl ester (Example no. 251, non-polar diastereoisomer) (820 mg, 2.09 mmol) in anhydrous methylene chloride (50 ml) and the mixture was stirred for 3 h at room temperature. The reaction mixture was concentrated i. vac., methylene chloride (30 ml) was added to the residue and the mixture was washed with saturated sodium bicarbonate solution (3×20 ml). The organic phase was dried with sodium sulfate and concentrated i. vac. The crude product (530 mg) was purified by flash chromatography (18 g, 20×2.0 cm) with methylene chloride/methanol (95:5) and 1% ammonia (25% in water).

Building Block No. 14 (Non-Polar Diastereoisomer)

Yield: 425 mg (70%), white solid $^1$H-NMR (CDCl$_3$): 1.46-1.56 (2H, m); 1.74-1.84 (2H, m); 1.86-2.09 (4H, m); 2.11 (6H, s); 2.115 (2H, s); 2.47 (3H, d, J=1.1 Hz); 3.22 (2H, s); 5.78 (1H, br s); 6.61 (1H, d, J=3.5 Hz); 6.67-6.69 (1H, m).

$^{13}$C-NMR (CDCl$_3$): 15.2; 32.6; 38.1; 38.8; 43.2; 52.7; 59.4; 124.5; 124.9; 137.9; 140.0; 177.4.

LC-MS: m/z: [M+H]$^+$=293.3, R$_t$=2.2 min.

Building Block No. 15

Step 1: 8-Dimethylamino-8-phenyl-2-azaspiro[4.5]decan-3-one

A suspension of 8-dimethylamino-3-oxo-2-azaspiro[4.5]decane-8-carbonitrile (536 mg, 2.4 mmol) in anhydrous tetrahydrofuran (30 ml) was added dropwise to a 2 M solution of phenylmagnesium chloride in tetrahydrofuran (3 ml, 6 mmol), cooled to 0° C., under argon and the mixture was then stirred for 18 h at room temperature. After addition of saturated ammonium chloride solution (15 ml) the phases were separated and the aqueous phase was extracted with ethyl acetate (3×30 ml). The combined organic phases were dried with sodium sulfate and concentrated i. vac.

Yield: 601 mg (92%), white solid (crude product)

Diastereoisomer mixture: Polar:non-polar ratio=1:2.

The diastereoisomer ratio was determined with the aid of the singlets of the HN—CH$_2$ group at 3.27 (polar diastereoisomer) and 3.02 ppm (non-polar diastereoisomer) in the $^1$H-NMR spectrum.

Step 2: 8-Dimethylamino-3-oxo-8-phenyl-2-azaspiro[4.5]decan-2-carboxylic acid tert-butyl ester A solution of di-tert-butyl dicarbonate (4.05 g, 18.6 mmol) in anhydrous tetrahydrofuran (30 ml) and 4-dimethylaminopyridine (206 mg, 1.69 mmol) was added to a solution of 8-dimethylamino-8-phenyl-2-azaspiro[4.5]decan-3-one (4.60 g, 16.9 mmol) in anhydrous acetonitrile (300 ml) and anhydrous tetrahydrofuran (100 ml) and the mixture was stirred for 3 d at room temperature. Since the reaction was not complete, a solution of di-tert-butyl dicarbonate (2.00 g, 9 mmol) in anhydrous acetonitrile (10 ml) was again added and the mixture was stirred for 3 h at 50° C. and 18 h at room temperature. The solvent was then removed i. vac., the residue was dissolved in methylene chloride (100 ml) and the solution was washed with water (3×50 ml) and saturated sodium chloride solution (50 ml). The organic phase was dried with sodium sulfate and concentrated i. vac. The crude product (7.00 g) was purified by flash chromatography (400 g, 20×7.5 cm) with ethyl acetate/methanol (9:1).

Non-Polar Diastereoisomer

Yield: 1.40 g (22%), white solid

Melting point: 174-176° C.

$^1$H-NMR (CDCl$_3$): 1.34-1.42 (2H, m); 1.53 (9H, 5); 1.72-1.82 (2H, m); 1.96-2.03 (2H, m); 2.04 (6H, 5); 2.10-2.24 (2H, m); 2.25 (2H, 5); 3.61 (2H, 5); 7.26-7.31 (3H, m); 7.36-7.41 (2H, m).

$^{13}$C-NMR (CDCl$_3$): 28.1; 30.0; 32.2; 34.3; 38.0; 45.8; 56.6; 60.1; 82.8; 126.8; 127.4; 127.8; 150.1; 173.4.

LC-MS: m/z: [M+H]$^+$=373.4, R$_t$=2.6 min.

Polar Diastereoisomer

Yield: 1.26 g (20%), white solid

Melting point: 176-181° C.

$^1$H-NMR (CDCl$_3$): 1.34-1.44 (2H, m); 1.48 (9H, s); 1.68-1.77 (2H, m); 1.90-2.03 (2H, m); 2.04 (6H, 5); 2.15-2.30 (2H, m); 2.48 (2H, 5); 3.36 (2H, 5); 7.28-7.32 (3H, m); 7.36-7.42 (2H, m).

$^{13}$C-NMR (CDCl$_3$): 28.0; 29.8; 32.3; 34.5; 38.0; 44.9; 57.6; 60.3; 60.5; 82.7; 126.8; 127.5; 127.8; 136.2; 150.1; 173.4.

LC-MS: m/z: [M+H]$^+$=373.4, R$_t$=3.0 min.

Step 3: 8-Dimethylamino-8-phenyl-2-azaspiro[4.5]decan-3-one (Non-Polar Diastereomer; Building Block No. 15)

Trifluoroacetic acid (5 ml) was added to a solution of 8-dimethylamino-3-oxo-8-phenyl-2-azaspiro[4.5]decane-2-carboxylic acid tert-butyl ester (non-polar diastereoisomer) (1.46 g, 3.9 mmol) in anhydrous methylene chloride (50 ml) and the mixture was stirred for 3 h at room temperature. The reaction mixture was concentrated i. vac., the residue was dissolved in methylene chloride (50 ml) and the solution was washed with saturated sodium bicarbonate solution (3×20 ml). The organic phase was dried with sodium sulfate and concentrated i. vac.

Yield: 1.03 g (96%), white solid

Melting point: >260° C.

$^1$H-NMR (CDCl$_3$): 1.37-1.46 (2H, m); 1.76-1.84 (2H, m); 1.90-2.02 (2H, br s); 2.04 (6H, s); 2.06 (2H, s); 2.15-2.27 (2H, br s); 3.27 (2H, s); 5.60 (1H, s); 7.26-7.32 (3H, m); 7.36-7.42 (2H, m).

Alkylating Agents 3-chloro-2,2-dimethylpropanenitrile

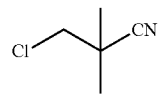

Isobutyronitrile (7 g, 101.2 mmol) was added to a LDA solution (76 mL, 2M in THF) at −78° C. The reaction mixture was stirred at −78° C. for 1 h. Then a solution of bromochloromethane (39.16 g, 303.6 mmol) was added at −78° C. and stirred for 16 h at RT. The reaction mixture was cooled to −70° C. and quenched with saturated ammonium chloride solution. The organic product was extracted with DCM (3×50 mL) and the combined organic layer was washed with brine, dried over anhydrous Na$_2$SO$_4$. Solvent was distilled under reduced pressure to give the crude compound. Purification by high vacuum distillation to collect pure fraction at 70-120° C. to give 7 g (43%) of 3-chloro-2,2-dimethylpropanenitrile as liquid.

121

3-cyano-3-methylbutyl-4-methylbenzenesulfonate

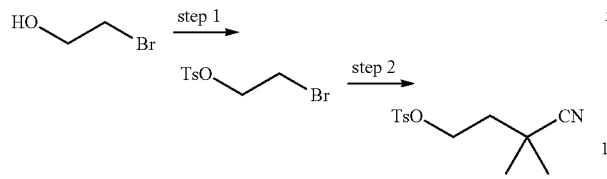

Step 1: 2-bromoethyl-4-methyl-benzene sulfonate

Pyridine (96.87 mL, 1.20 mol) was added drop-wise to p-toluenesulfonyl chloride (45.76 g, 240.05 mmol) at room temperature. To the reaction mixture was added 2-bromoethanol (30 g, 240.05 mmol) at room temperature and stirred for 2 h. The reaction mixture was cooled to 5° C. and quenched with 5N HCl. The organic product was extracted with diethyl ether (200 mL×3). The combined organic extracts were washed with water, brine, dried over anhydrous $Na_2SO_4$. Solvent was distilled under reduced pressure to give the crude compound. Purification by column chromatography over silica gel (60-120) by using 7-9% ethylacetate in pet ether as eluent to give 38 g (56%) of 2-bromoethyl-4-methyl-benzene sulfonate as liquid.

Step 2: 3-cyano-3-methylbutyl-4-methylbenzenesulfonate

Isobutyronitrile (20 g, 289.39 mmol) was added to a freshly prepared LDA solution (115.75 mL of 2.5M nBuLi was treated with 45.28 mL of disopropylamine in 1 L THF) at −78° C. The reaction mixture was stirred at −78° C. for 30 min. Then a solution of 2-bromoethyl-4-methyl-benzene sulfonate (38 g, 136.69 mmol) was added at −78° C. and stirred for 1 h. The reaction mixture was warmed to −10° C. and quenched with saturated ammonium chloride solution. The organic product was extracted with ethyl acetate (3×100 mL) and the combined organic layer was washed with brine, dried over anhydrous $Na_2SO_4$. Solvent was distilled under reduced pressure to give the crude compound. Purification by column chromatography over silica gel (100-200) by using 10% ethylacetate in pet ether as eluent to give 4.2 g (11%) of 3-cyano-3-methylbutyl-4-methylbenzenesulfonate as liquid.

tert-butyl 4-(2-((methylsulfonyl)oxy)ethyl)tetrahydro-2H-thiopyran-4-carboxylate 1,1-dioxide

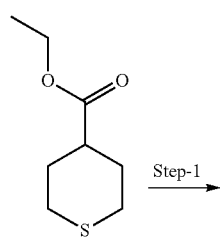

122

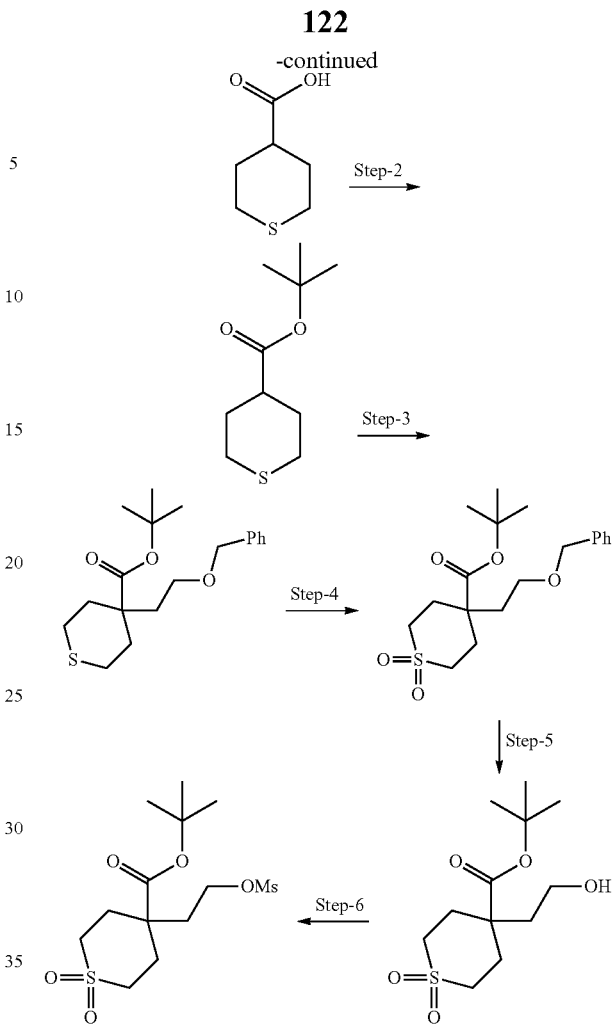

Step 1: Tetrahydro-thiopyran-4-carboxylic acid

To a stirring solution of tetrahydro-thiopyran-4-carboxylic acid ethyl ester (4.15 g, 23.8 mmol) in a mixture of tetrahydrofuran, methanol, and water (4:2:1) (168 ml) was added LiOH, $H_2O$ (3.0 g, 71.44 mmol). The reaction mixture then stirred for 16 h at room temperature. Evaporated all the solvents and the residue dissolved in water (100 ml) and washed by ether (2×50 ml). The aqueous layer then acidified by 2(N)HCl solution and then extracted by ethyl acetate (2×50 ml). The combined organic layer washed by water (2×50 ml) and brine (50 ml). The organic layer dried over anhydrous $Na_2SO_4$, concentrated in reduced pressure to afford the compound Tetrahydro-thiopyran-4-carboxylic acid (50% ethyl acetate/hexane; $R_f$-value-0.3) (3.3 g, 94.8%) as white solid.

Step 2: Tetrahydro-thiopyran-4-carboxylic acid tert-butyl ester

To a stirring solution of compound Tetrahydro-thiopyran-4-carboxylic acid (3.85 g, 26.333 mmol) in dichloromethane (75 ml) was added a solution of intermediate-1 (52.66 g, 263.33 mmol) in t-BuOH (75 ml). The reaction mixture then stirred for 24 h at room temperature. The reaction mixture was filtered through filter paper and the filtrate was diluted with ethyl acetate (250 ml). The organic layer washed by water (2×100 ml) and brine (100 ml). The organic layer dried over Na$_2$SO$_4$ to get the crude material. Crude was purified by column chromatography (100-200 mesh silica gel; 10% ethyl acetate/hexane; R$_f$-value-0.5) to afford compound Tetrahydro-thiopyran-4-carboxylic acid tert-butyl ester (4.8 g, 90.1%) as light yellow liquid.

Step 3: 4-(2-Benzyloxy-ethyl)-tetrahydro-thiopyran-4-carboxylic acid tert-butyl ester To a stirring solution of diisopropylamine (4.52 ml, 33.217 mmol) in tetrahydrofuran (100 ml) was drop wise added n-Buli (14.7 ml, 30.83 mmol) at −78° C. under argon atmosphere. The reaction mixture then stirred at 0° C. for 30 min. A solution of compound Tetrahydro-thiopyran-4-carboxylic acid tert-butyl ester (4.8 g, 23.72 mmol) in tetrahydrofuran (66 ml) was drop wise added to the reaction mixture at −78° C. and then stirred for 1 h at the same temperature. (2-Bromo-ethoxymethyl)-benzene (4.86 ml, 29.65 mmol) was then drop wise added to the reaction mixture at −78° C. and then stirred for 1 h at room temperature. The reaction mixture was quenched by addition of saturated ammonium chloride solution (50 ml). The organic layer was separated and the aqueous part then extracted by ethyl acetate (2×50 ml). The combined organic layer washed by water (2×100 ml) and brine (100 ml). The organic layer dried over anhydrous Na$_2$SO$_4$, concentrated in reduced pressure to get the crude material. Crude was purified by column chromatography (100-200 mesh silica gel; 10% ethyl acetate/hexane; R$_f$-value-0.4) to afford compound 4-(2-Benzyloxy-ethyl)-tetrahydro-thiopyran-4-carboxylic acid tert-butyl ester (5.9 g, 79.21%) as color less liquid.

Step 4: tert-butyl 4-(2-(benzyloxy)ethyl)tetrahydro-2H-thiopyran-4-carboxylate 1,1-dioxide To a stirring solution of compound 4-(2-Benzyloxy-ethyl)-tetrahydro-thiopyran-4-carboxylic acid tert-butyl ester (5.9 g, 18.789 mmol) in a mixture of tetrahydrofuran and water (3:1) (180 ml) was added oxone (46.14 g, 75.15 mmol). The reaction mixture then stirred for 2 h at room temperature. Evaporated all the solvent at reduced pressure and the residue then dissolved in water (200 ml). The aqueous part then extracted by ethyl acetate (2×200 ml). The combined organic layer washed by water (2×100 ml) and brine (100 ml). The organic layer dried over anhydrous Na$_2$SO$_4$, concentrated in reduced pressure to get the crude material which was purified by column chromatography (100-200 mesh silica gel; 40% ethyl acetate/hexane; R$_f$-value-0.4) to give tert-butyl 4-(2-(benzyloxy)ethyl)tetrahydro-2H-thiopyran-4-carboxylate 1,1-dioxide (5.8 g, 89.2%) as off white solid.

Step 5: tert-butyl 4-(2-hydroxyethyl)tetrahydro-2H-thiopyran-4-carboxylate 1,1-dioxide A solution of compound tert-butyl 4-(2-(benzyloxy)ethyl)tetrahydro-2H-thiopyran-4-carboxylate 1,1-dioxide (5.8 g, 16.76 mmol) in ethanol (290 ml) was deoxygenated well by argon gas. Pd/C (10%) (1.1 g) was then added to the reaction mixture under argon atmosphere. The reaction mixture again deoxygenated by argon and finally the reaction mixture was stirred at room temperature for 2 h under hydrogen atmosphere. The reaction mixture then filtered through celite bed and washed by ethanol (100 ml). The filtrate then concentrated in reduced pressure to get the compound tert-butyl 4-(2-hydroxyethyl)tetrahydro-2H-thiopyran-4-carboxylate 1,1-dioxide (60% ethyl acetate/hexane; R$_f$-value-0.4) (4.4 g, 94.43%) as off white solid.

Step 6: tert-butyl 4-(2-((methylsulfonyl)oxy)ethyl)tetrahydro-2H-thiopyran-4-carboxylate 1,1-dioxide To a stirring solution of compound tert-butyl 4-(2-hydroxyethyl)tetrahydro-2H-thiopyran-4-carboxylate 1,1-dioxide (4.4 g, 15.82 mmol) in dichloromethane (110 ml) was added triethyl amine (4.3 ml, 31.46 mmol). Methanesulfonylchloride (1.48 ml, 18.99 mmol) was then added to the reaction mixture drop wise at 0° C. The reaction mixture then stirred for 2 h at 0° C. The reaction mixture was diluted with dichloromethane (100 ml), washed by water (2×50 ml) and brine (50 ml). The organic layer dried over Na$_2$SO$_4$ to get the crude material. Crude was purified by column chromatography (230-400 mesh silica gel; 50% ethyl acetate/hexane; R-value-0.5) to afford compound tert-butyl 4-(2-((methylsulfonyl)oxy)ethyl)tetrahydro-2H-thiopyran-4-carboxylate 1,1-dioxide (4.5 g, 79.9%) as white solid.

tert-butyl 4-(2-((methylsulfonyl)oxy)ethyl)tetrahydro-2H-pyran-4-carboxylate

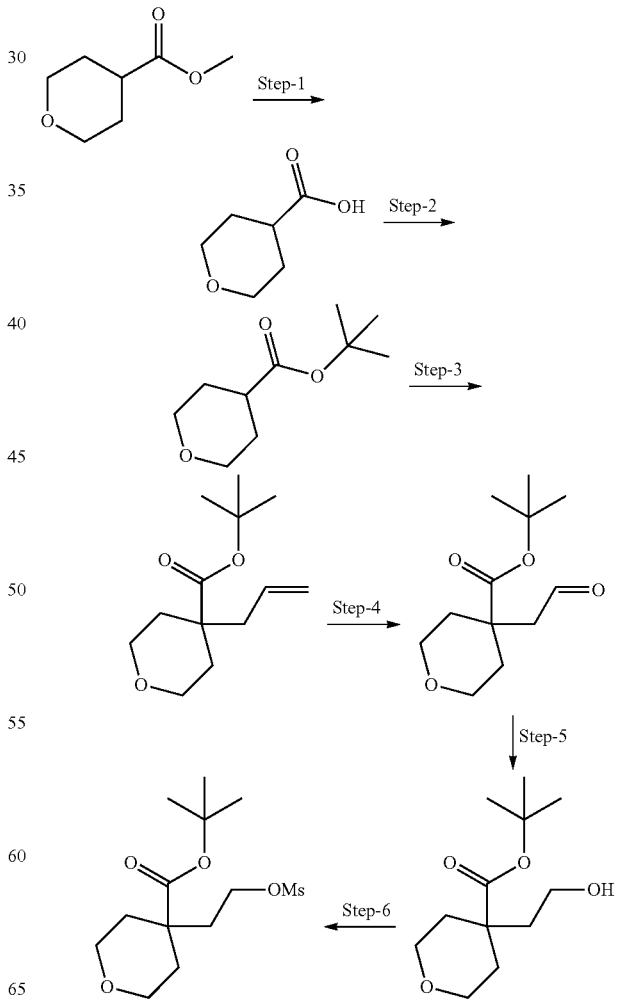

Step 1: Tetrahydro-pyran-4-carboxylic acid

To a stirring solution of tetrahydro-pyran-4-carboxylic acid methyl ester (2 g, 13.87 mmol) in a mixture of tetrahydrofura, methanol, and water (4:2:1) (70 ml) was added LiOH, $H_2O$ (1.74 g, 41.61 mmol). The reaction mixture was then stirred for 16 h at room temperature. Evaporated all the solvents and the residue dissolved in water (50 ml) and washed by ether (2×30 ml). The aqueous layer then acidified by 2(N) HCl solution and then extracted by ethyl acetate (2×50 ml). The combined organic layer washed by water (2×50 ml) and brine (50 ml). The organic layer dried over anhydrous $Na_2SO_4$, concentrated in reduced pressure to afford the compound Tetrahydro-pyran-4-carboxylic acid (50% ethyl acetate/hexane; $R_f$-value-0.3) (4.5 g, 49.9%) as white solid.

Step 2: Tetrahydro-pyran-4-carboxylic acid tert-butyl ester

To a stirring solution of compound Tetrahydro-pyran-4-carboxylic acid (0.46 g, 4.36 mmol) in dichloromethane (10 ml) was added a solution of intermediate-1 (7.07 g, 35.38 mmol) in t-BuOH (10 ml). The reaction mixture then stirred for 24 h at room temperature. The reaction mixture was filtered through filter paper and the filtrate was diluted with ethyl acetate (50 ml). The organic layer washed by water (2×30 ml) and brine (30 ml). The organic layer dried over $Na_2SO_4$ to get the crude material. Crude was purified by column chromatography (100-200 mesh silica gel; 10% ethyl acetate/hexane; $R_f$-value-0.5) to afford compound Tetrahydro-pyran-4-carboxylic acid tert-butyl ester (0.47 g, 71.32%) as light yellow liquid.

Step 3: 4-Allyl-tetrahydro-pyran-4-carboxylic acid tert-butyl ester

To a stirring solution of diisopropylamine (2.2 ml, 16.107 mmol) in tetrahydrofuran (45 ml) was drop wise added n-BuLi (7.36 ml, 15.456 mmol) at −78° C. under argon atmosphere. The reaction mixture was then stirred at 0° C. for 30 min. A solution of compound Tetrahydro-pyran-4-carboxylic acid tert-butyl ester (2.4 g, 12.88 mmol) in tetrahydrofuran (25 ml) was drop wise added to the reaction mixture at −78° C. and then stirred for 1 h at the same temperature. A solution of allyl bromide (2.18 g, 18.032 mmol) in tetrahydrofuran (25 ml) was drop wise added to the reaction mixture at −78° C. and then stirred for 1 h at room temperature. The reaction mixture was quenched by addition of saturated ammonium chloride solution (50 ml). The organic layer was separated and the aqueous part then extracted by ethyl acetate (2×50 ml). The combined organic layer washed by water (2×50 ml) and brine (50 ml). The organic layer dried over anhydrous $Na_2SO_4$, concentrated in reduced pressure to get the crude material. Crude was purified by column chromatography (100-200 mesh silica gel; 10% ethyl acetate/hexane; $R_f$-value-0.5) to afford compound 4-Allyl-tetrahydro-pyran-4-carboxylic acid tert-butyl ester (2.6 g, 89.3%) as light yellow liquid.

Step 4: 4-(2-Oxo-ethyl)-tetrahydro-pyran-4-carboxylic acid tert-butyl ester

To a stirring solution of compound 4-Allyl-tetrahydro-pyran-4-carboxylic acid tert-butyl ester (3.0 g, 13.274 mmol) in acetone (75 ml) and water (75 ml) was added potassium osmate dehydrate (0.166 gm, 0.4513 mmol). The reaction mixture was then cooled at 0° C. and sodium iodate (11.35 gm, 53.096 mmol) was added four times in 15 min interval. It was allowed for stir for 2 h. Acetone was distilled off under reduced pressure and the aqueous layer was extracted with dichloromethane (2×100 ml). The combined organic layer washed by water (2×50 ml) and brine (50 ml). The organic layer dried over anhydrous $Na_2SO_4$, concentrated in reduced pressure to get the compound 4-(2-Oxo-ethyl)-tetrahydro-pyran-4-carboxylic acid tert-butyl ester (10% ethyl acetate/hexane; $R_f$-value-0.4) (2.9 g, 95.8%) as light yellow liquid.

Step 5: 4-(2-Hydroxy-ethyl)-tetrahydro-pyran-4-carboxylic acid tert-butyl ester To a cold stirring solution of compound 4-(2-Oxo-ethyl)-tetrahydro-pyran-4-carboxylic acid tert-butyl ester (2.6 gm, 11.4 mmol) in methanol (20 ml) was portion wise added $NaHB_4$ (0.433 mmol, 11.4 mmol). The reaction mixture then stirred for 1 h at 0° C. The reaction mixture was quenched by addition of ice (10 g). The reaction mixture then concentrated in rotavapour and the residue dissolved in ethyl acetate (100 ml), washed by water (2×50 ml) and brine (50 ml). The organic layer dried over $Na_2SO_4$ to get the crude material. Crude was purified by column chromatography (230-400 mesh silica gel; 50% ethyl acetate/hexane; $R_f$-value-0.4) to afford compound 4-(2-Hydroxy-ethyl)-tetrahydro-pyran-4-carboxylic acid tert-butyl ester (1.3 g, 49.5%) as white solid.

Step 6: 4-(2-Methanesulfonyloxy-ethyl)-tetrahydro-pyran-4-carboxylic acid tert-butyl ester To a stirring solution of compound 4-(2-Hydroxy-ethyl)-tetrahydro-pyran-4-carboxylic acid tert-butyl ester (2.4 g, 10.42 mmol) in dichloromethane (55 ml) was added triethyl amine (2.84 ml, 20.48 mmol). Methanesulfonylchloride (1.43 g, 12.5 mmol) was then added to the reaction mixture drop wise at 0° C. The reaction mixture then stirred for 2 h at 0° C. The reaction mixture was diluted with dichloromethane (100 ml), washed by water (2×50 ml) and brine (50 ml). The organic layer dried over $Na_2SO_4$ to get the crude material. Crude was purified by column chromatography (230-400 mesh silica gel; 50% ethyl acetate/hexane; $R_f$-value-0.5) to afford compound 4-(2-Methanesulfonyloxy-ethyl)-tetrahydro-pyran-4-carboxylic acid tert-butyl ester (2.4 g, 74.78%) as white solid.

Example No. 1

(E)-1-[8-Benzyl-8-(dimethylamino)-3-azaspiro[4.5]decan-3-yl]-3-phenylprop-2-en-1-one Cinnamyl chloride (170 mg, 1.02 mmol) was added to a solution of (8-benzyl-3-azaspiro[4.5]decan-8-yl)-dimethylamine (polar diastereomer) (233 mg, 0.85 mmol) and triethylamine (128 mg, 176 µl, 1.3 mmol) in anhydrous methylene chloride (5 ml) and the mixture was stirred for 2 h at room temperature. The reaction mixture was diluted with methylene chloride (20 ml) and washed with 25% strength potassium carbonate solution (2×10 ml). The organic phase was dried with sodium sulfate and concentrated i. vac. The crude product (407 mg) was purified by flash chromatography on PharmPrep (40-63 µm, 18 g, 20×2.0 cm) with methylene chloride/methanol (50:1).

Example No. 1 (Polar Diastereoisomer)

Yield: 255 mg (74%), white solid
Melting point: 145-150° C.
$^1$H-NMR (CDCl$_3$): 1.10-1.29 (m, 3H); 1.57-1.80 (m, 7H); 2.30 and 2.31 (2 s, 6H); 2.62 and 2.65 (2s, 2H); 3.14 and 3.19 (2s, 2H); 3.57 (t, 1H, J=7.3 Hz); 3.62 (t, 1H, J=7.2 Hz); 6.50 and 6.68 (2 d, 1H, J=15.5 Hz); 7.05-7.55 (m, 10H); 7.61 and 7.65 (2 d, 1H, J=9.0 Hz).
$^{13}$C-NMR (CDCl$_3$): 29.6; 29.7; 29.8; 29.9; 36.9; 37.0; 37.1; 37.7; 39.7; 40.0; 42.2; 44.2; 44.9; 54.4; 54.8; 57.7; 118.6; 118.8; 125.7; 126.0; 127.8; 127.9; 128.0; 128.69; 128.72; 129.5; 130.5; 130.7; 135.4; 138.8; 139.2; 141.4; 141.6; 164.8; 164.9.
The NMR spectra show sometimes doubled signal sets (rotamers).
LC-MS: m/z: [M+H]$^+$=403.4, $R_f$=3.1 min.

Example No. 2

(E)-1-[8-Benzyl-8-(dimethylamino)-3-azaspiro[4.5]decan-3-yl]-3-phenylprop-2-en-1-one Cinnamyl chloride (120 mg, 0.72 mmol) was added to a solution of (8-benzyl-3-azaspiro[4.5]decan-8-yl)-dimethylamine (non-polar diastereomer) (165 mg, 0.6 mmol) and triethylamine (92 mg, 126 µl, 0.9 mmol) in anhydrous methylene chloride (5 ml) and the mixture was stirred for 2 h at room temperature. The reaction mixture was diluted with methylene chloride (20 ml) and washed with 25% strength potassium carbonate solution (2×10 ml). The organic phase was dried with sodium sulfate and concentrated i. vac. The crude product (253 mg) was purified by flash chromatography (10 g, 20×1.5 cm) with methylene chloride/methanol (30:1) and 1% ammonia (25% in water).

Example No. 2 (Non-Polar Diastereoisomer)

Yield: 208 mg (86%), colourless oil
$^1$H-NMR (CDCl$_3$): 1.15-1.28 (m, 4H); 1.47 and 1.56 (2 t, 2H, J=7.2 Hz); 1.65-1.90 (m, 4H); 2.30 (s, 6H); 2.64 (s, 2H); 3.30 and 3.35 (2 s, 2H); 3.53 and 3.56 (2 t 2H, J=7.1 Hz); 6.65 and 6.69 (2 d, 1H, J=6.2 Hz); 7.10-7.15 (m, 2H); 7.17-7.38 (m, 6H); 7.48-7.52 (m, 2H); 7.64 and 7.68 (2 d, 1H, J=7.0 Hz).
$^{13}$C-NMR (CDCl$_3$): 29.0; 29.1; 29.5; 29.6; 32.0; 33.6; 36.5; 36.6; 37.0; 39.9; 42.0; 44.8; 45.3; 57.6; 58.8; 59.9; 118.5; 118.9; 125.6; 125.7; 127.7; 127.75; 127.8; 128.7; 129.4; 130.6; 130.65; 135.4; 139.0; 139.3; 141.3; 141.5; 164.6; 164.7.
The NMR spectra show sometimes doubled signal sets (rotamers).
LC-MS: m/z: [M+H]$^+$=403.4, $R_f$=3.2 min.

Example No. 3

(3,8-Dibenzyl-3-azaspiro[4.5]decan-8-yl)-dimethylamine (Example No. 3, Non-Polar Diastereomer)

Benzaldehyde (117 mg, 111 µl, 1.1 mmol) and glacial acetic acid (500 µl) were added to a solution of (8-benzyl-3-azaspiro[4.5]decan-8-yl)-dimethylamine (non-polar diastereomer) (178 mg, 0.65 mmol) in methanol (5 ml) and the mixture was stirred for 2 h at room temperature. After addition of sodium cyanoborohydride (173 mg, 2.7 mmol) the mixture was stirred for 24 h at room temperature. The reaction mixture was then diluted with methylene chloride (20 ml), saturated sodium bicarbonate solution (25 ml) was added and the phases were separated. The aqueous phase was extracted with methylene chloride (3×20 ml). The combined organic phases were dried with sodium sulfate and concentrated i. vac. The crude product (231 mg) was purified by flash chromatography (10 g, 20×1.5 cm) with methylene chloride/methanol (95:5) and 1% ammonia (25% in water).

Example No. 3 (Non-Polar Diastereoisomer)

Yield: 163 mg (69%), white solid
Melting point: cannot be determined
$^1$H-NMR (CDCl$_3$): 1.14-1.28 (m, 4H); 1.33 (t, 2H, J=6.9 Hz); 1.58-1.70 (m, 4H); 2.27 (s, 8H); 2.47 (t, 2H, J=6.9 Hz); 2.61 (s, 2H); 3.51 (s, 2H); 7.10-7.29 (m, 10H).
$^{13}$C-NMR (CDCl$_3$): 29.5; 32.8; 35.2; 36.8; 37.1; 40.9; 54.1; 57.6; 60.7; 68.6; 125.5; 126.6; 127.7; 128.0; 128.6; 130.7; 139.5.
LC-MS: m/z: [M+H]$^+$=363.4, $R_f$=2.1 min.

Example No. 4

(E)-1-(8-Dimethylamino-8-thiophen-2-yl-3-azaspiro[4.5]decan-3-yl)-3-phenylprop-2-en-1-one (Example No. 4, Polar Diastereomer)

Cinnamyl chloride (90 mg, 0.54 mmol) was added to a solution of dimethyl-(8-thiophen-2-yl-3-azaspiro[4.5]decan-8-yl)-amine (polar diastereomer) (120 mg, 0.45 mmol) and triethylamine (68 mg, 93 µl, 0.68 mmol) in methylene chloride (5 ml) and the mixture was stirred for 1.5 h at room temperature. 1 M potassium carbonate solution (5 ml) was then added to the reaction mixture and the mixture was stirred for 15 min. The phases were separated and the aqueous phase was subsequently extracted with methylene chloride (2×5 ml). The combined organic phases were dried with sodium sulfate and concentrated i. vac. The residue (246 mg) was purified by flash chromatography (35 g, 24×2 cm) with methylene chloride/methanol (95:5).

Example No. 4 (Polar Diastereomer)

Yield: 143 mg (80%), yellow solid.
Melting point: 127-129° C.
$^1$H-NMR (DMSO-d$_6$): 1.28-1.38 (m, 2H); 1.59-1.78 (m, 4H); 2.01 (s, 10H); 3.29 (s, 1H); 3.44 (t, 1H, J=7.2 Hz); 3.55 (s, 1H); 3.69 (t, 1H, J=7.01 Hz); 6.92-7.00 (m, 2H); 7.03-7.12 (m, 2H); 7.34-7.51 (m, 4H); 7.65-7.76 (m, 2H).
$^{13}$C-NMR (CDCl$_3$): 31.2; 32.9; 33.5; 35.6; 38.1; 40.1; 42.1; 44.4; 45.0; 56.3; 59.9; 118.4; 118.6; 123.4; 123.7; 124.9; 125.2; 126.2; 126.4; 127.8; 127.9; 128.8; 129.5; 129.6; 135.3; 135.4; 141.8; 164.8; 165.0. Some C signals are doubled due to the amide structure.
LC-MS: [MH-HNMe$_2$]$^+$: m/z=350.2 (100%) and [M+H]$^+$: m/z=395.3 (10%), $R_f$=3.1 min.

Example No. 5

(E)-1-(8-Dimethylamino-8-thiophen-2-yl-3-azaspiro[4.5]decan-3-yl)-3-phenylprop-2-en-1-one (Example No. 5, Non-Polar Diastereomer)

Cinnamyl chloride (98 mg, 0.59 mmol) was added to a solution of dimethyl-(8-thiophen-2-yl-3-azaspiro[4.5]decan-8-yl)-amine (non-polar diastereomer) (130 mg, 0.49 mmol) and triethylamine (75 mg, 103 µl, 0.74 mmol) in methylene chloride (5 ml) and the mixture was stirred for 1 h at room temperature. Potassium carbonate solution (5 ml) was then added to the mixture and the mixture was stirred for 15 min. The phases were then separated and the aqueous phase was subsequently extracted with methylene chloride (3×5 ml). The combined organic phases were dried with sodium sulfate and concentrated i. vac. The crude product (200 mg) was purified by means of flash chromatography (18 g, 20×2.0 cm) with methylene chloride/methanol (95:5). Since the production obtained (125 mg) still contained impurities, the residue was taken up in ethyl acetate (20 ml) and the mixture was acidified with formic acid and extracted with water (3×10 ml). The acid aqueous phase was rendered alkaline with 1 M potassium carbonate solution and extracted with ethyl acetate (3×10 ml). The combined organic phases of the alkaline extraction were dried with sodium sulfate and concentrated i. vac.

Example No. 5 (Non-Polar Diastereoisomer)

Yield: 109 mg (57%), colourless oil
$^1$H-NMR (CDCl$_3$): 1.42-1.51 (m, 2H); 1.68-1.79 (m, 2H); 1.82 (t, 1H, J=7.2 Hz); 1.91 (t, 1H, J=7.2 Hz); 2.05-2.11 (m, 4H); 2.12 (s, 6H); 3.336 and 3.375 (2 s, 2H); 3.65 (t, 1H, J=7.3 Hz); 3.70 (t, 1H, J=7.3 Hz); 6.63 (d, 0.5H, J=15.5 Hz); 6.72 (d, 0.5H, J=15.5 Hz); 6.85 (dd, 0.5H, J=1.1, 3.6 Hz); 6.87 (dd, 0.5H, J=1.1, 3.6 Hz); 7.04 (dt, 1H, J=3.6, 5.2 Hz); 7.24 (ddd, 1H, J=1.1, 5.1, 6.1 Hz); 7.30-7.39 (m, 3H); 7.46-7.54 (m, 2H); 7.66 (d, 0.5H, J=15.5 Hz); 7.68 (d, 0.5H, J=15.5 Hz).
$^{13}$C-NMR (CDCl$_3$): 30.9; 31.0; 33.1; 38.1; 38.1; 40.1; 42.3; 44.6; 45.2; 53.4; 56.4; 57.5; 59.8; 118.5; 123.5; 124.9; 126.3; 127.8; 128.7; 129.5; 130.9; 135.3; 141.7; 164.9.
The NMR spectra show sometimes doubled signal sets (rotamers).
LC-MS: m/z: [MH-HNMe$_2$]$^+$=350.2 (100%) and [M+H]$^+$=395.3 (25%), R$_t$=3.04 min.

Example No. 6

8-Dimethylamino-N-ethyl-8-thiophen-2-yl-3-azaspiro[4.5]decane-3-carboxylic acid amide (Example No. 6, Polar Diastereomer)

Ethyl isocyanate (55 mg, 61 µl, 0.77 mmol) was added to a solution of dimethyl-(8-thiophen-2-yl-3-azaspiro[4.5]decan-8-yl)-amine (polar diastereomer) (130 mg, 0.49 mmol) in tetrahydrofuran (5 ml) and the mixture was stirred for 2 h at room temperature. 1 M potassium carbonate solution (1 ml) was then added to the reaction mixture and the mixture was stirred for 30 min and then concentrated i. vac. The residue was partitioned between ethyl acetate and potassium carbonate solution and the aqueous phase was extracted with ethyl acetate (3×15 ml). The combined organic phases were dried with sodium sulfate and concentrated i. vac. The crude product was purified by means of flash chromatography (10 g, 20×1.5 cm) with methylene chloride/methanol (9:1).

Example No. 6 (Polar Diastereomer)

Yield: 150 mg (91%), colourless oil
$^1$H-NMR (CDCl$_3$): 1.12 (t, 3H, J=7.3 Hz); 1.38 (ddd, 2H, J=3.5, 10.3, 13.6 Hz); 1.62 (t, 2H, J=7.1 Hz); 1.64-1.72 (m, 2H); 1.86-1.96 (m, 2H); 2.08 (s, 6H); 2.11-2.19 (m, 2H); 3.18 (br s, 2H); 3.23 (dd, 1H, J=5.6, 7.0 Hz); 3.27 (dd, 1H, J=5.5, 7.2 Hz); 3.35 (t, 2H, J=7.1 Hz); 4.11 (t, 1H, J=5.0 Hz); 6.84 (d, 1H, J=3.6 Hz); 7.02 (dd, 1H, J=3.6, 5.1 Hz); 7.22 (d, 1H, J=5.1 Hz).
$^{13}$C-NMR (CDCl$_3$): 15.7; 31.3; 33.2; 35.3; 36.7; 38.1; 41.6; 43.9; 55.1; 59.9; 123.4; 125.0; 126.2; 142.7; 156.9.
LC-MS: m/z: [MH-HNMe$_2$]$^+$=291.2 (100%) and [M+H]$^+$=336.3 (50%), R$_t$=2.5 min.

Example No. 7

(3-Benzyl-8-thiophen-2-yl-3-azaspiro[4.5]decan-8-yl)-dimethylamine (Example No. 7, Polar Diastereomer)

Benzaldehyde (79 mg, 75 µl, 0.74 mmol) and sodium cyanoborohydride (161 mg, 2.57 mmol) were added to a cloudy solution of dimethyl-(8-thiophen-2-yl-3-azaspiro [4.5]decan-8-yl)-amine (polar diastereomer) (150 mg, 0.57 mmol) in methanol (5 ml) and the mixture was stirred for 30 min at room temperature. After addition of acetic acid (0.57 ml) the mixture was stirred for a further 2 h at room temperature. The reaction mixture was then diluted with sodium bicarbonate solution (25 ml) and extracted with a mixture of methylene chloride/2-propanol (4:1, 3×20 ml). The combined organic phases were dried with sodium sulfate and concentrated i. vac. The crude product (209 mg) was purified by means of flash chromatography (20 g, 20×2.0 cm) with methanol and 0.1% ammonia (25% in H$_2$O).

Example No. 7 (Polar Diastereomer)

Yield: 153 mg (76%), white solid
Melting point: 59-60° C.
$^1$H-NMR (CDCl$_3$): 1.39 (ddd, 2H, J=3.2; 10.1 and 13.1 Hz); 1.52 (t, 2H, J=6.8 Hz); 1.65-1.75 (m, 2H); 1.78-1.94 (m, 2H); 2.08 (s, 6H); 2.08-2.16 (m, 2H); 2.40 (s, 2H); 2.55 (t, 2H, J=6.9 Hz); 3.57 (s, 2H); 6.84 (dd, 1H, J=1.0 and 3.5 Hz); 7.03 (dd, 1H, J=3.6 and 5.1 Hz); 7.20-7.32 (m, 6H).
$^{13}$C-NMR (CDCl$_3$): 33.8; 34.4; 38.1; 41.1; 53.7; 59.7; 60.8; 65.4 (br.); 123.1; 124.9; 126.1; 126.7; 128.2; 128.7; 139.5. A thienyl-C signal (approx. 143 ppm) could not be identified.
LC-MS: [MH-HNMe$_2$]±: m/z=310.3 (100%) and [M+H]$^+$: m/z=355.3 (8%), R$_t$=1.0 min.

Example No. 8

Dimethyl-[3-(pyridin-4-yl-methyl)-8-thiophen-2-yl-3-azaspiro[4.5]decan-8-yl]-amine (Example No. 8, Polar Diastereomer)

Pyridine-4-carbaldehyde (133 mg, 117 µl, 1.24 mmol) and sodium cyanoborohydride (270 mg, 4.3 mmol) were added to a cloudy solution of dimethyl-(8-thiophen-2-yl-3-azaspiro [4.5]decan-8-yl)-amine (polar diastereomer) (250 mg, 0.95 mmol) in methanol (9 ml) and the mixture was stirred for 30 min at room temperature. After addition of acetic acid (0.95 ml) the mixture was stirred for a further 3 h at room temperature. Pyridine-4-carbaldehyde (66 mg, 58 µl, 0.61 mmol) was again added to the reaction solution and the mixture was stirred for 1 h at room temperature. The reaction mixture was then diluted with sodium bicarbonate solution (30 ml) and extracted with methylene chloride/2-propanol (4:1, 3×30 ml). The combined organic phases were dried with sodium sulfate and concentrated i. vac. The crude product (480 mg) was purified by means of flash chromatography (45 g, 10×3.5 cm) with methanol and 0.2% ammonia (25% in H$_2$O).

Example No. 8 (Polar Diastereomer)

Yield: 155 mg (46%), yellow oil
$^1$H-NMR (CDCl$_3$): 1.40 (ddd, 2H, J=3.4; 10.0 and 13.3 Hz); 1.53 (t, 2H, J=6.9 Hz); 1.67-1.75 (m, 2H); 1.79-1.96 (m, 2H); 2.07 (s, 6H); 2.06-2.11 (m, 2H); 2.40 (s, 2H); 2.55 (t, 2H, J=6.9 Hz); 3.56 (s, 2H); 6.84 (dd, 1H, J=1.1 and 3.6 Hz); 7.03 (dd, 1H, J=3.5 and 5.1 Hz); 7.22 (dd, 1H, J=1.0 and 5.1 Hz); 7.24-7.26 (m, 2H); 8.52 (dd, 2H, J=1.6 and 4.4 Hz).
$^{13}$C-NMR (CDCl$_3$): 33.7; 34.2; 38.1 (2C); 41.2; 53.7; 59.4; 59.6; 65.5; 123.2; 123.5 (2C); 124.9; 126.1; 148.7; 149.7. A thienyl-C signal (approx. 143 ppm) could not be identified.
LC-MS: [MH-HNMe$_2$]$^+$: m/z=276.3 (100%) and [M+H]$^+$: m/z=321.3 (16%), R$_t$=0.3 min.

Example No. 9

8-Benzyl-8-(dimethylamino)-N-ethyl-3-azaspiro [4.5]decane-3-carboxylic acid amide (Example No. 9, Non-Polar Diastereomer)

Ethyl isocyanate (67 mg, 75 µl, 0.95 mmol) was added to a solution of (8-benzyl-3-azaspiro[4.5]decan-8-yl)-dimethylamine (non-polar diastereomer) (166 mg, 0.61 mmol) in anhydrous tetrahydrofuran (5 ml) and the mixture was stirred at room temperature overnight. After addition of methylene chloride (20 ml) the solution was washed with 25% strength potassium carbonate solution (2×15 ml). The organic phase was dried with sodium sulfate and concentrated i. vac. The crude product (200 mg) was purified by flash chromatography (10 g, 20×1.5 cm) with methylene chloride/methanol (95:5) and 1% ammonia (25% in water).

Example No. 9 (Non-Polar Diastereoisomer)

Yield: 167 mg (80%), white solid
Melting point: 45-47° C.
$^1$H-NMR (CDCl$_3$): 1.11 (t, 3H, J=7.1 Hz); 1.15-1.26 (m, 4H); 1.44 (t, 2H, J=7.1 Hz); 1.62-1.80 (m, 4H); 2.28 (s, 6H); 2.62 (s, 2H); 3.02 (s, 2H); 3.19-3.29 (m, 4H); 4.01 (br s, 1H); 6.99-7.28 (m, 5H).
$^{13}$C-NMR (CDCl$_3$): 15.8; 29.1; 29.7; 33.2; 35.3; 36.6; 37.0; 41.5; 44.3; 57.6; 58.6; 125.7; 127.8; 130.6; 139.2; 156.9.
LC-MS: m/z: [M+H]$^+$=344.4, R$_t$=2.6 min.

Example No. 10

(8-Benzyl-3-(pyridin-4-ylmethyl)-3-azaspiro[4.5] decan-8-yl)-dimethylamine (Example No. 10, Non-Polar Diastereomer)

4-Pyridinecarbaldehyde (117 mg, 104 µl, 1.1 mmol) and glacial acetic acid (500 µl) were added to a solution of (8-benzyl-3-azaspiro[4.5]decan-8-yl)-dimethylamine (non-polar diastereomer) (174 mg, 0.64 mmol) in methanol (5 ml) and the mixture was stirred for 2 h at room temperature. After addition of sodium cyanoborohydride (173 mg, 2.7 mmol) the mixture was stirred for 20 h at room temperature. After addition of saturated sodium bicarbonate solution (25 ml) the mixture was extracted with methylene chloride (3×20 ml). The organic phase was dried with sodium sulfate and concentrated i. vac. The crude product (197 mg) was purified by flash chromatography (10 g, 20×1.5 cm) with methylene chloride/methanol (95:5) and 1% ammonia (25% in water).

Example No. 10 (Non-Polar Diastereoisomer)

Yield: 75 mg (30%), colourless oil
$^1$H-NMR (CDCl$_3$): 1.01-1.28 (m, 4H); 1.34 (t, 2H, J=6.9 Hz); 1.59-1.72 (m, 4H); 2.72 (5, 2H); 2.78 (5, 6H); 2.47 (t, 2H, J=6.9 Hz); 2.61 (5, 2H); 3.50 (5, 2H); 7.10-7.13 (m, 2H); 7.15-7.25 (m, 5H); 8.48-8.50 (m, 2H).
$^{13}$C-NMR (CDCl$_3$): 29.4; 32.7; 35.1; 36.8; 37.1; 41.1; 54.1; 57.6; 59.4; 68.7; 123.5; 125.6; 127.7; 130.7; 139.5; 148.8; 149.6.
LC-MS: m/z: [M+H]$^+$=364.4, R$_t$=0.4 min.

Example No. 11

Step 1: N,N-Dimethyl-8-phenyl-3-azaspiro[4.5]decan-8-amine

A solution of 8-(dimethylamino)-8-phenyl-3-azaspiro [4.5]decan-2-one (non-polar diastereomer) (345 mg, 1.28 mmol) in anhydrous tetrahydrofuran (50 ml) was added to a suspension of lithium aluminium hydride (245 mg, 6.4 mmol) in anhydrous tetrahydrofuran (10 ml), while cooling with ice, and the mixture was then stirred overnight at 60° C. Water (200 µl), 1 N sodium hydroxide solution (500 µl) and again water (500 µl) were added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Yield: 329 mg (99%), oil
$^1$H-NMR (CDCl$_3$): 1.23-1.32 (m, 2H); 1.53-1.62 (m, 2H), 1.65 (t, 2H, J=7.0 Hz); 1.77 (br s, 2H); 1.87-1.96 (m, 2H); 2.04 (s, 6H); 2.23-2.35 (m, 1H); 2.52 (s, 2H); 2.94 (t, 2H, J=7.0 Hz); 7.27-7.33 (m, 3H); 7.34-7.40 (m, 2H).

Step 2: (E)-1-[8-(Dimethylamino)-8-phenyl-3-azaspiro[4.5]decan-3-yl]-3-phenylprop-2-en-1-one (Example No. 11, Non-Polar Diastereomer)

Triethylamine (94 mg, 129 µl, 0.93 mmol) and cinnamyl chloride (123 mg, 0.74 mmol) were added to a solution of N,N-dimethyl-8-phenyl-3-azaspiro[4.5]decan-8-amine (non-polar diastereomer) (160 mg, 0.62 mmol) in anhydrous methylene chloride (5 ml) and the mixture was stirred for 3 h at room temperature. After addition of methylene chloride (20 ml) the solution was washed with 25% strength potassium carbonate solution (2×20 ml) and the organic phase was dried with sodium sulfate and concentrated i. vac. The crude product (247 mg) was purified by flash chromatography (10 g, 20×1.5 cm) with methylene chloride/methanol (95:5) and 1% ammonia (25% in water).

Example No. 11 (Non-Polar Diastereoisomer)

Yield: 146 mg (60%), oil
$^1$H-NMR (CDCl$_3$): 1.34-1.44 (m, 2H); 1.64-1.76 (m, 2H); 1.86 and 1.95 (2 t, 2H, J=7.2 Hz); 2.05 (s, 6H); 2.06-2.28 (m, 4H); 3.30 and 3.31 (2 s, 2H); 3.66 and 3.72 (2 t, 2H, J=7.2 Hz); 6.60 and 6.72 (2 d, 1H, J=15.5 Hz); 7.24-7.41 (m, 8H); 7.46-7.54 (m, 2H); 7.64 and 7.68 (2 d, 1H, J=9.9 Hz).

$^{13}$C-NMR (CDCl$_3$): 30.4; 30.5; 31.1; 31.2; 34.2; 38.1; 40.3; 42.5; 44.6; 45.2; 56.7; 57.9; 60.6; 118.4; 118.7; 126.6; 127.4; 127.5; 127.6; 127.7; 127.8; 128.68; 128.74; 129.4; 129.5; 135.3; 135.4; 136.7; 141.6; 141.7; 164.8.

The NMR spectra show sometimes doubled signal sets (rotamers).

LC-MS: m/z: [M+H]$^+$=389.4, R$_t$=3.1 min.

Example No. 12

Step 1: N,N-Dimethyl-8-phenyl-3-azaspiro[4.5]decan-8-amine

A solution of 8-(dimethylamino)-8-phenyl-3-azaspiro[4.5]decan-2-one (non-polar diastereomer) (413 mg, 1.5 mmol) in anhydrous tetrahydrofuran (70 ml) was added to a suspension of lithium aluminium hydride (285 mg, 7.5 mmol) in anhydrous tetrahydrofuran (10 ml), while cooling with ice, and the mixture was then stirred at 60° C. overnight. Water (200 µl), 1 N sodium hydroxide solution (500 µl) and again water (500 µl) were added to the mixture, while cooling with ice, and the mixture was stirred for 1 h at room temperature. The suspension was filtered through sea sand and the residue was washed with tetrahydrofuran. The filtrate was dried with sodium sulfate and concentrated i. vac.

Yield: 374 mg (96%), oil $^1$H-NMR (CDCl$_3$): 1.23-1.35 (m, 2H); 1.39 (t, 2H, J=7.1 Hz); 1.56-1.67 (m, 2H); 1.78-1.95 (m, 4H); 2.03 (s, 6H); 2.17-2.33 (m, 1H); 2.79 (s, 2H); 2.88 (t, 2H, J=7.1 Hz); 7.24-7.33 (m, 3H); 7.34-7.40 (m, 2H).

Step 2: (E)-1-[8-(Dimethylamino)-8-phenyl-3-azaspiro[4.5]decan-3-yl]-3-phenylprop-2-en-1-one (Example No. 12, Polar Diastereomer)

Triethylamine (97 mg, 133 µl, 0.96 mmol) and cinnamyl chloride (128 mg, 0.77 mmol) were added to a solution of N,N-dimethyl-8-phenyl-3-azaspiro[4.5]decan-8-amine (polar diastereomer) (165 mg, 0.64 mmol) in anhydrous methylene chloride (5 ml) and the mixture was stirred for 3 h at room temperature. After addition of methylene chloride (20 ml) the solution was washed with 25% strength potassium carbonate solution (2×20 ml) and the organic phase was dried with sodium sulfate and concentrated i. vac. The crude product (290 mg) was purified by flash chromatography (10 g, 20×1.5 cm) with methylene chloride/methanol (95:5) and 1% ammonia (25% in water).

Example No. 12 (Polar Diastereoisomer)

Yield: 169 mg (68%), oil $^1$H-NMR (CDCl$_3$): 1.28-1.39 (m, 2H); 1.57-1.74 (m, 4H); 1.82-2.01 (m, 2H); 2.04 and 2.05 (2 s, 6H); 2.20-2.46 (m, 2H); 3.54-3.67 (m, 4H); 6.71 and 6.77 (2 d, 1H, J=15.4 Hz); 7.27-7.43 (m, 8H); 7.50-7.57 (m, 2H); 7.68 and 7.72 (2 d, 1H, J=5.6 Hz).

$^{13}$C-NMR (CDCl$_3$): 30.1; 31.0; 31.3; 31.4; 36.0; 38.0; 38.1; 40.3; 42.4; 44.4; 45.0; 55.5; 56.2; 60.8; 118.5; 118.7; 126.5; 126.7; 127.6; 127.7; 127.8; 127.81; 127.9; 128.7; 128.8; 129.5; 129.54; 135.3; 135.4; 137.4; 141.7; 164.87; 164.92.

The NMR spectra show sometimes doubled signal sets (rotamers).

LC-MS: m/z: [M+H]$^+$=389.4, R$_t$=3.1 min.

Example No. 13

(E)-1-[8-(Dimethylamino)-8-(5-methylthiophen-2-yl)-3-azaspiro[4.5]decan-3-yl]-3-phenylprop-2-en-1-one (Example No. 13, Polar Diastereomer)

Cinnamyl chloride (143 mg, 0.86 mmol) was added to a solution of 8-(dimethylamino)-8-(5-methylthiophen-2-yl)-3-azaspiro[4.5]decan-4-one (polar diastereomer) (200 mg, 0.72 mmol) and triethylamine (110 mg, 152 µl, 1.1 mmol) in absolute methylene chloride (10 ml) and the mixture was stirred for 2 h at room temperature. The reaction mixture was then adjusted to pH 9-10 with 1 M potassium carbonate solution and stirred for 15 min. The phases were separated and the aqueous phase was extracted with methylene chloride (3×50 ml). The combined organic phases were dried with sodium sulfate and concentrated i. vac. The residue (296 mg) was purified by flash chromatography (10 g, 20×1.5 cm) with ethyl acetate/methanol (4:1), as a result of which 210 mg were obtained. Since slight non-polar impurities were still present, the product was purified again by means of flash chromatography on spherical silica gel (PharmPrep 60 CC, 40-63 mm, 10 g, 20×1.5 cm) with ethyl acetate/methanol (97:3)→ethyl acetate/methanol (4:1).

Example No. 13 (Polar Diastereoisomer)

Yield: 185 mg (63%), colourless viscous oil $^1$H-NMR (DMSO-d$_6$): 1.29-1.38 (m, 2H); 1.58-1.68 (m, 3H); 1.73 (t, J=6.9 Hz, 1H); 1.88-1.98 (m, 4H); 2.01 (s, 6H); 2.41 (s, 3H); 3.27 (s, 1H); 3.43 (t, J=7.2 Hz, 1H); 3.54 (s, 1H); 3.69 (t, J=7.0 Hz, 1H); 6.69-6.73 (m, 2H); 7.35-7.49 (m, 5H); 7.66-7.74 (m, 2H).

$^{13}$C-NMR (DMSO-d$_6$): 15.3; 31.0; 32.8; 38.2; 38.3; 42.0; 44.5; 45.0; 120.1; 120.5; 125.1; 125.2; 125.3; 128.4; 128.5; 128.6; 129.1; 129.2; 129.3; 129.9; 130.0; 135.5; 135.6; 137.2; 140.6; 140.7; 164.2.

The NMR spectra show sometimes doubled signal sets (rotamers).

LC-MS: m/z: [MH-HNMe$_2$]$^+$=364.2, R$_t$=3.2 min.

Example No. 14

3-Benzyl-8-(dimethylamino)-8-thiophen-2-yl-3-azaspiro[4.5]decan-2-one (Example No. 14, Polar Diastereomer)

A mixture of 8-(dimethylamino)-8-thiophen-2-yl-2-azaspiro[4.5]decan-3-one (polar diastereoisomer) (200 mg, 0.72 mmol) and potassium tert-butylate (98 mg, 0.87 mmol) in N,N-dimethylformamide (6 ml) was stirred for 40 min at room temperature, before benzyl bromide (149 mg, 104 µl, 0.87 mmol) was added and stirring was carried out for a further 3 h at room temperature. The reaction mixture was then diluted with ethyl acetate (50 ml) and washed with water (3×10 ml). The organic phase was dried with sodium sulfate and concentrated i. vac. The crude product was purified by means of flash chromatography (38 g, 20×2.5 cm) with methylene chloride/methanol (95:5)+1% ammonia (25% in H$_2$O). Since the product obtained (155 mg) still contained impurities, it was purified again by means of flash chromatography (10 g, 20×1.5 cm) with methylene chloride/methanol (95:5)+1% ammonia (25% in H$_2$O).

Example No. 14 (Polar Diastereoisomer)

Yield: 120 mg (45%), colourless oil
$^1$H-NMR (CDCl$_3$): 1.43 (ddd, 2H, J=3.7, 9.1, 13.1 Hz); 1.64-1.73 (m, 2H); 1.83-1.95 (m, 2H); 1.97-2.05 (m, 2H); 2.05 (s, 6H); 2.24 (s, 2H); 3.07 (s, 2H); 4.43 (s, 2H); 6.83 (dd, 1H, J=1.1, 3.6 Hz); 7.04 (dd, 1H, J=3.6, 5.1 Hz); 7.21-7.25 (m, 3H); 7.27-7.36 (m, 3H).
$^{13}$C-NMR (CDCl$_3$): 32.6; 32.7; 35.4; 38.0; 44.3; 46.5; 57.2; 59.3; 123.5; 124.9; 126.3; 127.6; 128.2; 128.7; 136.5; 173.6.
LC-MS: m/z: [M+H]$^+$=369.3, R$_t$=2.5 min.

Example No. 15

3-Benzyl-8-(dimethylamino)-8-thiophen-2-yl-3-azaspiro[4.5]decan-2-one (Example No. 15, Non-Polar Diastereomer)

A mixture of 8-(dimethylamino)-8-thiophen-2-yl-2-azaspiro[4.5]decan-3-one (non-polar diastereoisomer) (135 mg, 0.49 mmol) and potassium tert-butylate (66 mg, 0.59 mmol) in N,N-dimethylformamide (5 ml) was stirred for 40 min at room temperature, before benzyl bromide (101 mg, 70 µl, 0.59 mmol) was added and stirring was carried out for a further 3 h at room temperature. The reaction mixture was then diluted with ethyl acetate (50 ml) and washed with water (3×10 ml). The organic phase was dried with sodium sulfate and concentrated i. vac. The crude product was purified by means of flash chromatography (10 g, 20×1.5 cm) with methylene chloride/methanol (95:5)+1% ammonia (25% in H$_2$O).

Example No. 15 (Non-Polar Diastereoisomer)

Yield: 113 mg (62%), colourless oil
$^1$H-NMR (CDCl$_3$): 1.35-1.43 (m, 2H); 1.67-1.76 (m, 2H); 1.92-2.06 (m, 4H); 2.09 (s, 6H); 2.39 (s, 2H); 2.92 (s, 2H); 4.40 (s, 2H); 6.80 (dd, 1H, J=1.1, 3.6 Hz); 7.00 (dd, 1H, J=3.5, 5.1 Hz); 7.16-7.22 (m, 3H); 7.24-7.32 (m, 3H).
$^{13}$C-NMR (CDCl$_3$): 32.6; 32.7; 35.5; 38.1; 43.5; 46.5; 57.9; 59.6; 123.5; 125.0; 126.2; 127.5; 128.1; 128.6; 136.4; 142.6; 173.7.
LC-MS: m/z: [MH-HNMe$_2$]$^+$=324.2 (100%) and [M+H]$^+$=369.3 (65%), R$_t$=2.9 min.

Example No. 16

[3-Benzyl-8-(5-methylthiophen-2-yl)-3-azaspiro[4.5]decan-8-yl]-dimethylamine (Example No. 16, Polar Diastereomer)

Benzaldehyde (99 mg, 95 µl, 0.9 mmol), acetic acid (720 µl) and sodium cyanoborohydride (204 mg, 3.2 mmol) were added successively to a solution of dimethyl-[8-(5-methyl-thiophen-2-yl)-3-azaspiro[4.5]decan-8-yl]-amine (polar diastereomer) (200 mg, 0.72 mmol) in absolute methanol (5 ml) and the mixture was stirred for 4 h at room temperature. Saturated potassium bicarbonate solution (30 ml) was then added to the reaction mixture and the mixture was extracted with methylene chloride/2-propanol (4:1) (3×50 ml). The combined organic phases were washed with saturated sodium chloride solution (50 ml), dried with sodium sulfate and concentrated i. vac. The residue (248 mg) was purified by flash chromatography on spherical silica gel (PharmPrep 60 CC, 40-63 mm, 10 g, 20×1.5 cm) with methanol which contained 1% ammonia (25% in H$_2$O).

Example No. 16 (Polar Diastereoisomer)

Yield: 139 mg (52%), colourless viscous oil
$^1$H-NMR (CDCl$_3$): 1.39 (ddd, J=13.5, 10.4, 3.4 Hz, 2H); 1.52 (t, J=6.9 Hz, 2H); 1.64-1.70 (m, 4H); 1.73-1.85 (m, 2H); 2.08 (s, 6H); 2.39 (s, 2H); 2.46 (d, J=1.0 Hz, 3H); 2.54 (t, J=6.9 Hz, 2H); 3.57 (s, 2H); 6.60 (d, J=3.5 Hz, 1H); 6.67 (td, J=3.1, 1.0 Hz, 1H); 7.20-7.24 (m, 1H); 7.27-7.33 (m, 4H).
$^{13}$C-NMR (CDCl$_3$): 15.3; 33.6; 35.0; 38.2; 41.0; 53.7; 59.8; 60.8; 76.8; 77.5; 124.3; 124.9; 126.7; 128.1; 128.7; 137.5; 139.4.
LC-MS: m/z: [m+H]$^+$369.2, R$_t$=1.8 min.

Example No. 17

[8-(Dimethylamino)-8-(5-methylthiophen-2-yl)-3-azaspiro[4.5]decan-3-yl]-phenylmethanone Example No. 17, Polar Diastereomer Benzoyl chloride (121 mg, 99 µl, 0.86 mmol) was added to a solution of dimethyl-[8-(5-methylthiophen-2-yl)-3-azaspiro[4.5]decan-8-yl]-amine (polar diastereomer) (200 mg, 0.72 mmol) and triethylamine (110 mg, 152 µl, 1.1 mmol) in absolute methylene chloride (10 ml) and the mixture was stirred for 2 h at room temperature. The reaction mixture was then adjusted to pH 9-10 with 1 M potassium carbonate solution and stirred for 15 min. The phases were separated, the aqueous phase was extracted with methylene chloride (3×50 ml) and the combined organic phases were dried with sodium sulfate and concentrated i. vac. The residue (289 mg) was purified by flash chromatography on spherical silica gel (PharmPrep 60 CC, 40-63 mm, 10 g, 20×1.5 cm) with ethyl acetate/methanol (4:1).

Example No. 17 (Polar Diastereoisomer)

Yield: 197 mg (72%), yellow viscous oil
$^1$H-NMR (CDCl$_3$): 1.35-1.49 (m, 2H); 1.57-1.62 (m, 2H); 1.65 (t, J=7.4 Hz, 1.4H); 1.70 (t, J=7.1 Hz, 2.6H); 1.87-2.03 (m, 2H); 2.05 (s, 4H); 2.14 (s, 2H); 2.47 (s, 3H); 3.31 (s, 1.3H); 3.45 (t, J=7.0 Hz, 0.7H); 3.55 (s, 0.7H); 3.66 (t, J=7.4 Hz, 1.3H); 6.60 (d, J=3.4 Hz, 0.7H); 6.63 (d, J=3.5 Hz, 0.3H); 6.67 (d, J=1.0 Hz, 0.7H); 6.68 (d, J=1.0 Hz, 0.3H); 7.37-7.41 (m, 3H); 7.47-7.50 (m, 2H). Some H signals are doubled due to the amide structure (rotamers).
$^{13}$C-NMR (CDCl$_3$): 15.3; 30.8; 31.5; 32.7; 33.1; 35.9; 38.0; 38.1; 40.3; 42.1; 44.4; 47.8; 58.9; 60.4; 124.4; 124.5; 125.0; 125.2; 127.0; 127.1; 127.9; 128.2; 128.4; 129.7; 129.9; 137.0; 137.8; 138.0; 169.9; 170.0. Some C signals are doubled due to the amide structure (rotamers).
LC-MS: m/z: [M+H]$^+$=383.2, R$_t$=3.1 min.

Example No. 33

[8-(Dimethylamino)-8-thiophen-2-yl-3-azaspiro[4.5]decan-3-yl]-(1H-imidazol-1-yl)-methanone (Example No. 33, Polar Diastereomer)

Carbonyldiimidazole (487 mg, 3 mmol) was added to a solution of cyclopropylacetic acid (250 mg, 242 µl, 2.5 mmol) in absolute tetrahydrofuran (10 ml) and the mixture was stirred for 30 min at room temperature. A solution of dimethyl-(8-thiophen-2-yl-3-azaspiro[4.5]decan-8-yl)-amine (Example no. 21) (397 mg, 1.5 mmol) in tetrahydrofuran (10 ml) was added to this and the mixture was stirred for 2 h at room temperature. The reaction mixture was then concentrated i. vac., 1 M potassium carbonate solution (20 ml) was added to the residue and the mixture was extracted with methylene chloride (3×10 ml). The combined organic phases were dried with sodium sulfate and concentrated i. vac. The crude product was purified by means of flash chromatography (38 g, 20×2.5 cm) with ethyl acetate/methanol (1:1)+1% acetic acid.

Example No. 33 (Polar Diastereoisomer)

Yield: 250 mg (47%), yellow oil
$^1$H-NMR (CDCl$_3$): 1.38-1.49 (2H, m); 1.66-1.75 (2H, m); 2.03 (6H, s); 2.09-2.18 (2H, m); 2.24 (6H, s); 2.27-2.34 (2H, m); 2.35 (2H, s); 3.58 (2H, s); 3.67 (2H, t, J=7.2 Hz); 6.97 (1H, dd, J=3.6 and 1.1 Hz); 7.08-7.11 (2H, m); 7.12-7.19 (2H, m); 7.22-7.27 (2H, m); 7.36 (1H, dd, J=5.1 and 1.0 Hz); 7.40 (1H, s); 8.11 (1H, s); 10.45 (2H, br s).
$^{13}$C-NMR (CDCl$_3$): 21.3; 31.1; 31.2; 37.4; 46.7; 56.1; 65.1; 117.9; 127.4; 127.6; 128.4; 129.0; 136.5; 137.1; 149.4; 176.6.

The substance contains one molar equivalent of imidazole.
LC-MS: m/z: [MH-HNMe$_2$]$^{+=314.3}$ (100%), R$_t$=2.1 min.

Example No. 46

Step 1: 10-Benzyl-1,4-dioxa-10-azadispiro[4.2.4.2] tetradecan-9-one

A solution of substance D (equation 1) (1.4 g, 6.6 mmol), and potassium tert-butanolate (892 mg, 7.95 mmol) in N,N-dimethylformamide (15 ml) was stirred for 30 min at room temperature and benzyl bromide (1.36 g, 950 µl, 7.95 mmol) was then added. After 4 h at room temperature the reaction mixture was diluted with ethyl acetate (100 ml) and washed with water (3×40 ml). The organic phase was dried with sodium sulfate and concentrated i. vac.

Yield: 1.94 g (97%), brown oil
$^1$H-NMR (CDCl$_3$): 1.44-1.65 (4H, m); 1.83-1.95 (4H, m); 2.00-2.09 (2H, m); 3.14 (2H, dd, J=6.6 and 7.3 Hz); 3.92-3.97 (4H, m); 4.45 (2H, s); 7.17-7.23 (2H, m); 7.26-7.35 (3H, m).

Step 2: 10-Benzyl-1,4-dioxa-10-azadispiro[4.2.4.2] tetradecane

A solution of 10-benzyl-1,4-dioxa-10-azadispiro[4.2.4.2] tetradecan-9-one (1.94 g, 6.43 mmol) in tetrahydrofuran (40 ml) was added to a suspension of lithium aluminium hydride (962 mg, 25.7 mmol) in tetrahydrofuran (8 ml) at room temperature and the mixture was stirred for 18 h at 60° C. The reaction mixture was cooled to 0° C., water (1 ml), 1 N sodium hydroxide solution (1 ml) and again water (3 ml) were added and the mixture was stirred for 1 h at room temperature. The suspension was filtered through sodium sulfate and the residue was washed with tetrahydrofuran (20 ml). The filtrate was concentrated, and dried i. vac.

Yield: 1.80 g (97%), yellowish oil.
$^1$H-NMR (CDCl$_3$): 1.54-1.65 (10H, m); 2.36 (2H, s); 2.56 (2H, t, J=6.9 Hz); 3.56 (2H, s); 3.91 (4H, m); 7.18-7.36 (5H, m).
LC-MS: [M+H]$^+$: m/z=288.3, R$_t$=2.1 min.

Step 3: 2-Benzyl-2-azaspiro[4.5.]decan-8-one

A solution of 10-benzyl-1,4-dioxa-10-azadispiro[4.2.4.2] tetradecane (1.80 g, 6.2 mmol) in 1 M sulfuric acid (60 ml) was stirred for 20 h at room temperature. The reaction solution was then washed with diethyl ether (2×25 ml), rendered alkaline (pH~9) with 4 M sodium hydroxide solution and extracted with methylene chloride (3×25 ml). The combined organic methylene chloride phases were dried with sodium sulfate and concentrated i. vac.

Yield: 1.10 g (73%), colourless oil
$^1$H-NMR (CDCl$_3$): 1.78 (2H, t, J=6.9 Hz); 1.87 (4H, t, J=6.9 Hz); 2.25-2.40 (4H, m); 2.49 (2H, s); 2.67 (2H, t, J=6.9 Hz); 3.62 (2H, s); 7.22-7.35 (5H, m).

Step 4: 2-Benzyl-8-dimethylamino-2-azaspiro[4.5] decane-8-carbonitrile

4 N hydrochloric acid (1.35 ml, 5.4 mmol) and then a solution of 2-benzyl-2-azaspiro[4.5]decan-8-one (1.10 g, 4.5 mmol) in methanol (10 ml) and tetrahydrofuran (4 ml) were added to a 40% strength aqueous dimethylamine solution (2.3 ml, 18.1 mmol), cooled to 0° C. Potassium cyanide (586 mg, 9 mmol) was added to this mixture and the mixture was stirred for 20 h at room temperature. After addition of water (30 ml) the mixture was extracted with methylene chloride (3×50 ml). The combined organic extracts were dried with sodium sulfate and concentrated.

Yield: 1.27 g (95%), yellowish oil.
$^1$H-NMR (CDCl$_3$): 1.53-1.79 (8H, m); 2.00-2.09 (2H, m); 2.31 (1H, m); 2.32 (3H, s); 2.35 (3H, s); 2.36-2.37 (1H, m); 2.55-2.61 (2H, m); 3.56 (2H, s); 7.20-7.26 (1H, m); 7.28-7.32 (4H, m).

Step 5: (3-Benzyl-8-thiophen-2-yl-3-azaspiro[4.5] decan-8-yl)-dimethylamine (Example No. 46, Non-Polar Diastereomer)

A 1 M solution of 2-thienyllithium in tetrahydrofuran (15 ml, 15 mmol) was added dropwise to a solution of 2-benzyl-8-dimethylamino-2-azaspiro[4.5]decane-8-carbonitrile (1.50 g, 5 mmol) in anhydrous tetrahydrofuran (15 ml) at 0° C. under argon. The reaction solution was stirred for 20 h at room temperature and thereafter heated for 2 h under reflux. 20% strength ammonium chloride solution (20 ml) was then added to the reaction mixture at room temperature. The phases were separated and the aqueous phase was extracted with methylene chloride (2×20 ml). The combined organic phases were dried with sodium sulfate and concentrated i. vac. The residue was taken up in tetrahydrofuran (5 ml), 2 M hydrochloric acid (20 ml) was added and the mixture was stirred for 20 h at room temperature. The reaction solution was then washed with diethyl ether (20 ml), rendered alkaline (pH~9-10) with 4 M sodium hydroxide solution and extracted with methylene chloride (3×20 ml). The combined organic phases were dried with sodium sulfate and concentrated i. vac. The crude product (1.25 g) was purified by flash chromatography (80 g, 20×4 cm) with methylene chloride/methanol/ammonia (25% in H$_2$O) (100:5:0.2). The impure non-polar diastereoisomer (360 mg) was purified again by flash chromatography (30 g, 21×2.5 cm) with methanol and 0.5% ammonia (25% in H$_2$O).

Isolation of the known polar diastereoisomer was not carried out.

Example No. 46 (Non-Polar Diastereoisomer)

Yield: 225 mg (12%) brown oil
$^1$H-NMR (CDCl$_3$): 1.35-1.45 (2H, m); 1.61-1.72 (4H, m); 1.85-2.00 (2H, m); 2.01-2.13 (2H, m); 2.10 (6H, s); 2.23 (2H, s); 2.59 (2H, t, J=6.9 Hz); 3.53 (2H, s); 6.82 (1H, dd, J=3.5 and 1.0 Hz); 7.01 (1H, dd, J=5.1 and 3.5 Hz); 7.17-7.30 (6H, m).

$^{13}$C-NMR (CDCl$_3$): 33.5; 34.3; 38.2; 41.0; 54.1; 59.8; 60.7; 66.9; 123.2; 125.0; 126.1; 126.7; 128.1; 128.6; 139.5.
LC-MS: [M+H]$^+$: m/z=355.4, R$_f$=2.0 min.

Example No. 58

Step 1: 8-(5-Chlorothiophen-2-yl)-8-dimethylamino-2-azaspiro[4.5]decan-4-one

A suspension of 8-(dimethylamino)-1-oxo-2-azaspiro [4.5]decane-8-carbonitrile (1.76 g, 7.9 mmol) in absolute tetrahydrofuran (75 ml) was slowly added dropwise to a 0.5 M suspension of 5-chloro-2-thienylmagnesium bromide (5.29 g, 48 ml, 23.9 mmol) in tetrahydrofuran under argon, a clear solution being formed. The solution was then stirred overnight at 50° C. After addition of saturated ammonium chloride solution (100 ml) the tetrahydrofuran was removed i. vac. The aqueous solution obtained was extracted with methylene chloride (3×50 ml) and the combined organic phases were washed with saturated sodium chloride solution (50 ml), dried with sodium sulfate and concentrated i. vac. The crude product (2.45 g) was purified by means of flash chromatography (100 g, 20×4.0 cm) with ethyl acetate/methanol (97:3).

Yield: 1.47 g (59%), yellow solid.
Melting point: 198-201° C.
$^1$H-NMR (CDCl$_3$): 1.28-1.34 (2H, m); 1.61-1.68 (2H, m); 2.01 (2H, t, J=6.9 Hz); 2.12 (6H, s); 2.17 (2H, dt, J=13.1 and 3.1 Hz), 2.32-2.40 (2H, m); 3.28-3.32 (2H, m); 5.90 (1H, br s); 6.60 (1H, d, J=3.8 Hz); 6.83 (1H, d, J=3.8 Hz).
$^{13}$C-NMR (CDCl$_3$): 27.9; 31.5; 32.7; 37.9; 38.7; 43.1; 58.9; 123.1; 125.2; 127.4; 144.4; 182.4.
LC-MS: m/z: [MH-HNMe$_2$]$^+$=268.2, R$_f$=2.6 min.

Step 2: [8-(5-Chloro-2-thiophen-2-yl)-2-azaspiro [4.5]dec-8-yl]-dimethylamine

A 2 M solution of boron-dimethyl sulfide complex in tetrahydrofuran (6.42 ml, 12.8 mmol) was added to a solution of 8-(5-chlorothiophen-2-yl)-8-dimethylamino-2-azaspiro[4.5]decan-4-one (1.34 g, 4.3 mmol) in absolute tetrahydrofuran (150 ml) and the mixture was stirred for 4 h under reflux and overnight at 50° C. Since the reaction was not yet complete, the same amount of 2 M borane-dimethyl sulfide complex was again added and the mixture was stirred for a further 6 h under reflux and over the weekend at room temperature. Water (100 ml) was added to the reaction solution and the mixture was concentrated i. vac. Toluene, methanol and methylene chloride (3×30 ml of each) were added in succession to the residue and the mixture was again concentrated i. vac. The crude product was reacted further without purification.

Yield: 1.95 g (151%), viscous yellow oil
The $^1$H-NMR spectrum shows all the expected signals.
LC-MS: m/z: [MH-HNMe$_2$]$^+$=254.3, R$_f$=2.7 min.
The product content is a maximum of 66%.

Step 3: (E)-1-[8-(5-Chlorothiophen-2-yl)-8-dimethylamino-2-azaspiro[4.5]dec-2-yl]-3-phenylpropenone (Example 58, a Diastereomer)

Cinnamyl chloride (268 mg, 1.6 mmol) was added to a solution of [8-(5-chloro-2-thiophen-2-yl)-2-azaspiro[4.5] dec-8-yl]-dimethylamine (400 mg of crude product, max. 0.9 mmol) and triethylamine (203 mg, 279 µl, 2.0 mmol) in absolute methylene chloride (30 ml) and the mixture was stirred for 2 h at room temperature. Since the reaction was not yet complete, the same amount of triethylamine and cinnamyl chloride was again added and the mixture was stirred for a further 24 h at room temperature. The reaction mixture was then adjusted to pH 9-10 with 1 M potassium carbonate solution and stirred for 15 min. The phases were separated and the aqueous phase was extracted with methylene chloride (3×50 ml). The combined organic phases were washed with saturated sodium chloride solution (50 ml), dried with sodium sulfate and concentrated i. vac. The residue (800 mg) was purified by flash chromatography on spherical silica gel (PharmPrep 60 CC, 40-63 µm, 38 g, 20×2.5 cm) with ethyl acetate/methanol (97:3) which contained 1% ammonia (25% in water).

Example No. 58 (a Diastereoisomer)

Yield: 220 mg (58%), yellow foam.
$^1$H-NMR (DMSO-d$_6$): 1.38-1.49 (2H, m); 1.66-1.73 (3H, m); 1.78 (1H, t, J=7.2 Hz); 1.85-2.02 (4H, m); 2.11 (4H, s); 2.13 (2H, s); 3.50 (2H, d, J=7.1 Hz); 3.62 (1.3H, d, J=7.2 Hz); 3.67 (0.7H, d, J=7.2 Hz); 6.59-6.63 (1H, m); 6.69-6.74 (1H, m); 6.82-6.87 (1H, m); 7.35-7.39 (3H, m); 7.51-7.55 (2H, m); 7.67-7.72 (1H, m).
$^{13}$C-NMR (DMSO-d$_6$): 27.9; 31.1; 31.5; 32.5; 32.7; 33.1; 35.6; 37.2; 37.9; 38.1; 38.6; 40.0; 42.1; 44.4; 45.0; 118.4; 118.6; 125.4; 125.6; 127.8; 128.8; 129.5; 129.6; 135.3; 135.4; 141.9; 164.9. Some C signals are doubled due to the amide structure (rotamers).
LC-MS: m/z: [MH-NHMe$_2$]$^+$=384.3, R$_f$=3.3 min.

Example No. 61

Step 1: 8-Dimethylamino-8-(5-fluorothiophen-2-yl)-2-azaspiro[4.5]decane-2-carboxylic acid tert-butyl ester A 2.5 M solution of n-butyllithium in hexane (2.2 ml, 5.5 mmol) was added dropwise to a solution of 8-dimethylamino-8-thiophen-2-yl-3-azaspiro[4.5]decane-3-carboxylic acid tert-butyl ester (Example no. 79) (1.55 g, 4.3 mmol) in absolute tetrahydrofuran (100 ml) in a thoroughly heated apparatus at −78° C. under argon and the mixture was stirred for 30 min at this temperature. The solution became yellow in colour. A solution of N-benzenesulfonyl-N-fluorobenzenesulfonamide (1.74 g, 5.5 mmol) in absolute tetrahydrofuran (50 ml) was added dropwise to this and the mixture was then warmed slowly to room temperature and further stirred for 18 h at this temperature. The solution became red in colour. After addition of saturated ammonium chloride solution (50 ml) the tetrahydrofuran was removed i. vac. The aqueous solution obtained was extracted with methylene chloride (3×30 ml) and the combined organic phases were washed with saturated sodium chloride solution (50 ml), dried with sodium sulfate and concentrated i. vac. The crude product (2.50 g) was purified by flash chromatography on spherical silica gel (PharmPrep 60 CC, 40-63 µm, 100 g, 20×4.0 cm) with ethyl acetate/isopropanol (99:1).

Yield: cannot be determined since various mixed fractions of differing purity were obtained, orange-coloured viscous oil
$^1$H-NMR (CDCl$_3$): 1.34-1.42 (2H, m); 1.46 (9H, s); 1.57-1.66 (4H, m); 1.78-1.97 (4H, m); 2.11 (2H, s); 2.13 (4H, s); 3.18 (0.7H, s); 3.22 (1.3H, s); 3.32 (0.7H, t, J=7.1 Hz); 3.37 (1.3H, t, J=7.1 Hz); 6.35-6.40 (1H, m); 6.42 (1H, t, J=3.5 Hz).

$^{13}$C-NMR (DMSO-d$_6$): 28.6; 31.3; 32.1; 32.9; 36.6; 37.0; 38.1; 40.7; 41.5; 44.0; 44.4; 55.6, 60.2; 79.1; 106.3; 121.3; 154.8; 162.5; 165.4.

Some C signals are doubled due to the amide structure (rotamers). For this reason, also no C—F coupling constants were determined.

LC-MS: m/z: [MH-NHMe$_2$]$^+$=383.4, R$_t$=3.3 min.

Step 2: [8-(5-Fluorothiophen-2-yl)-2-azaspiro[4.5]dec-8-yl]-dimethylamine

Trifluoroacetic acid (15 ml) was added to a solution of 8-dimethylamino-8-(5-fluorothiophen-2-yl)-2-azaspiro[4.5]decane-2-carboxylic acid tert-butyl ester (1.35 g, max. 3.5 mmol, slightly contaminated) in absolute methylene chloride (60 ml) and the mixture was stirred for 1 h at room temperature. The reaction solution was concentrated I. vac. and methylene chloride (50 ml) was added to the residue. The solution obtained was washed with saturated potassium bicarbonate solution (3×30 ml) and saturated sodium chloride solution (50 ml), dried with sodium sulfate and concentrated i. vac. The crude product was reacted further without purification.

Yield: 738 mg (crude product), orange-coloured viscous oil $^1$H-NMR (CDCl$_3$): 1.43 (2H, ddd, J=13.1, 8.1 and 4.9 Hz); 1.61 (2H, t, J=7.3 Hz); 1.68-1.74 (2H, m); 1.86-1.99 (4H, m); 2.10 (6H, s); 2.88 (2H, s); 3.09 (2H, t, J=7.3 Hz); 5.02 (1H, br. s); 6.38 (1H, dd, J=4.0 and 1.7 Hz); 6.42 (1H, dd, J=4.0 and 3.1 Hz).

Step 3: (E)-1-[8-(Dimethylamino)-8-(5-fluorothiophen-2-yl)-3-azaspiro[4.5]decan-3-yl]-3-phenylprop-2-en-1-one (Example No. 61, Polar Diastereomer)

Cinnamyl chloride (170 mg, 1.0 mmol) was added to a solution of [8-(5-fluorothiophen-2-yl)-2-azaspiro[4.5]dec-8-yl]-dimethylamine (240 mg, 0.8 mmol, crude product) and triethylamine (129 mg, 177 µl, 1.3 mmol) in absolute methylene chloride (20 ml) and the mixture was stirred for 18 h at room temperature. The reaction mixture was then adjusted to pH 9-10 with 1 M potassium carbonate solution and stirred for 15 min. The phases were separated and the aqueous phase was extracted with methylene chloride (3×10 ml). The combined organic phases were washed with saturated sodium chloride solution (10 ml), dried with sodium sulfate and concentrated i. vac. The residue (354 mg) was purified by flash chromatography on spherical silica gel (PharmPrep 60 CC, 40-63 µm, 18 g, 20×2.0 cm) with ethyl acetate/methanol (9:1).

Example No. 61 (Polar Diastereoisomer)

Yield: 190 mg (54%), pale solid foam.
Melting point: 61-63° C.
$^1$H-NMR (DMSO-d$_6$): 1.38-1.49 (2H, m); 1.67-1.71 (3H, m); 1.78 (1H, t, J=7.2 Hz); 1.84-2.02 (4H, m); 2.12 (3H, s); 2.13 (3H, s); 3.50 (1H, s); 3.51 (1H, s); 3.63 (1H, t, J=7.1 Hz); 3.68 (1H, t, J=7.1 Hz); 6.39 (1H, ddd, J=12.9, 4.0 and 1.7 Hz); 6.43-6.45 (1H, m); 6.72 (1H, dd, J=15.5 and 4.2 Hz); 7.33-7.41 (3H, m); 7.51-7.55 (2H, m); 7.70 (1H, dd, J=15.5 and 5.4 Hz).
$^{13}$C-NMR (DMSO-d$_6$): 31.09; 31.15; 32.2; 32.5; 32.9; 35.6; 37.2; 37.90; 37.94; 38.06; 38.08; 40.1; 42.1; 42.2; 44.4; 45.0; 55.6; 56.3; 60.1; 60.2; 106.1; 106.2; 106.4; 106.5; 118.4; 118.6; 121.1; 121.4; 127.32; 127.34; 127.8; 127.9; 128.8; 129.2; 129.5; 129.6; 131.9; 133.2; 135.3; 135.4; 141.8; 141.9; 162.5; 164.88; 164.92; 165.4.

Some C signals are doubled due to the amide structure (rotamers). For this reason, also no C—F coupling constants were determined.

LC-MS: m/z: [MH-NHMe$_2$]$^+$=368.3, R$_t$=3.2 min.

Example No. 67

Step 1: 8-Cyclopent-1-enyl-8-dimethylamino-2-azaspiro[4.5]decan-1-one

A solution of cyclopentenylmagnesium bromide (maximum 17 mmol) was added dropwise to a solution of 8-(dimethylamino)-1-oxo-2-azaspiro[4.5]decane-8-carbonitrile (958 mg, 4.32 mmol) in anhydrous tetrahydrofuran (20 ml) and the mixture was stirred for 1 h at room temperature. The mixture was heated to 60° C. and stirred for 1 h at this temperature. Saturated ammonium chloride solution (25 ml) and water (20 ml) were added to the suspension, while cooling with ice. The phases were separated and the aqueous phase was extracted with ethyl acetate (2×30 ml). The combined organic phases were dried with sodium sulfate and concentrated i. vac. The residue (900 mg) was purified by flash chromatography (85 g, 4.0×20 cm) with methylene chloride/methanol (9:1) and 1% ammonia (25% in water).

Yield: 527 mg (46%), white solid
$^1$H-NMR (CDCl$_3$): 1.18-1.26 (2H, m); 1.31-1.41 (2H, m); 1.75-1.85 (2H, m); 1.97 (2H, t, J=6.9 Hz); 2.01-2.10 (2H, m); 2.11-2.20 (2H, m); 2.18 (6H, s); 2.22-2.36 (4H, m); 3.25-3.30 (2H, m); 5.44 (1H, m); 6.38 (1H, br s).
$^{13}$C-NMR (CDCl$_3$): 23.6; 28.2; 29.1; 31.9; 32.9; 34.0; 38.3; 38.6; 38.8; 43.2; 56.9; 125.8; 146.0; 183.2.
LC-MS: [M+H]$^+$: m/z=263.4, R$_t$=2.3 min.

Step 2: 8-Cyclopentyl-8-dimethylamino-2-azaspiro[4.5]decan-1-one

5% rhodium on aluminium oxide (960 mg, 0.47 mmol) was added to a solution of 8-cyclopent-1-enyl-8-dimethylamino-2-azaspiro[4.5]decan-1-one (2.5 g, 9.5 mmol) in anhydrous methanol (20 ml) and the mixture was stirred for 3 h under a hydrogen pressure of 2 bar. Methanol (20 ml) was again added to the mixture and the mixture was stirred for a further 2 h under a hydrogen pressure of 2 bar. Since the educt had not yet reacted, the reaction mixture was diluted with methanol (110 ml), 5% rhodium on aluminium oxide (1.92 g, 0.95 mmol) was again added and hydrogenation was carried out for 20 h under a hydrogen pressure of 4 bar. The suspension was filtered through Celite, the residue was washed with methanol and the filtrate was concentrated i. vac. The residue was partitioned between ethyl acetate and 10% strength citric acid solution (40 ml of each). The organic phase was washed with 10% strength citric acid solution (3×80 ml). The combined acid, aqueous phases were rendered alkaline with 4 M sodium hydroxide solution and extracted with methylene chloride (4×50 ml). The combined organic phases were dried with sodium sulfate and concentrated i. vac. The crude product was purified by flash chromatography (85 g, 20×4.0 cm) with methylene chloride/methanol (95:5) and 1% ammonia (25% in water).

Yield: 757 mg (30%), white solid
$^1$H-NMR (CDCl$_3$): 1.14 (2H, dd, J=11.8 and 1.2 Hz); 1.20-1.34 (4H, m); 1.40-1.63 (6H, m); 1.73 (2H, dd, J=14.9 and 2.8 Hz); 1.98-2.14 (5H, m); 2.28 (6H, s); 3.29-3.30 (2H, m); 6.20 (1H, s).

$^{13}$C-NMR (CDCl$_3$): 25.0; 26.5; 27.3; 28.3; 31.9; 37.9; 38.9; 44.2; 44.4; 57.4; 183.4.

LC-MS: [M+H]$^+$: m/z=265.4.4, Rt=2.2 min.

Step 3: 8-Cyclopentyl-8-dimethylamino-2-azaspiro [4.5]decan-1-one

A solution of 8-cyclopentyl-8-dimethylamino-2-azaspiro [4.5]decan-1-one (758 mg, 2.8 mmol) in anhydrous tetrahydrofuran (30 ml) was added dropwise to a suspension of lithium aluminium hydride (542 mg, 14.3 mmol) in anhydrous tetrahydrofuran (10 ml), while cooling with ice. The suspension was stirred for 4 h at 50° C. Water (560 µl), 1 M sodium hydroxide solution (1.1 ml) and again water (1.1 ml) were added to the mixture, while cooling with ice. The suspension was stirred for 1 h at room temperature and then filtered through sodium sulfate. The residue was washed with tetrahydrofuran and the filtrate was concentrated i. vac.

Yield: 689 mg (96%), colourless oil $^1$H-NMR (CDCl$_3$): 1.11-1.20 (2H, m); 1.22-1.36 (4H, m); 1.40-1.70 (12H, m); 1.98 (1H, br s); 2.05 (1H, m); 2.26 (6H, s); 2.61 (2H, s); 2.93 (2H, t, J=7.0 Hz).

LC-MS: [M+H]$^+$: m/z=251.4, R$_t$=0.3 min.

Step 4: (8-Cyclopentyl-8-dimethylamino-3-azaspiro [4.5.]decan-3-ylphenylmethanone (Example No. 67, a Diastereomer)

Benzoyl chloride (231 mg, 189 µl, 1.64 mmol) was added to a solution of 8-cyclopentyl-8-dimethylamino-2-azaspiro [4.5]decan-1-one (345 mg, 1.37 mmol) and triethylamine (207 mg, 284 µl, 2.05 mmol) in anhydrous methylene chloride (12 ml) and the mixture was stirred for 5 h at room temperature. 25% strength potassium carbonate solution (13 ml) was then added to the reaction mixture and the mixture was stirred for 15 min at room temperature. The phases were separated and the aqueous phase was extracted with methylene chloride (2×15 ml). The combined organic phases were dried with sodium sulfate and concentrated i. vac. The residue was taken up in diethyl ether (20 ml) and the solution was extracted with 10% strength formic acid solution (3×40 ml). The combined acid, aqueous phases were rendered alkaline with 4 M sodium hydroxide solution and extracted with methylene chloride (4×30 ml). The combined organic phases were dried with sodium sulfate and concentrated i. vac.

Example No. 67 (a Diastereoisomer)

Yield: 460 mg (94%), colourless oil $^1$H-NMR (CDCl$_3$): 1.11-1.39 (6H, m); 1.40-1.86 (12H, m); 2.05 (1H, m); 2.20 (4H, s); 2.28 (2H, s); 3.17 (1.3H, s); 3.41 (0.7H, s); 3.47 (0.6H, t, J=7.0 Hz); 3.71 (1.4H, t, J=7.3 Hz); 7.35-7.41 (3H, m); 7.45-7.52 (2H, m).

$^{13}$C-NMR (CDCl$_3$): 25.1; 26.9; 27.0; 28.4; 29.2; 30.0; 32.0; 33.9; 37.7; 37.9; 40.9; 42.7; 44.0; 44.3; 44.9; 48.2; 57.8; 57.9; 59.5; 62.9; 127.0; 128.2; 129.5; 137.3; 169.8.

LC-MS: [M+H]$^+$: m/z=355.4, R$_t$=2.9 min.

Example No. 69 and Example No. 70

Step 1: 10-Benzyl-1,4-dioxa-10-azadispiro[4.2.4.2.] tetradecan-9-one

A solution of substance D (equation 1) (1.4 g, 6.6 mmol) and potassium tert-butanolate (892 mg, 7.95 mmol) in N,N-dimethylformamide (15 ml) was stirred for 30 min at room temperature and benzyl bromide (1.36 g, 950 µl, 7.95 mmol) was then added. After 4 h at room temperature the reaction mixture was diluted with ethyl acetate (100 ml) and washed with water (3×40 ml). The organic phase was dried with sodium sulfate and concentrated i. vac.

Yield: 1.94 g (97%), brown oil $^1$H-NMR (CDCl$_3$): 1.44-1.65 (4H, m); 1.83-1.95 (4H, m); 2.00-2.09 (2H, m); 3.14 (2H, dd, J=6.6 and 7.3 Hz); 3.92-3.97 (4H, m); 4.45 (2H, s); 7.17-7.23 (2H, m); 7.26-7.35 (3H, m).

Step 2: 10-Benzyl-1,4-dioxa-10-azadispiro[4.2.4.2] tetradecane

A solution of 10-benzyl-1,4-dioxa-10-azadispiro[4.2.4.2] tetradecan-9-one (1.94 g, 6.43 mmol) in tetrahydrofuran (40 ml) was added to a suspension of lithium aluminium hydride (962 mg, 25.7 mmol) in tetrahydrofuran (8 ml) at room temperature and the mixture was stirred for 18 h at 60° C. The reaction mixture was cooled to 0° C., water (1 ml), 1 N sodium hydroxide solution (1 ml) and again water (3 ml) were added and the mixture was stirred for 1 h at room temperature. The suspension was filtered through sodium sulfate and the residue was washed with tetrahydrofuran (20 ml). The filtrate was concentrated, and dried i. vac.

Yield: 1.80 g (97%), yellowish oil.

$^1$H-NMR (CDCl$_3$): 1.54-1.65 (10H, m); 2.36 (2H, s); 2.56 (2H, t, J=6.9 Hz); 3.56 (2H, s); 3.91 (4H, m); 7.18-7.36 (5H, m).

LC-MS: [M+H]$^+$: m/z=288.3, R$_t$=2.1 min.

Step 3: 2-Benzyl-2-azaspiro[4.5.]decan-8-one

A solution of 10-benzyl-1,4-dioxa-10-azadispiro[4.2.4.2] tetradecane (1.80 g, 6.2 mmol) in 1 M sulfuric acid (60 ml) was stirred for 20 h at room temperature. The reaction solution was then washed with diethyl ether (2×25 ml), rendered alkaline (pH~9) with 4 M sodium hydroxide solution and extracted with methylene chloride (3×25 ml). The combined organic methylene chloride phases were dried with sodium sulfate and concentrated i. vac.

Yield: 1.10 g (73%), colourless oil $^1$H-NMR (CDCl$_3$): 1.78 (2H, t, J=6.9 Hz); 1.87 (4H, t, J=6.9 Hz); 2.25-2.40 (4H, m); 2.49 (2H, s); 2.67 (2H, t, J=6.9 Hz); 3.62 (2H, s); 7.22-7.35 (5H, m).

Step 4: 2-Benzyl-8-dimethylamino-2-azaspiro[4.5.] decane-8-carbonitrile

4 N hydrochloric acid (1.35 ml, 5.4 mmol) and then a solution of 2-benzyl-2-azaspiro[4.5]decan-8-one (1.10 g, 4.5 mmol) in methanol (10 ml) and tetrahydrofuran (4 ml) were added to a 40% strength aqueous dimethylamine solution (2.3 ml, 18.1 mmol), cooled to 0° C. Potassium cyanide (586 mg, 9 mmol) was added to this mixture and the mixture was stirred for 20 h at room temperature. After addition of water (30 ml) the mixture was extracted with methylene chloride (3×50 ml). The combined organic extracts were dried with sodium sulfate and concentrated.

Yield: 1.27 g (95%), yellowish oil.

$^1$H-NMR (CDCl$_3$): 1.53-1.79 (8H, m); 2.00-2.09 (2H, m); 2.31 (1H, m); 2.32 (3H, s); 2.35 (3H, s); 2.36-2.37 (1H, m); 2.55-2.61 (2H, m); 3.56 (2H, s); 7.20-7.26 (1H, m); 7.28-7.32 (4H, m).

Step 5: [3-Benzyl-8-(dimethylamino)-3-azaspiro[4.5]decan-8-yl]-phenylmethanone (Example No. 69, Non-Polar Diastereomer and Example No. 70, Polar Diastereomer)

A 1.8 M solution of phenyllithium in di-n-butyl ether (2.1 ml, 3.78 mmol) was added dropwise to a solution of 2-benzyl-8-dimethylamino-2-azaspiro[4.5]decane-8-carbonitrile (927 mg, 3.1 mmol) in anhydrous tetrahydrofuran (8 ml) at 0° C. under argon. The reaction solution was warmed slowly to room temperature and then stirred for 20 h. Thereafter, 2 M hydrochloric acid (5.5 ml) was added at 0° C., the mixture was stirred for 5 h at room temperature, water (5 ml) was added and the mixture was rendered alkaline (pH~9-10) with 4 M sodium hydroxide solution. The phases were separated and the aqueous phase was extracted with methylene chloride (3×20 ml). The combined organic phases were dried with sodium sulfate and concentrated i. vac. The crude product was purified by flash chromatography (60 g, silica gel PharmPrep 60 CC, 13×4 cm) with ethyl acetate/cyclohexane (1:4) and 0.5% ammonia (25% in $H_2O$).

Example No. 69 (Non-Polar Diastereoisomer)

Yield: 40 mg (3%), yellowish oil.
$^1$H-NMR ($CDCl_3$): 1.24-1.31 (2H, m); 1.45 (2H, t, J=6.9 Hz); 1.47-1.56 (4H, m); 1.97-2.04 (2H, m); 2.23 (6H, s); 2.37 (2H, s); 2.45 (2H, t, J=6.9 Hz); 3.54 (2H, s); 7.14-7.34 (7H, m); 7.37-7.43 (1H, m); 8.14-8.16 (1H, m); 8.16-8.18 (1H, m).
$^{13}$C-NMR ($CDCl_3$): 25.5; 35.0; 38.4; 39.7; 41.4; 52.9; 60.5; 63.5; 69.0; 126.9; 127.8; 128.2; 128.6; 129.5; 131.5; 138.1; 203.9.
LC-MS: $[M+H]^+$: m/z=377.4, $R_t$=2.0 min.

Example No. 70 (Polar Diastereoisomer)

Yield: 40 mg (3%), yellowish oil.
$^1$H-NMR ($CDCl_3$): 1.25-1.35 (2H, m); 1.47-1.55 (2H, m); 1.62-1.72 (4H, m); 2.02-2.10 (2H, m); 2.22 (2H, s); 2.32 (6 h, s); 2.58 (2H, t, J=6.8 Hz); 3.53 (2H, s); 7.18-7.38 (7H, m); 7.43-7.48 (1H, m); 8.19-8.24 (2H, m).
$^{13}$C-NMR ($CDCl_3$): 42.7; 34.5; 34.7; 38.4; 41.2; 54.2; 60.5; 68.7; 69.2; 126.9; 127.8; 128.2; 128.7; 129.5; 131.5; 138.0; 203.9.
LC-MS: $[M+H]^+$: m/z=377.4, $R_t$=2.3 min.

Example No. 71 and Example No. 72

[3-Benzyl-8-(dimethylamino)-3-azaspiro[4.5]decan-8-yl]-thiophen-2-ylmethanone (Example No. 71, Non-Polar Diastereomer and Example No. 72, Polar Diastereomer)

A 1 M solution of 2-thienyllithium in tetrahydrofuran (9.7 ml, 9.68 mmol) was added dropwise to a solution of 2-benzyl-8-dimethylamino-2-azaspiro[4.5]decane-8-carbonitrile (Example no. 178, step 4) (2.4 g, 8.1 mmol) in anhydrous tetrahydrofuran (24 ml) at 0° C. under argon. The reaction solution was warmed slowly to room temperature and stirred for 20 h. 2 M hydrochloric acid (20 ml) was then added at 0° C., the mixture was stirred for 5 h at room temperature and thereafter the mixture was rendered alkaline (pH~9-10) with 4 M sodium hydroxide solution and extracted with methylene chloride (3×50 ml). The combined organic phases were dried with sodium sulfate and concentrated i. vac. Since the imine hydrolysis was not complete, 2 M hydrochloric acid was added to the residue (2.8 g) and the mixture was stirred for 48 h at room temperature. The reaction mixture was then washed with diethyl ether (10 ml), rendered alkaline (pH~9-10) with 4 M sodium hydroxide solution and extracted with methylene chloride (3×25 ml). The combined organic phases were dried with sodium sulfate and concentrated i. vac. The crude product (2 g) was purified by flash chromatography (200 g, 26×5 cm) with ethyl acetate/cyclohexane (1:2) and 0.5% ammonia (25% in $H_2O$). The impure polar diastereoisomer (170 mg) was purified again by flash chromatography (16 g, 20×2 cm) with ethyl acetate/cyclohexane (1:2) and 0.5% ammonia (25% in $H_2O$).

Example No. 71 (Non-Polar Diastereoisomer)

Yield: 170 mg (6%), yellow oil
$^1$H-NMR ($CDCl_3$): 1.52-1.65 (8H, m); 1.94-2.02 (2H, m); 2.20-2.31 (6H, m); 2.44 (2H, s); 2.53 (2H, t, J=7.0 Hz); 3.61 (2H, s); 7.04 (1H, t, J=4.3 Hz); 7.27-7.38 (5H, m); 7.45 (1H, d, J=5.0 Hz); 7.93 (1H, d, J=3.2 Hz).
$^{13}$C-NMR ($CDCl_3$): 26.0; 34.9; 38.5; 39.7; 41.3; 53.0; 60.5; 63.4; 68.1; 126.5; 126.9; 128.2, 128.6, 133.5; 133.8; 138.4; 197.9.
LC-MS: $[M+H]^+$: m/z=383.3, $R_t$=2.3 min.

Example No. 72 (Polar Diastereoisomer)

Yield: 140 mg (4%), yellow oil
$^1$H-NMR ($CDCl_3$): 1.50-1.72 (8H, m); 1.93-2.00 (2H, m); 2.27 (2H, m); 2.29 (6H, s); 2.59 (2H, t, J=6.8 Hz); 3.54 (2H, s); 7.03 (1H, dd, J=5.0 Hz); 7.18-7.33 (5H, m); 7.45 (1H, br dd, J=5.0 and 1.0 Hz); 7.91 (1H, br dd, J=3.8 and 1.1 Hz).
LC-MS: $[M+H]^+$: m/z=377.4, $R_t$=2.3 min.

Example No. 73

Step 1: 2-[4-(Azetidin-1-yl)-4-(2-thienyl)cyclohexylidene]-acetic acid ethyl ester Potassium tert-butylate (2.82 g, 25.1 mmol) was added to a solution of phosphonoacetic acid triethyl ester (5.60 g, 4.8 ml, 25.1 mmol) in anhydrous N,N-dimethylformamide (30 ml) under argon and the mixture was stirred for 10 min at room temperature. A solution of 4-(azetidin-1-yl)-4-(thiophen-2-yl)cyclohexanone (3.96 g, 16.8 mmol) in anhydrous N,N-dimethylformamide (60 ml) was then added to the mixture and the mixture was stirred for 1 h at room temperature and then poured into ice-water (80 g). The aqueous suspension was extracted with diethyl ether (4×40 ml). The combined organic extracts were dried with sodium sulfate and concentrated i. vac.

Yield: 4.79 g (93%), brownish oil
$^1$H-NMR ($CDCl_3$): 1.26 (t, 3H, J=7.1 Hz); 1.76-1.85 (m, 2H); 1.87-2.02 (m, 4H); 2.12-2.20 (m, 1H); 2.44-2.57 (m, 1H); 2.89-3.05 (m, 2H); 3.11 (t, 4H, J=6.9 Hz); 4.13 (q, 2H, J=7.1 Hz); 5.61 (br s, 1H); 6.89 (d, 1H, J=3.5 Hz); 7.08 (dd, 1H, J=5.1, 1.5 Hz); 7.25-7.28 (m, 1H, overlapped by the $CDCl_3$ signal).

Step 2: 2-[4-(Azetidin-1-yl)-1-(nitromethyl)-4-(2-thienyl)cyclohexyl]-acetic acid ethyl ester Nitromethane (1.24 g, 1.09 ml, 20.3 mmol) was added to a mixture of 2-[4-(azetidin-1-yl)-4-(2-thienyl)cyclohexylidene]-acetic acid ethyl ester (4.79 g, 15.7 mmol) and tetra-n-butylammonium fluoride trihydrate (5.43 g, 17.2 mmol) in tetrahydrofuran (150 ml) and the mixture was stirred for 6 h at 70° C. and 18 h at 45° C. The reaction mixture was then concentrated i. vac. and the crude product (12.0 g) was purified by flash chromatography (200 g, 20×5.7 cm) with ethyl acetate/cyclohexane (9:1).

Yield: 4.18 g (74%), yellowish oil.

$^1$H-NMR (DMSO-d$_6$): 1.10-1.24 (m, 3H); 1.37-1.47 (m, 2H); 1.63-1.86 (m, 8H); 2.42 and 2.46 (2 s, 2H); 2.92-2.99 (m, 4H); 3.98-4.05 (m, 2H); 4.68 and 4.69 (2 s, 2H); 6.96 (dt, 1H, J=3.5, 1.1 Hz); 7.09-7.12 (m, 1H); 7.47 (dd, 1H, J=5.1, 1.0 Hz).

This is a diastereoisomer mixture in the ratio of approx. 2:3.

Step 3: 8-(Azetidin-1-yl)-8-(2-thienyl)-3-azaspiro [4.5]decan-2-one

A solution of 2-[4-(azetidin-1-yl)-1-(nitromethyl)-4-(2-thienyl)cyclohexyl]-acetic acid ethyl ester (3.90 g, 10.7 mmol) in ethanol (100 ml) was added to a mixture of iron powder (2.84 g, 53 mmol), ammonium chloride (14.2 g, 265 mmol) and water (10 ml) and the mixture was then stirred for 4 h at 80° C. The mixture was filtered and the residue was washed with ethanol. The filtrate was rendered alkaline by addition of 5% strength sodium bicarbonate solution (8 ml) and then concentrated i. vac. The crude product (6.30 g) was purified by flash chromatography (200 g, 20×5.7 cm) with methylene chloride/methanol (95:5) and 1% ammonia (25% in water). The mixture of non-polar and polar diastereoisomer isolated (1.60 g) was purified by medium pressure chromatography under 8-10 bar on a PuriFlash cartridge (PF-15SIHP, 40 g, 15 μm) and 2 PuriFlash cartridges (PF-15SIHP, 120 g, 15 μm) with methylene chloride/isopropanol (9:1) and 1% ammonia (25% in water).

Non-Polar Diastereoisomer

Yield: 504 mg (16%), white solid

Melting point: 180-183° C.

$^1$H-NMR (DMSO-d$_6$): 1.31-1.40 (m, 2H); 1.63-1.77 (m, 8H); 2.02 (s, 2H); 2.93 (s, 2H); 2.96 (t, 4H, J=6.9 Hz); 6.95 (d, 1H, J=3.5 Hz); 7.10 (dd, 1H, J=8.6, 3.5 Hz); 7.41 (br s, 1H); 7.46 (d, 1H, J=5.1 Hz).

Polar Diastereoisomer

Yield: 772 mg (25%), white solid

Melting point: 170-172° C.

$^1$H-NMR (DMSO-d$_6$): 1.30-1.40 (m, 2H); 1.62-1.82 (m, 8H); 1.93 (s, 2H); 2.96 (t, 4H, J=6.9 Hz); 3.03 (s, 2H); 6.95 (dd, 1H, J=3.5 Hz, 1.1 Hz); 7.10 (dd, 1H, J=5.1, 3.5 Hz); 7.45 (br s, 1H); 7.46 (dd, 2H, J=5.1 Hz, 1.0 Hz).

Step 4: 8-(Azetidin-1-yl)-8-(2-thienyl)-3-azaspiro [4.5]decan-2-one (Polar Diastereomer)

A solution of 8-(azetidin-1-yl)-8-(2-thienyl)-3-azaspiro [4.5]decan-2-one (polar diastereoisomer) (765 mg, 2.63 mmol) in anhydrous tetrahydrofuran (50 ml) was added dropwise to a suspension of lithium aluminium hydride (500 mg, 13.1 mmol) in anhydrous tetrahydrofuran (20 ml) at 0° C. under argon and the mixture was then stirred at 60° C. overnight. After addition of water (500 μl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.

Yield: 696 mg (96%), colourless oil $^1$H-NMR (CDCl$_3$): 1.35 (ddd, 2H, J=13.1, 9.4, 3.7 Hz); 1.40-1.46 (m, 3H), 1.60-1.90 (m, 8H); 2.75 (s, 2H); 2.89 (t, 2H, J=7.1 Hz); 3.07 (t, 4H, J=7.0 Hz); 6.88 (dd, 1H, J=3.5, 1.1 Hz); 7.09 (dd, 1H, J=5.1, 3.5 Hz); 7.27 (dd, 1H, J=5.1, 1.1 Hz).

Step 5: (E)-1-[8-(Azetidin-1-yl)-8-thiophen-2-yl-3-azaspiro[4.5]decan-3-yl]-3-phenylprop-2-en-1-one (Example No. 73, Polar Diastereomer)

Triethylamine (94 mg, 129 μl, 0.93 mmol) and cinnamyl chloride (122 mg, 0.73 mmol) were added to a solution of 8-(azetidin-1-yl)-8-(2-thienyl)-3-azaspiro[4.5]decane (polar diastereomer) (170 mg, 0.61 mmol) in anhydrous methylene chloride (5 ml) and the mixture was stirred for 5 h at room temperature. After addition of methylene chloride (20 ml) the solution was washed with 25% strength potassium carbonate solution (2×10 ml) and the organic phase was dried with sodium sulfate and concentrated i. vac. The crude product (271 mg) was purified by flash chromatography (10 g, 20×1.5 cm) with methylene chloride/methanol (95:5) and 1% ammonia (25% in water).

Example No. 73 (Polar Diastereoisomer)

Yield: 130 mg (52%), white solid $^1$H-NMR (CDCl$_3$): 1.35-1.46 (m, 2H); 1.64 (t, 1H, J=7.2 Hz); 1.67-2.03 (m, 9H); 3.07 (dd, 4H, J=14.7, 7.6 Hz); 3.50 and 3.52 (2 s, 2H); 3.60 and 3.65 (2 t, 2H, J=7.2 Hz); 6.71 and 6.73 (2 d, 1H, J=15.5 Hz); 6.87-6.89 (m, 1H); 7.08 and 7.11 (2 dd, 1H, J=5.1, 3.5 Hz); 7.26-7.31 (m, 1H); 7.32-7.42 (m, 3H); 7.49-7.57 (m, 2H); 7.69 and 7.70 (2 d, 1H, J=15.5 Hz).

$^{13}$C-NMR (CDCl$_3$): 16.0; 16.1; 30.9; 31.0; 31.7; 35.4; 36.7; 40.2; 42.3; 44.4; 45.0; 46.7; 46.8; 56.0; 56.6; 58.8; 59.0; 118.5; 118.6; 123.5; 123.7; 124.7; 125.1; 126.4; 126.6; 127.8; 127.9; 128.73; 128.75; 129.48; 129.53; 135.3; 135.4; 141.7; 164.8; 164.9.

The NMR spectra show sometimes doubled signal sets (rotamers).

LC-MS: m/z: [M+H]$^+$=407.4, R$_t$=3.1 min.

Example No. 74

Step 1: 8-(Azetidin-1-yl)-8-(2-thienyl)-3-azaspiro [4.5]decane (Non-Polar Diastereomer)

A solution of 8-(azetidin-1-yl)-8-(2-thienyl)-3-azaspiro [4.5]decan-2-one (non-polar diastereoisomer) (504 mg, 1.73 mmol) in anhydrous tetrahydrofuran (50 ml) was added dropwise to a suspension of lithium aluminium hydride (330 mg, 8.65 mmol) in anhydrous tetrahydrofuran (20 ml) at 0° C. under argon and the mixture was then stirred overnight at 60° C. After addition of water (300 μl), 1 N sodium hydroxide solution (800 μl) and water again (800 μl) the mixture was stirred for 1 h at room temperature and thereafter was filtered through sea sand. The filtrate was dried with sodium sulfate and concentrated i. vac.

Yield: 414 mg (87%), oil $^1$H-NMR (CDCl$_3$): 1.35 (ddd, 2H, J=13.4, 9.9, 3.7 Hz); 1.56-1.64 (m, 3H); 1.70-1.93 (m, 8H); 2.55 (s, 2H); 2.94 (t, 2H, J=7.1 Hz); 3.08 (t, 4H, J=7.1 Hz); 6.87 (dd, 1H, J=3.5, 1.1 Hz); 7.08 (dd, 1H, J=5.1, 3.5 Hz); 7.27 (dd, 1H, J=5.1, 1.1 Hz).

Step 2: (E)-1-[8-(Azetidin-1-yl)-8-thiophen-2-yl-3-azaspiro[4.5]decan-3-yl]-3-phenylprop-2-en-1-one (Example No. 74, Non-Polar Diastereomer)

Triethylamine (111 mg, 152 μl, 1.1 mmol) and cinnamyl chloride (143 mg, 0.86 mmol) were added to a solution of 8-(azetidin-1-yl)-8-(2-thienyl)-3-azaspiro[4.5]decane (non-polar diastereomer) (200 mg, 0.72 mmol) in anhydrous methylene chloride (5 ml) and the mixture was stirred for 3 h at room temperature. After addition of methylene chloride (20 ml) the solution was washed with 25% strength potassium carbonate solution (2×20 ml) and the organic phase was dried with sodium sulfate and concentrated i. vac. The crude product (330 mg) was purified by flash chromatography (10 g, 20×1.5 cm) with methylene chloride/methanol (95:5) and 1% ammonia (25% in water).

Example No. 74 (Non-Polar Diastereoisomer)

Yield: 226 mg (77%), colourless oil
$^1$H-NMR (CDCl$_3$): 1.38-1.48 (m, 2H); 1.62 (s, 1H); 1.68-1.88 (m, 8H); 1.92 (t, 1H, J=7.2 Hz); 3.09 (t, 4H, J=6.9 Hz); 3.35 (d, 2H, J=2.7 Hz); 3.65 (t, 1H, J=7.3 Hz); 3.70 (t, 1H, J=7.1 Hz); 6.63 (d, 0.5H, J=15.5 Hz); 6.71 (d, 0.5H, J=15.5 Hz); 6.87 (dd, 1H, J=8.9, 3.5 Hz); 7.06-7.11 (m, 1H); 7.26-7.39 (m, 4H); 7.47-7.54 (m, 2H); 7.66 (dd, 1H, J=15.5, 7.4 Hz).
$^{13}$C-NMR (CDCl$_3$): 15.9; 30.8; 30.85; 31.3; 40.2; 42.4; 44.6; 45.1; 46.7; 118.4; 118.7; 123.6; 126.5; 127.81; 127.83; 128.69; 128.75; 129.47; 129.5; 135.3; 135.4; 141.69; 141.74; 164.8.
The NMR spectra show sometimes doubled signal sets (rotamers).
LC-MS: m/z: [M+H]$^+$=407.3, R$_f$=3.0 min.

Example No. 78

Step 1: (4-Azetidin-1-yl-4-phenylcyclohexylidene)acetic acid ethyl ester

Potassium tert-butylate (3.52 g, 31.4 mmol) was added to a solution of phosphonoacetic acid triethyl ester (7.03 g, 6.2 ml, 31.4 mmol) in anhydrous N,N-dimethylformamide (30 ml) under argon and the mixture was stirred for 10 min at room temperature. A solution of 4-(azetidin-1-yl)-4-phenyl-cyclohexanone (4.81 g, 21 mmol) in anhydrous N,N-dimethylformamide (60 ml) was then added to the mixture and the mixture was stirred for 1 h at room temperature and then poured into ice-water (80 g). The aqueous suspension was extracted with diethyl ether (4×40 ml). The combined organic extracts were dried with sodium sulfate and concentrated i. vac.
Yield: 6.30 g (100%), yellowish oil.
$^1$H-NMR (DMSO-d$_6$): 1.18 (t, 3H, J=7.1 Hz); 1.65 (quin, 2H, J=7.0 Hz); 1.75-1.90 (m, 2H); 1.96-2.10 (m, 3H); 2.73-2.82 (m, 2H); 2.88-2.96 (m, 1H); 2.90 (t, 4H, J=6.9 Hz); 4.05 (q, 2H, J=7.1 Hz); 5.62 (s, 1H); 7.23-7.45 (m, 5H).

Step 2: (4-Azetidin-1-yl-1-nitromethyl-4-phenylcyclohexyl)acetic acid ethyl ester Nitromethane (1.65 g, 1.45 ml, 27.1 mmol) was added to a mixture of (4-azetidin-1-yl-4-phenylcyclohexylidene)acetic acid ethyl ester (6.30 g, 21 mmol) and tetra-n-butylammonium fluoride trihydrate (7.26 g, 23 mmol) in tetrahydrofuran (150 ml) and the mixture was stirred for 6 h at 70° C. and 18 h at 45° C. Since the reaction was not complete, tetra-n-butylammonium fluoride trihydrate (2.42 g, 7.6 mmol) and nitromethane (550 mg, 483 µl, 9 mmol) were again added and the mixture was stirred for a further 5 h at 70° C. and 18 h at 45° C. The reaction mixture was concentrated in vacuo and the residue (17.0 g) was purified by flash chromatography (200 g, 20×5.7 cm) with ethyl acetate/methanol (95:5).
Yield: 4.92 g (65%), brownish oil
$^1$H-NMR (DMSO-d$_6$): 1.10 and 1.18 (2 t, 3H, J=7.1 Hz); 1.30-1.42 (m, 2H); 1.62 (t, 2H, J=6.8 Hz); 1.70-1.80 (m, 4H); 1.85-1.95 (m, 2H); 2.36 (s, 1H); 2.84 (t, 4H, J=6.8 Hz); 3.95-4.08 (m, 2H); 4.63 and 4.73 (m, 2H); 7.26-7.45 (m, 5H).
LC-MS: m/z: [M+H]$^+$=361.4, R$_f$=2.6 and 2.7 min.
A diastereoisomer mixture in the ratio of 4:3 is present.

Step 3: 8-Azetidin-1-yl-8-phenyl-2-azaspiro[4.5.]decan-3-one

A solution of (4-azetidin-1-yl-1-nitromethyl-4-phenylcyclohexyl)acetic acid ethyl ester (4.92 g, 13.5 mmol) in ethanol (130 ml) was added to a mixture of iron powder (3.58 g, 67 mmol), ammonium chloride (17.9 g, 334 mmol) and water (13 ml) and the mixture was then stirred for 4 h at 80° C. and overnight at 65° C. The mixture was filtered and the residue on the filter was washed with ethanol. The filtrate was rendered alkaline by addition of 5% strength sodium bicarbonate solution (8 ml) and then concentrated i. vac. The residue (10.0 g) was purified by flash chromatography (400 g, 20×7.5 cm) with methylene chloride/methanol (95:5) and 1% ammonia (25% in water). The mixture of non-polar and polar diastereoisomer isolated (1.80 g) was purified by flash chromatography on two columns with PharmPrep (40-63 µm, 200 g, 20×5.7 cm) and the mixed fractions (670 mg) thereby obtained were purified on a PuriFlash cartridge (PF-15SIHP, 200 g, 15 µm), in each case with methylene chloride/ethanol (95:5) and 1% ammonia (25% in water).
Non-Polar Diastereoisomer
Yield: 719 mg (19%), white solid
Melting point: 180-187° C.
$^1$H-NMR (DMSO-d$_6$): 1.21-1.31 (m, 2H); 1.56-1.84 (m, 8H); 2.06 (s, 2H); 2.85 (t, 4H, J=6.8 Hz); 2.88 (s, 2H); 7.22-7.46 (m, 6H).
LC-MS: m/z: [M+H]$^+$=285.4, R$_f$=1.9 min.
Polar Diastereoisomer
Yield: 907 mg (24%), white solid
Melting point: 150-155° C.
$^1$H-NMR (DMSO-d$_6$): 1.20-1.33 (m, 2H); 1.58-1.87 (m, 8H); 1.88 (s, 2H); 2.84 (t, 4H, J=6.8 Hz); 3.07 (s, 2H); 7.25-7.49 (m, 6H).
LC-MS: m/z: [M+H]$^+$=285.4, R$_f$=1.8 min.

Step 4: 8-Azetidin-1-yl-8-phenyl-2-azaspiro[4.5]decane (Polar Diastereomer)

A solution of 8-azetidin-1-yl-8-phenyl)-2-azaspiro[4.5]decan-3-one (polar diastereoisomer) (892 mg, 3.14 mmol) in anhydrous tetrahydrofuran (80 ml) was added dropwise to a suspension of lithium aluminium hydride (599 mg, 15.7 mmol) in anhydrous tetrahydrofuran (20 ml) at 0° C. under argon and the mixture was then stirred at 60° C. overnight. After addition of water (500 µl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.
Yield: 830 mg (98%), colourless oil
$^1$H-NMR (DMSO-d$_6$): 1.12-1.22 (m, 2H); 1.23-1.30 (m, 2H); 1.52-1.66 (m, 4H); 1.70-1.81 (m, 3H); 2.53 (s, 2H);

2.70 (t, 2H, J=7.1 Hz); 2.82 (t, 4H, J=6.8 Hz); 3.34-3.42 (m, 2H); 7.24-7.34 (m, 3H); 7.37-7.43 (m, 2H).

LC-MS: m/z: [M+H]$^+$=271.4, R$_t$=0.4 min.

Step 5: (E)-1-[8-(Azetidin-1-yl)-8-phenyl-3-azaspiro [4.5]decan-3-yl]-3-phenylprop-2-en-1-one (Example No. 78, Polar Diastereomer)

Triethylamine (93 mg, 127 µl, 0.92 mmol) and cinnamyl chloride (119 mg, 0.72 mmol) were added to a solution of 8-azetidin-1-yl-8-phenyl)-3-azaspiro[4.5]decane (polar diastereoisomer) (162 mg, 0.6 mmol) in anhydrous methylene chloride (5 ml) and the mixture was stirred for 2 h at room temperature. After addition of methylene chloride (20 ml) the solution was washed with 25% strength potassium carbonate solution (2×20 ml) and the organic phase was dried with sodium sulfate and concentrated i. vac. The crude product (241 mg) was purified by flash chromatography (10 g, 20×1.5 cm) with methylene chloride/methanol (95:5) and 1% ammonia (25% in water).

Example No. 78 (Polar Diastereoisomer)

Yield: 139 mg (58%), white solid

Melting point: 65-69° C.

$^1$H-NMR (CDCl$_3$): 1.20-1.40 (m, 2H); 1.51 (t, 1H, J=7.2 Hz); 1.60-1.90 (m, 7H); 1.90-2.20 (m, 2H); 3.00 (t, 4H, J=6.8 Hz); 3.50-3.67 (m, 4H); 6.70 (t, 1H, J=15.8 Hz); 7.25-7.50 (m, 8H); 7.50-7.64 (m, 2H); 7.70 (dd, 1H, J=15.5, 5.4 Hz).

$^{13}$C-NMR (CDCl$_3$): 16.5; 16.8; 28.5; 29.5; 31.0; 31.1; 40.4; 42.4; 44.3; 44.9; 46.6; 46.7; 55.7; 56.4; 59.3; 59.6; 118.5; 118.7; 126.6; 126.8; 127.5; 127.7; 127.8; 127.85; 127.9; 128.0; 128.72; 128.75; 129.47; 129.51; 135.3; 135.4; 138.1; 141.7; 164.8; 164.9.

The NMR spectra show sometimes doubled signal sets (rotamers).

LC-MS: m/z: [M+H]$^+$=401.4, R$_t$=3.2 min.

Example No. 79

Step 1: 8-Azetidin-1-yl-8-phenyl-2-azaspiro[4.5] decane (Non-Polar Diastereomer)

A solution of 8-azetidin-1-yl-8-phenyl)-3-azaspiro[4.5] decan-2-one (non-polar diastereoisomer) (701 mg, 2.46 mmol) in anhydrous tetrahydrofuran (100 ml) was added dropwise to a suspension of lithium aluminium hydride (470 mg, 12.3 mmol) in anhydrous tetrahydrofuran (20 ml) at 0° C. under argon and the mixture was then stirred at 60° C. overnight. After addition of water (500 µl), 1 N sodium hydroxide solution (1.3 ml) and water again (1.3 ml) the mixture was stirred for one hour at room temperature and thereafter filtered through sea sand and the filtrate was dried with sodium sulfate and concentrated i. vac.

Yield: 663 mg (95%), colourless oil $^1$H-NMR (DMSO-d$_6$): 1.10-1.20 (m, 2H); 1.48 (t, 2H, J=7.0 Hz); 1.50-1.66 (m, 4H); 1.70-1.80 (m, 3H); 2.34 (s, 2H); 2.74 (t, 2H, J=7.0 Hz); 2.84 (t, 4H, J=6.8 Hz); 3.20-3.40 (m, 2H); 7.23-7.34 (m, 3H); 7.36-7.42 (m, 2H).

LC-MS: m/z: [M+H]$^+$=271.4, R$_t$=0.2 min.

Step 2: (E)-1-[8-(Azetidin-1-yl)-8-phenyl-3-azaspiro [4.5]decan-3-yl]-3-phenylprop-2-en-1-one (Example No. 79, Non-Polar Diastereomer)

Triethylamine (98 mg, 134 µl, 0.96 mmol) and cinnamyl chloride (125 mg, 0.75 mmol) were added to a solution of 8-azetidin-1-yl-8-phenyl)-3-azaspiro[4.5]decane (non-polar diastereoisomer) (170 mg, 0.63 mmol) in anhydrous methylene chloride (5 ml) and the mixture was stirred for 2 h at room temperature. After addition of methylene chloride (20 ml) the solution was washed with 25% strength potassium carbonate solution (2×20 ml) and the organic phase was dried with sodium sulfate and concentrated i. vac. The crude product (240 mg) was purified by flash chromatography on PharmPrep (40-63 µm, 10 g, 20×1.5 cm) with methylene chloride/methanol (95:5) and 1% ammonia (25% in water).

Example No. 79 (Non-Polar Diastereoisomer)

Yield: 160 mg (63%), white solid

Melting point: 53-56° C.

$^1$H-NMR (CDCl$_3$): 1.30-1.40 (m, 2H); 1.60-2.01 (m, 10H); 2.98 (t, 4H, J=6.9 Hz); 3.28 (s, 2H); 3.65 (t, 1H, J=7.2 Hz); 3.71 (t, 1H, J=7.2 Hz); 6.65 (2 d, 1H, J=15.5 Hz); 7.27-7.52 (m, 10H); 7.65 (dd, 1H, J=15.5, 9.4 Hz).

$^{13}$C-NMR (CDCl$_3$): 16.5; 16.6; 28.8; 28.9; 29.0; 30.9; 31.0; 40.4; 42.6; 44.6; 45.2; 46.7; 56.5; 57.6; 59.2; 118.5; 118.7; 126.67; 126.7; 127.5; 127.6; 127.8; 127.85; 127.9; 128.67; 128.7; 129.4; 129.5; 135.3; 135.4; 137.7; 141.6; 141.7; 164.79; 164.8.

The NMR spectra show sometimes doubled signal sets (rotamers).

LC-MS: m/z: [M+H]$^+$=401.4, R$_t$=3.1 min.

Example No. 96 and Example No. 97

Step 1: Bromo-(5-methyl-2-thienyl)magnesium

Magnesium powder (0.06-0.3 mm, 875 mg, 36 mmol) was heated with an iodine crystal in a three-necked flask with a dropping funnel, reflux condenser and argon inlet until iodine gas was evolved. After 10 min anhydrous diethyl ether (10 ml) and a further iodine crystal were added. A solution of 2-bromo-5-methylthiophene (6.37 g, 4.06 ml, 36 mmol) in anhydrous diethyl ether (2 ml) was added dropwise to the boiling suspension such that the mixture boiled without heating. The mixture was then heated for a further 50 min under reflux and thereafter the solution was cooled to room temperature.

Yield: 12 ml of a 3 M solution of bromo-(5-methyl-2-thienyl)magnesium in diethyl ether.

Step 2: (1,4-Dioxaspiro[4.5.]dec-8-ylidene)acetic acid ethyl ester

Potassium tert-butylate (10.7 g, 95.6 mmol) was added to a solution of phosphonoacetic acid triethyl ester (21.4 g, 19 ml, 95.6 mmol) in anhydrous N,N-dimethylformamide (90 ml) under argon and the mixture was stirred for 10 min at room temperature. A solution of 1,4-dioxaspiro[4.5]decan-8-one (10.0 g, 64 mmol) in anhydrous N,N-dimethylformamide (160 ml) was then added to the mixture and the mixture was stirred for 1 h at room temperature and then poured into ice-water (240 g). The aqueous suspension was extracted with diethyl ether (4×100 ml). The combined organic extracts were dried with sodium sulfate and concentrated i. vac.

Yield: 14.4 g (100%), yellowish oil.

$^1$H-NMR (CDCl$_3$): 1.27 (3H, t, J=7.1 Hz); 1.73-1.80 (4H, m); 2.35-2.40 (2H, m); 2.92-3.02 (2H, m); 3.97 (4H, 5); 4.15 (2H, q, J=7.1 Hz); 5.66 (1H, s).

Step 3: 8-(2-Nitromethyl)-1,4-dioxaspiro[4.5.]decan-8-acetic acid ethyl ester Nitromethane (5.00 g, 4.4 ml, 82 mmol) was added to a mixture of (1,4-dioxaspiro[4.5]dec-8-ylidene)acetic acid ethyl ester (14.4 g, 63.6 mmol) and tetra-n-butylammonium fluoride trihydrate (21.9 g, 69.6 mmol) in tetrahydrofuran (150 ml) and the mixture was stirred for 6 h at 70° C. and 18 h at 45° C. The reaction mixture was then concentrated in vacuo and the crude product (40.0 g) was purified by flash chromatography (400 g, 20×7.5 cm) with methyl tert-butyl ether/cyclohexane (1:3).

Yield: 14.8 g (81%), colourless oil $^1$H-NMR (CDCl$_3$): 1.27 (3H, t, J=7.1 Hz); 1.64-1.75 (8H, m); 2.55 (2H, 5); 3.94 (4H, 5); 4.15 (2H, q, J=7.1 Hz); 4.71 (2H, s).

Step 4: 1,4-Dioxa-10-azadispiro[4.2.4.2]tetradecan-11-one

A solution of 8-(2-nitromethyl-1,4-dioxaspiro[4.5]decane-8-acetic acid ethyl ester (5.00 g, 17.4 mmol) in ethanol (170 ml) was added to a mixture of iron powder (4.85 g, 87 mmol), ammonium chloride (23.0 g, 430 mmol) and water (17 ml) and the mixture was then stirred for 6 h at 80° C. The mixture was filtered, the residue on the filter was washed with ethanol and the filtrate was concentrated i. vac. The white solid obtained (10 g) was taken up in water (80 ml) and the mixture was extracted with methylene chloride (4×50 ml).

Yield: 3.04 g (83%), white solid $^1$H-NMR (CDCl$_3$): 1.62-1.68 (4H, m); 1.70-1.75 (4H, m); 2.22 (2H, 5); 3.19 (2H, 5); 3.94 (4H, s); 5.80 (1H, br s).

Step 5: 2-Azaspiro[4.5]decane-3,8-dione

A solution of 1,4-dioxa-10-azadispiro[4.2.4.2]tetradecan-11-one (3.01 g, 14.2 mmol) in 5% strength sulfuric acid (70 ml) was stirred for 20 h at room temperature. The solution was then adjusted to pH 9 with 2 N sodium hydroxide solution, while cooling with ice, and then extracted with methylene chloride (10×30 ml). The combined organic phases were dried with sodium sulfate and concentrated i. vac.

Yield: 1.80 g (76%), white solid $^1$H-NMR (CDCl$_3$): 1.90-2.04 (4H, m); 2.36-2.42 (6H, m); 3.33 (2H, s); 6.34 (1H, br s).

$^{13}$C-NMR (CDCl$_3$): 36.1; 37.9; 38.8; 41.6; 52.5; 176.8; 209.6.

Step 6: 8-Dimethylamino-3-oxo-2-azaspiro[4.5]decane-8-carbonitrile

A 40% strength aqueous dimethylamine solution (4.81 ml, 34.1 mmol), then a solution of 2-azaspiro[4.5]decane-3,8-dione (1.19 g, 7.12 mmol) in methanol (10 ml) and thereafter potassium cyanide (1.11 g, 17.1 mmol) were added to a solution of methanol (2.3 ml) and 4 N hydrochloric acid (1.78 ml), while cooling with ice. The mixture was stirred for 72 h at room temperature, then diluted with water (20 ml) and extracted with diethyl ether (3×10 ml) and methylene chloride (3×20 ml). The combined organic phases were dried with sodium sulfate and concentrated i. vac.

Yield: 1.30 g (83%), white solid $^1$H-NMR (CDCl$_3$): 1.58-1.74 (4H, m); 1.78-1.88 (2H, m); 2.00-2.17 (2H, m); 2.19 and 2.23 (2H, 2 s); 2.35 and 2.36 (6H, 2 s); 3.17 and 3.20 (2H, 2 s); 5.90 (1H, br s).

This is a diastereoisomer mixture.

Step 7: 8-(Dimethylamino)-8-(5-methylthiophen-2-yl)-3-azaspiro[4.5]decan-2-one A suspension of 8-dimethylamino-3-oxo-2-azaspiro[4.5] decane-8-carbonitrile (852 mg, 3.85 mmol) in anhydrous tetrahydrofuran (50 ml) was added dropwise to a 3 M solution of bromo-(5-methyl-2-thienyl)magnesium (3.2 ml, 9.6 mmol) in anhydrous diethyl ether under argon and the mixture was then stirred at room temperature overnight. After addition of saturated ammonium chloride solution (15 ml) the phases were separated and the aqueous phase was extracted with ethyl acetate (3×30 ml). The combined organic phases were dried with sodium sulfate and concentrated i. vac.

Yield: 870 mg (78%), slightly orange-coloured solid

The diastereoisomers are present in the ratio of 1:2.

The diastereoisomer ratio was determined with the aid of the singlets of the HN—CH$_2$ group at 3.22 (polar diastereoisomer) and 3.07 ppm (non-polar diastereoisomer) in the $^1$H-NMR spectrum.

LC-MS: m/z: [M+H]$^+$=293.3, R$_f$=2.2 min.

Step 8: 8-(Dimethylamino)-8-(5-methylthiophen-2-yl)-2-oxo-3-azaspiro[4.5]decane-3-carboxylic acid tert-butyl ester (Example No. 96, Non-Polar Diastereomer and Example 97, Polar Diastereomer)

A solution of di-tert-butyl dicarbonate (2.14 g, 9.8 mmol) in anhydrous acetonitrile (30 ml) and 4-dimethylaminopyridine (110 mg, 0.89 mmol) was added to a solution of 8-(dimethylamino)-8-(5-methylthiophen-2-yl)-3-azaspiro [4.5]decan-2-one (diastereomer mixture) (2.60 g, 8.9 mmol) in anhydrous acetonitrile (140 ml) and anhydrous tetrahydrofuran (60 ml) and the mixture was stirred for 24 h at room temperature. Since the reaction was not complete, a solution of di-tert-butyl dicarbonate (700 mg, 2.9 mmol) in anhydrous acetonitrile (10 ml) was again added and the mixture was stirred over the weekend at room temperature. The solvent was then removed i. vac., the residue was dissolved in methylene chloride (100 ml) and the solution was washed with water (3×50 ml) and saturated sodium chloride solution (50 ml). The organic phase was dried with sodium sulfate and concentrated i. vac. The crude product (4.14 g) was purified by flash chromatography (400 g, 20×7.5 cm) with ethyl acetate/methanol (9:1).

Example No. 96 (Non-Polar Diastereoisomer)

Yield: 926 mg (26%), ochre-coloured solid

Melting point: 138-140° C.

$^1$H-NMR (CDCl$_3$): 1.40-1.51 (2H, m); 1.52 (9H, 5); 1.70-1.81 (2H, m); 1.90-2.08 (4H, m); 2.11 (6H, 5); 2.30 (2H, 5); 2.46 (3H, 5); 3.57 (2H, s); 6.61 (1H, d, J=3.4 Hz); 6.68 (1H, dd, J=3.3 and 0.8 Hz).

$^{13}$C-NMR (CDCl$_3$): 15.2; 28.1; 32.2; 32.4; 34.1; 38.1; 45.8; 56.5; 59.5; 82.8; 124.5; 14.9; 138.0; 150.1; 173.5.

LC-MS: m/z: [M+H]$^+$=393.4, R$_f$=2.8 min.

Example No. 97 (Polar Diastereoisomer)

Yield: 1.05 g (30%), sand-coloured solid

Melting point: 165-167° C.

$^1$H-NMR (CDCl$_3$): 1.44-1.54 (2H, m); 1.49 (9H, 5); 1.68-1.77 (2H, m); 1.86-2.10 (4H, m); 2.11 (6H, 5); 2.43

(2H, 5); 2.47 (3H, d, J=1.0 Hz); 3.42 (2H, 5); 6.62 (1H, d, J=3.5 Hz); 6.68 (1H, dd, J=3.4 and 1.1 Hz).

$^{13}$C-NMR (CDCl$_3$): 15.2; 28.0; 32.2; 32.3; 34.2; 38.1; 45.0; 57.3; 59.6; 82.7; 124.5; 125.0; 138.1; 150.1; 173.3.

LC-MS: m/z: [M+H]$^+$=393.4, R$_t$=3.1 min.

Example No. 102

Step 1: 8-Dimethylamino-8-phenyl-2-azaspiro[4.5]decan-3-one (Polar Diastereomer)

Trifluoroacetic acid (5 ml) was added to a solution of 8-dimethylamino-3-oxo-8-phenyl-2-azaspiro[4.5]decane-2-carboxylic acid tert-butyl ester (polar diastereoisomer) (1.28 g, 3.43 mmol) in anhydrous methylene chloride (50 ml) and the mixture was stirred for 3 h at room temperature. The reaction mixture was concentrated i. vac., the residue was dissolved in methylene chloride (50 ml) and the solution was washed with saturated sodium bicarbonate solution (3×20 ml). The organic phase was dried with sodium sulfate and concentrated i. vac.

Yield: 875 mg (94%), white solid

Melting point: 220-222° C.

$^1$H-NMR (CDCl$_3$): 1.34-1.44 (2H, m); 1.72-1.81 (2H, m); 1.86-2.02 (2H, br s); 2.04 (6H, s); 2.16-2.29 (2H, m); 2.30 (2H, s); 3.01 (2H, s); 5.60 (1H, s); 7.26-7.32 (3H, m); 7.36-7.41 (2H, m).

Step 2: 3-Benzyl-8-dimethylamino-8-phenyl-3-azaspiro[4.5]decan-2-one (Example No. 102, Polar Diastereomer)

Potassium tert-butylate (74 mg, 0.66 mmol) was added to a suspension of 8-dimethylamino-8-phenyl-2-azaspiro[4.5]decan-3-one (polar diastereomer) (150 mg, 0.55 mmol) in anhydrous N,N-dimethylformamide (10 ml) and the mixture was stirred for 40 min at room temperature. Benzyl bromide (113 mg, 79 μl, 0.66 mmol) was then added and the mixture was stirred for 18 h at room temperature. After addition of ethyl acetate (50 ml) the mixture was washed with water (3×20 ml). The organic phase was then extracted with 5% strength formic acid (3×20 ml). The combined aqueous, acid phases were adjusted to pH 10 with 5 N sodium hydroxide solution and extracted with ethyl acetate (3×20 ml). The combined organic phases were dried with sodium sulfate and concentrated i. vac. The crude product (136 mg) was purified by flash chromatography (5 g, 15×0.9 cm) with methylene chloride/methanol (95:5) and 0.5% ammonia (25% in water).

Example No. 102 (Polar Diastereoisomer)

Yield: 102 mg (51%), colourless oil $^1$H-NMR (CDCl$_3$): 1.22-1.32 (2H, m); 1.63-1.72 (2H, m); 1.74-1.98 (2H, m); 2.00 (6H, s); 2.04-2.26 (2H, m); 2.42 (2H, m); 2.85 (2H, s); 4.38 (2H, s); 7.14-7.18 (2H, m); 7.20-7.26 (4H, m); 7.27-7.38 (4H, m).

$^{13}$C-NMR (CDCl$_3$): 30.0; 30.1; 32.9; 35.8; 38.0; 43.5; 46.4; 58.2; 60.4; 126.6; 127.48; 127.5; 127.67; 127.73; 128.1; 128.6; 128.7; 136.5; 173.7.

LC-MS: m/z: [M+H]$^+$=363.4, R$_t$=3.0 min.

Example No. 119

3-(8-Dimethylamino-3-oxo-8-phenyl-2-azaspiro[4.5]dec-3-yl)-2,2-dimethylpropionamide Step 1: 8-Dimethylamino-8-phenyl-2-azaspiro[4.5]decan-3-one A suspension of 8-dimethylamino-3-oxo-2-azaspiro[4.5]decane-8-carbonitrile (536 mg, 2.4 mmol) in anhydrous tetrahydrofuran (30 ml) was added dropwise to a 2 M solution of phenylmagnesium chloride in tetrahydrofuran (3 ml, 6 mmol), cooled to 0° C., under argon and the mixture was then stirred for 18 h at room temperature. After addition of saturated ammonium chloride solution (15 ml) the phases were separated and the aqueous phase was extracted with ethyl acetate (3×30 ml). The combined organic phases were dried with sodium sulfate and concentrated i. vac.

Yield: 601 mg (92%), white solid (crude product)

Diastereoisomer mixture: Polar:non-polar ratio=1:2.

The diastereoisomer ratio was determined with the aid of the singlets of the HN—CH$_2$ group at 3.27 (polar diastereoisomer) and 3.02 ppm (non-polar diastereoisomer) in the $^1$H-NMR spectrum.

Step 2: 8-Dimethylamino-3-oxo-8-phenyl-2-azaspiro[4.5]decan-2-carboxylic acid tert-butyl ester A solution of di-tert-butyl dicarbonate (4.05 g, 18.6 mmol) in anhydrous tetrahydrofuran (30 ml) and 4-dimethylaminopyridine (206 mg, 1.69 mmol) was added to a solution of 8-dimethylamino-8-phenyl-2-azaspiro[4.5]decan-3-one (4.60 g, 16.9 mmol) in anhydrous acetonitrile (300 ml) and anhydrous tetrahydrofuran (100 ml) and the mixture was stirred for 3 d at room temperature. Since the reaction was not complete, a solution of di-tert-butyl dicarbonate (2.00 g, 9 mmol) in anhydrous acetonitrile (10 ml) was again added and the mixture was stirred for 3 h at 50° C. and 18 h at room temperature. The solvent was then removed i. vac., the residue was dissolved in methylene chloride (100 ml) and the solution was washed with water (3×50 ml) and saturated sodium chloride solution (50 ml). The organic phase was dried with sodium sulfate and concentrated i. vac. The crude product (7.00 g) was purified by flash chromatography (400 g, 20×7.5 cm) with ethyl acetate/methanol (9:1).

Non-Polar Diastereoisomer

Yield: 1.40 g (22%), white solid

Melting point: 174-176° C.

$^1$H-NMR (CDCl$_3$): 1.34-1.42 (2H, m); 1.53 (9H, s); 1.72-1.82 (2H, m); 1.96-2.03 (2H, m); 2.04 (6H, s); 2.10-2.24 (2H, m); 2.25 (2H, s); 3.61 (2H, s); 7.26-7.31 (3H, m); 7.36-7.41 (2H, m).

$^{13}$C-NMR (CDCl$_3$): 28.1; 30.0; 32.2; 34.3; 38.0; 45.8; 56.6; 60.1; 82.8; 126.8; 127.4; 127.8; 150.1; 173.4.

LC-MS: m/z: [M+H]$^+$=373.4, R$_t$=2.6 min.

Polar Diastereoisomer

Yield: 1.26 g (20%), white solid

Melting point: 176-181° C.

$^1$H-NMR (CDCl$_3$): 1.34-1.44 (2H, m); 1.48 (9H, s); 1.68-1.77 (2H, m); 1.90-2.03 (2H, m); 2.04 (6H, s); 2.15-2.30 (2H, m); 2.48 (2H, s); 3.36 (2H, s); 7.28-7.32 (3H, m); 7.36-7.42 (2H, m).

¹³C-NMR (CDCl₃): 28.0; 29.8; 32.3; 34.5; 38.0; 44.9; 57.6; 60.3; 60.5; 82.7; 126.8; 127.5; 127.8; 136.2; 150.1; 173.4.

LC-MS: m/z: [M+H]⁺=373.4, R$_t$=3.0 min.

Step 3: 8-Dimethylamino-8-phenyl-2-azaspiro[4.5] decan-3-one (Non-Polar Diastereomer)

Trifluoroacetic acid (5 ml) was added to a solution of 8-dimethylamino-3-oxo-8-phenyl-2-azaspiro[4.5]decane-2-carboxylic acid tert-butyl ester (non-polar diastereoisomer) (1.46 g, 3.9 mmol) in anhydrous methylene chloride (50 ml) and the mixture was stirred for 3 h at room temperature. The reaction mixture was concentrated i. vac., the residue was dissolved in methylene chloride (50 ml) and the solution was washed with saturated sodium bicarbonate solution (3×20 ml). The organic phase was dried with sodium sulfate and concentrated i. vac.

Yield: 1.03 g (96%), white solid
Melting point: >260° C.
¹H-NMR (CDCl₃): 1.37-1.46 (2H, m); 1.76-1.84 (2H, m); 1.90-2.02 (2H, br s); 2.04 (6H, s); 2.06 (2H, s); 2.15-2.27 (2H, br s); 3.27 (2H, s); 5.60 (1H, s); 7.26-7.32 (3H, m); 7.36-7.42 (2H, m).

3-(8-Dimethylamino-3-oxo-8-phenyl-2-azaspiro[4.5] dec-3-yl)-2,2-dimethylpropionamide Example 119

A suspension of sodium hydroxide (112 mg, 2.8 mmol) in anhydrous dimethylsulfoxide (10 ml) was stirred for 20 min at room temperature. 8-Dimethylamino-8-phenyl-2-azaspiro [4.5]decan-3-one (non-polar diastereomer) (190 mg, 0.7 mmol) and a solution of 3-chloro-2,2-dimethylpropanenitrile (98 mg, 0.84 mmol) in anhydrous dimethylsulfoxide (2 ml) were then added to the suspension. The reaction mixture was stirred for 18 h at 130° C. and thereafter three more times a solution of 3-chloro-2,2-dimethylpropanenitrile (96 mg, 0.84 mmol each time) in anhydrous dimethylsulfoxide (1 ml) was added and the mixture was stirred for a further 30 h in total at 130° C. Sodium hydroxide (112 mg, 2.8 mmol) and a solution of 3-chloro-2,2-dimethylpropanenitrile (98 mg, 0.84 mmol) in anhydrous dimethylsulfoxide (1 ml) were then again added to the reaction mixture and the mixture was stirred for a further 18 h at 130° C., before a solution of 3-chloro-2,2-dimethylpropanenitrile (98 mg, 0.84 mmol) in anhydrous dimethylsulfoxide (1 ml) was again added and the mixture was stirred again for 18 h at 130° C. Water (100 ml) was then added to the mixture and the mixture was extracted with ethyl acetate (4×25 ml). The combined organic phases were extracted with 10% strength aqueous formic acid (4×25 ml) and the combined acid, aqueous phases were rendered alkaline with 4 M sodium hydroxide solution and extracted with methylene chloride (4×25 ml). The combined organic phases were dried with sodium sulfate and concentrated i. vac. The product was isolated from the crude product by preparative thin layer chromatography [layer thickness 1 mm, 20×20 cm, concentration zone, 2-propanol/cyclohexane (9:1) and 1% NH₃ (25% in water)].

Example 119

Yield: 31 mg (12%), yellow oil which is still contaminated
¹H-NMR (CDCl₃): 1.16-1.28 (6H, m); 1.30-1.48 (2H, m); 1.64-1.84 (2H, m); 1.92-2.20 (12H, m); 3.34 (2H, s); 3.43 (2H, s); 5.44 (1H, br s); 6.53 (1H, br s); 7.24-7.32 (3H, m); 7.34-7.42 (2H, m).
¹³C-NMR (CDCl₃): 24.2; 24.3; 24.8; 29.5; 29.8; 30.1; 32.4; 32.6; 35.9; 36.1; 37.8; 43.5; 43.9; 51.5; 60.2; 126.8; 127.4; 127.6; 175.3; 175.5; 179.0; 179.7.

Example No. 124

Step 1: 8-Butyl-8-dimethylamino-2-azaspiro[4.5] decan-3-one

A suspension of 8-(dimethylamino)-3-oxo-2-azaspiro [4.5]decane-8-carbonitrile (2.21 g, 10 mmol) in anhydrous tetrahydrofuran (140 ml) was added dropwise to a 2 M solution of n-butylmagnesium chloride in anhydrous tetrahydrofuran (20 ml, 40 mmol) at 0° C. under argon and the mixture was stirred for 20 h at room temperature. Saturated ammonium chloride solution (50 ml) was then added to the solution. The phases were separated and the aqueous phase was extracted with methylene chloride (3×20 ml). The combined organic phases were dried with sodium sulfate and concentrated i. vac. The crude product (3.97 g) was taken up in methylene chloride and the suspension was washed with potassium carbonate solution. The organic phase was then dried with sodium sulfate and concentrated i. vac.

Yield: 1.88 g (75%), colourless oil which crystallized over time
¹H-NMR (CDCl₃): 0.90 and 0.91 (3H, 2 t, J=7.2 Hz); 1.14-1.47 (10H, m); 1.51-1.61 (2H, m); 1.67-1.82 (2H, m); 2.18 and 2.19 (2H, 2 s); 2.21 (s, 6H); 3.15 and 3.18 (2H, 2 s); 5.90 and 5.93 (1H, br s).

This is a diastereoisomer mixture in the ratio of approx. 1:1.

LC/MS: m/z: [M+H]⁺=253.3, R$_t$=1.3 min.

Step 2: 8-Butyl-8-dimethylamino-3-oxo-2-azaspiro [4.5]decane-2-carboxylic acid tert-butyl ester (Polar and Non-Polar Diastereoisomer)

Di-tert-butyl dicarbonate (2.71 g. 12.4 mmol) and 4-dimethylaminopyridine (90 mg, 0.75 mmol) were added to a solution of 8-butyl-8-dimethylamino-2-azaspiro[4.5]decan-3-one (1.84 g, 7.3 mmol) in anhydrous acetonitrile (60 ml) and anhydrous tetrahydrofuran (20 ml). The reaction mixture was stirred for 72 h at 50° C. It was then concentrated i. vac. The residue was taken up in methylene chloride (100 ml) and the solution was washed with water (3×80 ml) and saturated sodium chloride solution (50 ml). The organic phase was dried with sodium sulfate and concentrated i. vac. The crude product (2.37 g) was purified by flash chromatography (220 g, 20×5.7 cm) with methylene chloride/ methanol (95:5-9:1-4:1).

Non-Polar Diastereoisomer:
Yield: 819 mg (32%), orange-coloured solid
¹H-NMR (CDCl₃): 0.90 (3H, t, J=7.1 Hz); 1.17-1.40 (10H, m); 1.51 (9H, s); 1.54-1.76 (4H, m); 2.21 (6H, s); 2.39 (2H, s); 3.49 (2H, s).

Polar Diastereoisomer:
Yield: 647 mg (25%), yellow oil
¹H-NMR (CDCl₃): 0.90 (3H, t, J=7.1 Hz); 1.22-1.48 (10H, m); 1.53 (9H, s); 1.58-1.76 (4H, m); 2.25 (6H, s); 2.39 (2H, s); 3.52 (2H, s).

Mixed Fraction:
Yield: 310 mg (12%), yellow oil

Step 3: 8-Butyl-8-dimethylamino-2-azaspiro[4.5] decan-3-one (Polar Diastereoisomer)

Trifluoroacetic acid (12.5 ml) was added to a solution of 8-butyl-8-dimethylamino-3-oxo-2-azaspiro[4.5]decane-2-carboxylic acid tert-butyl ester—polar diastereoisomer (603 mg, 1.71 mmol) in anhydrous methylene chloride (50 ml) and the mixture was stirred for 4 h at room temperature. The reaction mixture was then concentrated i. vac., the residue was taken up in methylene chloride (50 ml) and the solution was washed with 25% strength potassium carbonate solution (3×20 ml). The organic phase was dried with sodium sulfate and concentrated i. vac.

Polar Diastereoisomer:
Yield: 365 mg (85%), yellowish solid
$^1$H-NMR (CDCl$_3$): 0.90 (3H, t, J=7.2 Hz); 1.11-1.48 (10H, m); 1.53-1.64 (2H, m); 1.69-1.79 (2H, m); 2.17 (2H, s); 2.21 (6H, s); 3.17 (2H, s); 6.10 (br s, 1H).
$^{13}$C-NMR (CDCl$_3$): 14.1; 23.7; 26.5; 28.3; 30.7 (2C); 31.9 (2C); 37.3 (2C); 39.0; 44.0; 52.6; 56.2; 177.9.

Step 4: 8-Butyl-8-dimethylamino-2-azaspiro[4.5] decan-3-one (Non-Polar Diastereoisomer)

Trifluoroacetic acid (12.5 ml) was added to a solution of 8-butyl-8-dimethylamino-3-oxo-2-azaspiro[4.5]decane-2-carboxylic acid tert-butyl ester—non-polar diastereoisomer (740 mg, 2.09 mmol) in anhydrous methylene chloride (50 ml) and the mixture was stirred for 2 h at room temperature. The reaction mixture was then concentrated i. vac., the residue was taken up in methylene chloride (50 ml) and the solution was washed with 25% strength potassium carbonate solution (3×20 ml). The organic phase was dried with sodium sulfate and concentrated i. vac.

Non-Polar Diastereoisomer:
Yield: 416 mg (79%), yellow solid.
$^1$H-NMR (CDCl$_3$): 0.90 (3H, t, J=7.2 Hz); 1.16-1.43 (10H, m); 1.58-1.78 (4H, m); 2.19 (2H, s); 2.22 (6H, s); 3.14 (2H, s); 5.97 (br s, 1H).
$^{13}$C-NMR (CDCl$_3$): 14.1; 23.8; 26.6; 28.6; 30.6 (2C); 31.8 (2C); 37.3 (2C); 39.1; 42.1; 54.6; 177.7.

Step 5: 3-Benzyl-8-butyl-8-(dimethylamino)-3-azaspiro[4.5]decan-2-one (Example No. 124, Polar Diastereoisomer)

A suspension of sodium hydroxide (96 mg, 2.39 mmol) in anhydrous dimethylsulfoxide (5 ml) was stirred for 40 min at room temperature. 8-Butyl-8-dimethylamino-2-azaspiro [4.5]decan-3-one (polar diastereoisomer, 151 mg, 0.6 mmol) and benzyl bromide (102 mg, 71 µl, 0.6 mmol) were then added to the suspension and the mixture was stirred for 5 h at room temperature. Twice more benzyl bromide (71 µl, 0.6 mmol each time) was added to the suspension and the mixture was stirred for 36 h in total at 50° C. Water (100 ml) was then added to the reaction mixture and the solution was extracted with ethyl acetate (4×25 ml). The combined organic phases were extracted with 10% strength aqueous formic acid (4×25 ml). The combined acid, aqueous phases were rendered alkaline with 4 M sodium hydroxide solution and extracted with methylene chloride (4×25 ml). The combined organic phases were dried with sodium sulfate and concentrated i. vac. The crude product was purified by flash chromatography (18 g, 20×2.0 cm) with methylene chloride/methanol (95:5) and 1% ammonia (25% in water).

Example No. 124 (Polar Diastereoisomer)

Yield: 76 mg (37%), colourless oil
$^1$H-NMR (CDCl$_3$): 0.88 (3H, t, J=7.2 Hz); 1.07-1.80 (12H, m); 2.15-2.25 (2H, m); 2.19 (6H, s); 2.31 (2H, s); 3.03 (2H, s); 4.44 (2H, s); 7.18-7.40 (5H, m).
$^{13}$C-NMR (CDCl$_3$): 14.1; 26.4; 28.3; 30.6; 32.0; 35.6; 37.2; 46.5; 55.8; 57.3; 127.5; 128.0; 128.4; 136.5; 174.0.
LC-MS: [M+H]$^+$: m/z=343.4, R$_f$=3.0 min.

Example No. 125

Step 1: 4-[2-(8-Dimethylamino-8-phenyl-2-azaspiro [4.5]dec-2-yl)-2-oxoethyl]-piperidine-1-carboxylic acid tert-butyl ester N,N'-Carbonyldiimidazole (211 mg, 1.3 mmol) was added to a solution of 1-Boc-4-piperidine-acetic acid (317 mg, 1.3 mmol) in absolute tetrahydrofuran (10 ml) and the mixture was stirred for 2 h under reflux (evolution of CO$_2$). A solution of dimethyl-(8-phenyl-3-azaspiro[4.5]decan-8-yl)-amine (Example no. 119; 260 mg, 1.0 mmol) in tetrahydrofuran (10 ml) was then added to the solution at room temperature and the mixture was stirred for a further 2 h under reflux. The reaction mixture was concentrated i. vac., the residue was dissolved in ethyl acetate (50 ml) and the solution was washed with water (2×10 ml). The organic phase was dried with sodium sulfate and concentrated i. vac. The crude product (570 mg) was purified by means of flash chromatography (40 g, 18×2.6 cm) with methylene chloride/methanol (95:5).

Yield: 256 mg (53%), colourless oil
$^1$H-NMR (CDCl$_3$): 1.05-1.19 (2H, m); 1.25-1.34 (2H, m); 1.44 (4H, s); 1.45 (5H, s); 1.51-1.77 (6H, m); 1.81-1.99 (3H, m); 2.03 (3H, s); 2.05 (3H, s); 2.12-2.20 (2H, m); 2.20-2.28 (1H, m); 2.32-2.44 (1H, m); 2.63-2.80 (2H, m); 3.30-3.30 (4H, m); 3.98-4.17 (2H, m); 7.23-7.33 (3H, m); 7.33-7.43 (2H, m).

The NMR spectra show sometimes a doubled signal set (rotamers).
LC-MS: m/z: [M+H]$^+$=484.4, R$_f$=3.2 min.

Step 2: 1-(8-Dimethylamino-8-phenyl-2-azaspiro [4.5]dec-2-yl)-2-piperidin-4-ylethanone A 4 M solution of hydrogen chloride in 1,4-dioxane (2 ml) was added to a solution of 4-[2-(8-dimethylamino-8-phenyl-2-azaspiro[4.5]dec-2-yl)-2-oxoethyl]-piperidine-1-carboxylic acid tert-butyl ester (110 mg, 0.23 mmol) in absolute 1,4-dioxane (2 ml) and the mixture was stirred for 2 h at room temperature. The volatile constituents were then removed i. vac., the residue (130 mg) was dissolved in methanol (15 ml) and 1 M potassium carbonate solution (0.5 ml, 0.5 mmol) was added to the solution. The solvent was then again removed i. vac. and the residue was dried i. vac.
Yield: 200 mg (crude product)
LC-MS: m/z: [M+H]$^+$=384.4, R$_f$=2.0 min.

Step 3: 1-[8-(Dimethylamino)-8-phenyl-3-azaspiro [4.5]decan-3-yl]-2-(1-methylpiperidine-4-yl)-ethanone (Example No. 125, Diastereoisomer 1)

A 37% strength aqueous formalin solution (430 µl, 5.75 mmol) and sodium cyanoborohydride (58 mg, 0.96 mmol)

were added to a solution of the crude product 1-(8-dimethylamino-8-phenyl-2-azaspiro[4.5]dec-2-yl)-2-piperidin-4-ylethanone (240 mg, max. 0.22 mmol) in methanol (5 ml) and the mixture was stirred for 30 min at room temperature. After addition of acetic acid (0.3 ml) the mixture was stirred again for a further 2 h at room temperature. Saturated potassium carbonate solution (10 ml) was then added to the reaction solution and the mixture was extracted with methylene chloride (20 ml and 3×10 ml). The combined organic phases were washed with saturated sodium chloride solution (10 ml), dried with sodium sulfate and concentrated i. vac. This crude product (84 mg) and the crude product of OG1567 (70 mg) were combined and purified by means of flash chromatography (12 g, 18×1.6 cm) with methylene chloride/methanol (95:5) and 1% ammonia (25% in water) followed by methanol and 0.5% ammonia (25% in water).

Example No. 125 (Diastereoisomer 1)

Yield: 96 mg (54%), colourless, viscous oil
$^1$H-NMR (CDCl$_3$): 1.23-1.37 (4H, m); 1.52-1.57 (1H, m); 1.58-1.68 (3H, m); 1.72-1.80 (2H, m); 1.80-1.91 (3H, m); 1.91-2.01 (3H, m); 2.025 (2.7H, s); 2.034 (3.3H, s); 2.14-2.19 (2H, m); 2.25 (1.3H, s); 2.26 (1.7H, s); 2.28-2.37 (1H, m); 2.77-2.87 (2H, m); 3.33 (1H, s); 3.38-3.49 (3H, m); 7.26-7.33 (3H, m); 7.41-7.34-7.41 (2H, m).
The NMR spectra show sometimes a doubled signal set (rotamers).
$^{13}$C-NMR (CDCl$_3$): 30.1; 30.9; 31.2; 31.4; 32.2, 32.3; 32.5; 35.9; 38.0; 38.1; 403; 41.0; 41.4; 42.3; 43.9; 45.2; 46.4; 55.2; 55.8; 56.6; 60.7; 126.5; 126.7; 127.56; 127.61, 127.68; 127.75; 170.8.
LC-MS: m/z: [M+H]$^+$=398.4 (100%) and [MH-NHMe$_2$]$^+$=353.3 (28%), R$_f$=2.2 min.

Example No. 126

Step 1: 4-[2-(8-Dimethylamino-8-thiophen-2-yl-2-azaspiro[4.5]dec-2-yl)-2-oxoethyl]-piperidine-1-carboxylic acid tert-butyl ester N,N'-Carbonyldiimidazole (422 mg, 2.6 mmol) was added to a solution of 1-Boc-4-piperidine-acetic acid (640 mg, 2.6 mmol) in absolute tetrahydrofuran (20 ml) and the mixture was stirred for 2 h under reflux (evolution of CO$_2$). A solution of dimethyl-(8-thiophen-2-yl-3-azaspiro[4.5]decan-8-yl)-amine (Example no. 21; 529 mg, 2.0 mmol) in tetrahydrofuran (20 ml) was then added to the solution at room temperature and the mixture was stirred for a further 3 h under reflux. The reaction mixture was concentrated i. vac., the residue was dissolved in ethyl acetate (80 ml) and the solution was washed with water (3×15 ml). The organic phase was dried with sodium sulfate and concentrated i. vac. The crude product (1.3 g) was purified by means of flash chromatography (80 g, 18×4 cm) with methylene chloride/methanol (95:5→9:1).
Yield: 540 mg (55%), white, solid foam
$^1$H-NMR (CDCl$_3$): 1.05-1.18 (2H, m); 1.33-1.42 (2H, m); 1.44 (4H, s); 1.45 (5H, s); 1.58-1.63 (1H, m); 1.63-1.76 (6H, m); 1.84-1.96 (1H, m); 1.97-2.07 (2H, m); 2.08 (3H, s); 2.11 (3H, s); 2.13-2.24 (3H, m); 2.80-2.65 (2H, m); 3.29 (1.2H, s); 3.36 (0.8H, s); 3.43 (0.8H, t, J=7.1 Hz); 3.47 (1.2H, t, J=7.3 Hz); 3.99-4.15 (2H, m); 6.83-6.87 (1H, m); 7.00-7.07 (1H, m); 7.20-7.26 (1H, m).
The NMR spectra show sometimes a doubled signal set (rotamers).
LC-MS: m/z: [M+H]$^+$=490.4, R$_f$=3.2 min.

Step 2: 1-(8-Dimethylamino-8-thiophen-2-yl-2-azaspiro[4.5]dec-2-yl)-2-piperidin-4-ylethanone A 4 M solution of hydrogen chloride in 1,4-dioxane (3 ml) was added to a solution of 4-[2-(8-dimethylamino-8-thiophen-2-yl-2-azaspiro[4.5]dec-2-yl)-2-oxoethyl]-piperidine-1-carboxylic acid tert-butyl ester (525 mg, 1.07 mmol) in absolute 1,4-dioxane (3 ml) and the mixture was stirred for 1.5 h at room temperature. The volatile constituents were then removed i. vac. 1,4-Dioxane (×2) was repeatedly added to the residue and the mixture was in each case concentrated again i. vac. The crude product (870 mg) was dissolved in methanol (5 ml) and 1 M potassium carbonate solution (2.2 ml, 2.2 mmol) was added to the solution. The solvent was then again removed i. vac. and the residue was dried i. vac.
Yield: 550 mg (crude product)
LC-MS: m/z: [M+H]$^+$=390.3, R$_f$=2.0 min.

Step 3: 1-[8-(Dimethylamino)-8-thiophen-2-yl-3-azaspiro[4.5]decan-3-yl]-2-(1-methylpiperidin-4-yl)-ethanone (Example No. 126, Diastereoisomer 1)

A 37% strength aqueous formalin solution (2 ml, 26.8 mmol) and sodium cyanoborohydride (282 mg, 4.5 mmol) were added to a solution of the crude product 1-(8-dimethylamino-8-thiophen-2-yl-2-azaspiro[4.5]dec-2-yl)-2-piperidin-4-ylethanone (540 mg, max. 1.07 mmol) in methanol (20 ml) and the mixture was stirred for 30 min at room temperature. After addition of acetic acid (1.0 ml) the mixture was stirred again for a further 2 h at room temperature. Saturated potassium carbonate solution (30 ml) was then added to the reaction solution and the mixture was extracted with methylene chloride (40 ml and 3×30 ml). The combined organic phases were washed with saturated sodium chloride solution (10 ml), dried with sodium sulfate and concentrated i. vac. The crude product (621 mg) was purified by means of flash chromatography (55 g, 24×2.8 cm) with methylene chloride/methanol (95:5) and 1% ammonia (25% in water).

Example No. 126 (Diastereoisomer 1)

Yield: 287 mg (66%), colourless viscous oil
$^1$H-NMR (CDCl$_3$): 1.28-1.45 (4H, m); 1.57-1.81 (6H, m); 1.82-2.07 (6H, m); 2.09 (2.5H, s); 2.11 (3.5H, s); 2.13-2.20 (3H, m); 2.29 (3H, s); 2.82-2.90 (2H, m); 3.30 (1.2H, s); 3.36 (0.8H, s); 3.41-3.50 (2H, m); 6.83-6.86 (1H, m); 7.01-7.06 (1H, m); 7.21-7.26 (1H, m).
$^{13}$C-NMR (CDCl$_3$): 31.1; 31.2; 32.1; 32.2; 32.2; 32.9; 33.4; 35.5; 37.0; 38.1; 40.1; 40.9; 41.3; 42.0; 43.9; 45.2; 46.2; 46.3; 55.4; 55.7; 56.7; 59.9; 123.3; 123.5; 124.9; 125.0; 126.2; 126.3; 170.7.
The NMR spectra show sometimes a doubled signal set (rotamers).
LC-MS: m/z: [M+H]$^+$=404.3 (100%) and [MH-NHMe$_2$]$^+$=359.3 (18%), R$_f$=0.4 min.

Example No. 127

Step 1: 3-(8-Dimethylamino-8-phenyl-2-azaspiro[4.5]dec-2-ylmethyl)-azetidine-1-carboxylic acid tert-butyl ester 3-Formylazetidine-1-carboxylic acid tert-butyl ester (270 mg, 1.46 mmol) and sodium cyanoborohydride (385 mg, 6.13 mmol) were added to a solution of dimethyl-(8-phenyl-3-azaspiro[4.5]decan-8-yl)-amine (Example no. 119; 377 mg, 1.46 mmol) in methanol (15 ml) and the mixture was stirred for 30 min at room temperature. After addition of acetic acid (1.5 ml) the mixture was stirred again for a further 4 h at room temperature. Saturated sodium bicarbonate solution (30 ml) was then added to the reaction solution and the mixture was extracted with methylene chloride (3×30 ml). The combined organic phases were washed with saturated sodium chloride solution (10 ml), dried with sodium sulfate and concentrated i. vac. The crude product (630 mg) was purified by means of flash chromatography (60 g, 12×4 cm) with methylene chloride/methanol (9:1) and 1.2% ammonia (25% in water).

Yield: 420 mg (67%), colourless oil
$^1$H-NMR (CDCl$_3$): 1.21-1.32 (2H, m); 1.44 (11H, m); 1.60-1.70 (2H, m); 1.78-1.96 (2H, m); 2.04 (6H, s); 2.25 (2H, br s); 2.42 (2H, s); 2.46 (2H, t, J=6.8 Hz); 2.59-2.64 (2H, m); 2.65-2 73 (1H, m); 3.60 (2H, dd, J=8.4 and 5.3 Hz); 4.00 (2H, t, J=8.1 Hz); 7.23-7.34 (3H, m); 7.34-7.42 (2H, m).
LC-MS: m/z: [M+H]$^+$=428.6, R$_t$=2.2 min.

Step 2: (2-Azetidin-3-ylmethyl-8-phenyl-2-azaspiro[4.5]dec-8-yl)-dimethylamine

A 4 M solution of hydrogen chloride in 1,4-dioxane (4 ml) was added to a solution of 3-(8-dimethylamino-8-phenyl-2-azaspiro[4.5]dec-2-ylmethyl)-azetidine-1-carboxylic acid tert-butyl ester (412 mg, 0.96 mmol) in absolute 1,4-dioxane (4 ml) and the mixture was stirred for 2.5 h at room temperature. The volatile constituents were then removed i. vac. 1,4-Dioxane (×2) was repeatedly added to the residue and the mixture was in each case concentrated again i. vac. The crude product (480 mg) was dissolved in methanol (8 ml) and 4 M sodium hydroxide solution (750 µl, 3.0 mmol) was added to the solution. The solvent was then again removed i. vac. and the residue was dried i. vac.

Yield: 390 mg (crude product)
LC-MS: m/z: [M+H]$^+$=328.3, R$_t$=0.2 min.

Step 3: 1-[3-[[8-(Dimethylamino)-8-phenyl-3-azaspiro[4.5]decan-3-yl]-methyl]-azetidin-1-yl]-ethanone (Example No. 127, Diastereoisomer 1)

Acetic anhydride (196 mg, 180 µl, 1.92 mmol) was added to a solution of the crude product (2-azetidin-3-ylmethyl-8-phenyl-2-azaspiro[4.5]dec-8-yl)dimethylamine (390 mg, max. 0.96 mmol in methylene chloride (15 ml) and triethylamine (194 ml, 266 µl, 1.92 mmol) and the mixture was then stirred for 20 h at room temperature. Thereafter saturated sodium bicarbonate solution (10 ml) was added, the phases were separated and the aqueous phase was extracted with methylene chloride (3×10 ml). The combined organic phases were dried with sodium sulfate and the solvent was removed i. vac. The crude product (400 mg) was purified by means of flash chromatography (30 g, 23×2.5 cm) with methylene chloride/methanol (9:1) and 1% ammonia (25% in water).

Example No. 127 (Diastereoisomer 1)

Yield: 160 mg (45%), colourless oil
$^1$H-NMR (CDCl$_3$): 1.22-1.32 (2H, m); 1.43 (2H, t, J=6.9 Hz); 1.61-1.70 (2H, m); 1.85 (3H, s); 1.95-2.10 (2H, m); 2.03 (6H, s); 2.26 (2H br s); 2.36-2.54 (4H, m); 2.55-2.67 (2H, m); 2.66-2.78 (1H, m); 3.65 (1H, dd, J=9.8 and 5.4 Hz); 3.80 (1H, dd, J=8.4 and 5.3 Hz); 4.03-4.09 (1H, m); 4.18 (1H, t, J=8.1 Hz); 7.27-7.42 (5H, m).
$^{13}$C-NMR (CDCl$_3$): 18.6; 27.7; 31.0; 34.4; 38.0; 41.3; 50.8, 51.9; 53.7; 54.8; 60.1, 65.7, 126.5, 127.6; 127.7; 170.7.
LC-MS: m/z: [M+H]$^+$=370.4, R$_t$=0.3 min.

In accordance with the general synthesis instructions described and analogously to the concrete synthesis examples given by way of example, the following examples were prepared from the polar and non-polar precursors (8-benzyl-8-(dimethylamino)-3-azaspiro[4.5]decan-4-one, (8-benzyl-3-azaspiro[4.5]decan-8-yl)-dimethylamine, 8-dimethylamino-8-phenyl-3-azaspiro[4.5]decan-4-one, 8-(dimethylamino)-8-phenyl-3-azaspiro[4.5]decan-2-one, 8-butyl-8-dimethylamino-3-azaspiro[4.5]decan-4-one, 8-dimethylamino-8-thiophen-2-yl-3-azaspiro[4.5]decan-4-one, dimethyl-(8-thiophen-2-yl-3-azaspiro[4.5]decan-8-yl)-amine, 8-(dimethylamino)-8-thiophen-2-yl-2-azaspiro[4.5]decan-3-one, 8-(dimethylamino)-8-(5-methylthiophen-2-yl)-3-azaspiro[4.5]decan-4-one, dimethyl-[8-(5-methylthiophen-2-yl)-3-azaspiro[4.5]decan-8-yl]-amine, dimethyl-(8-phenyl-3-azaspiro[4.5]decan-8-yl)-amine, 8-(cyclohexylmethyl)-8-dimethylamino-3-azaspiro[4.5]decan-4-one, 8-(cyclopentylmethyl)-N,N-dimethyl-2-azaspiro[4.5]decan-8-amine, 8-cyclopentyl-N,N-dimethyl-2-azaspiro[4.5]decan-8-amine, (8-(dimethylamino)-2-azaspiro[4.5]decan-8-yl)(phenyl)methanone (8-(dimethylamino)-2-azaspiro[4.5]decan-8-yl)(thiophen-2-yl)methanone 8-(azetidin-1-yl)-8-(thiophen-2-yl)-2-azaspiro[4.5]decane, 8-(azetidin-1-yl)-8-phenyl-2-azaspiro[4.5]decane, 8-(5-chlorothiophen-2-yl)-8-dimethylamino-3-azaspiro[4.5]decan-4-one, 8-(dimethylamino)-8-(5-methylthiophen-2-yl)-3-azaspiro[4.5]decan-2-one) by acylation, arylation, alkylation, reductive amination or reduction of amides.

| Ex. no. | Diastereomer* | Building block/ Method/ Yield | LC-MS [M + H]$^+$/R$_t$ | NMR spectrum |
|---|---|---|---|---|
| 18 | 1 | Building Block no. 1/ Acylation/36% | [M + H]$^+$ = 384.6, R$_t$ = 1.4 min | $^1$H-NMR (CDCl$_3$): 1.38-1.46 (2 H, m); 1.58-1.74 (6 H, m); 2.05 (6 H, m); 2.13 (2 H, s); 2.46 (3 H, s); 3.33 (1 H, s); 3.48 (1 H, t); 3.56 (1 H, s); 6.68 (1 H, t); 6.59-6.68 (2 H, m); 7.34 (1 H, m); 7.83 (1 H, m); 8.63 (1 H, m); 8.76 (1 H, s). |
| 19 | 1 | Building Block no. 1/ Acylation/24% | [M + H]$^+$ = 384.5, R$_t$ = 1.7 min | $^1$H-NMR (CDCl$_3$): 1.15-1.40 (2 H, m); 1.52-1.71 (6 H, m); 1.98 (6 H, s); 2.06 (2 H, s); 2.40 (3 H, s); 3.20 (1 H, s); 3.35 (1 H, m); 3.48 (1 H, s); 3.61 (1 H, m); 6.56 (1 H, m); 6.61 (1 H, m); 7.30 (2 H, m); 8.62 (2 H, m). |
| 20 | 1 | Building Block no. 1/ Acylation/11% | [M + H]$^+$ = 384.1, R$_t$ = 3.1 min | $^1$H-NMR (CDCl$_3$): 1.36-1.47 (2 H, m); 1.63-1.67 (4 H, m); 1.70-1.76 (2 H, m); 2.05 (4 H, s); 2.10 (4 H, s); 2.44 (3 H, s); 3.56 (1 H, s); 3.60 (1 H, s); 3.67 (1 H, t); 3.77 (1 H, t); 6.64 (2 H, m); 7.30 (1 H, m); 7.76 (2 H, m); 8.55 (1 H, m). |

-continued

| Ex. no. | Dia-stereomer* | Building block/ Method/ Yield | LC-MS [M + H]+/Rt | NMR spectrum |
|---|---|---|---|---|
| 21 | 1 | Building Block no. 1/ Alkylation/9% | [M + H]+ = 355.1, Rt = 4.1 min | 1H-NMR (CDCl3): 1.43-1.50 (2 H, m); 1.69-1.77 (4 H, m); 1.90 (2 H, m); 2.14 (6 H, s); 2.18 (2 H, m); 2.49 (3 H, s); 3.21 (2 H, s); 3.31 (2 H, t); 6.54 (2 H, d); 6.67 (3 H, m); 7.23 (2 H, m). |
| 22 | 1 | Ex. no. 18/ Reduction/ 51% | [M + H]+ = 370.1, Rt = 1.7 min | 1H-NMR (CDCl3): 1.34-1.41 (2 H, m); 1.50 (2 H, t); 1.62-1.68 (2 H, bm); 1.76 (2 H, bs); 2.06 (8 H, s); 2.37 (2 H, s); 2.44 (3 H, s); 2.53 (2 H, m); 3.55 (2 H, s); 6.58 (1 H, m); 6.65 (1 H, m); 7.20 (1 H, m); 7.62 (1 H, m); 8.46 (1 H, m); 8.53 (1 H, m). |
| 23 | 1 | Ex. no. 19/ Reduction/ 39% | [M + H]+ = 370.1, Rt = 1.7 min | 1H-NMR (CDCl3): 1.40 (2 H, m); 1.52 (2 H, t); 1.64-1.70 (2 H, bm); 1.78 (2 H, bs); 2.07 (8 H, s); 2.39 (2 H, s); 2.45 (3 H, s); 2.54 (2 H, t); 3.55 (2 H, s); 6.60 (1 H, m); 6.66 (1 H, m); 7.23 (2 H, m); 8.50 (2 H, m). |
| 24 | 1 | Building Block no. 2/ Acylation/82% | [M + H]+ = 369.2, Rt = 2.8 min | 1H-NMR (DMSO-d6): 1.41 (2 H, m); 1.60-1.80 (5 H, m); 2.03 (4 H, s); 2.12 (5 H, m); 3.31 (1 H, s); 3.45 (1 H, t); 3.55 (1 H, s); 3.66 (1 H, t); 6.85 (1 H, m); 7.04 (1 H, m); 7.24 (1 H, m); 7.38 (3 H, m); 7.49 (2 H, m). |
| 25 | 1 | Building Block no. 2/ Acylation/84% | [M + H]+ = 370.2, Rt = 2.0 min | 1H-NMR (CDCl3): 1.35 (2 H, m); 1.51-1.72 (4 H, b m); 1.94 (4 H, s); 2.02 (4 H, s); 3.17 (2 H, d); 3.30 (2 H, m); 3.45 (1 H, s); 3.56 (1 H, t); 6.74 (1 H, m); 6.93 (1 H, m); 7.14 (1 H, m); 7.27 (2 H, m); 8.58 (2 H, m). |
| 26 | 1 | Building Block no. 2/ Acylation/81% | [M + H]+ = 370.1, Rt = 2.1 min | 1H-NMR (CDCl3): 1.32-1.41 (2 H, b m); 1.54-1.72 (5 H, b m); 1.95 (4 H, s); 2.03 (4 H, s); 3.26 (2 H, m); 3.41 (1 H, t); 3.60 (2 H, m); 6.75 (1 H, m); 6.95 (1 H, m); 7.16 (1 H, m); 7.27 (1 H, m); 7.76 (1 H, m); 8.58 (1 H, m); 8.69 (1 H, m). |
| 27 | 1 | Building Block no. 2/ Acylation/65% | [M + H]+ = 370.2, Rt = 1.6 min | 1H-NMR (CDCl3): 1.34 (2 H, m); 1.59 (3 H, m); 1.74 (2 H, m); 2.03 (5 H, s); 2.06 (4 H, m); 3.52 (1 H, s); 3.56 (1 H, s); 3.63 (1 H, t); 3.73 (1 H, t); 6.79 (1 H, m); 6.96 (1 H, m); 7.15 (1 H, m); 7.25 (1 H, m); 7.70 (2 H, m); 8.51 (1 H, m). |
| 29 | 1 | Ex. no. 25/ Reduction/ 33% | [M + H]+ = 356.2, Rt = 0.6 min | 1H-NMR (CDCl3): 1.35 (2 H, m); 1.51-1.72 (4 H, b m); 1.94 (4 H, s); 2.02 (4 H, s); 3.17 (2 H, d); 3.30 (2 H, m); 3.45 (1 H, s); 3.56 (1 H, t); 6.74 (1 H, m); 6.93 (1 H, m); 7.14 (1 H, m); 7.27 (2 H, m); 8.58 (2 H, m). |
| 30 | 1 | Ex. no. 26/ Reduction/ 81% | [M + H]+ = 356.2, Rt = 0.6 min | 1H-NMR (CDCl3): 1.37 (2 H, m); 1.51 (2 H, t); 1.68 (2 H, m); 1.85 (3 H, b s); 2.06 (7 H, s); 2.38 (2 H, s); 2.53 (2 H, t); 3.56 (2 H, s); 6.82 (1 H, d); 7.02 (1 H, t); 7.22 (2 H, m); 7.63 (1 H, m); 8.47 (1 H, m); 8.54 (1 H, d). |
| 31 | 1 | Building Block no. 2/ Alkylation/ 16% | [M + H]+ = 341.2, Rt = 2.3 min | 1H-NMR (CDCl3): 1.45 (2 H, m); 1.75 (4 H, t); 1.97 (2 H, t); 2.14 (6 H, s); 2.21 (2 H, b s); 3.21 (2 H, s); 3.33 (2 H, t); 6.53 (2 H, d); 6.66 (1 H, t); 6.88 (1 H, m); 7.07 (1 H, m); 7.23 (3 H, m). |
| 32 | 1 | Building Block no. 2/ Acylation/76% | [M + H]+ = 365.2, Rt = 3.3 min | 1H-NMR (CDCl3): 1.38 (2 H, ddd, J = 13.6, 10.3 und 3.6 Hz); 1.46 (9 H, s); 1.54-1.61 (2 H, m); 1.62-1.72 (2 H, m); 1.88 (1.2 H, t, J = 11.9 Hz); 1.98 (0.8 H, t, J = 11.9 Hz); 2.09 (2 H, s); 2.11 (4 H, s); 2.17-2.25 (2 H, m); 3.19 (1.2 H, s); 3.23 (0.8 H, s); 3.31 (0.8 H, t, J = 7.3 Hz); 3.36 (1.2 H, t, J = 7.1 Hz); 6.85 (1 H, dd, J = 3.5 und 1.0 Hz); 7.02-7.06 (1 H, m); 7.22-7.25 (1 H, m). 13C-NMR (DMSO-d6): 28.6; 31.3; 31.4; 32.9; 33.5; 36.6; 36.8; 38.1; 40.7; 41.5; 44.0; 44.7; 55.6; 60.0; 78.9; 79.0; 123.3; 123.4; 124.9; 125.1; 126.1; 126.3; 154.8. |
| 34 | 1 | Building Block no. 2/ Acylation/61% | [MH − HNMe2]+ = 344.2 (100%) [M + H]+ = 389.3 (35%), Rt = 3.0 min. | 1H-NMR (CDCl3): 1.44 (2 H, ddd, J = 13.4, 10.1 und 3.6 Hz); 1.63-1.79 (4 H, m); 1.84-2.04 (2 H, m); 2.05-2.23 (2 H, m); 2.10 (6 H, s); 2.50 (3 H, s); 3.52-3.81 (4 H, m); 6.71-6.74 (1 H, m); 6.86 (1 H, d, J = 3.5 Hz); 7.02-7.11 (1 H, m); 7.20-7.28 (1 H, m); 7.33 (1 H, d, J = 3.7 Hz). 13C-NMR (CDCl3): 15.4; 31.1; 32.9; 33.3; 35.2; 37.6; 38.1; 39.7; 42.6; 45.5; 47.1; 53.4; 57.0; 58.5; 59.9; 123.4; 124.9; 125.6; 126.3; 130.2; 136.6; 144.7; 162.0. |
| 35 | 1 | Building Block no. 2/ Reductive amination/ 64% | [MH − HNMe2]+ = 316.2 (100%) [M + H]+ = 361.3 (6%), Rt = 1.0 min. | 1H-NMR (CDCl3): 1.38 (2 H, ddd, J = 13.6, 10.4 und 3.4 Hz); 1.53 (2 H, t, J = 6.9 Hz); 1.67-1.75 (2 H, m); 1.83-1.97 (2 H, m); 2.08-2.18 (2 H, m); 2.11 (6 H, s); 2.49 (2 H, s); 2.61 (2 H, t, J = 6.9 Hz); 3.80 (2 H, s); 6.86 (1 H, dd, J = 3.5 und 1.0 Hz); 6.89-6.91 (1 H, m); 6.93 (1 H, dd, J = 5.9 und 3.4 Hz); 7.04 (1 H, dd, J = 5.0 und 1.3 Hz); 7.20 (1 H, dd, J = 5.0 und 1.3 Hz); 7.24 (1 H, dd, J = 5.1 und 1.0 Hz). 13C-NMR (CDCl3): 33.6; 34.2; 38.1; 41.0; 53.2; 53.4; 54.6; 60.2; 64.6; 123.5; 124.6; 125.3; 126.3; 126.3; 142.5. |
| 36 | 1 | Ex. no. 36/ Reduction/ 82% | [MH − HNMe2]+ = 330.3 (100%) [M + H]+ = 375.3 (15%), Rt = 2.1 min. | 1H-NMR (CDCl3): 1.38 (2 H, ddd, J = 13.5, 10.4 und 3.4 Hz); 1.53 (2 H, t, J = 6.9 Hz); 1.67-1.75 (2 H, m); 1.84-1.95 (2 H, m); 2.06-2.19 (2 H, m); 2.11 (6 H, s); 2.45 (3 H, d, J = 0.7 Hz); 2.49 (2 H, s); 2.61 (2 H, t, J = 6.9 Hz); 3.72 (2 H, s), 6.55-6.57 (1 H, m); 6.68 (1 H, d, J = 3.2 Hz); 6.86 (1 H, dd, J = 3.5 und 0.8 Hz); 7.04 (1 H, dd, J = 5.1 und 3.6 Hz); 7.24 (1 H, dd, J = 5.0 und 0.7 Hz). 13C-NMR (CDCl3): 15.4; 29.9; 33.6; 34.2; 38.1; 41.0; 53.1; 54.7; 60.1; 64.4; 123.5; 124.4; 125.4; 126.2; 139.2. |

-continued

| Ex. no. | Dia-stereomer* | Building block/ Method/ Yield | LC-MS [M + H]⁺/R_t | NMR spectrum |
|---|---|---|---|---|
| 28 | 1 | Building Block no. 2/ Acylation/75% | [MH − HNMe₂]⁺ = 330.3 (100%) [M + H]⁺ = 375.3 (80%), R_t = 2.8 min. | ¹H-NMR (CDCl₃): 1.45 (2 H, ddd, J = 13.5, 10.0 und 3.6 Hz); 1.66-1.80 (4 H, m); 1.86-2.24 (4 H, m); 2.11 (6 H, s); 3.58 (0.7 H, s); 3.65 (1.3 H, s); 3.70 (1.3 H, t, J = 7.2 Hz); 3.79 (0.7 H, t, J = 7.2 Hz); 6.87 (1 H, d, J = 3.1 Hz); 7.03-7.09 (2 H, m); 7.23-7.28 (1 H, m); 7.46 (1 H, dd, J = 5.0 und 0.6 Hz); 7.51 (1 H, d, J = 3.2 Hz). 13C-NMR (CDCl₃): 31.0; 31.2; 32.9; 33.2; 35.2; 37.6; 38.0; 39.7; 42.6; 45.6; 47.3; 57.0; 58.6; 59.9; 123.4; 124.9; 126.2; 126.4; 127.1; 129.5; 129.6; 139.3; 162.1. |
| 36 | 1 | Building Block no. 2/ Acylation/64% | [MH − HNMe₂]⁺ = 344.2 (95%) [M + H]⁺ = 389.3 (100%), R_t = 2.9 min. | ¹H-NMR (CDCl₃): 1.36-1.46 (2 H, m); 1.63-1.72 (4 H, m); 1.76-1.92 (2 H, m); 1.98-2.22 (8 H, m); 2.32 (3 H, s); 3.30-3.70 (4 H, m); 6.82-6.86 (2 H, m); 7.04 (1 H, dd, J = 5.1 und 3.6 Hz); 7.22-7.25 (2 H, m). 13C-NMR (CDCl₃): 15.0; 30.8; 33.2; 35.6; 38.1; 41.9; 44.4; 58.4; 60.0; 123.5; 125.0; 125.4; 126.3; 130.0; 131.0; 138.3; 164.4. |
| 39 | 1 | Building Block no. 2/ Acylation/62% | [MH − HNMe₂]⁺ = 348.2 (100%) [M + H]⁺ = 393.3 (60%), R_t = 2.9 min. | ¹H-NMR (CDCl₃): 1.40-1.49 (2 H, m); 1.64-1.82 (4 H, m); 1.88-2.05 (2 H, m); 2.06-2.24 (2 H, m); 2.11 (6 H, s); 3.52-3.81 (4 H, m); 6.46 (1 H, d, J = 3.5 Hz); 6.85-6.87 (1 H, m); 7.03-7.07 (1 H, m); 7.15 (1 H, t, J = 3.8 Hz); 7.23-7.27 (1 H, m). 13C-NMR (CDCl₃): 31.0; 32.9; 33.3; 35.0; 37.5; 38.1; 42.8; 45.9; 47.0; 57.2; 58.3; 59.9; 108.2 (d, J = 12 Hz); 123.5; 124.9; 126.3; 127.0 (d, J = 5 Hz); 128.7 (d, J = 3 Hz); 142.1; 143.5; 161.1; 168.8 (d, J = 294 Hz). |
| 40 | 1 | Ex. no. 39/ Reduction/ 46% | [MH − HNMe₂]⁺ = 334.2 (100%) [M + H]⁺ = 379.3 (5%), R_t = 1.9 min. | ¹H-NMR (CDCl₃): 1.38 (2 H, ddd, J = 13.4 und 10.3 Hz); 1.52 (2 H, t, J = 6.9 Hz); 1.66-1.74 (2 H, m); 1.80-1.94 (2 H, m); 2.06-2.19 (8 H, m); 2.44 (2 H, s); 2.57 (2 H, t, J = 7.0 Hz); 3.62 (2 H, s, J = 2.9 Hz); 6.24 (1 H, dd, J = 3.8 und 1.7 Hz); 6.43-6.46 (1 H, m); 6.85 (1 H, dd, J = 3.6 und 0.7 Hz); 7.04 (1 H, dd, J = 5.0 und 3.6 Hz); 7.23 (1 H, dd, J = 5.1 und 0.7 Hz). 13C-NMR (CDCl₃): 33.8; 34.2; 38.1; 41.1; 53.2; 55.4; 59.7; 64.8; 105.7 (d, J = 11 Hz); 120.5 (d, J = 4 Hz); 123.3; 125.0; 126.2; 131.8; 164.9 (d, J = 288 Hz). |
| 41 | 1 | Building Block no. 2/ Reductive amination/ 39% | [MH − HNMe₂]⁺ = 329.3 (100%), R_t = 0.6 min. | ¹H-NMR (CDCl₃): 1.35-1.44 (2 H, m); 1.53 (2 H, t, J = 6.9 Hz); 1.66-1.74 (2 H, m); 1.78-1.92 (2 H, m); 2.07 (6 H, s); 2.08-2.15 (2 H, m); 2.40 (2 H, s); 2.54 (2 H, t, J = 6.9 Hz); 3.60 (2 H, s); 6.84 (1 H, dd, J = 3.5 und 1.0 Hz); 7.03 (1 H, dd, J = 5.1 und 1.5 Hz); 7.22 (1 H, dd, J = 5.1 und 0.9 Hz); 7.39-7.44 (1 H, m); 8.33-8.37 (2 H, m). 13C-NMR (CDCl₃): 33.7; 34.2; 38.1; 41.2; 53.6; 57.0 (d, J = 1 Hz); 59.6; 65.5; 122.7 (d, J = 18 Hz); 123.2; 124.9; 126.2; 136.2 (d, J = 23 Hz); 137.0 (d, J = 3 Hz); 145.6 (d, J = 4 Hz); 159.7 (d, J = 256 Hz). |
| 42 | 1 | Building Block no. 2/ Reductive amination/ 38% | [MH − HNMe₂]⁺ = 329.2 (100%), R_t = 0.5 min. | ¹H-NMR (CDCl₃): 1.34-1.44 (2 H, m); 1.52 (2 H, t, J = 6.9 Hz); 1.65-1.74 (2 H, m); 1.75-2.05 (4 H, m); 2.07 (6 H, s); 2.44 (2 H, s); 2.58 (2 H, t, J = 6.9 Hz); 3.61 (2 H, s); 6.83 (1 H, dd, J = 3.5 und 1.1 Hz); 7.02 (1 H, dd, J = 5.1 und 1.5 Hz); 7.12-7.17 (1 H, m); 7.21 (1 H, dd, J = 5.1 und 1.0 Hz); 7.80-7.87 (1 H, m); 8.08 (1 H, d, J = 4.8 Hz). 13C-NMR (CDCl₃): 33.6; 34.2; 38.0; 41.2; 52.3 (d, J = 3 Hz); 53.4; 59.6; 65.3; 121.1; 121.3 (d, J = 4 Hz); 123.2; 124.8; 126.1; 141.0 (d, J = 6 Hz); 145.6 (d, J = 15 Hz); 161.7 (d, J = 227 Hz). |
| 43 | 1 | Building Block no. 2/ Reductive amination/ 34% | [MH − HNMe₂]⁺ = 329.2 (100%), R_t = 0.5 min. | ¹H-NMR (CDCl₃): 1.34-1.42 (2 H, m); 1.52 (2 H, t, J = 6.9 Hz); 1.65-1.73 (2 H, m); 1.75-1.90 (2 H, m); 2.07 (6 H, s); 2.08-2.15 (2 H, m); 2.38 (2 H, s); 2.53 (2 H, t, J = 6.9 Hz); 3.55 (2 H, s); 6.84 (1 H, dd, J = 3.5 und 1.1 Hz); 6.87 (1 H, dd, J = 8.4 und 2.9 Hz); 7.03 (1 H, dd, J = 5.1 und 3.5 Hz); 7.22 (1 H, dd, J = 5.1 und 1.1 Hz); 7.76 (1 H, dt, J = 8.1 und 2.4 Hz); 8.12 (1 H, d, J = 2.2 Hz). 13C-NMR (CDCl₃): 33.7; 34.2; 38.1; 41.1; 53.3; 56.8 (d, J = 1 Hz); 59.6; 65.3; 109.0 (d, J = 37 Hz); 123.2; 124.9; 126.1; 132.6 (d, J = 5 Hz); 141.5 (d, J = 8 Hz); 147.3 (d, J = 14 Hz); 162.8 (d, J = 244 Hz). |
| 44 | 1 | Building Block no. 2/ Reductive amination/ 34% | [M + H]⁺ = 374.3, R_t = 1.3 min. | ¹H-NMR (CDCl₃): 1.40 (2 H, ddd, J = 13.4 und 9.9 und 3.4 Hz); 1.54 (2 H, t, J = 6.9 Hz); 1.67-1.77 (2 H, m); 1.78-1.92 (2 H, m); 2.07 (6 H, s); 2.08-2.18 (2 H, m); 2.45 (2 H, s); 2.60 (2 H, t, J = 6.9 Hz); 3.70 (2 H, s); 6.84 (1 H, dd, J = 3.5 und 1.1 Hz); 7.03 (1 H, dd, J = 5.1 und 3.5 Hz); 7.22 (1 H, dd, J = 5.1 und 1.1 Hz); 7.40 (1 H, dt, J = 8.5 und 2.8 Hz); 7.40 (1 H, dt, J = 8.9 und 4.8 Hz); 8.38 (1 H, d, J = 2.8 Hz). 13C-NMR (CDCl₃): 33.8; 34.3; 38.1; 41.2; 53.8; 59.7; 61.6; 65.0; 123.0; 123.2 (d, J = 3 Hz); 123.5 (d, J = 5 Hz); 125.0; 126.2; 137.0 (d, J = 23 Hz); 155.5 (d, J = 5 Hz); 158.4 (d, J = 253 Hz). |
| 45 | 1 | Building Block no. 2/ Reductive amination/ 19% | [M + H]⁺ = 374.3, R_t = 0.6 min. | ¹H-NMR (CDCl₃): 1.35-1.44 (2 H, m); 1.54 (2 H, t, J = 6.9 Hz); 1.67-1.75 (2 H, m); 1.78-1.95 (2 H, m); 2.08 (6 H, s); 2.08-2.15 (2 H, m); 2.45 (2 H, s); 2.59 (2 H, t, J = 6.9 Hz); 3.66 (2 H, s); 6.84 (1 H, dd, J = 3.5); 7.01-7.05 (1 H, m); 7.22 (1 H, dd, J = 5.1 und 1.1 Hz); 7.41 (1 H, t, J = 5.5 Hz); 8.36 (1 H, d, J = 4.8 Hz); 8.38 (1 H, s). 13C-NMR (CDCl₃): 33.7; 34.2; 37.9; 38.1; 41.3; 51.6; 53.6; 59.6; 65.2; 123.2; 124.7 (d, J = 2 Hz); 124.9; 126.2; 135.0 (d, J = 12 Hz); 137.7 (d, J = 24 Hz); 145.6 (d, J = 5 Hz); 158.0 (d, J = 255 Hz). |

-continued

| Ex. no. | Dia-stereomer* | Building block/ Method/ Yield | LC-MS [M + H]+/Rt | NMR spectrum |
|---|---|---|---|---|
| 47 | 1 | Building Block no. 2/ Reductive amination/ 21% | [MH − HNMe2]+ = 312.3 (100%), Rt = 0.3 min. | 1H-NMR (CDCl3): 1.38 (2 H, ddd, J = 13.3 und 9.8 und 3.5 Hz); 1.52 (2 H, t, J = 6.9 Hz); 1.64-1.73 (2 H, m); 1.78-1.92 (2 H, m); 2.06 (6 H, s); 2.07-2.15 (2 H, m); 2.40 (2 H, s); 2.54 (2 H, t, J = 6.9 Hz); 3.57 (2 H, s); 6.83 (1 H, dd, J = 3.5 und 1.1 Hz); 7.02 (1 H, dd, J = 5.1 und 3.5 Hz); 7.21 (1 H, dd, J = 5.1 und 1.0 Hz); 8.68 (2 H, s); 9.10 (1 H, s). 13C-NMR (CDCl3): 33.7; 34.2; 37.8; 38.1; 41.2; 53.6; 55.3; 59.6; 65.3; 123.2; 124.9; 126.2; 132.6; 157.0; 157.6. |
| 48 | 1 | Building Block no. 2/ Alkylation/ 51% | [MH − HNMe2]+ = 312.2 (100%) [M + H]+ = 357.3 (10%), Rt = 0.6 min. | 1H-NMR (CDCl3): 1.33-1.46 (2 H, m); 1.57 (2 H, t, J = 6.9 Hz); 1.69-1.77 (2 H, m); 1.80-1.95 (2 H, m); 2.08 (6 H, s); 2.09-2.18 (2 H, m); 2.49 (2 H, s); 2.64 (2 H, t, J = 6.9 Hz); 3.72 (2 H, s); 6.85 (1 H, d, J = 3.5 Hz); 7.04 (1 H, dd, J = 5.1 und 3.5 Hz); 7.23 (1 H, d, J = 5.1 Hz); 7.48 (1 H, dt, J = 5.1 und 0.6 Hz); 8.67 (1 H, d, J = 5.1 Hz); 9.12 (1 H, d, J = 1.1 Hz). 13C-NMR (CDCl3): 33.7; 34.1; 37.9; 38.1; 41.4; 53.8; 59.6; 61.3; 65.5; 119.9; 123.2; 124.9; 126.2; 157.0; 158.5; 168.5. |
| 49 | 1 | Building Block no. 3/ Acylation/82% | [M + H]+ = 364.2, Rt = 2.1 min | 1H-NMR (CDCl3): 1.30 (2 H, m); 1.59-1.67 (4 H, m); 1.75 (2 H, m); 1.98-2.06 (6 H, m); 2.27 (2 H, m); 3.30-3.66 (4 H, m); 7.25-7.40 (7 H, m); 7.27 (1 H, m); 7.36 (1 H, m). |
| 50 | 1 | Building Block no. 3/ Acylation/78% | [M + H]+ = 363.2, Rt = 2.8 min | 1H-NMR (CDCl3): 1.27 (2 H, m); 1.54-1.64 (4 H, m); 1.74 (2 H, m); 2.00-2.10 (6 H, m); 2.32 (2 H, m); 3.36-3.66 (4 H, m); 7.28 (3 H, m); 7.34-7.42 (5 H, m); 7.48 (2 H, m). |
| 51 | 1 | Ex. no. 50/ Reduction/ 68% | [M + H]+ = 349.2, Rt = 1.7 min | 1H-NMR (CDCl3): 1.28 (2 H, m); 1.47 (2 H, m); 1.67 (2 H, m); 1.83 (2 H, m); 2.03 (6 H, s); 2.28 (2 H, s); 2.48 (2 H, s); 2.55 (2 H, m); 3.60 (2 H, s); 7.22-7.40 (10 H, m). |
| 52 | 1 | Building Block no. 3/ Acylation/64% | [M + H]+ = 364.2, Rt = 2.5 min | 1H-NMR (CDCl3): 1.30 (2 H, m); 1.59-1.66 (4 H, m); 1.73 (2 H, m); 1.98-2.05 (6 H, m); 2.23 (1 H, m); 2.33 (1 H, m); 3.63-3.79 (4 H, m); 7.24-7.40 (6 H, m); 7.75-7.85 (2 H, m); 8.54-8.60 (1 H, m). |
| 53 | 1 | Building Block no. 3/ Acylation/36% | [M + H]+ = 364.2, Rt = 2.2 min | 1H-NMR (CDCl3): 1.30 (2 H, m); 1.58-1.78 (6 H, m); 1.95-2.04 (6 H, m); 2.26 (2 H, m); 3.36-3.67 (4 H, m); 7.24-7.38 (6 H, m); 7.83 (1 H, m); 8.62-8.76 (2 H, m). |
| 54 | 1 | Ex. no. 49/ Reduction/ 85% | [M + H]+ = 350.3, Rt = 0.6 min | 1H-NMR (CDCl3): 1.29 (2 H, m); 1.47 (2 H, m); 1.67 (2 H, m); 1.81 (2 H, m); 2.00 (6 H, m); 2.26 (2 H, m); 2.45 (2 H, s); 2.53 (2 H, m); 3.57 (2 H, s); 7.25-7.38 (7 H, m); 8.52 (2 H, m). |
| 55 | 1 | Ex. no. 52/ Reduction/ 62% | [M + H]+ = 350.3, Rt = 0.8 min | 1H-NMR (CDCl3): 1.28 (2 H, m); 1.48 (2 H, m); 1.67 (2 H, m); 1.79 (2 H, m); 1.99 (6 H, m); 2.26 (2 H, m); 2.50 (2 H, s); 2.60 (2 H, m); 3.74 (2 H, s); 7.13 (1 H, m); 7.23-7.41 (6 H, m); 7.63 (1 H, m); 8.53 (1 H, m). |
| 56 | 1 | Ex. no. 53/ Reduction/ 56% | [M + H]+ = 350.3, Rt = 0.6 min | 1H-NMR (CDCl3): 1.27 (2 H, m); 1.45 (2 H, m); 1.63 (2 H, m); 1.78 (2 H, m); 1.98 (6 H, m); 2.24 (2 H, m); 2.42 (2 H, s); 2.51 (2 H, m); 3.57 (2 H, s); 7.20-7.37 (6 H, m); 7.63 (1 H, m); 8.47 (1 H, m); 8.54 (1 H, m). |
| 57 | 1 | Building Block no. 3/ Acylation/25% | [M + H]+ = 401.3, Rt = 2.5 min. | 1H-NMR (CDCl3): 1.25-1.33 (2 H, m); 1.56 (2 H, dd, J = 14.8 und 7.5 Hz); 1.60-1.68 (2 H, m); 1.70-1.96 (2 H, m); 2.03 und 2.04 (6 H, 2 s); 2.18-2.35 (2 H, m); 2.37 (0.5 H, dd, J = 5.8 und 1.7 Hz); 2.41 (0.5 H, dd, J = 5.8 und 1.7 Hz); 2.64 (0.5 H, dd, J = 9.1 und 6.6 Hz); 2.69 2.64 (0.5 H, dd, J = 9.1 und 6.6 Hz); 2.85-2.95 (1 H, m); 3.25 (1 H, s); 3.29-3.34 (2 H, m); 3.39 (1 H, t, J = 7.2 Hz); 4.08-4.13 (1 H, m); 4.15-4.22 (2 H, m); 4.43 (1 H, dt, J = 9.2 und 7.5 Hz); 7.26-7.32 (3 H, m); 7.34-7.41 (2 H, m). 13C-NMR (CDCl3): 30.3; 30.6; 31.1; 31.3; 34.7; 34.9; 36.9; 37.3; 38.0; 38.1; 39.2; 41.1; 42.0; 44.2; 44.7; 55.4; 55.9; 60.8; 65.1; 65.2; 70.4; 70.5; 126.5; 126.7; 127.6; 127.7; 154.3; 154.4; 176.2. |
| 49 | 3 | Ex. no. 58 Step 2/ Reductive amination/ 39% | [MH − HNMe2]+ = 344.3, Rt = 2.3 min. | 1H-NMR (CDCl3): 1.38 (2 H, ddd, J = 13.4, 10.1 und 3.5 Hz); 1.55 (2 H, t, J = 6.9 Hz); 1.66-1.72 (2 H, m); 1.75-1.86 (2 H, m); 1.96-2.05 (2 H, m); 2.08 (6 H, m); 2.41 (2 H, s); 2.58 (2 H, t, J = 6.9 Hz); 3.59 (2 H, s); 6.59 (1 H, d, J = 3.8 Hz); 6.83 (1 H, d, J = 3.8 Hz); 7.21-7.29 (1 H, m); 7.30 (2 H, d, J = 2.0 Hz); 7.31 (2 H, s). 13C-NMR (CDCl3): 33.3; 34.2; 38.1; 41.0; 53.6; 60.1; 60.6; 124.4; 125.4; 126.9; 127.5; 128.2; 128.7. |
| 60 | 3 | Ex. no. 58 Step 2/ Acylation/ 44% | [MH − HNMe2]+ = 358.2, Rt = 3.1 min. | 1H-NMR (CDCl3): 1.35-1.47 (2 H, m); 1.64-1.74 (4 H, m); 1.99-2.03 (2 H, m); 2.039 (2 H, s); 2.042 (4 H, s); 2.115 (0.7 H, s); 2.124 (1.3 H, s); 3.30 (1.3 H, s); 3.46 (0.7 H, t, J = 6.9 Hz); 3.54 (0.7 H, s); 3.68 (1.3 H, t, J = 7.4 Hz); 6.58-6.59 (0.7 H, m); 6.60-6.62 (0.3 H, m); 6.82 (0.3 H, d, J = 3.7 Hz); 6.84 (0.7 H, d, J = 3.9 Hz), 7.36-7.42 (3 H, m); 7.48-7.49 (2 H, m). 13C-NMR (CDCl3): 27.9; 30.6; 31.3; 31.5; 32.5; 32.9; 35.5; 37.9; 38.0; 38.1; 38.6; 40.3; 42.1; 44.4; 47.8; 59.2; 60.4; 124.3; 124.4; 125.2; 125.4; 125.6; 127.0; 127.1; 127.8; 128.1; 128.4; 129.8; 129.9; 137.0; 170.0. |
| 62 | 1 | Ex. no. 61 Step 2/ Acylation/ 69% | [MH − HNMe2]+ = 342.3, Rt = 2.9 min. | 1H-NMR (CDCl3): 1.36-1.49 (2 H, m); 1.59-1.75 (6 H, m); 1.95-2.00 (2 H, m); 2.04 (2 H, s); 2.05 (4 H, s); 3.30 (1.3 H, s); 3.46 (0.7 H, t, J = 6.9 Hz); 3.55 (0.7 H, s); 3.68 (1.3 H, t, J = 7.4 Hz); 6.36-6.44 (2 H, m); 7.37-7.42 (3 H, m); 7.47-7.50 (2 H, m). |

| Ex. no. | Dia-stereomer* | Building block/ Method/ Yield | LC-MS [M + H]$^+$/R$_t$ | NMR spectrum |
|---|---|---|---|---|
| 63 | 3 | Building Block no. 4/ Acylation/ 98% | [M + H]$^+$ = 383.3, geringe UV-Aktivität | 13C-NMR (CDCl$_3$): 30.6; 31.4; 32.2; 32.7; 35.5; 37.4; 38.0; 38.1; 40.3; 42.1; 44.4; 47.8; 56.0; 59.1; 60.0; 106.1; 106.2; 121.0; 121.2; 127.03; 127.07; 128.2; 128.4; 129.8; 129.9; 136.96; 137.0; 162.5; 165.4; 170.0. $^1$H-NMR (CDCl$_3$): 0.88-1.02 (2 H, m); 1.10-1.44 (10 H, m); 1.46-1.87 (11 H, m); 2.09 (4 H, s); 2.19 (2 H, s); 3.19 (1.3 H, s); 3.43-3.51 (1.4 H, m); 3.68-3.74 (1.3 H, m); 7.33-7.42 (3 H, m); 7.44-7.52 (2 H, m). 13C-NMR (CDCl$_3$): 26.1; 26.2; 26.7; 28.8; 29.2; 29.4; 30.5; 32.8; 33.0; 33.4; 35.7; 35.9; 36.1; 36.9; 37.1; 37.7; 37.9; 40.4; 42.1; 44.9; 48.0; 53.4; 57.0; 57.2; 58.0; 62.2; 127.1; 128.1; 129.63; 129.68; 137.1; 137.2; 169.7. |
| 64 | 3 | Ex. no. 63/ Reduction/ 80% | [M + H]$^+$ = 369.3, geringe UV-Aktivität | $^1$H-NMR (CDCl$_3$): 0.88-1.01 (2 H, m); 1.06-1.42 (10 H, m); 1.47-1.75 (11 H, m); 2.15 (6 H, s); 2.33 (2 H, s); 2.57 (2 H, t, J = 6.8 Hz); 3.56 (2 H, s); 7.18-7.38 (5 H, m). 13C-NMR (CDCl$_3$): 26.2; 26.7; 29.3; 33.2; 33.3; 36.1; 36.3; 37.1; 37.8; 41.1; 54.1; 56.9; 60.7; 68.0; 126.5; 128.1; 128.7; 139.5. |
| 65 | 3 | Building Block no. 12/ Acylation/ 98% | [M + H]$^+$ = 369.3, geringe UV-Aktivität | $^1$H-NMR (CDCl$_3$): 1.00-1.12 (2 H, m); 1.18-1.27 (2 H, m); 1.30-1.87 (17 H, m); 2.10 (3.8 H, s); 2.20 (2.2 H, s); 3.19 (1.3 H, s); 3.45 (0.7 H, s); 3.47 (0.7 H, t, J = 7.2 Hz); 3.70 (1.3 H, t, J = 7.2 Hz); 7.34-7.40 (3 H, m); 7.45-7.52 (2 H, m). 13C-NMR (CDCl$_3$): 25.1; 29.0; 29.3; 29.4; 30.5; 32.8; 35.2; 35.7; 36.0; 36.6; 36.9; 37.2; 40.4; 42.1; 44.7; 48.0; 56.7; 56.9; 57.9; 62.0; 127.1; 128.2; 129.5; 137.0; 137.1; 169.7. |
| 66 | 3 | Ex. no. 65/ Reduction/ 45% | [M + H]$^+$ = 355.3, geringe UV-Aktivität | $^1$H-NMR (CDCl$_3$): 1.00-1.12 (2 H, m); 1.24-1.86 (19 H, m); 2.17 (6 H, s); 2.33 (2 H, s); 2.57 (2 H, t, J = 6.8 Hz); 3.56 (2 H, s); 7.19-7.35 (5 H, m). 13C-NMR (CDCl$_3$): 25.0; 29.7; 33.2; 35.1; 36.0; 36.2; 36.9; 37.1; 41.1; 54.1; 56.8; 60.8; 67.8; 126.7; 128.1; 128.7; 139.4. |
| 68 | 3 | Ex. no. 67/ Reduction/ 56% | [M + H]$^+$ = 341.4, R$_t$ = 2.1 min. | $^1$H-NMR (CDCl$_3$): 1.20-1.35 (6 H, m); 1.38-1.70 (12 H, m); 2.04 (1 H, m); 2.25 (6 H, s); 2.30 (2 H, s); 2.58 (2 H, t, J = 6.8 Hz); 3.55 (2 H, s); 7.19-7.35 (5 H, m). 13C-NMR (CDCl$_3$): 25.0; 27.2; 28.4; 33.1; 35.0; 37.9; 41.6; 44.4; 54.4; 57.6; 60.9; 69.0; 126.5; 128.1; 128.6; 139.5. |
| 75 | 1 | Ex. no. 73 Step 4/ Acylation/ 75% | [M + H]$^+$ = 381.3, R$_t$ = 2.84 min. | $^1$H-NMR (CDCl$_3$): 1.30-1.50 (m, 2H); 1.50-1.93 (m, 10H); 3.01 und 3.08 (2 t, 4H, J = 7.0 Hz); 3.31 und 3.55 (2 s, 2H); 3.44 und 3.6 (2 t, 2H, J = 7.2 Hz); 6.85 und 6.87 (2 d, $^1$H, J = 3.5 Hz); 7.06-7.11 (m, $^1$H); 7.26-7.29 (m, 2H); 7.36-7.45 (m, 2H); 7.47-7.51 (m, 2H). 13C-NMR (CDCl$_3$): 15.96; 16.0; 30.5; 31.1; 31.2; 31.6; 40.4; 42.3; 44.5; 46.7; 47.9; 59.0; 123.5; 123.7; 124.6; 125.0; 126.4; 126.6; 127.0; 128.2; 128.4; 129.7; 129.8; 137.1; 170.0. |
| 76 | 2 | Ex. no. 74 Step 1/ Acylation/ 56% | [M + H]$^+$ = 381.3, R$_t$ = 2.80 min. | $^1$H-NMR (CDCl$_3$): 1.20-1.51 (m, 2H); 1.60-1.84 (m, 8H); 1.84-1.91 (m, 2H); 3.04-3.15 (m, 4H); 3.12 und 3.39 (2 s, 2H); 3.48 und 3.70 (2 t, 2H, J = 7.2 Hz); 6.81 und 6.89 (2 d, $^1$H, J = 3.0 Hz); 7.04 und 7.09 (2 dd, $^1$H, J = 5.0, 1.4 Hz); 7.23 (dd, 0.6H, J = 5.0, 0.7 Hz); 7.29 (d, 0.4H, J = 4.8 Hz); 7.31-7.50 (m, 5H). 13C-NMR (CDCl$_3$): 15.9; 16.0; 30.4; 31.0; 31.1; 31.3; 40.4; 42.3; 44.7; 46.7; 47.9; 59.0; 60.1; 123.7; 124.9; 126.5; 127.0; 127.1; 128.2; 128.3; 129.7; 137.0; 169.8; 169.9. |
| 77 | 1 | Ex. no. 73 Step 4/ Reductive amination/ 55% | [M + H]$^+$ = 367.4, R$_t$ = 1.8 min. | $^1$H-NMR (CDCl$_3$): 1.31-1.39 (m, 2H); 1.49 (t, 2H, J = 6.9 Hz); 1.57-1.72 (m, 4H); 1.76 (q, 2H, J = 7.0 Hz); 1.81-1.93 (m, 2H); 2.40 (s, 2H); 2.54 (t, 2H, J = 6.9 Hz); 3.04 (t, 4H, J = 6.9 Hz); 3.57 (s, 2H); 6.86 (dd, $^1$H, J = 3.5, 1.1 Hz); 7.08 (dd, $^1$H, J = 5.1, 3.5 Hz); 7.20-7.26 (m, $^1$H); 7.26-7.29 (m, $^1$H); 7.29-7.34 (m, 4H). 13C-NMR (CDCl$_3$): 14.2; 16.1; 31.9; 34.2; 39.0; 41.1; 46.7; 53.7; 58.8; 60.7; 123.4; 124.9; 126.4; 126.7; 128.1; 128.6; 139.5. |
| 80 | 1 | Ex. no. 78 Step 4/ Acylation/ 67% | [M + H]$^+$ = 375.4, R$_t$ = 2.9 min. | $^1$H-NMR (CDCl$_3$): 1.20-1.38 (m, 2H); 1.46-1.90 (m, 8H); 1.96-2.10 (m, 2H); 2.89 und 2.98 (2 t, 4H, J = 6.9 Hz); 3.35 und 3.59 (2s, 2H); 3.42 und 3.63 (2 t, 2H, J = 7.2 Hz); 7.24-7.52 (m, 10H). 13C-NMR (CDCl$_3$): 16.5; 16.7; 28.5; 29.4; 30.5; 31.4; 35.9; 40.7; 42.6; 44.4; 46.6; 47.8; 59.2; 59.6; 126.5; 126.7; 127.0; 127.1; 127.5; 127.7; 127.90; 127.93; 128.2; 128.4; 129.7; 129.8; 137.1; 169.9; 170.0. |
| 81 | 2 | Ex. no. 79 Step 1/ Acylation/ 51% | [M + H]$^+$ = 375.4, R$_t$ = 2.8 min. | $^1$H-NMR (CDCl$_3$): 1.17-1.46 (m, 2H); 1.57-2.05 (m, 10H); 2.90-3.02 (m, 4H); 3.06 und 3.34 (2s, 2H); 3.50 (t, 0.7H, J = 6.9 Hz); 3.70 (2 t, 1.3H, J = 7.4 Hz); 7.20-7.50 (m, 10H). 13C-NMR (CDCl$_3$): 16.6; 28.7; 29.0; 30.5; 31.1; 34.2; 40.6; 42.6; 44.7; 46.6; 48.0; 56.8; 59.4; 60.5; 126.5; 126.7; 127.0; 127.1; 127.5; 127.9; 128.2; 128.4; 129.7; 137.0; 169.6; 169.8. |

-continued

| Ex. no. | Dia-stereomer* | Building block/ Method/ Yield | LC-MS [M + H]⁺/R$_t$ | NMR spectrum |
|---|---|---|---|---|
| 82 | 1 | Ex. no. 78 Step 4/ Reductive amination/ 40% | [M + H]⁺ = 361.4, R$_t$ = 2.1 min. | ¹H-NMR (CDCl₃): 1.20-1.30 (m, 2H); 1.44 (t, 2H, J = 6.9 Hz); 1.56-1.76 (m, 6H); 1.94-2.08 (m, 2H); 2.44 (s, 2H); 2.52 (t, 2H, J = 6.8 Hz); 2.92 (t, 4H, J = 6.9 Hz); 3.58 (s, 2H); 7.20-7.34 (m, 8H); 7.37-7.44 (m, 2H). 13C-NMR (CDCl₃): 16.7; 29.6; 34.3; 38.2; 41.5; 46.6; 59.1; 60.8; 65.6; 126.4; 126.7; 127.8; 127.9; 128.1; 128.7; 139.5. |
| 83 | 2 | Ex. no. 79 Step 1/ Reductive amination/ 34% | [M + H]⁺ = 361.4, R$_t$ = 2.2 min. | ¹H-NMR (CDCl₃): 1.19-1.29 (m, 2H); 1.55-1.68 (m, 2H); 1.69-1.79 (m, 6H); 2.00 (br s, 2H); 2.13 (s, 2H); 2.58 (t, 2H, J = 6.9 Hz); 2.96 (t, 4H, J = 6.9 Hz); 3.50 (s, 2H); 7.15-7.32 (m, 8H); 7.35-7.41 (m, 2H). 13C-NMR (CDCl₃): 16.7; 29.1; 34.1; 36.5; 41.5; 46.6; 54.2; 60.7; 67.2; 126.4; 126.7; 127.8; 127.9; 128.1; 128.6; 139.5. |
| 84 | 3 | Building Block no. 5/ Alkylation/ 88% | [M + H]⁺ = 369.3, R$_t$ = 2.8 min. | ¹H-NMR (CDCl₃): 1.28 (br d, 2H, J = 13.1 Hz); 1.68 (dt, 2H, J = 13.7 Hz); 1.87 (t, 2H, J = 7.0 Hz); 2.12 (s, 6H); 2.26 (dt, 2H, J = 13.0 Hz); 2.46 (br d, 2H, J = 13.7 Hz); 3.09-3.16 (m, 2H); 4.46 (s, 2H); 6.85 (dd, ¹H, J = 1.1 und 3.5 Hz); 7.02 (dd, ¹H, J = 3.6 und 5.0 Hz); 7.18-7.35 (m, 6H). 13C-NMR (CDCl₃): 28.2; 30.2; 31.8 (2C); 38.0 (2C); 43.3 (2C); 44.5; 46.7; 58.4; 122.7; 123.6; 125.9; 127.4; 128.0 (2C); 128.6 (2C); 136.9; 145.8; 178.9. |
| 85 | 3 | Building Block no. 5/ Alkylation/ 43% | [M + H]⁺ = 370.3 (100%) [MH − HNMe₂]⁺ = 325.2 (86%), R$_t$ = 1.9 min. | ¹H-NMR (CDCl₃): 1.30 (br d, 2H, J = 13.3 Hz); 1.70 (dt, 2H, J = 13.5 Hz); 1.93 (t, 2H, J = 7.0 Hz); 2.13 (s, 6H); 2.27 (dt, 2H, J = 3.3 und 13.0 Hz); 2.48 (d, 2H, J = 13.6 Hz); 3.17 (t, 2H, J = 7.0 Hz); 4.47 (s, 2H); 6.86 (dd, ¹H, J = 1.0 und 3.5 Hz); 7.03 (dd, ¹H, J = 3.6 und 5.1 Hz); 7.13 (br d, 2H, J = 6.0 Hz); 7.21 (dd, ¹H, J = 1.0 und 5.1 Hz); 8.56 (dd, 2H, J = 1.6 und 4.5 Hz). 13C-NMR (CDCl₃): 28.2; 30.3; 31.7; 37.9; 43.5; 43.6; 44.2; 45.7; 58.4; 122.7; 123.7; 126.0; 145.8; 150.1; 179.3. |
| 86 | 2 | Building Block no. 7/ Alkylation/ 66% | [M + H]⁺ = 377.3, R$_t$ = 3.1 min. | ¹H-NMR (DMSO-d₆): 1.02-1.18 (m, 4H); 1.57 (t, 2H, J = 7.0 Hz); 1.76 (d, 2H, J = 12.0 Hz); 2.16 (dt, 2H, J = 13.3, 3.1 Hz); 2.32 (s, 6H); 2.62 (s, 2H); 2.97-3.02 (m, 2H); 4.41 (s, 2H); 7.08-7.32 (m, 10H). 13C-NMR (DMSO-d₆): 25.1; 28.5; 29.4; 36.9; 37.0; 43.2; 44.6; 46.6; 57.1; 125.6; 127.3; 127.7; 127.9; 128.5; 130.6; 136.9; 139.4; 179.3. |
| 87 | 1 | Building Block no. 6/ Alkylation/ 41% | [M + H]⁺ = 377.3, R$_t$ = 2.9 min. | ¹H-NMR (CDCl₃): 1.54-1.64 (m, 4H); 1.72-1.79 (m, 2H); 1.82 (t, 2H; J = 6.9 Hz); 1.88-1.96 (m, 2H); 2.28 (s, 6H); 2.82 (s, 2H); 3.09 (t, 2H, J = 6.9 Hz); 4.39 (s, 2H); 7.15-7.33 (m, 10H). 13C-NMR (CDCl₃): 28.4; 29.4; 32.7; 36.9; 37.5; 42.9; 43.1; 46.4; 57.6; 125.7; 127.3; 127.8; 127.9; 128.6; 130.8; 136.9; 129.3; 178.9. |
| 88 | 1 | Building Block no. 8/ Alkylation/ 28% | [MH − HNMe₂]⁺ = 325.3 (100%), R$_t$ = 0.4 min. | ¹H-NMR (CDCl₃): 1.42-1.50 (m, 2H); 1.68-1.77 (m, 2H); 1.87-2.05 (m, 4H); 2.06 (s, 6H); 2.27 (s, 2H); 3.10 (s, 2H); 4.43 (s, 2H); 6.83 (dd, ¹H, J = 1.1, 3.6 Hz); 7.04 (dd, ¹H, J = 3.6, 5.1 Hz); 7.14 (dd, 2H, J = 1.6, 4.4 Hz); 7.24 (dd, ¹H, J = 1.1, 5.1 Hz); 8.58 (dd, 2H, J = 1.6, 4.4 Hz). 13C-NMR (CDCl₃): 32.6; 32.7; 35.7; 38.0; 38.1; 43.8; 45.6; 57.6; 59.2; 122.8; 123.5; 124.8; 126.3; 145.5; 150.2; 174.0. |
| 89 | 2 | Building Block no. 9/ Alkylation/ 15% | [MH − HNMe₂]⁺ = 325.3 (100%) [M + H]⁺ = 370.3 (20%), R$_t$ = 0.7 min. | ¹H-NMR (CDCl₃): 1.39-1.46 (m, 2H); 1.70-1.79 (m, 2H); 1.92-2.05 (m, 4H); 2.09 (s, 6H); 2.41 (s, 2H); 2.96 (s, 2H); 4.40 (s, 2H); 6.80 (dd, ¹H, J = 1.0, 3.6 Hz); 7.00 (dd, 1H, J = 3.6, 5.1 Hz); 7.08-7.11 (m, 2H); 7.21 (dd, 1H, J = 1.0, 5.1 Hz); 8.54 (dd, 2H, J = 1.5, 4.4 Hz). 13C-NMR (CDCl₃): 32.6; 32.8; 35.7; 38.1; 43.2; 45.5; 58.2; 59.4; 122.7; 123.5; 124.9; 126.2; 142.2; 145.5; 150.2; 174.1. |
| 90 | 1 | Building Block no. 8/ Acylation/ 20% | [M + H]⁺ = 379.4, R$_t$ = 2.6 min. | ¹H-NMR (CDCl₃): 1.42-1.51 (2 H, m); 1.53 (9 H, s); 1.75-1.84 (2 H, m); 2.00-2.07 (4 H, m); 2.11 (6 H, s); 2.31 (2 H, s); 3.58 (2 H, s); 6.83-6.87 (1 H, m); 7.03-7.07 (1 H, m); 7.23-7.27 (1 H, m). 13C-NMR (CDCl₃): 28.1; 32.1; 32.6; 34.2; 38.1; 45.6; 56.9; 59.3; 82.8; 123.5; 124.9; 126.3; 150.1; 173.4. |
| 91 | 2 | Building Block no. 9/ Acylation/ 35% | [M + H]⁺ = 379.4, R$_t$ = 2.9 min. | ¹H-NMR (CDCl₃): 1.50 (9 H, s); 1.51-1.55 (2 H, m); 1.72-1.82 (2 H, m); 1.95-2.10 (4 H, m); 2.10 (6 H, s); 2.44 (2 H, s); 3.43 (2 H, s); 6.84-6.88 (1 H, m); 7.03-7.08 (1 H, m); 7.24-7.30 (1 H, m). 13C-NMR (CDCl₃): 28.0; 32.1; 32.5; 34.2; 38.1; 45.1; 57.2; 59.5; 82.8; 123.6; 125.0; 126.3; 150.1; 173.3. |
| 92 | 1 | Building Block no. 8/ Alkylation/ 45% | [M + H]⁺ = 389.3, R$_t$ = 2.7 min. | ¹H-NMR (CDCl₃): 1.39-1.47 (2 H, m); 1.68-1.76 (2 H, m); 1.85-2.06 (4 H, m); 2.07 (6 H, s); 2.20 (2 H, s); 2.44 (3 H, d, J = 0.7 Hz); 3.15 (2 H, s); 4.52 (2 H, s); 6.56-6.59 (1 H, m); 6.71 (1 H, d, J = 3.4 Hz); 6.83 (1 H, dd, J = 3.5 und 1.0 Hz); 7.04 (1 H, dd, J = 3.5 und 5.1 Hz); 7.23 (1 H, dd, J = 5.1 und 0.9 Hz). 13C-NMR (CDCl₃): 15.4; 32.6; 32.8; 35.4; 38.0; 41.2; 44.3; 56.8; 59.3; 123.4; 124.8; 124.9; 126.3; 126.7; 136.4; 140.1; 173.3. |
| 93 | 2 | Building Block no. 9/ Alkylation/ 65% | [MH − HNMe₂]⁺ = 344.3 (100%), R$_t$ = 3.0 min. | ¹H-NMR (CDCl₃): 1.38-1.46 (2 H, m); 1.68-1.77 (2 H, m); 1.90-2.08 (4 H, m); 2.09 (6 H, s); 2.35 (2 H, s); 2.42 (3 H, d, J = 0.8 Hz); 3.00 (2 H, s); 4.49 (2 H, s); 6.54 (1 H, qd, J = 3.3 und 1.1 Hz); 6.67 (1 H, d, J = 3.4 Hz); 6.82 (1 H, dd, J = 3.6 und 1.1 Hz); 7.02 (1 H, dd, J = 3.5 und 5.1 Hz); 7.22 (1 H, dd, J = 5.1 und 1.1 Hz). |

-continued

| Ex. no. | Diastereomer* | Building block/ Method/ Yield | LC-MS [M + H]⁺/R_t | NMR spectrum |
|---|---|---|---|---|
| 94 | 1 | Building Block no. 8/ Alkylation/ 50% | [M + H]⁺ = 375.3, R_t = 2.4 min. | 13C-NMR (CDCl₃): 15.3; 32.7; 35.5; 38.1; 41.2; 43.7; 57.6; 59.4; 123.4; 124.7; 124.9; 126.2; 126.5; 136.5; 140.0; 173.3. ¹H-NMR (CDCl₃): 1.38-1.48 (2 H, m); 1.66-1.76 (2 H, m); 1.80-2.06 (4 H, m); 2.07 (6 H, s); 2.21 (2 H, s); 3.16 (2 H, s); 4.62 (2 H, s); 6.83 (1 H, dd, J = 3.5 und 1.1 Hz); 6.94-6.97 (2 H, m); 7.04 (1 H, dd, J = 5.1 und 3.5 Hz); 7.22-7.25 (2 H, m). |
| 95 | 2 | Building Block no. 9/ Alkylation/ 65% | [M + H]⁺ = 375.3, R_t = 2.8 min. | 13C-NMR (CDCl₃): 32.5; 32.8; 35.5; 38.0; 40.9; 44.2; 56.9; 59.3; 123.5; 124.9; 125.5; 126.3; 126.7; 126.8; 139.0; 173.3. ¹H-NMR (CDCl₃): 1.37-1.46 (2 H, m); 1.68-1.78 (2 H, m); 1.92-2.07 (4 H, m); 2.09 (6 H, s); 2.36 (2 H, s); 3.01 (2 H, s); 4.58 (2 H, s); 6.81 (1 H, dd, J = 3.6 und 1.1 Hz); 6.89-6.93 (2 H, m); 7.02 (1 H, dd, J = 5.1 und 3.6 Hz); 7.19-7.23 (2 H, m). |
| 98 | 2 | Building Block no. 14/ Alkylation/ 52% | [M + H]⁺ = 383.3, R_t = 2.7 min. | 13C-NMR (CDCl₃): 32.6; 35.6; 38.1; 40.9; 43.7; 57.6; 59.4; 123.4; 124.9; 125.4; 126.2; 126.6; 126.8; 139.0; 173.4. ¹H-NMR (CDCl₃): 1.39-1.48 (2 H, m); 1.60-1.70 (2 H, m); 1.74-1.90 (2 H, m); 1.92-2.03 (2 H, m); 2.07 (6 H, s); 2.23 (2 H, s); 2.46 (3 H, s); 3.08 (2 H, s); 4.43 (2 H, s); 6.58-6.62 (1 H, m); 6.66-6.69 (1 H, m); 7.20-7.24 (2 H, m); 7.27-7.36 (3 H, m). |
| 99 | 1 | Building Block no. 13/ Alkylation/ 42% | [MH − HNMe₂]⁺ = 338.3 (100%) [M + H]⁺ = 383.3 (10%), R_t = 3.1 min. | 13C-NMR (CDCl₃): 15.2; 32.6; 32.7; 35.4; 38.0; 44.5; 46.5; 56.6; 59.7; 124.6; 127.6; 128.2; 128.7; 136.5; 173.6. ¹H-NMR (CDCl₃): 1.35-1.44 (2 H, m); 1.65-1.74 (2 H, m); 1.85-2.06 (4 H, m); 2.11 (6 H, s); 2.38 (2 H, s); 2.44 (3 H, d, J = 1.1 Hz); 2.91 (2 H, s); 4.40 (2 H, s); 6.57 (1 H, d, J = 3.5 Hz); 6.63-6.65 (1 H, m); 7.16-7.20 (2 H, m); 7.23-7.32 (3 H, m). |
| 100 | 2 | Building Block no. 14/ Alkylation/ 12% | [MH − HNMe₂]⁺ = 339.3 (100%), R_t = 2.0 min. | 13C-NMR (CDCl₃): 15.2; 32.4; 32.8; 35.5; 38.1; 43.2; 46.4; 58.0; 124.5; 125.1; 127.5; 128.1; 128.6; 136.5; 173.7. ¹H-NMR (CDCl₃): 1.39-1.49 (2 H, m); 1.65-1.74 (2 H, m); 1.90-2.12 (4 H, m); 2.15 (6 H, s); 2.23 (2 H, s); 2.45 (3 H, s); 3.14 (2 H, s); 4.41 (2 H, s); 6.65 (1 H, br s); 6.68 (1 H, br s); 7.14 (2 H, d, J = 5.9 Hz); 8.55 (2 H, dd, J = 4.4 und 1.5 Hz). |
| 101 | 2 | Building Block no. 15/ Alkylation/ 58% | [M + H]⁺ = 363.4, R_t = 2.5 min. | 13C-NMR (CDCl₃): 15.2; 32.1; 32.7; 35.5; 37.8; 44.0; 45.5; 57.0; 122.8; 124.8; 145.4; 150.2; 173.8. ¹H-NMR (CDCl₃): 1.30-1.38 (2 H, m); 1.62-1.71 (2 H, m); 1.75-1.95 (2 H, m); 2.19 (6 H, s); 2.05-2.22 (4 H, m); 3.11 (2 H, s); 4.44 (2 H, s); 7.22-7.40 (10 H, m). |
| 103 | 2 | Building Block no. 15/ Alkylation/ 21% | [M + H]⁺ = 364.3, R_t = 0.6 min. | 13C-NMR (CDCl₃): 30.2; 32.8; 35.6; 38.0; 44.5; 46.6; 57.2; 60.1; 126.7; 127.4; 127.6; 127.7; 128.2; 128.3; 128.7; 136.5; 173.7. ¹H-NMR (CDCl₃): 1.30-1.40 (2 H, m); 1.67-1.76 (2 H, m); 2.00-2.05 (1 H, m); 2.10 (6 H, s); 2.18 (3 H, s); 2.20-2.40 (2 H, m); 3.20 (2 H, s); 4.42 (2 H, s); 7.14 (1 H, d, J = 1.6 Hz); 7.16 (1 H, d, J = 1.6 Hz); 7.28-7.45 (5 H, m); 8.57 (1 H, d, J = 1.6 Hz); 8.58 (1 H, d, J = 1.6 Hz). |
| 104 | 1 | Ex. no. 103 Step 1/ Alkylation/ 15% | [M + H]⁺ = 364.3, R_t = 1.1 min. | 13C-NMR (CDCl₃): 29.6; 32.7; 35.7; 37.7; 44.2; 45.6; 57.1; 122.8; 127.7; 128.2; 145.4; 150.2; 173.8. ¹H-NMR (CDCl₃): 1.25-1.36 (2 H, m); 1.67-1.75 (2 H, m); 1.90-2.00 (2 H, m); 2.02 (6 H, s); 2.10-2.28 (2 H, m); 2.44 (2 H, s); 2.90 (2 H, s); 4.38 (2 H, s); 7.07-7.10 (2 H, m); 7.22-7.38 (5 H, m); 8.52 (1 H, d, J = 1.6 Hz); 8.53 (1 H, d, J = 1.6 Hz). |
| 105 | 2 | Building Block no. 15/ Alkylation/ 58% | [M + H]⁺ = 369.4, R_t = 2.5 min. | 13C-NMR (CDCl₃): 30.0; 33.0; 35.9; 43.2; 45.4; 58.5; 60.3; 122.7; 127.5; 127.7; 145.5; 150.2; 174.1. ¹H-NMR (CDCl₃): 1.30-1.39 (2 H, m); 1.65-1.73 (2 H, m); 1.80-1.95 (2 H, m); 2.00 (6 H, s); 2.13-2.25 (2 H, m); 2.16 (2 H, s); 3.20 (2 H, s); 4.62 (2 H, s); 6.95-6.98 (2 H, m); 7.23-7.30 (4 H, m); 7.35-7.40 (2 H, m). |
| 106 | 1 | Ex. no. 102 Step 1/ Alkylation/ 50% | [M + H]⁺ = 369.2 | 13C-NMR (CDCl₃): 30.2; 32.7; 35.7; 38.0; 41.0; 44.6; 56.9; 60.1; 125.5; 126.72; 126.74; 126.8; 127.4; 127.8; 139.0; 173.4. ¹H-NMR (CDCl₃): 1.25-1.35 (2 H, m); 1.64-1.72 (2 H, m); 1.80-2.00 (2 H, m); 2.05-2.30 (2 H, m); 2.38 (2 H, s); 2.94 (2 H, s); 4.56 (2 H, s); 6.86-6.91 (2 H, m); 7.18 (1 H, dd, J = 4.9 und 1.4 Hz); 7.22-7.27 (3 H, m); 7.32-7.37 (2 H, m). |
| 107 | 2 | Building Block no. 15/ Alkylation/ 48% | [M + H]⁺ = 383.3, R_t = 2.7 min. | 13C-NMR (CDCl₃): 30.0; 32.8; 35.8; 38.0; 40.9; 43.5; 57.9; 60.4; 125.4; 126.5; 126.5; 126.7; 127.5; 127.7; 136.5; 139.0; 173.4. ¹H-NMR (CDCl₃): 1.30-1.39 (2 H, m); 1.65-1.74 (2 H, m); 1.80-1.99 (2 H, m); 2.00 (6 H, s); 2.14 (2 H, s); 2.15-2.30 (2 H, m); 2.45 (3 H, d, J = 0.9 Hz); 3.19 (2 H, s); 4.52 (2 H, s); 6.57-6.60 (1 H, m); 6.72 (1 H, d, J = 3.4 Hz); 7.26-7.30 (3 H, m); 7.35-7.40 (2 H, m). |
| 108 | 1 | Ex. no. 102 Step 1/ Alkylation/ 55% | [M + H]⁺ = 383.3, R_t = 3.0 min. | 13C-NMR (CDCl₃): 15.4; 30.2; 32.7; 35.7; 38.0; 41.2; 44.6; 56.9; 60.2; 124.8; 126.69; 126.7; 127.5; 127.7; 136.5; 140.1; 173.3. ¹H-NMR (CDCl₃): 1.26-1.36 (2 H, m); 1.65-1.73 (2 H, m); 1.86-2.00 (2 H, m); 2.02 (6 H, s); 2.08-2.28 (2 H, m); 2.39 (2 H, s); 2.41 (3 H, d, J = 0.9 Hz); 2.94 (2 H, s); 4.47 (2 H, s); 6.50-6.52 (1 H, m); 6.62 (1 H, d, J = 3.3 Hz); 7.23-7.29 (3 H, m); 7.33-7.39 (2 H, m). 13C-NMR (CDCl₃): 15.3; 30.0; 32.8; 35.8; 38.0; 41.1; 43.6; 57.9; 60.4; 124.7; 126.5; 126.6; 127.5; 127.7; 136.5; 140.0; 173.4. |

| Ex. no. | Dia-stereomer* | Building block/ Method/ Yield | LC-MS [M + H]+/Rt | NMR spectrum |
|---|---|---|---|---|
| 109 | 2 | Building Block no. 15/ Alkylation/ 33% | [M + H]+ = 387.3, Rt = 2.7 min. | 1H-NMR (CDCl3): 1.30-1.39 (2 H, m); 1.65-1.78 (3 H, m); 1.82-1.97 (2 H, m); 2.00 (6 H, s); 2.15 (2 H, s); 2.16-2.30 (1 H, m); 3.19 (2 H, s); 4.45 (2 H, d, J = 2.5 Hz); 6.30 (1 H, dd, J = 3.9 und 1.7 Hz); 6.54-6.57 (1 H, m); 7.25-7.30 (3 H, m); 7.35-7.41 (2 H, m). 13C-NMR (CDCl3): 30.2; 32.7; 35.7; 38.0; 41.8; 44.4; 56.8; 60.1; 106.4 (d, J = 11 Hz); 123.0 (d, J = 4 Hz); 126.7; 127.38; 127.4; 127.7; 135.9; 165.2 (d, J = 280 Hz); 173.5. |
| 110 | 1 | Building Block no. 2/ Alkylation/ 58% | m/z: [MH − HNMe2]+ = 319.3 (45%) [M + H]+ = 364.3 (100%), Rt = 0.5 min. | 1H-NMR (CDCl3): 1.39 (2 H, ddd, J = 13.3, 9.8 und 3.5 Hz); 1.53 (2 H, t, J = 7.0 Hz); 1.66-1.74 (2 H, m); 1.83-1.97 (2 H, m); 2.06-2.16 (2 H, m); 2.09 (6 H, s); 2.48-2.62 (6 H, m); 2.75-2.80 (2 H, m); 2.93 (3 H, s); 3.01 (3 H, s); 6.84 (1 H, dd, J = 3.6 und 1.1 Hz); 7.03 (1 H, dd, J = 5.1 und 3.6 Hz); 7.22 (1 H, dd, J = 5.1 und 1.1 Hz). 13C-NMR (CDCl3): 32.5; 33.7; 34.3; 35.3; 37.2; 38.1; 41.00; 41.01; 52.3; 53.8; 59.6; 65.6; 123.2; 125.0; 126.2; 171.5. |
| 111 | 1 | Building Block no. 2/ Alkylation/ 29% | m/z: [MH − HNMe2]+ = 305.3 (100%) [M + H]+ = 351.3 (77%), Rt = 0.3 min. | 1H-NMR (CDCl3): 1.38 (2 H, ddd, J = 13.2. 9.7 und 3.6 Hz); 1.52 (2 H, t, J = 7.0 Hz); 1.67-1.75 (2 H, m); 1.86-1.99 (2 H, m); 2.02-2.12 (2 H, m); 2.09 (6 H, s); 2.50 (2 H, s); 2.61 (2 H, t, J = 7.0 Hz); 2.93 (3 H, s); 3.08 (3 H, s); 3.25 (2 H, s); 6.85 (1 H, d, J = 3.5 Hz); 7.03 (1 H, dd, J = 5.1 und 3.6 Hz); 7.22 (1 H, d, J = 5.0 Hz). 13C-NMR (CDCl3): 33.5; 34.0; 35.5; 36.9; 38.1; 41.2; 53.3; 58.6; 59.8; 65.3; 123.2; 124.9; 126.1; 170.1. |
| 112 | 1 | Building Block no. 2/ Alkylation/ 41% | m/z: [MH − HNMe2]+ = 317.2 (100%) [M + H]+ = 362.3 (26%), Rt = 0.4 min. | 1H-NMR (CDCl3): 1.38 (2 H, ddd, J = 13.3, 19.8 und 3.5 Hz); 1.51 (2 H, t, J = 6.9 Hz); 1.67-1.74 (2 H, m); 1.85-2.15 (4 H, m); 2.09 (6 H, s); 2.22-2.30 (2 H, m); 2.49 (2 H, s); 2.59 (2 H, t, J = 6.9 Hz); 3.08 (2 H, s); 4.03 (2 H, t, J = 7.8 Hz); 4.22 (2 H, t, J = 7.7 Hz); 6.84 (1 H, dd, J = 3.6 und 1.1 Hz); 7.03 (1 H, dd, J = 5.1 und 3.6 Hz); 7.22 (1 H, dd, J = 5.1 und 1.1 Hz). 13C-NMR (CDCl3): 15.8; 33.6; 34.1; 38.1; 41.3; 48.1; 50.9; 53.5; 56.8; 59.8; 65.6; 123.2; 125.0; 126.1; 143.0; 170.1. |
| 113 | 1 | Building Block no. 2/ Alkylation/ 67% | m/z: [MH − HNMe2]+ = 331.3 (50%) [M + H]+ = 376.3 (100%), Rt = 0.6 min. | 1H-NMR (CDCl3): 1.37 (2 H, dd, J = 13.3, 10.0 und 3.4 Hz); 1.51 (2 H, t, J = 6.9 Hz); 1.64-1.73 (2 H, m); 1.81-1.96 (2 H, m); 2.04-2.19 (2 H, m); 2.09 (6 H, s); 2.21-2.29 (4 H, m); 2.45 (2 H, s); 2.54 (2 H, t, J = 6.9 Hz); 2.69-2.74 (2 H, m); 4.00 (2 H, t, J = 7.8 Hz); 4.14 (2 H, t, J = 7.6 Hz); 6.83 (1 H, dd, J = 3.5 und 0.9 Hz); 7.02 (1 H, dd, J = 5.1 und 3.6 Hz); 7.22 (1 H, dd, J = 5.1 und 0.8 Hz). 13C-NMR (CDCl3): 15.0; 30.6; 33.7; 34.3; 38.1; 41.0; 47.8; 50.1; 51.9; 53.7; 59.6; 65.5; 123.3; 124.9; 126.1; 142.9; 171.8. |
| 114 | 2 | Building Block no. 10/ Alkylation/ 80% | [M + H]+: m/z = 355.4, Rt = 2.7 min. | 1H-NMR (CDCl3): 1.16-1.38 (6 H, m); 1.40-1.80 (10 H, m); 2.04 (1 H, m); 2.21 (6 H, s); 2.34 (2 H, s); 2.96 (2 H, s); 4.42 (" H, s); 7.18-7.38 (5 H, m). 13C-NMR (CDCl3): 25.1; 26.9; 28.5; 31.5; 36.3; 37.7; 42.1; 44.2; 46.3; 57.5; 60.1; 127.3; 128.0; 128.6; 136.5; 174.0. |
| 115 | 2 | Building Block no. 9/ Alkylation + Deprotection + Alkylation/3 steps 62% | m/z: [M + H]+ = 404.3 (100%) [MH − NHMe2]+ = 349.3 (45%), Rt = 0.6 min. | 1H-NMR (CDCl3): 1.21-1.32 (3 H, m); 1.41-1.49 (4 H, m); 1.67-1.79 (4 H, m); 1.85-1.91 (2 H, m); 1.95-2.08 (4 H, m); 2.10 (6 H, s); 2.18 (2 H, s), 2.25 (3 H, s); 2.79-2.85 (2 H, m); 3.19 (2 H, s); 3.27-3.31 (2 H, m); 6.85 (1 H, dd, J = 5.1 und 3.5 Hz); 7.24 (1 H, dd, J = 5.1 und 1.0 Hz). 13C-NMR (CDCl3): 31.8; 32.3; 32.7; 32.8; 33.0; 33.8; 35.5; 38.1; 40.1; 44.3; 46.5; 52.3; 55.9; 59.3; 123.5; 124.9; 126.3; 173.5. |
| 116 | 2 | Building Block no. 9/ Alkylation + Deprotection + Alkylation/3 steps 52% | m/z: [M + H]+ = 390.3 (100%) [MH − NHMe2]+ = 345.3 (82%), | 1H-NMR (CDCl3): 1.25-1.36 (2 H, m); 1.44-1.50 (2 H, m); 1.58-1.70 (4 H, m); 1.74-1.80 (2 H, m); 1.89 (2 H, dt, J = 11.7 und 2.2 Hz); 1.99-2.08 (3 H, m); 2.10 (6 H, s); 2.20 (2 H, s), 2.25 (3 H, s); 2.80-2.85 (2 H, m); 3.13 (2 H, d, J = 6.7 Hz); 3.22 (2 H, s); 6.85 (1 H, dd, J = 3.6 und 1.1 Hz); 7.05 (1 H, dd, J = 5.1 und 3.6 Hz); 7.24 (1 H, dd, J = 5.1 und 1.1 Hz). 13C-NMR (CDCl3): 29.8; 30.2; 32.7; 32.8; 34.1; 35.7; 38.1; 44.2; 46.4; 48.3; 52.0; 55.4; 59.3; 123.5; 124.9; 126.3; 174.0. |
| 117 | 2 | Building Block no. 9/ Alkylation/ Deprotection/ Reductive amination/3 steps 48% | m/z: [M + H]+ = 376.3 (100%) [MH − NHMe2]+ = 331.3 (34%), Rt = 0.5 min. | 1H-NMR (CDCl3): 1.42-1.49 (2 H, m); 1.73-1.81 (4 H, m); 1.99-2.07 (4 H, m); 2.11 (6 H, s); 2.17 (2 H, s), 2.34 (3 H, s); 2.39-2.47 (1 H, m); 2.93 (2 H, t, J = 6.6 Hz); 3.18-3.23 (4 H, m); 3.49 (2 H, t, J = 7.6 Hz); 6.85 (1 H, dd, J = 3.6 und 0.7 Hz); 7.05 (1 H, dd, J = 5.1 und 3.6 Hz); 7.25 (1 H, dd, J = 5.1 und 0.7 Hz). 13C-NMR (CDCl3): 28.3; 31.6; 32.7; 35.6; 38.1; 40.4; 44.1; 45.6; 59.4; 61.9; 123.5; 125.0; 126.3; 173.6. |
| 118 | 2 | Building Block no. 9/ Alkylation/ Deprotection/ Reductive amination/3 steps 39% | m/z: [M + H]+ = 362.3 (100%) [MH − NHMe2]+ = 317.2 (28%), Rt = 0.3 min. | 1H-NMR (CDCl3): 1.42-1.48 (2 H, m); 1.72-1.78 (2 H; m), 1.97-2.07 (4 H, m); 2.10 (6 H, s); 2.17 (2 H, s), 2.29 (3 H, s); 2.61-2.68 (1 H, m); 2.87 (2 H, t, J = 7.2 Hz); 3.17 (2 H, s); 3.40-3.44 (4 H, m); 6.84 (1 H, dd, J = 3.6 und 1.1 Hz); 7.04 (1 H, dd, J = 5.1 und 3.6 Hz); 7.24 (1 H, dd, J = 5.1 und 1.1 Hz). 13C-NMR (CDCl3): 29.5; 32.6; 32.8; 38.0; 45.9; 46.0; 59.3; 60.6; 123.5; 124.9; 126.3; 173.8. |
| 120 | 1 | Building Block no. 3/ Acylation/97% | [M + H]+: m/z = 369.3, Rt = 2.9 min. | 1H-NMR (CDCl3): 1.29-1.40 (2 H, m); 1.56-1.92 (6 H, m); 1.94-2.08 (6 H, m); 2.16-2.42 (2 H, m); 3.54-3.84 (4 H, m); 7.02-7.10 (0.7 H, m); 7.24-7.54 (7.3 H, m). |

-continued

| Ex. no. | Dia-stereomer* | Building block/ Method/ Yield | LC-MS [M + H]+/Rt | NMR spectrum |
|---|---|---|---|---|
| 121 | 1 | Building Block no. 3/ Acylation/98% | [M + H]+: m/z = 383.3, Rt = 3.0 min. | 13C-NMR (CDCl3): 30.0; 30.9; 31.1; 31.4; 35.4; 37.9; 39.9; 42.7; 45.4; 47.1; 53.4; 56.9; 58.6; 60.8; 126.5; 126.7; 127.0; 127.6; 127.7; 129.3; 129.4; 139.2; 162.1<br>1H-NMR (CDCl3): 1.28-1.39 (2 H, m); 1.50-1.90 (6 H, m); 2.02 (6 H, s); 2.12-2.42 (2 H, m); 2.50 (3 H, m); 3.54-3.82 (4 H, m); 6.70-6.75 (1 H, m); 7.23-7.43 (6 H, m).<br>13C-NMR (CDCl3): 15.4; 30.0; 30.9; 31.2; 31.4; 35.5; 38.0; 39.9; 42.9; 45.5; 47.1; 56.7; 58.4; 60.7; 125.4; 126.2; 126.49; 126.65; 127.5; 127.6; 129.7; 130.0; 136.5; 144.7; 162.1. |
| 122 | 1 | Building Block no. 3/ Acylation/60% | [M + H]+: m/z = 387.3, Rt = 2.9 min. | 1H-NMR (CDCl3): 1.29-1.40 (2 H, m); 1.55-1.77 (4 H, m); 1.78-1.96 (2 H, m); 2.03 (6 H, s); 2.12-2.50 (2 H, m); 3.44-3.84 (4 H, m); 6.46 (1 H, d, J = 2.6 Hz); 7.12-7.18 (1 H, m); 7.26-7.34 (3 H, m); 7.35-7.42 (2 H, m).<br>13C-NMR (CDCl3): 30.0; 30.8; 31.0; 35.2; 38.0; 43.0; 45.7; 46.8; 57.0; 58.1; 60.8; 108.2; 108.3; 126.7; 126.90; 126.94; 127.6; 127.7; 128.71; 128.73; 161.0; 167.2; 170.3. |
| 123 | 1 | Building Block no. 11/ Acylation/30% | m/z: [M + H]+ = 377.4 (100%), Rt = 3.1 min. | 1H-NMR (CDCl3): 0.91 (3 H, t, J = 7.1 Hz); 1.16-1.43 (10 H, m); 1.47-1.67 (4 H, m); 1.71 (1 H, t, J = 7.2 Hz); 1.78 (1 H, t, J = 7.1 Hz); 2.21 (3 H, s); 2.22 (3 H, s); 2.43 (3 H, s); 3.27 (1 H, s); 3.31 (1 H, s); 3.51-3.55 (2 H, m); 3.71 (1 H, s); 3.72 (1 H, s); 6.55 (1 H, m); 6.66 (1 H, d, J = 3.3 Hz).<br>13C-NMR (CDCl3): 14.16; 14.18; 15.2; 23.7; 23.8; 26.1; 26.5; 28.0; 28.5; 30.2; 30.5; 30.8; 34.0; 36.3; 36.6; 37.3; 37.4; 40.4; 42.4; 44.6; 45.5; 56.6; 56.9; 58.4; 124.7; 125.8; 134.1; 139.0; 139.1; 168.6; 168.7. |
| 129 | 1 | Building Block no. 2/3 steps analogous to Ex. no. 127/ 25% | m/z: [M + H]+ 376.3 (82%) [MH − NHMe2]+ = 331.3 (100%), Rt = 0.2 min. | 1H-NMR (CDCl3): 1.31-1.42 (2 H, m); 1.49 (2 H, t, J = 6.8 Hz); 1.63-1.72 (2 H, m); 1.84 (3 H, s); 1.94 (2 H, br. s); 1.99-2.23 (2 H, m); 2.11 (6 H, s); 2.35-2.42 (2 H, m); 2.44-2.54 (2 H, m); 2.56-2.66 (2 H, m); 2.66-2.76 (1 H, m); 3.64 (1 H, dd, J = 9.8 und 5.4 Hz); 3.79 (1 H, dd, J = 8.3 und 5.3 Hz); 4.05 (1 H, t, J = 9.0 Hz); 4.18 (1 H, t, J = 8.2 Hz); 6.84-6.87 (1 H, m); 7.01-7.07 (1 H, m); 7.23 (1 H, d, J = 4.9 Hz).<br>13C-NMR (CDCl3): 18.59; 27.7; 29.7; 33.6; 34.2; 38.1; 41.0; 51.9; 53.7; 54.8; 60.0; 65.6; 123.4; 125.0; 126.2; 170.6. |

*1 = polar, 2 = non-polar, 3 = a diastereomer

Additional Examples

Synthesis of Cis-3-(8-Dimethylamino-3-oxo-8-phenyl-2-azaspiro[4.5]decan-2-yl)-2,2-dimethyl-propionic acid hydrochloride Salt (Example SC-1045)

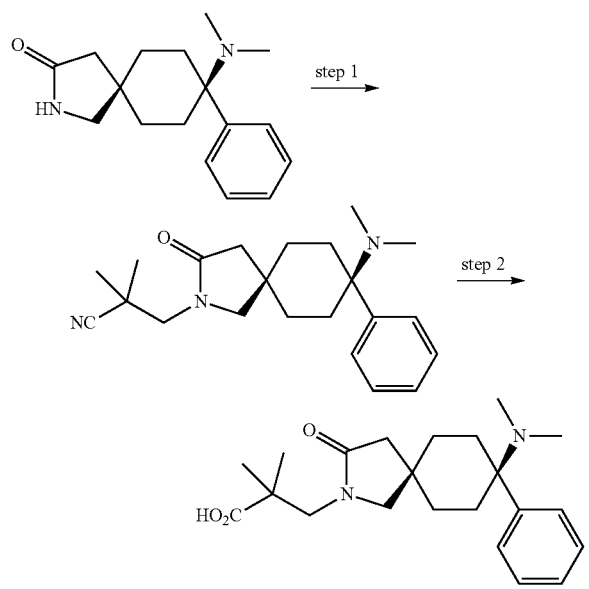

Step 1: cis-3-(8-Dimethylamino-3-oxo-8-phenyl-2-azaspiro[4.5]decan-2-yl)-2,2-dimethyl-propionitrile KOtBu (3.95 g, 35.28 mmol) was added to a suspension Cis-8-(dimethylamino)-8-phenyl-2-azaspiro[4.5]decan-3-one (3.2 g, 11.76 mmol) in DMSO (20 mL) at RT. 3-chloro-2,2-dimethylpropane nitrile (7.5 g, 47.04 mmol) was added to the reaction mixture and stirred for 16 h at 130° C. The reaction mixture was quenched with cold water (5 mL) and the organic product was extracted with ethyl acetate (2×20 mL). The combined organic layer was washed with water, brine, dried over anhydrous Na2SO4 and solvent was evaporated under reduced pressure to afford crude, which was purified by silica column chromatography eluted with 6% MeOH in DCM to yield 1.75 g (42%) of cis-3-(8-Dimethylamino-3-oxo-8-phenyl-2-azaspiro[4.5]decan-2-yl)-2,2-dimethyl-propionitrile as a pale brown solid.

Step 2: cis-3-(8-Dimethylamino-3-oxo-8-phenyl-2-azaspiro[4.5]decan-2-yl)-2,2-dimethyl-propionic acid hydrochloride Salt 12N hydrochloric acid (15 mL) was added to cis-3-(8-Dimethylamino-3-oxo-8-phenyl-2-azaspiro[4.5]decan-2-yl)-2,2-dimethyl-propionitrile (1.75 g, 4.95 mmol) and the resultant solution was refluxed for 16 h. The reaction mixture was concentrated under reduced pressure to get the residue which was co-distilled with toluene. Then the residue was washed with acetone (2×8 mL), diethyl ether (20 mL), hexane (20 mL) to give 1.8 g (97%) of cis-3-(8-Dimethylamino-3-oxo-8-phenyl-2-azaspiro[4.5]decan-2- yl)-2,2-dimethyl-propionic acid hydrochloride salt as solid, which was further purified by titration with acetone and diethyl ether to get pure compound as cis-3-(8-Dimethylamino-3-oxo-8-phenyl-2-azaspiro[4.5]decan-2-yl)-2,2-dimethyl-propionic acid hydrochloride salt as solid.

Analogues Syntheses

The following compounds have been prepared in analogy to Cis-3-(8-Dimethylamino-3-oxo-8-phenyl-2-azaspiro[4.5]decan-2-yl)-2,2-dimethyl-propionic acid hydrochloride salt:

Example SC-1043: cis-3-(8-Dimethylamino-3-oxo-8-pyridin-2-yl-2-azaspiro[4.5]decan-2-yl)-2,2-dimethyl-propionic acid hydrochloride Example SC-1077: cis-4-(8-Dimethylamino-3-oxo-8-phenyl-2-azaspiro[4.5]decan-2-yl)-2,2-dimethyl-butyric acid Example SC-1044: cis-4-(8-Dimethylamino-3-oxo-8-phenyl-2-azaspiro[4.5]decan-2-yl)-2,2-dimethyl-butyric acid hydrochloride Analogues Syntheses The following compounds have been prepared in analogy to cis-3-(8-Dimethylamino-3-oxo-8-phenyl-2-azaspiro[4.5]decan-2-yl)-2,2-dimethyl-propionitrile:

Example SC-1050: cis-2-(8-Dimethylamino-3-oxo-8-phenyl-2-azaspiro[4.5]decan-2-yl)-acetic acid methyl ester.

4-(cis-8-(dimethylamino)-3-oxo-8-(pyridin-2-yl)-2-azaspiro[4.5]decan-2-yl)butanoic acid hydrochloride (Example SC-1042)

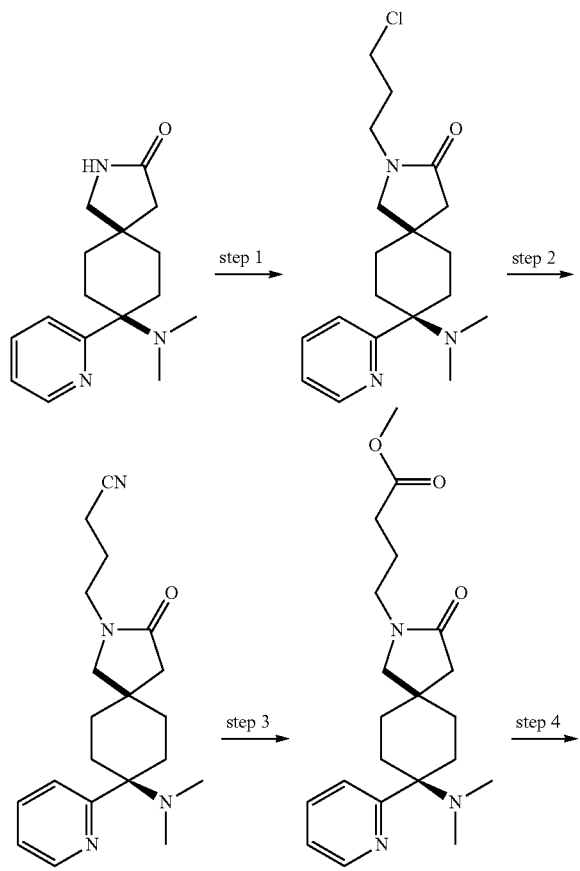

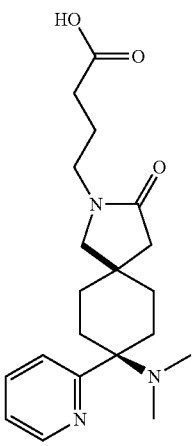

Step 1: cis-2-(3-chloropropyl)-8-(dimethylamino)-8-(pyridin-2-yl)-2-azaspiro[4.5]decan-3-one 60% NaH (87 mg, 3.66 mmol) was added to a suspension cis-8-(dimethylamino)-8-(pyridin-2-yl)-2-azaspiro[4.5]decan-3-one (500 mg, 1.83 mmol) in THF (15 mL) at 0° C. & stirred for 30 min at 50° C. A solution of 1-Bromo-3-chloro propane (0.9 mL, 9.15 mmol) in THF (5 mL) was added at 50° C. and the whole then stirred for 18 h at 80° C. The reaction mixture was quenched with cold water and extracted with ethyl acetate (2×70 mL). The combined organic layer was washed with water, brine, dried over $Na_2SO_4$ and distilled under reduced pressure to afford crude, which was purified by Flash Silica column chromatography (using 100-200 mesh silica gel and 0-5% MeOH in DCM as eluent) to afford 0.5 g (79%) cis-2-(3-chloropropyl)-8-(dimethylamino)-8-(pyridin-2-yl)-2-azaspiro[4.5]decan-3-one as a Pale yellow liquid Step 2: 4-(cis-8-(dimethylamino)-3-oxo-8-(pyridin-2-yl)-2-azaspiro[4.5]decan-2-yl)butanenitrile NaCN (105 mg, 2.14 mmol) and NaI (214 mg, 1.43 mmol) were added to a suspension cis-2-(3-chloropropyl)-8-(dimethylamino)-8-(pyridin-2-yl)-2-azaspiro[4.5]decan-3-one (500 mg, 1.43 mmol) in DMSO (1 mL) at RT, The resultant mixture was stirred for 16 h at 90° C. The reaction mixture was quenched with water (5 mL) and extracted with ethyl acetate (5×25 mL). The combined organic layer was washed with brine, dried over anhydrous $Na_2SO_4$ and distilled under reduced pressure to afford crude, which was purified by Flash Silica column chromatography (using 100-200 mesh silica gel and 0-5% MeOH in DCM as eluent) to afford 300 mg (62%) of 4-(cis-8-(dimethylamino)-3-oxo-8-(pyridin-2-yl)-2-azaspiro[4.5]decan-2-yl)butanenitrile as a pale yellow thick liquid Step 3: methyl 4-(cis-8-(dimethylamino)-3-oxo-8-(pyridin-2-yl)-2-azaspiro[4.5]decan-2-yl)butanoate Conc. HCl (3 mL) was added to 4-(cis-8-(dimethylamino)-3-oxo-8-(pyridin-2-yl)-2-azaspiro[4.5]decan-2-yl)butanenitrile (300 mg, 0.882 mmol), stirred for 6 h at 100° C. Volatiles were distilled under reduced pressure to afford crude, which was successively washed with acetone (2×5 mL), ether (5 mL) and pentane (10 mL) to afford 310 mg (quantitative) of 4-(cis-8-(dimethylamino)-3-oxo-8-(pyridin-2-yl)-2-azaspiro[4.5]decan-2-yl)butanoic acid hydrochloride as crude pale yellow hygroscopic solid (TLC system: 10% MeOH in DCM $R_f$: 0.10) (having good amount of NH$_4$Cl contaminated in it) which was dissolved in methanol (5 mL) and cooled to 0° C. Thionyl chloride (0.41 g, 3.45 mmol), was added and the whole then stirred for 3 h at 80° C. The reaction completion was monitored by TLC. Volatiles were evaporated. Residue was dissolved in sat NaHCO$_3$ solution (5 mL) and extracted with DCM (3×10 mL). The combined organic layer was dried (Na$_2$SO$_4$) and concentrated in vacuo. The crude product was purified by column chromatography (using 100-200 mesh silica gel and 0-5% MeOH in DCM as eluent) to afford 0.2 g of methyl 4-(cis-8-(dimethylamino)-3-oxo-8-(pyridin-2-yl)-2-azaspiro[4.5]decan-2-yl)butanoate (62%) as pale brown liquid.

Step 4: 4-(cis-8-(dimethylamino)-3-oxo-8-(pyridin-2-yl)-2-azaspiro[4.5]decan-2-yl)butanoic acid hydrochloride Methyl 4-(cis-8-(dimethylamino)-3-oxo-8-(pyridin-2-yl)-2-azaspiro[4.5]decan-2-yl)butan-oate (80 mg, 0.214 mmol) was added to 6N.HCl (3.0 mL) and the whole then stirred for 16 h at 100° C. Volatiles were distilled under reduced pressure to afford crude, which was washed with acetone (5 mL), and lyophilized over 16 h to afford 50 mg (65%) of 4-(cis-8-(dimethylamino)-3-oxo-8-(pyridin-2-yl)-2-azaspiro[4.5]decan-2-yl)butanoic acid hydrochloride as a solid.

Analogues Synthesis

The following compounds were prepared in analogy to cis-2-(3-chloropropyl)-8-(dimethylamino)-8-(pyridin-2-yl)-2-azaspiro[4.5]decan-3-one:

Example SC-1080: cis-2-(8-Dimethylamino-3-oxo-8-pyridin-2-yl-2-azaspiro[4.5]decan-2-yl)-acetic acid tert-butyl ester.

Analogues Synthesis

The following compounds were prepared in analogy to methyl 4-(cis-8-(dimethylamino)-3-oxo-8-(pyridin-2-yl)-2-azaspiro[4.5]decan-2-yl)butanoate:

Example SC-1089: cis-4-(8-Dimethylamino-3-oxo-8-pyridin-2-yl-2-azaspiro[4.5]decan-2-yl)-butyric acid methyl ester.

Synthesis of Cis-2-(8-Di methylami no-3-oxo-8-phenyl-2-azaspiro[4.5]decan-2-yl)-acetic acid hydrochloride Salt

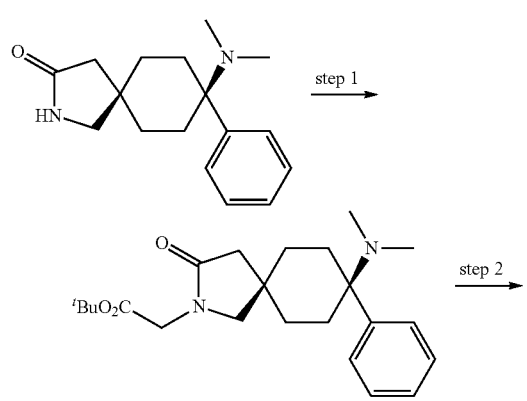

Step 1: cis-2-(8-Dimethylamino-3-oxo-8-phenyl-2-azaspiro[4.5]decan-2-yl)-acetic acid tert-butyl ester NaH-60% (1.9 g, 47.7941 mmol) was added to a suspension of Cis-8-(dimethylamino)-8-phenyl-2-azaspiro[4.5]decan-3-one (10 g, 36.7647 mmol) in THF (200 mL) at 0° C. and heated the reaction mass to 50° C. and stirred for 30 min at 50° C. A solution of t-butyl bromoacetate (8.14 mL, 55.1470 mmol) in THF (10 mL) was added to the reaction mass at 50° C. The reaction mixture was stirred at 70° C. for 6 h. The reaction completion was monitored by TLC. Quenched with saturated NH$_4$Cl solution and the organic product was extracted with ethyl acetate (2×300 mL). The combined organic layer was dried (anhydrous Na$_2$SO$_4$) and concentrated in vacuo to afford 12 g (crude) of cis-2-(8-Dimethylamino-3-oxo-8-phenyl-2-azaspiro[4.5]decan-2-yl)-acetic acid tert-butyl ester as brown solid.

Step 2: Cis-2-(8-Dimethylamino-3-oxo-8-phenyl-2-azaspiro[4.5]decan-2-yl)-acetic acid hydrochloride Salt 4M. HCl in dioxane (72 mL) was added to cis-2-(8-Dimethylamino-3-oxo-8-phenyl-2-azaspiro[4.5]decan-2-yl)-acetic acid tert-butyl ester (12 g, 31.0462 mmol) in DCM (72 mL) at 0° C. and the reaction mixture was stirred at RT for 16 h. The reaction completion was monitored by LCMS. The reaction mixture was concentrated under reduced pressure to get the residue which was co-distilled with DCM. Then the residue was washed with DCM (30 mL), diethyl ether (30 mL), acetone (30 mL) to give 7.6 g (67%) Cis-2-(8-Dimethylamino-3-oxo-8-phenyl-2-azaspiro[4.5]decan-2-yl)-acetic acid hydrochloride salt as brown solid.

Analogues Syntheses

The following compounds have been prepared in analogy to Cis-2-(8-Dimethylamino-3-oxo-8-phenyl-2-azaspiro[4.5]decan-2-yl)-acetic acid hydrochloride salt: tert-butyl-2-(cis-8-(dimethylamino)-3-oxo-8-(pyridin-2-yl)-2-azaspiro[4.5]decan-2-yl)acetate Example SC-1201: 2-(8-Dimethylamino-3-oxo-8-phenyl-2-azaspiro[4.5]decan-2-yl)-acetic acid

Synthesis of cis-2-(8-Dimethylamino-3-oxo-8-phenyl-2-azaspiro[4.5]decan-2-yl)-acetic acid methyl ester (Example SC-1050)

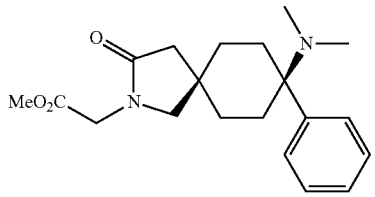 [SMILES: COC(=O)CN1C[C@]2(CC[C@@](c3ccccc3)(N(C)C)CC2)CC1=O]

Cis-8-(dimethylamino)-8-phenyl-2-azaspiro[4.5]decan-3-one (0.1 g, 0.367 mmol) was dissolved in THF (0.5 mL) and treated with KOtBu (0.7 mL, 2 mol/L in THF) at 0° C. After stirring for 30 min methyl bromoacetate (168 mg, 1.10 mmol) was added. The reaction was stirred for 2 h at rt. Then water (2 mL) was added. The aqueous layer was extracted with DCM (3×5 mL) and the combined organic layers were dried over Na2SO4 and concentrated in vacuo. After purification by silica chromatography cis-2-(8-Dimethylamino-3-oxo-8-phenyl-2-azaspiro[4.5]decan-2-yl)-acetic acid methyl ester (65 mg) was isolated as a colorless solid.

Analogues Syntheses

The following example compounds have been prepared in analogy to cis-2-(8-dimethylamino-3-oxo-8-phenyl-2-azaspiro[4.5]decan-2-yl)-acetic acid hydrochloride salt:

| | |
|---|---|
| SC-1049 | cis-N-[3-(8-Dimethylamino-3-oxo-8-phenyl-2-azaspiro[4.5]decan-2-yl)-propyl]-carbamic acid tert-butyl ester |
| SC-1051 | cis-4-[2-(8-Dimethylamino-3-oxo-8-phenyl-2-azaspiro[4.5]decan-2-yl)-ethyl]-tetrahydro-pyran-4-carboxylic acid tert-butyl ester |
| SC-1052 | cis-4-[2-(8-Dimethylamino-3-oxo-8-phenyl-2-azaspiro[4.5]decan-2-yl)-ethyl]-1,1-dioxo-thiane-4-carboxylic acid tert-butyl ester |
| SC-1053 | cis-4-(8-Dimethylamino-3-oxo-8-phenyl-2-azaspiro[4.5]decan-2-yl)-2,2-dimethyl-butyric acid methyl ester |
| SC-1054 | cis-8-Dimethylamino-8-phenyl-2-(pyridin-2-yl-methyl)-2-azaspiro[4.5]decan-3-one |
| SC-1055 | cis-8-Dimethylamino-8-phenyl-2-(pyridin-3-yl-methyl)-2-azaspiro[4.5]decan-3-one |

Synthesis of trans-3-(8-Dimethylamino-3-oxo-8-pyridin-2-yl-2-azaspiro[4.5]decan-2-yl)-2,2-dimethyl-propionamide 2,2,2-trifluoro acetate (Example SC-1101)

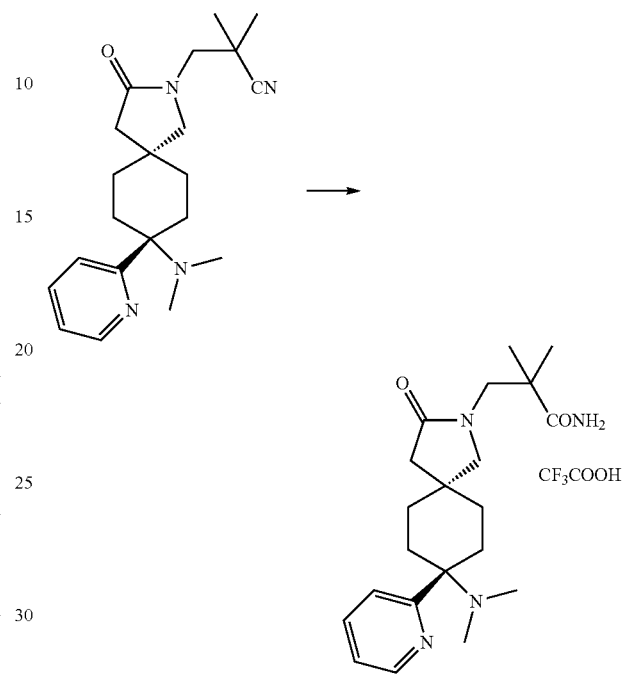

30% aqueous $H_2O_2$ (0.12 mL, 1.10 mmol) was added to a suspension of 3-(trans-8-(dimethylamino)-3-oxo-8-(pyridin-2-yl)-2-azaspiro[4.5]decan-2-yl)-2,2-dimethylpropanenitrile (130 mg, 0.367 mmol) and sodium hydroxide (22 mg, 0.55 mmol) in DMSO at 10-15° C. The resultant reaction mixture was warmed to room temperature and stirred for 18 h. The reaction mixture was neutralized (pH~7) with 10% TFA in DCM at RT and the resultant mixture was concentrated in vacuo at below 40° C. to give the crude compound which was purified by preparative HPLC to give 100 mg of trans-3-(8-Dimethylamino-3-oxo-8-pyridin-2-yl-2-azaspiro[4.5]decan-2-yl)-2,2-dimethyl-propionamide as TFA salt.

Analogues Syntheses

The following compounds have been prepared in analogy to trans-3-(8-Dimethylamino-3-oxo-8-pyridin-2-yl-2-azaspiro[4.5]decan-2-yl)-2,2-dimethyl-propionamide 2,2,2-trifluoro acetate

| | |
|---|---|
| SC-1091 | Cis-4-(8-Dimethylamino-3-oxo-8-phenyl-2-azaspiro[4.5]decan-2-yl)-2,2-dimethyl-butyramide |
| SC-1092 | Cis-4-(8-Dimethylamino-3-oxo-8-phenyl-2-azaspiro[4.5]decan-2-yl)-butyramide |
| SC-1093 | Cis-1-[(8-Dimethylamino-3-oxo-8-phenyl-2-azaspiro[4.5]decan-2-yl)-methyl]-cyclobutane-1-carboxylic acid amide |
| SC-1094 | Cis-4-[8-Dimethylamino-8-(3-methoxy-propyl)-3-oxo-2-azaspiro[4.5]decan-2-yl]-butyramide 2,2,2-trifluoro acetate |
| SC-1095 | Cis-3-[8-Dimethylamino-8-(3-methoxy-propyl)-3-oxo-2-azaspiro[4.5]decan-2-yl]-2,2-dimethyl-propionamide 2,2,2-trifluoro acetate |
| SC-1096 | Cis-4-[8-Dimethylamino-8-(3-methoxy-propyl)-3-oxo-2-azaspiro[4.5]decan-2-yl]-2,2-dimethyl-butyramide 2,2,2-trifluoro acetate |
| SC-1097 | Cis-3-(8-Dimethylamino-3-oxo-8-pyrazin-2-yl-2-azaspiro[4.5]decan-2-yl)-2,2-dimethyl-propionamide |
| SC-1098 | Cis-4-(8-Dimethylamino-3-oxo-8-pyrazin-2-yl-2-azaspiro[4.5]decan-2-yl)-2,2-dimethyl-butyramide |

| | |
|---|---|
| SC-1099 | Cis-3-(8-Dimethylamino-3-oxo-8-pyridin-2-yl-2-azaspiro[4.5]decan-2-yl)-2,2-dimethyl-propionamide 2,2,2-trifluoro acetate |
| SC-1100 | Cis-4-(8-Dimethylamino-3-oxo-8-pyridin-2-yl-2-azaspiro[4.5]decan-2-yl)-2,2-dimethyl-butyramide |

Synthesis of cis-2-(8-Dimethylamino-3-oxo-8-pyridin-2-yl-2-azaspiro[4.5]decan-2-yl)-acetamide (SC-1011)

Synthesis of cis-4-[2-(8-Dimethylamino-3-oxo-8-phenyl-2-azaspiro[4.5]decan-2-yl)-ethyl]-tetrahydro-pyran-4-carboxylic acid 2,2,2-trifluoro acetate (Example SC-1194)

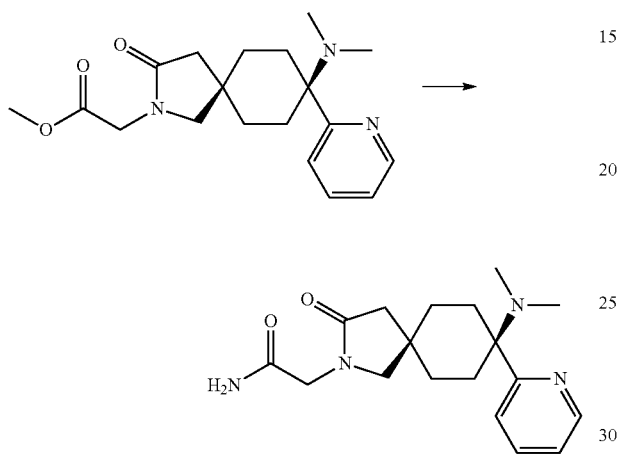

7M ammonia in methanol (5.0 mL) was added to a solution of methyl 2-(cis-8-(dimethylamino)-3-oxo-8-(pyridin-2-yl)-2-azaspiro[4.5]decan-2-yl)acetate (100 mg, 0.289 mol) in methanol (3.0 mL) at 0° C. and then stirred for 16 h at RT in a sealed tube. Volatiles was distilled under reduced pressure to afford crude, which was purified by adding 0.5 mL of DCM heated and then cooled to room temperature. Added 4 mL of n-Pentane stirred, filtered and dried to afford the yield 0.07 g (73%) cis-2-(8-Dimethylamino-3-oxo-8-pyridin-2-yl-2-azaspiro[4.5]decan-2-yl)-acetamide as a solid.

Analogues Syntheses

The following compounds have been prepared in analogy to cis-2-(8-Dimethylamino-3-oxo-8-pyridin-2-yl-2-azaspiro[4.5]decan-2-yl)-acetamide cis-4-[2-(8-Dimethylamino-3-oxo-8-phenyl-2-azaspiro[4.5]decan-2-yl)-ethyl]-tetrahydro-pyran-4-carboxylic acid tert-butyl ester (200 mg, 0.4 mmol) is dissolved in trifluoro acetic acid (1.6 mL) and stirred at 40° C. for 10 min. All volatiles are removed in vacuo. The residue was triturated with diethyl ether to obtain cis-4-[2-(8-Dimethylamino-3-oxo-8-phenyl-2-azaspiro[4.5]decan-2-yl)-ethyl]-tetrahydro-pyran-4-carboxylic acid 2,2,2-trifluoro acetate as a white solid (220 mg, 98%).

| | |
|---|---|
| SC-1006 | Cis-2-[8-Dimethylamino-8-(3-methoxy-propyl)-3-oxo-2-azaspiro[4.5]decan-2-yl]-acetamide |
| SC-1007 | Cis-3-[8-Dimethylamino-8-(3-methoxy-propyl)-3-oxo-2-azaspiro[4.5]decan-2-yl]-propionamide |
| SC-1008 | Cis-2-(8-Dimethylamino-3-oxo-8-pyrazin-2-yl-2-azaspiro[4.5]decan-2-yl)-acetamide |
| SC-1009 | Cis-3-(8-Dimethylamino-3-oxo-8-pyrazin-2-yl-2-azaspiro[4.5]decan-2-yl)-propionamide |
| SC-1010 | Cis-4-(8-Dimethylamino-3-oxo-8-pyrazin-2-yl-2-azaspiro[4.5]decan-2-yl)-butyramide |
| SC-1012 | Cis-3-(8-Dimethylamino-3-oxo-8-pyridin-2-yl-2-azaspiro[4.5]decan-2-yl)-propionamide |
| SC-1013 | Cis-4-(8-Dimethylamino-3-oxo-8-pyridin-2-yl-2-azaspiro[4.5]decan-2-yl)-butyramide |

Analogues Syntheses

The following compounds have been prepared in analogy to cis-4-[2-(8-Dimethylamino-3-oxo-8-phenyl-2-azaspiro[4.5]decan-2-yl)-ethyl]-tetrahydro-pyran-4-carboxylic acid 2,2,2-trifluoro acetate.

Example SC-1195 cis-4-[2-(8-Dimethylamino-3-oxo-8-phenyl-2-azaspiro[4.5]decan-2-yl)-ethyl]-1,1-dioxo-thiane-4-carboxylic acid 2,2,2-trifluoro acetate.

Synthesis of cis-3-(8-Dimethylamino-3-oxo-8-pyridin-2-yl-2-azaspiro[4.5]decan-2-yl)-propionic acid hydrochloride (Example SC-1047)

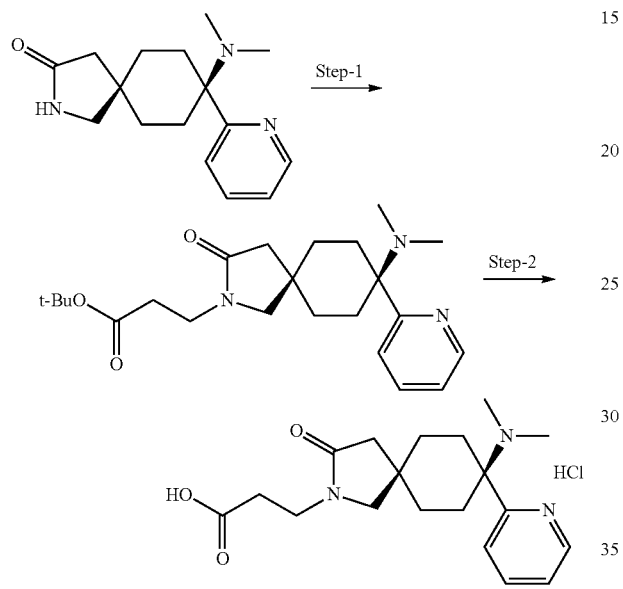

Step 1: tert-butyl-3-(cis-8-(dimethylamino)-3-oxo-8-(pyridin-2-yl)-2-azaspiro[4.5]decan-2-yl) propanoate NaH (60% in mineral oil; 58 mg, 1.46 mmol) was added to a suspension (5s,8s)-8-(dimethylamino)-8-(pyridin-2-yl)-2-azaspiro[4.5]decan-3-one (400 mg, 1.46 mmol) in THF (20 mL) at 0° C. and then stirred for 30 min at RT. A solution of t-butyl acrylate (0.21 mL, 1.46 mmol) in THF (2 mL) was added at 0° C. over a period of 1 h. The resultant mixture was stirred for 4 h at RT. The reaction mixture was quenched with saturated $NH_4Cl$ solution and extracted with ethyl acetate (3×25 mL). The combined organic layer was washed with water, brine, dried over anhydrous $Na_2SO_4$ and distilled under reduced pressure to afford crude, which was purified by preparative HPLC to give 350 mg (60%) of tert-butyl3-((5s,8s)-8-(dimethylamino)-3-oxo-8-(pyridin-2-yl)-2-azaspiro-[4.5]-decan-2-yl)-propanoate as a solid.

Step 2: cis-3-(8-Dimethylamino-3-oxo-8-pyridin-2-yl-2-azaspiro[4.5]decan-2-yl)-propionic acid hydrochloride 4M HCl in dioxane (3.0 mL) was added to tert-butyl-3-(cis-8-(dimethylamino)-3-oxo-8-(pyridin-2-yl)-2-azaspiro[4.5]decan-2-yl)-propanoate (100 mg, 0.24 mmol) at 0° C. and the whole then stirred for 16 h at RT. Volatiles were distilled under reduced pressure to afford crude, which was successively washed with acetone (2 mL), ether (5 mL) and pentane (10 mL) to yield 55 mg (57%) of cis-3-(8-Dimethylamino-3-oxo-8-pyridin-2-yl-2-azaspiro[4.5]decan-2-yl)-propionic acid hydrochloride as a solid.

Analogues Syntheses

The following compounds have been prepared in analogy to cis-3-(8-Dimethylamino-3-oxo-8-pyridin-2-yl-2-azaspiro[4.5]decan-2-yl)-propionic acid hydrochloride Example SC-1046 cis-2-(8-Dimethylamino-3-oxo-8-pyridin-2-yl-2-azaspiro[4.5]decan-2-yl)-acetic acid hydrochloride Example SC-1048 cis-2-(8-Dimethylamino-3-oxo-8-phenyl-2-azaspiro[4.5]decan-2-yl)-acetic acid hydrochloride Example SC-1201 cis-2-(8-Dimethylamino-3-oxo-8-phenyl-2-azaspiro[4.5]decan-2-yl)-acetic acid.

Analogues Syntheses

The following compounds have been prepared in analogy to tert-butyl-3-(cis-8-(dimethylamino)-3-oxo-8-(pyridin-2-yl)-2-azaspiro[4.5]decan-2-yl) propanoate:

Example SC-1078: 2-(8-Dimethylamino-3-oxo-8-pyridin-2-yl-2-azaspiro[4.5]decan-2-yl)-acetic acid methyl ester Example SC-1079: 3-(8-Dimethylamino-3-oxo-8-pyridin-2-yl-2-azaspiro[4.5]decan-2-yl)-propionic acid methyl ester Example SC-1081: 3-(8-Dimethylamino-3-oxo-8-pyridin-2-yl-2-azaspiro[4.5]decan-2-yl)-propionic acid tert-butyl ester

N-(2-cyanopropan-2-yl)-2-(cis-8-(dimethylamino)-3-oxo-8-phenyl-2-azaspiro[4, 5] decan-2-yl) acetamide (Example SC-1115)

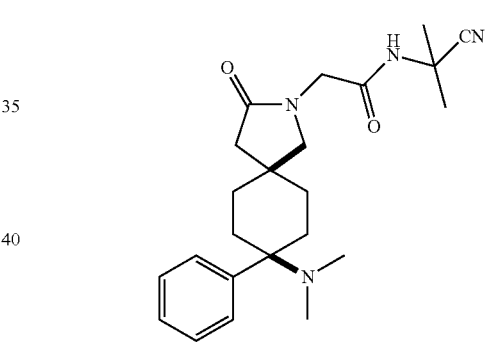

50% propylphosphonic anhydride (T3P) solution in DMF (0.86 mL, 1.3623 mmol) was added to a suspension of 2-(cis-8-(dimethylamino)-3-oxo-8-phenyl-2-azaspiro[4,5]decan-2-yl)acetic acid hydrochloride (250 mg, 0.68 mmol), 2-amino-2-methylpropanenitrile (0.069 mL, 0.74 mmol) and diisopropylethylamine (0.50 mL, 2.72 mmol) in THF (10 mL) at 0° C. The reaction mixture was warmed to RT and stirred for 16 h. The reaction mixture was quenched with water, the organic product was extracted with ethyl acetate (3×25 mL). The combined organic extracts were washed with water, brine, dried over anhydrous $Na_2SO_4$. Solvent was distilled under reduced pressure to give the crude compound. Purification by column chromatography over silica gel (100-200 mesh) by using 10% methanol in DCM as eluent to give 168 mg of compound which was further purified by preparative TLC by using 5% methanol in DCM as mobile phase to give 120 mg (44%) of N-(2-cyanopropan-2-yl)-2-(cis-8-(dimethylamino)-3-oxo-8-phenyl-2-azaspiro[4, 5] decan-2-yl) acetamide as a solid.

Analogues Syntheses:

The following compounds have been prepared in analogy to Example SC-1115:

| | |
|---|---|
| SC-1110 | Cis-N-(3-Cyano-propyl)-2-(8-dimethylamino-3-oxo-8-phenyl-2-azaspiro[4.5]decan-2-yl)-acetamide |
| SC-1111 | Cis-4-(8-Dimethylamino-3-oxo-8-phenyl-2-azaspiro[4.5]decan-2-yl)-N-methyl-butyramide |
| SC-1112 | Cis-8-Dimethylamino-2-[4-(4-methylsulfonyl-piperazin-1-yl)-4-oxo-butyl]-8-phenyl-2-azaspiro[4.5]decan-3-one |
| SC-1113 | Cis-8-Dimethylamino-2-[4-(1,1-dioxo-[1,4]thiazinan-4-yl)-4-oxo-butyl]-8-phenyl-2-azaspiro[4.5]decan-3-one |
| SC-1114 | Cis-2-(8-Dimethylamino-3-oxo-8-phenyl-2-azaspiro[4.5]decan-2-yl)-N-(2-hydroxy-2-methyl-propyl)-acetamide |
| SC-1115 | Cis-N-(1-Cyano-1-methyl-ethyl)-2-(8-dimethylamino-3-oxo-8-phenyl-2-azaspiro[4.5]decan-2-yl)-acetamide |
| SC-1116 | Cis-N-(2-Cyano-2-methyl-propyl)-2-(8-dimethylamino-3-oxo-8-phenyl-2-azaspiro[4.5]decan-2-yl)-acetamide |
| SC-1117 | Cis-2-(8-Dimethylamino-3-oxo-8-phenyl-2-azaspiro[4.5]decan-2-yl)-N-[2-(trifluoromethyl)-pyrimidin-5-yl]-acetamide |
| SC-1118 | Cis-2-(8-Dimethylamino-3-oxo-8-phenyl-2-azaspiro[4.5]decan-2-yl)-N-(pyridin-4-yl-methyl)-acetamide |
| SC-1119 | Cis-2-(8-Dimethylamino-3-oxo-8-phenyl-2-azaspiro[4.5]decan-2-yl)-N-(pyrimidin-4-yl-methyl)-acetamide |
| SC-1120 | Cis-2-(8-Dimethylamino-3-oxo-8-phenyl-2-azaspiro[4.5]decan-2-yl)-N-(pyrimidin-5-yl-methyl)-acetamide |
| SC-1123 | Cis-2-(8-Dimethylamino-3-oxo-8-phenyl-2-azaspiro[4.5]decan-2-yl)-N-(2-methylsulfonyl-ethyl)-acetamide |
| SC-1124 | Cis-8-Dimethylamino-2-[2-(1,1-dioxo-[1,4]thiazinan-4-yl)-2-oxo-ethyl]-8-phenyl-2-azaspiro[4.5]decan-3-one |
| SC-1125 | Cis-2-[[2-(8-Dimethylamino-3-oxo-8-phenyl-2-azaspiro[4.5]decan-2-yl)-acetyl]amino]-N,N-dimethyl-acetamide |
| SC-1126 | Cis-2-[[2-(8-Dimethylamino-3-oxo-8-phenyl-2-azaspiro[4.5]decan-2-yl)-acetyl]amino]-acetamide |
| SC-1127 | Cis-2-[[2-(8-Dimethylamino-3-oxo-8-phenyl-2-azaspiro[4.5]decan-2-yl)-acetyl]amino]-N-methyl-acetamide |
| SC-1128 | Cis-2-[[2-(8-Dimethylamino-3-oxo-8-phenyl-2-azaspiro[4.5]decan-2-yl)-acetyl]amino]-N,2-dimethyl-propionamide |
| SC-1129 | Cis-2-(8-Dimethylamino-3-oxo-8-phenyl-2-azaspiro[4.5]decan-2-yl)-N-[(dimethyl-carbamoyl)-methyl]-N-methyl-acetamide |
| SC-1130 | Cis-N-(Carbamoyl-methyl)-2-(8-dimethylamino-3-oxo-8-phenyl-2-azaspiro[4.5]decan-2-yl)-N-methyl-acetamide |
| SC-1131 | Cis-2-(8-Dimethylamino-3-oxo-8-phenyl-2-azaspiro[4.5]decan-2-yl)-N-methyl-N-(methylcarbamoyl-methyl)-acetamide |
| SC-1132 | Cis-2-[[2-(8-Dimethylamino-3-oxo-8-phenyl-2-azaspiro[4.5]decan-2-yl)-acetyl]-methyl-amino]-N,2-dimethyl-propionamide |
| SC-1133 | Cis-3-(8-Dimethylamino-3-oxo-8-phenyl-2-azaspiro[4.5]decan-2-yl)-N-(2-hydroxy-ethyl)-2,2-dimethyl-propionamide |
| SC-1134 | Cis-3-(8-Dimethylamino-3-oxo-8-phenyl-2-azaspiro[4.5]decan-2-yl)-N-(2-methoxy-ethyl)-2,2-dimethyl-propionamide |
| SC-1135 | Cis-8-Dimethylamino-2-[3-(1,1-dioxo-[1,4]thiazinan-4-yl)-2,2-dimethyl-3-oxo-propyl]-8-phenyl-2-azaspiro[4.5]decan-3-one |
| SC-1136 | Cis-3-(8-Dimethylamino-3-oxo-8-phenyl-2-azaspiro[4.5]decan-2-yl)-N,2,2-trimethyl-propionamide |
| SC-1137 | Cis-4-(8-Dimethylamino-3-oxo-8-phenyl-2-azaspiro[4.5]decan-2-yl)-2,2-dimethyl-N-phenyl-butyramide |
| SC-1138 | Cis-N-Benzyl-4-(8-dimethylamino-3-oxo-8-phenyl-2-azaspiro[4.5]decan-2-yl)-2,2-dimethyl-butyramide |
| SC-1139 | Cis-4-(8-Dimethylamino-3-oxo-8-phenyl-2-azaspiro[4.5]decan-2-yl)-2,2-dimethyl-N-(pyridin-4-yl-methyl)-butyramide |
| SC-1140 | Cis-4-(8-Dimethylamino-3-oxo-8-phenyl-2-azaspiro[4.5]decan-2-yl)-2,2-dimethyl-N-[(2-methyl-pyrimidin-4-yl)-methyl]-butyramide |
| SC-1141 | Cis-4-(8-Dimethylamino-3-oxo-8-phenyl-2-azaspiro[4.5]decan-2-yl)-N-(2-methoxy-ethyl)-2,2-dimethyl-butyramide |
| SC-1142 | Cis-4-(8-Dimethylamino-3-oxo-8-phenyl-2-azaspiro[4.5]decan-2-yl)-N-(2-hydroxy-2-methyl-propyl)-2,2-dimethyl-butyramide |
| SC-1145 | Cis-4-(8-Dimethylamino-3-oxo-8-phenyl-2-azaspiro[4.5]decan-2-yl)-N,2,2-trimethyl-butyramide |
| SC-1146 | Cis-N-(Cyano-methyl)-4-(8-dimethylamino-3-oxo-8-phenyl-2-azaspiro[4.5]decan-2-yl)-2,2-dimethyl-butyramide |
| SC-1147 | Cis-N-(2-Cyanoethyl)-4-(8-dimethylamino-3-oxo-8-phenyl-2-azaspiro[4.5]decan-2-yl)-2,2-dimethyl-butyramide |
| SC-1148 | Cis-N-(Carbamoyl-methyl)-4-(8-dimethylamino-3-oxo-8-phenyl-2-azaspiro[4.5]decan-2-yl)-2,2-dimethyl-butyramide |
| SC-1149 | Cis-4-(8-Dimethylamino-3-oxo-8-phenyl-2-azaspiro[4.5]decan-2-yl)-2,2-dimethyl-N-(methylcarbamoyl-methyl)-butyramide |
| SC-1150 | Cis-4-(8-Dimethylamino-3-oxo-8-phenyl-2-azaspiro[4.5]decan-2-yl)-N-[(dimethyl-carbamoyl)-methyl]-2,2-dimethyl-butyramide |
| SC-1151 | Cis-4-(8-Dimethylamino-3-oxo-8-phenyl-2-azaspiro[4.5]decan-2-yl)-2,2-dimethyl-N-(2-methylsulfonyl-ethyl)-butyramide |
| SC-1152 | Cis-4-(8-Dimethylamino-3-oxo-8-phenyl-2-azaspiro[4.5]decan-2-yl)-N-(1,1-dioxo-thian-4-yl)-2,2-dimethyl-butyramide |
| SC-1153 | Cis-4-(8-Dimethylamino-3-oxo-8-phenyl-2-azaspiro[4.5]decan-2-yl)-N-[(1,1-dioxo-thian-4-yl)-methyl]-2,2-dimethyl-butyramide |

| | |
|---|---|
| SC-1154 | Cis-3-(8-Dimethylamino-3-oxo-8-phenyl-2-azaspiro[4.5]decan-2-yl)-N-methyl-propionamide |
| SC-1179 | Cis-8-Dimethylamino-2-[2,2-dimethyl-3-(4-methylsulfonyl-piperazin-1-yl)-3-oxo-propyl]-8-phenyl-2-azaspiro[4.5]decan-3-one |
| SC-1180 | Cis-2-(8-Dimethylamino-3-oxo-8-phenyl-2-azaspiro[4.5]decan-2-yl)-N-(1,1-dioxo-thian-4-yl)-acetamide |
| SC-1181 | Cis-3-(8-Dimethylamino-3-oxo-8-phenyl-2-azaspiro[4.5]decan-2-yl)-2,2-dimethyl-N-(2-methylsulfonyl-ethyl)-propionamide |
| SC-1182 | Cis-8-Dimethylamino-2-[2,2-dimethyl-3-oxo-3-(3-oxo-piperazin-1-yl)-propyl]-8-phenyl-2-azaspiro[4.5]decan-3-one |
| SC-1183 | Cis-2-(8-Dimethylamino-3-oxo-8-phenyl-2-azaspiro[4.5]decan-2-yl)-N-[(1,1-dioxo-thian-4-yl)-methyl]-acetamide |
| SC-1184 | Cis-3-(8-Dimethylamino-3-oxo-8-phenyl-2-azaspiro[4.5]decan-2-yl)-2,2-dimethyl-N-(2-pyrimidin-5-yl-ethyl)-propionamide |
| SC-1185 | Cis-4-(8-Dimethylamino-3-oxo-8-phenyl-2-azaspiro[4.5]decan-2-yl)-N-(2-hydroxy-ethyl)-2,2-dimethyl-butyramide |
| SC-1186 | Cis-4-(8-Dimethylamino-3-oxo-8-phenyl-2-azaspiro[4.5]decan-2-yl)-N-(3-hydroxy-propyl)-2,2-dimethyl-butyramide |
| SC-1187 | Cis-4-(8-Dimethylamino-3-oxo-8-phenyl-2-azaspiro[4.5]decan-2-yl)-N-(3-hydroxy-3-methyl-butyl)-2,2-dimethyl-butyramide |
| SC-1189 | Cis-8-Dimethylamino-2-[4-(1,1-dioxo-[1,4]thiazinan-4-yl)-3,3-dimethyl-4-oxo-butyl]-8-phenyl-2-azaspiro[4.5]decan-3-one |
| SC-1190 | Cis-2-(8-Dimethylamino-3-oxo-8-phenyl-2-azaspiro[4.5]decan-2-yl)-N-(5-methoxy-pyrazin-2-yl)-acetamide |
| SC-1155 | Cis-1-(8-Dimethylamino-8-phenyl-2-azaspiro[4.5]decan-2-yl)-2-pyridin-2-yl-ethanone |
| SC-1156 | Cis-1-(8-Dimethylamino-8-phenyl-2-azaspiro[4.5]decan-2-yl)-2-pyridin-3-yl-ethanone |
| SC-1157 | Cis-1-(8-Dimethylamino-8-phenyl-2-azaspiro[4.5]decan-2-yl)-2-pyridin-4-yl-ethanone |
| SC-1158 | Cis-1-(8-Dimethylamino-8-phenyl-2-azaspiro[4.5]decan-2-yl)-3-pyridin-2-yl-propan-1-one |
| SC-1159 | Cis-1-(8-Dimethylamino-8-phenyl-2-azaspiro[4.5]decan-2-yl)-3-pyridin-3-yl-propan-1-one |
| SC-1160 | Cis-1-(8-Dimethylamino-8-phenyl-2-azaspiro[4.5]decan-2-yl)-3-pyridin-4-yl-propan-1-one |
| SC-1161 | Cis-1-(8-Dimethylamino-8-phenyl-2-azaspiro[4.5]decan-2-yl)-4-pyridin-2-yl-butan-1-one |
| SC-1162 | Cis-N-[3-(8-Dimethylamino-8-phenyl-2-azaspiro[4.5]decan-2-yl)-3-oxo-propyl]-acetamide |
| SC-1163 | Cis-N-[2-(8-Dimethylamino-8-phenyl-2-azaspiro[4.5]decan-2-yl)-2-oxo-ethyl]-acetamide |
| SC-1164 | Cis-1-(8-Dimethylamino-8-phenyl-2-azaspiro[4.5]decan-2-yl)-3-phenyl-propan-1-one |
| SC-1165 | Cis-1-(8-Dimethylamino-8-phenyl-2-azaspiro[4.5]decan-2-yl)-3-(2-methoxyphenyl)-propan-1-one |
| SC-1166 | Cis-1-(8-Dimethylamino-8-phenyl-2-azaspiro[4.5]decan-2-yl)-3-(3-methoxyphenyl)-propan-1-one |
| SC-1167 | Cis-1-(8-Dimethylamino-8-phenyl-2-azaspiro[4.5]decan-2-yl)-3-(4-methoxyphenyl)-propan-1-one |
| SC-1168 | Cis-1-(8-Dimethylamino-8-phenyl-2-azaspiro[4.5]decan-2-yl)-4-pyridin-4-yl-butan-1-one |
| SC-1169 | Cis-1-(8-Dimethylamino-8-phenyl-2-azaspiro[4.5]decan-2-yl)-4-pyridin-3-yl-butan-1-one |
| SC-1191 | Cis-2-(8-Dimethylamino-3-oxo-8-phenyl-2-azaspiro[4.5]decan-2-yl)-N-(3-hydroxy-3-methyl-butyl)-acetamide |
| SC-1192 | Cis-N-[3-(8-Dimethylamino-3-oxo-8-phenyl-2-azaspiro[4.5]decan-2-yl)-propyl]-2-isoxazol-3-yl-acetamide |
| SC-1193 | Cis-N-[3-(8-Dimethylamino-3-oxo-8-phenyl-2-azaspiro[4.5]decan-2-yl)-propyl]-4-methyl-isoxazole-5-carboxylic acid amide |
| SC-1170 | Cis-N-[3-(8-Dimethylamino-3-oxo-8-phenyl-2-azaspiro[4.5]decan-2-yl)-propyl]-pyridine-2-carboxylic acid amide |
| SC-1171 | Cis-N-[3-(8-Dimethylamino-3-oxo-8-phenyl-2-azaspiro[4.5]decan-2-yl)-propyl]-pyridine-3-carboxylic acid amide |
| SC-1172 | Cis-N-[3-(8-Dimethylamino-3-oxo-8-phenyl-2-azaspiro[4.5]decan-2-yl)-propyl]-pyridine-4-carboxylic acid amide |
| SC-1173 | Cis-N-[3-(8-Dimethylamino-3-oxo-8-phenyl-2-azaspiro[4.5]decan-2-yl)-propyl]-pyrimidine-5-carboxylic acid amide |
| SC-1174 | Cis-N-[3-(8-Dimethylamino-3-oxo-8-phenyl-2-azaspiro[4.5]decan-2-yl)-propyl]-5-methyl-oxazole-4-carboxylic acid amide |
| SC-1175 | Cis-N-[3-(8-Dimethylamino-3-oxo-8-phenyl-2-azaspiro[4.5]decan-2-yl)-propyl]-pyrimidine-4-carboxylic acid amide |
| SC-1176 | Cis-N-[3-(8-Dimethylamino-3-oxo-8-phenyl-2-azaspiro[4.5]decan-2-yl)-propyl]-3-methyl-pyrazine-2-carboxylic acid amide |
| SC-1177 | Cis-N-[3-(8-Dimethylamino-3-oxo-8-phenyl-2-azaspiro[4.5]decan-2-yl)-propyl]-3-methyl-isoxazole-5-carboxylic acid amide |
| SC-1178 | Cis-N-[3-(8-Dimethylamino-3-oxo-8-phenyl-2-azaspiro[4.5]decan-2-yl)-propyl]-benzamide |

| | |
|---|---|
| SC-1198 | Cis-N-Butyl-2-(8-dimethylamino-3-oxo-8-phenyl-2-azaspiro[4.5]decan-2-yl)-acetamide |
| SC-1199 | Cis-N-(Cyclopropyl-methyl)-2-(8-dimethylamino-3-oxo-8-phenyl-2-azaspiro[4.5]decan-2-yl)-acetamide |
| SC-1200 | Cis-2-(8-Dimethylamino-3-oxo-8-phenyl-2-azaspiro[4.5]decan-2-yl)-N-propyl-acetamide |

Cis-8-Dimethylamino-2,8-diphenyl-2-azaspiro[4.5]decan-3-one (Example SC-1070)

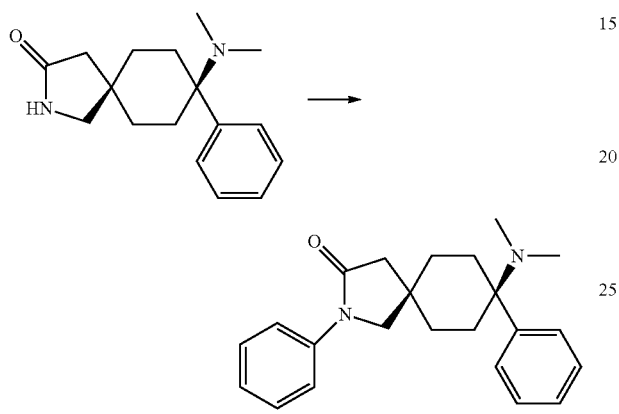

Cis-8-Dimethylamino-8-phenyl-2-azaspiro[4.5]decan-3-one (60 mg, 0.22 mmol), K3PO4 (187 mg, 0.88 mmol), CuI (21 mg, 0.11 mmol) and iodobenzene (0.098 mL, 0.88 mmol) were suspended in N,N'-dimethyl ethylenediamine (0.42 mL) and heated under a Nitrogen atmosphere to 120° C. overnight. The crude reaction mixture was diluted with water (2 mL) and extracted with DCM (3×5 mL). The combined organic layers were dried over Na₂SO₄, dried in vacuo and purified by column chromatography to yield Cis-8-Dimethyl-amino-2,8-diphenyl-2-azaspiro[4.5]decan-3-one (21 mg) as a white solid.

Analogues Syntheses:

The following compounds have been prepared in analogy to Example SC-1070:

| | |
|---|---|
| SC-1056 | trans-8-Dimethylamino-2-(6-methoxy-pyridin-3-yl)-8-phenyl-2-azaspiro[4.5]decan-3-one |
| SC-1057 | trans-8-Dimethylamino-2-(2-methoxy-pyrimidin-5-yl)-8-phenyl-2-azaspiro[4.5]decan-3-one |
| SC-1058 | trans-8-Dimethylamino-2-(5-methoxy-pyrimidin-2-yl)-8-phenyl-2-azaspiro[4.5]decan-3-one |
| SC-1059 | trans-8-Dimethylamino-2-(3-methoxy-pyridin-2-yl)-8-phenyl-2-azaspiro[4.5]decan-3-one |
| SC-1060 | trans-8-Dimethylamino-2-(5-methoxy-pyrazin-2-yl)-8-phenyl-2-azaspiro[4.5]decan-3-one |
| SC-1061 | trans-8-Dimethylamino-2-(5-methyl-pyrazin-2-yl)-8-phenyl-2-azaspiro[4.5]decan-3-one |
| SC-1062 | trans-8-Dimethylamino-2-(5-fluoro-pyridin-2-yl)-8-phenyl-2-azaspiro[4.5]decan-3-one |
| SC-1063 | trans-8-Dimethylamino-8-phenyl-2-pyrazin-2-yl-2-azaspiro[4.5]decan-3-one |
| SC-1064 | trans-8-Dimethylamino-8-phenyl-2-(2-pyridin-4-yl-thiazol-4-yl)-2-azaspiro[4.5]decan-3-one |
| SC-1065 | Cis-5-Chloro-2-(8-dimethylamino-3-oxo-8-phenyl-2-azaspiro[4.5]decan-2-yl)-benzonitrile |
| SC-1066 | Cis-8-Dimethylamino-2-(6-methyl-pyridazin-3-yl)-8-phenyl-2-azaspiro[4.5]decan-3-one |
| SC-1067 | Cis-8-Dimethylamino-8-phenyl-2-[2-(trifluoromethyl)-pyrimidin-5-yl]-2-azaspiro[4.5]decan-3-one |
| SC-1068 | Cis-2-([2,1,3]Benzothiadiazol-4-yl)-8-dimethylamino-8-phenyl-2-azaspiro[4.5]decan-3-one |
| SC-1069 | Trans-8-Dimethylamino-2,8-diphenyl-2-azaspiro[4.5]decan-3-one |
| SC-1071 | Cis-4-(8-Dimethylamino-3-oxo-8-phenyl-2-azaspiro[4.5]decan-2-yl)-benzonitrile |
| SC-1072 | Cis-3-(8-Dimethylamino-3-oxo-8-phenyl-2-azaspiro[4.5]decan-2-yl)-benzonitrile |
| SC-1073 | Cis-2-(8-Dimethylamino-3-oxo-8-phenyl-2-azaspiro[4.5]decan-2-yl)-benzonitrile |
| SC-1074 | Cis-4-(8-Dimethylamino-3-oxo-8-phenyl-2-azaspiro[4.5]decan-2-yl)-benzoic acid methyl ester |
| SC-1075 | Cis-2-(8-Dimethylamino-3-oxo-8-phenyl-2-azaspiro[4.5]decan-2-yl)-5-methyl-benzonitrile |

Synthesis of cis-4-(8-Dimethylamino-3-oxo-8-phenyl-2-azaspiro[4.5]decan-2-yl)-2,2-dimethyl-N-(pyrimidin-4-yl-methyl)-butyramide (Example SC-1030)

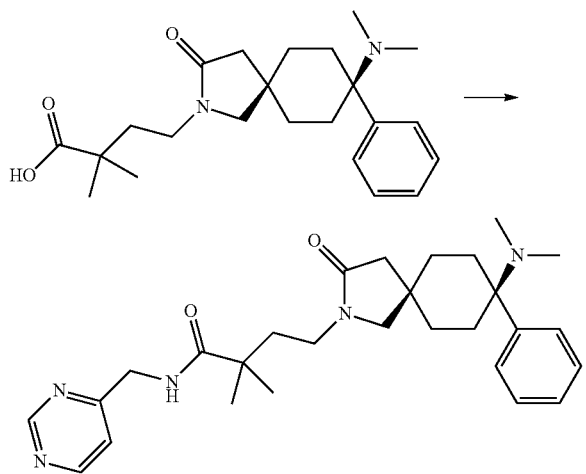

To a stirred solution of 4-(cis-8-(dimethylamino)-3-oxo-8-phenyl-2-azaspiro[4.5]decan-2-yl)-2,2-dimethylbutanoic acid hydrochloride (300 mg, 0.71 mmol) in THF (10 mL), diisopropylethylamine (490 mg, 3.80 mmol) and HATU (541 mg, 1.43 mmol) were added at RT. The reaction mixture was stirred at RT for 45 min and then pyrimidin-4-yl-methanamine (114 mg, 1.045 mmol) was added at 0° C. The reaction mixture was warmed to RT and stirred for 16 h. The reaction mixture was quenched with saturated NaHCO3 Solution, extracted with 10% methanol in DCM (3×25 mL). The combined organic extracts were dried over anhydrous $Na_2SO_4$ and concentrated under reduced pressure to give the crude compound. Purification by column chromatography over silica gel (100-200 mesh) by using 10% methanol in DCM with traces of ammonia as eluent to give 160 mg of compound which was further purified by preparative TLC by using 5% methanol in DCM as mobile phase to give 110 mg (33%) of cis-4-(8-Dimethylamino-3-oxo-8-phenyl-2-azaspiro[4.5]decan-2-yl)-2,2-dimethyl-N-(pyrimidin-4-yl-methyl)-butyramide as solid.

Analogues Syntheses:

The following compounds have been prepared in analogy to Example SC-1030:

| | |
|---|---|
| SC-1014 | Cis-N-Benzyl-2-(8-dimethylamino-3-oxo-8-phenyl-2-azaspiro[4.5]decan-2-yl)-acetamide |
| SC-1015 | Cis-2-(8-Dimethylamino-3-oxo-8-phenyl-2-azaspiro[4.5]decan-2-yl)-N-(2-methoxy-ethyl)-acetamide |
| SC-1016 | Cis-N-(2-Cyanoethyl)-2-(8-dimethylamino-3-oxo-8-phenyl-2-azaspiro[4.5]decan-2-yl)-acetamide |
| SC-1017 | Cis-3-(8-Dimethylamino-3-oxo-8-phenyl-2-azaspiro[4.5]decan-2-yl)-N-(3-methoxy-propyl)-propionamide |
| SC-1018 | Cis-N-(Cyano-methyl)-2-(8-dimethylamino-3-oxo-8-phenyl-2-azaspiro[4.5]decan-2-yl)-acetamide |
| SC-1019 | Cis-N-(2-Cyanoethyl)-3-(8-dimethylamino-3-oxo-8-phenyl-2-azaspiro[4.5]decan-2-yl)-propionamide |
| SC-1020 | Cis-N-(Cyano-methyl)-3-(8-dimethylamino-3-oxo-8-phenyl-2-azaspiro[4.5]decan-2-yl)-propionamide |
| SC-1021 | Cis-N-(3-Cyano-propyl)-3-(8-dimethylamino-3-oxo-8-phenyl-2-azaspiro[4.5]decan-2-yl)-propionamide |
| SC-1022 | Cis-3-(8-Dimethylamino-3-oxo-8-phenyl-2-azaspiro[4.5]decan-2-yl)-N-pyridin-2-yl-propionamide |
| SC-1023 | Cis-3-(8-Dimethylamino-3-oxo-8-phenyl-2-azaspiro[4.5]decan-2-yl)-N-(2-phenyl-ethyl)-propionamide |
| SC-1024 | Cis-3-(8-Dimethylamino-3-oxo-8-phenyl-2-azaspiro[4.5]decan-2-yl)-N-(2-methoxy-ethyl)-propionamide |
| SC-1025 | Cis-N-Benzyl-3-(8-dimethylamino-3-oxo-8-phenyl-2-azaspiro[4.5]decan-2-yl)-propionamide |
| SC-1026 | Cis-2-(8-Dimethylamino-3-oxo-8-phenyl-2-azaspiro[4.5]decan-2-yl)-N-(3-methoxy-propyl)-acetamide |
| SC-1027 | Cis-2-(8-Dimethylamino-3-oxo-8-phenyl-2-azaspiro[4.5]decan-2-yl)-N-(2-phenyl-ethyl)-acetamide |
| SC-1028 | Cis-3-(8-Dimethylamino-3-oxo-8-phenyl-2-azaspiro[4.5]decan-2-yl)-N-pyridin-3-yl-propionamide |
| SC-1029 | Cis-4-(8-Dimethylamino-3-oxo-8-phenyl-2-azaspiro[4.5]decan-2-yl)-2,2-dimethyl-N-pyridin-4-yl-butyramide |
| SC-1031 | Cis-4-(8-Dimethylamino-3-oxo-8-phenyl-2-azaspiro[4.5]decan-2-yl)-2,2-dimethyl-N-(pyrimidin-5-yl-methyl)-butyramide |
| SC-1038 | Cis-N-(1-Cyano-cyclopropyl)-4-(8-dimethylamino-3-oxo-8-phenyl-2-azaspiro[4.5]decan-2-yl)-2,2-dimethyl-butyramide |
| SC-1039 | Cis-3-(8-Dimethylamino-3-oxo-8-phenyl-2-azaspiro[4.5]decan-2-yl)-N-(1,1-dioxo-thian-4-yl)-2,2-dimethyl-propionamide |
| SC-1040 | Cis-8-Dimethylamino-2-[3-[2-(hydroxymethyl)-morpholin-4-yl]-2,2-dimethyl-3-oxo-propyl]-8-phenyl-2-azaspiro[4.5]decan-3-one |
| SC-1033 | Cis-3-(8-Dimethylamino-8-phenyl-2-azaspiro[4.5]decan-2-yl)-3-oxo-propionamide |
| SC-1034 | Cis-3-(8-Dimethylamino-8-phenyl-2-azaspiro[4.5]decan-2-yl)-2,2-dimethyl-3-oxo-propionamide |
| SC-1032 | Cis-2-(8-Dimethylamino-3-oxo-8-phenyl-2-azaspiro[4.5]decan-2-yl)-N-pyrimidin-4-yl-acetamide |
| SC-1041 | Cis-3-(8-Dimethylamino-3-oxo-8-phenyl-2-azaspiro[4.5]decan-2-yl)-propionamide |

| | |
|---|---|
| SC-1035 | Cis-2-(8-Dimethylamino-3-oxo-8-phenyl-2-azaspiro[4.5]decan-2-yl)-acetamide |
| SC-1036 | Cis-4-[2-(8-Dimethylamino-3-oxo-8-phenyl-2-azaspiro[4.5]decan-2-yl)-ethyl]-tetrahydro-pyran-4-carboxylic acid amide |
| SC-1037 | Cis-4-[2-(8-Dimethylamino-3-oxo-8-phenyl-2-azaspiro[4.5]decan-2-yl)-ethyl]-1,1-dioxo-thiane-4-carboxylic acid amide |

Synthesis of cis-2,2-Dimethyl-4-(8-methylamino-3-oxo-8-pyridin-2-yl-2-azaspiro[4.5]decan-2-yl)-butyramide (Example SC-1087)

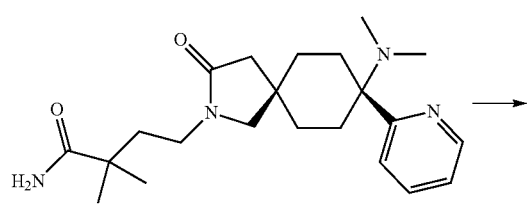

N-Iodo succinimide (174 mg, 0.51 mmol) was added to a suspension of 4-(cis-8-(dimethylamino)-3-oxo-8-(pyridin-2-yl)-2-azaspiro[4.5]decan-2-yl)-2,2-dimethylbutanamide (200 mg, 0.51 mmol) in a mixture of acetonitrile and THF (1:1 v/v, 10 mL) at RT and the resultant mixture was stirred for 16 h at RT. The reaction mixture was basified with 2N NaOH solution to pH~10 and the organic product was extracted with DCM (10 mL×3). The combined organic extracts were dried over anhydrous sodium sulphate and solvent was concentrated in vacuo to get the residue which was stirred vigorously with a mixture of 10% aqueous citric acid solution (5 mL) and DCM (10 mL) at RT for 10 min. The reaction mixture was basified with 5N NaOH solution to pH~10 and extracted with DCM (10 mL×3). The combined organic layer was dried over anhydrous sodium sulphate and solvent was concentrated in vacuo to get the crude which was purified by preparative TLC by using 5% methanol in DCM with traces of ammonia drops as mobile phase to get the compound. This was washed with diethyl ether (3 mL) to give 109 mg (56%) of cis-2,2-Dimethyl-4-(8-methylamino-3-oxo-8-pyridin-2-yl-2-azaspiro[4.5]decan-2-yl)-butyramide as a solid Analogues Syntheses:

The following compounds have been prepared in analogy to Example SC-1087:

| | |
|---|---|
| SC-1083 | Cis-2-(8-Methylamino-3-oxo-8-pyridin-2-yl-2-azaspiro[4.5]decan-2-yl)-acetamide |
| SC-1084 | Cis-3-(8-Methylamino-3-oxo-8-pyridin-2-yl-2-azaspiro[4.5]decan-2-yl)-propionamide |
| SC-1085 | Cis-4-(8-Methylamino-3-oxo-8-pyridin-2-yl-2-azaspiro[4.5]decan-2-yl)-butyramide 2,2,2-trifluoro acetate |
| SC-1086 | Cis-2,2-Dimethyl-3-(8-methylamino-3-oxo-8-pyridin-2-yl-2-azaspiro[4.5]decan-2-yl)-propionamide 2,2,2-trifluoro acetate |
| SC-1088 | Trans-2,2-Dimethyl-3-(8-methylamino-3-oxo-8-pyridin-2-yl-2-azaspiro[4.5]decan-2-yl)-propionamide |
| SC-1082 | Cis-2,2-Dimethyl-3-(8-methylamino-3-oxo-8-phenyl-2-azaspiro[4.5]decan-2-yl)-propionamide |

Synthesis of building block: cis-8-Dimethylamino-4-(methoxymethyl)-8-phenyl-2-azaspiro[4.5]decan-3-one (BB-16 and BB-17)

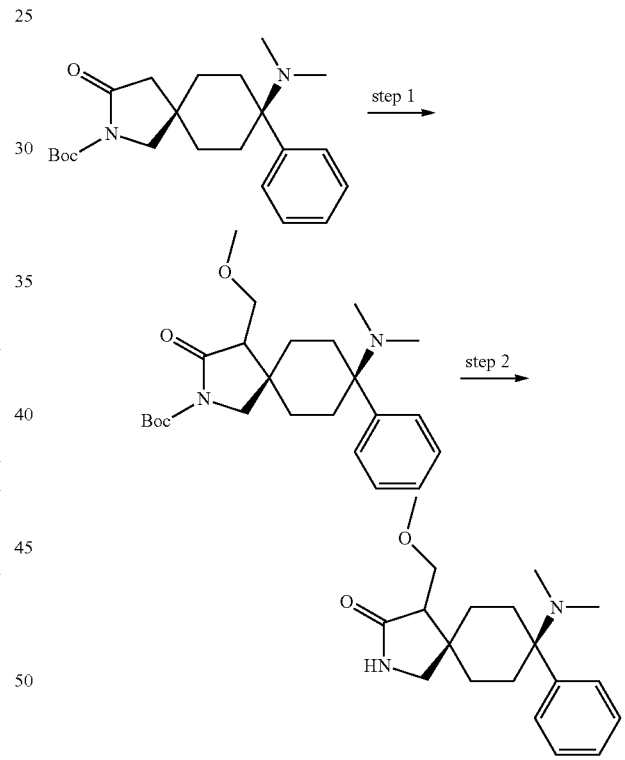

Step 1: cis-tert-butyl 8-(dimethylamino)-4-(methoxymethyl)-3-oxo-8-phenyl-2-azaspiro[4.5]decane-2-carboxylate To a stirred solution of compound cis-tert-butyl 8-(dimethylamino)-3-oxo-8-phenyl-2-azaspiro[4.5]decane-2-carboxylate (1.4 g, 3.76 mmol) in THF (15 mL) at −78° C. under argon atmosphere was added LHMDS (1M in THF) (5.5 mL, 5.64 mmol), stirred for 15 min then added bromomethyl methyl ether (0.37 mL, 4.5 mmol), stirred for another 1.5 h at −78° C. The RM was quenched with sat. NH$_4$Cl, extracted with DCM (2×20 mL), washed with brine (10 mL), dried (Na$_2$SO$_4$) and evaporated under reduced pressure to get crude compound cis-tert-butyl 8-(dimethylamino)-4-(methoxymethyl)-3-oxo-8-phenyl-2-azaspiro[4.5]decane-2-carboxylate (1.40 g, crude) as off white solid.

Step 2: cis-8-Dimethylamino-4-(methoxymethyl)-8-phenyl-2-azaspiro[4.5]decan-3-one To a stirred solution of compound cis-tert-butyl 8-(dimethylamino)-4-(methoxymethyl)-3-oxo-8-phenyl-2-azaspiro[4.5]decane-2-carboxylate (1.4 g, 3.36 mmol) in DCM (15 mL) was added TFA (1.4 mL) at RT and stirred for 1 h. The RM was evaporated and diluted with DCM (20 mL), washed with sat. NaHCO₃ solution, dried (Na₂SO₄) and evaporated under reduced pressure to get crude compound. The crude compound was purified by column chromatography (Neutral alumina) using 2% MeOH in DCM to get compound cis-8-Dimethylamino-4-(methoxymethyl)-8-phenyl-2-azaspiro[4.5]decan-3-one (1.0 g, ~94%) as white solid Chiral resolution of cis-8-Dimethylamino-4-(methoxymethyl)-8-phenyl-2-azaspiro[4.5]decan-3-one Cis-rac 8-Dimethylamino-4-(methoxymethyl)-8-phenyl-2-azaspiro[4.5]decan-3-one was subjected to preparative chiral-SFC (Chiralcel-OX—H column, co-solvent iPrOH+ 0.5% iso propylamine) to give cis-Enantiomer 1 (BB 16) and cis-Enantiomer 2 (BB-17)

Cis-Enantiomer 1 (BB-16)—analytical SFC: Chiralcel OX—H (250×4.6 mm 5μ), 4 g/min, RT, 40% iPrOH (+0.5% isopropylamine), Ret. Time 1.82; ee>95%

Cis-Enantiomer 2 (BB-17)—analytical SFC: Chiralcel OX—H (250×4.6 mm 5μ), 4 g/min, RT, 40% iPrOH (+0.5% isopropylamine), Ret. Time 3.13; ee>95%

Analogues Syntheses:

The following compounds have been prepared in analogy to cis-tert-butyl 8-(dimethylamino)-4-(methoxymethyl)-3-oxo-8-phenyl-2-azaspiro[4.5]decane-2-carboxylate:

Example SC-1104: cis-4-Benzyl-8-dimethylamino-3-oxo-8-phenyl-2-azaspiro[4.5]decane-2-carboxylic acid tert-butyl ester.

Synthesis of cis-N-[3-(8-Dimethylamino-3-oxo-8-phenyl-2-azaspiro[4.5]decan-2-yl)-propyl]-pyridine-2-sulfonic acid amide (Example SC-1109)

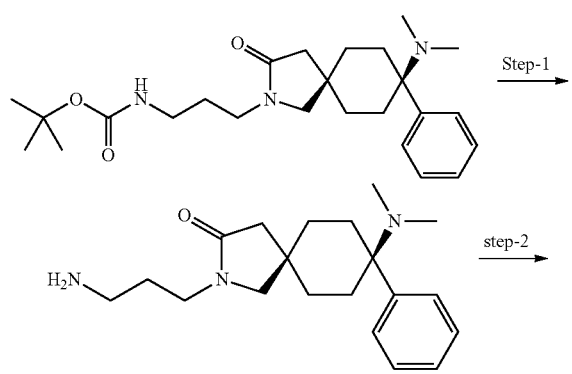

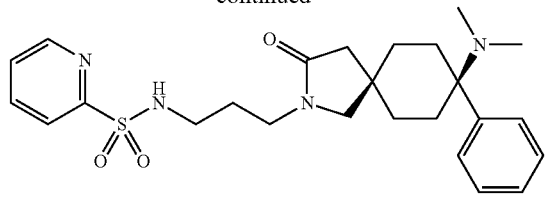

Step 1: cis-8-Dimethylamino-4-(methoxymethyl)-8-phenyl-2-azaspiro[4.5]decan-3-one tert-butyl (3-(cis-8-(dimethylamino)-3-oxo-8-phenyl-2-azaspiro[4.5]decan-2-yl)propyl) carbamate (1 g, 0.43 mmol) is dissolved in DCM (15 mL) and TFA (2.5 mL, 32 mmol) is added dropwise at 0° C. After stirring for 2 h, DCM (50 mL) and 1M NaOH is added until a pH of 9 is reached. Then the organic layer is separated and washed with 1M NaHCO3 (3×50 mL), dried over Na2SO4 and concentrated in vacuo to yield cis-8-Dimethylamino-4-(methoxymethyl)-8-phenyl-2-azaspiro[4.5]decan-3-one (0.6 g) as a colorless oil Step 2: cis-8-Dimethylamino-4-(methoxymethyl)-8-phenyl-2-azaspiro[4.5]decan-3-one cis-8-Dimethylamino-4-(methoxymethyl)-8-phenyl-2-azaspiro[4.5]decan-3-one (50 mg, 0.15 mmol) is dissolved in THF (1 mL) and N-ethyl-diisoproyl-amine (0.05 mL, 0.3 mmol) and 2-pyridyl-sulfonylchloride are added subsequently. The reaction mixture is stirred at RT for 24 h, and then diluted with water. The organic phase is separated, dried and concentrated in vacuo to obtain the crude reaction product. The crude reaction product is purified by column chromatography to yield cis-8-Dimethylamino-4-(methoxymethyl)-8-phenyl-2-azaspiro[4.5]decan-3-one (0.04 g) as a colorless oil.

Synthesis of cis-4-(8-Dimethylamino-3-oxo-8-phenyl-2-azaspiro[4.5]decan-2-yl)-2,2-dimethyl-N-pyrimidin-4-yl-butyramide (Example SC-1005)

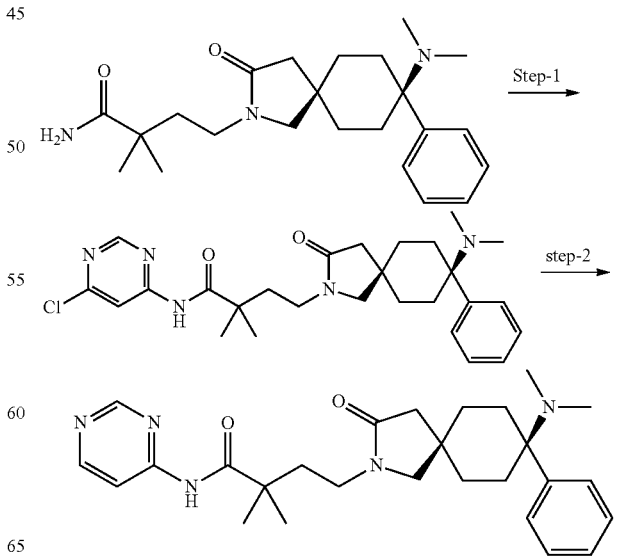

Step 1: N-(6-chloropyrimidin-4-yl)-4-(cis-8-(dimethylamino)-3-oxo-8-phenyl-2-azaspiro[4.5]decan-2-yl)-2,2-dimethylbutanamide A suspension of 4-(cis-8-(dimethylamino)-3-oxo-8-phenyl-2-azaspiro[4.5]decan-2-yl)-2,2-dimethylbutanamide (400 mg, 1.03 mmoL), 4,6-dichloropyrimidine (154 mg, 1.03 mmol), cesium carbonate (508 mg, 1.55 mmol), Xantphos (30 mg, 0.051 mmol) in 1,4-dioxane (10 mL) was purged with argon for 10 min. Then $Pd(PPh_3)_4$ (60 mg, 0.051 mmol) was added and again purged with argon for 10 min. The reaction mass was heated to 120° C. and stirred for 10 h. The reaction mixture was filtered and the filtrate was concentrated in vacuo to get the crude compound which was partitioned between water (20 mL) and 5% MeOH in DCM (40 mL). The organic layer was separated and concentrated under reduced pressure to get crude which was purified by preparative TLC by using 5% methanol in DCM as mobile phase to get 120 mg (23%) of N-(6-chloropyrimidin-4-yl)-4-(cis-8-(dimethylamino)-3-oxo-8-phenyl-2-azaspiro[4.5]decan-2-yl)-2,2-dimethylbutanamide as solid

Step 2: cis-4-(8-Dimethylamino-3-oxo-8-phenyl-2-azaspiro[4.5]decan-2-yl)-2,2-dimethyl-N-pyrimidin-4-yl-butyramide 10% Pd—C (50 mg) was added to a solution of N-(6-chloropyrimidin-4-yl)-4-(cis-8-(dimethylamino)-3-oxo-8-phenyl-2-azaspiro[4.5]decan-2-yl)-2,2-dimethylbutanamide (120 mg, 0.24 mmol) in methanol at RT and the reaction mixture was hydrogenated under balloon pressure at RT for 1 h. The reaction mixture was filtered through celite and the filtrate was concentrated in vacuo to get the crude compound. Purification by preparative TLC by using 5% methanol in DCM as mobile phase afforded 64 mg (57%) of cis-4-(8-Dimethylamino-3-oxo-8-phenyl-2-azaspiro[4.5]decan-2-yl)-2,2-dimethyl-N-pyrimidin-4-yl-butyramide as solid.

Analogues Syntheses:

The following compounds have been prepared in analogy to cis-4-(8-Dimethylamino-3-oxo-8-phenyl-2-azaspiro[4.5]decan-2-yl)-2,2-dimethyl-N-pyrimidin-4-yl-butyramide:

SC-1102 cis-4-(8-Dimethylamino-3-oxo-8-phenyl-2-azaspiro[4.5]decan-2-yl)-2,2-dimethyl-N-[2-(trifluoromethyl)-pyrimidin-5-yl]-butyramide SC-1103 cis-4-(8-Dimethylamino-3-oxo-8-phenyl-2-azaspiro[4.5]decan-2-yl)-2,2-dimethyl-N-(2-methyl-pyrimidin-4-yl)-butyramide

Synthesis of cis-2-(8-Dimethylamino-3-oxo-8-phenyl-2-azaspiro[4.5]decan-2-yl)-N-pyridin-2-yl-acetamide (Example SC-1001)

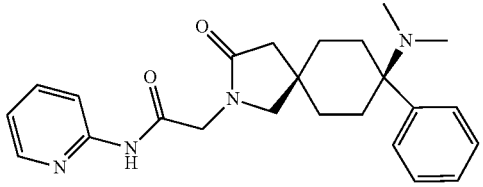

2-aminopyridine (0.02 g, 0.2 mmol) is dissolved in toluene (1.5 mL) and a 2M solution of trimethylaluminium in toluene (0.22 mL, 0.4 mmol) is added at 0° C. After stirring for 30 min methyl 2-(cis-8-(dimethylamino)-3-oxo-8-phenyl-2-azaspiro[4.5]decan-2-yl)acetate (50 mg, 0.15 mmol) is added. The reaction is heated to 110° C. for 1 h and then 1M NaOH (5 mL is added upon cooling to 0° C. The aqueous layer is extracted with DCM (3×20 mL), the combined organic layers are washed with brine and dried over Na2SO4. Purification by silica chromatography yielded cis-2-(8-Dimethylamino-3-oxo-8-phenyl-2-azaspiro[4.5]decan-2-yl)-N-pyridin-2-yl-acetamide (23 mg) as a white solid.

Analogues Syntheses:

The following compounds have been prepared in analogy to cis-2-(8-Dimethylamino-3-oxo-8-phenyl-2-azaspiro[4.5]decan-2-yl)-N-pyridin-2-yl-acetamide:

Example SC-1002 cis-2-(8-Dimethylamino-3-oxo-8-phenyl-2-azaspiro[4.5]decan-2-yl)-N-pyridin-3-yl-acetamide.

Synthesis of cis-4-(8-Dimethylamino-3-oxo-8-phenyl-2-azaspiro[4.5]decan-2-yl)-2,2-dimethyl-N-pyrimidin-5-yl-butyramide (Example SC-1004)

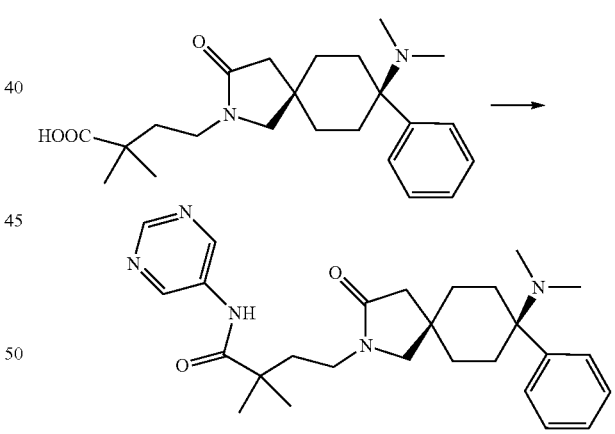

EDC.HCl (272 mg, 1.425 mmol) was added to a suspension of 4-(cis-8-(dimethylamino)-3-oxo-8-phenyl-2-azaspiro[4.5]decan-2-yl)-2,2-dimethylbutanoic acid hydrochloride (300 mg, 0.71 mmol), pyrimidin-5-amine (135 mg, 1.425 mmol) and pyridine (281 mg, 3.56 mmol) in DCM (10 mL) at 0° C. The reaction mixture was warmed to RT and stirred for 16 h. The reaction mixture was quenched with minimum amount of water, the organic product was extracted with 10% MeOH:DCM (3×25 mL). The combined organic extracts were dried over anhydrous $Na_2SO_4$. Solvent was distilled under reduced pressure to give the crude compound. Purification by column chromatography over silicagel (100-200 mesh) using 6% methanol in DCM with traces of ammonia as eluant to give 150 mg of compound which was further purified by Preparative TLC by using 5% methanol in DCM with traces of ammonia as mobile phase to get the compound. This was further washed with n-pentane (10 mL) to give 100 mg (30%) cis-4-(8-Dimethylamino-3-oxo-8-phenyl-2-azaspiro[4.5]decan-2-yl)-2,2-dimethyl-N-pyrimidin-5-yl-butyramide as off white solid.

Analogues Syntheses:

The following compounds have been prepared in analogy to cis-4-(8-Dimethylamino-3-oxo-8-phenyl-2-azaspiro[4.5]decan-2-yl)-2,2-dimethyl-N-pyrimidin-5-yl-butyramide:

Example SC-1003: cis-4-(8-Dimethylamino-3-oxo-8-phenyl-2-azaspiro[4.5]decan-2-yl)-N-[(1,1-dioxo-thian-4-yl)-methyl]-butyramide Synthesis of cis-3-(8-Dimethylamino-3-oxo-8-pyridin-2-yl-2-azaspiro[4.5]decan-2-yl)-2,2-dimethyl-propionic acid methyl ester (SC-1090)

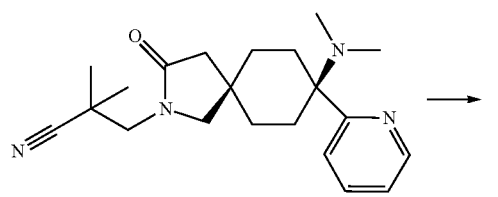

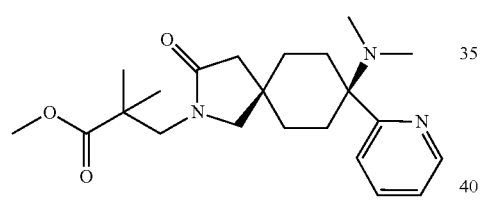

12N HCl (2 mL) was added to 3-(cis-8-(dimethylamino)-3-oxo-8-(pyridin-2-yl)-2-azaspiro[4.5]decan-2-yl)-2,2-dimethylpropanenitrile (150 mg, 0.423 mmol), the reaction mixture was stirred for 16 h at 100° C. The reaction mixture was evaporated under reduced pressure to afford crude, which was successively washed with acetone (2×5 mL), ether (5 mL) and pentane (10 mL) to afford 150 mg (crude) of 3-(cis-8-(dimethylamino)-3-oxo-8-(pyridin-2-yl)-2-azaspiro[4.5]decan-2-yl)-2,2-dimethylpropanoic acid hydrochloride as pale yellow hygroscopic solid (TLC system: 10% MeOH in DCM $R_f$: 0.10) which was dissolved in methanol (5 mL) and cooled to 0° C. To the solution was added thionyl chloride (0.229 g, 1.60 mmol) and the reaction mixture was stirred for 6 h at 80° C. The reaction completion was monitored by TLC. The reaction mixture were evaporated under reduced pressure. To the residue was added saturated NaHCO₃ solution (5 mL) and the organic product was extracted with DCM (3×10 mL). The combined organic layer was dried over anhydrous Na₂SO₄ and solvent was concentrated in vacuo. The crude product was purified by prep TLC, the product eluted with 5% MeOH in DCM to afford 0.1 g of cis-3-(8-Dimethylamino-3-oxo-8-pyridin-2-yl-2-azaspiro[4.5]decan-2-yl)-2,2-dimethyl-propionic acid methyl ester (64%) as off-white solid.

Synthesis of cis-4-(8-Dimethylamino-3-oxo-8-phenyl-2-azaspiro[4.5]decan-2-yl)-2,2-dimethyl-butyric acid (Example SC-1077)

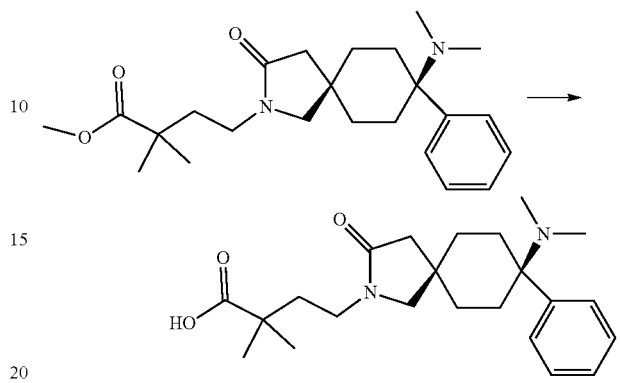

Methyl-4-(cis-8-(dimethylamino)-3-oxo-8-phenyl-2-azaspiro[4.5]decan-2-yl)-2,2-dimethyl-butanoate (40 mg, 0.1 mmol) is dissolved in a mixture of THF (1.9 mL) and water (0.5 mL); then lithium hydroxide (5 mg, 0.2 mmol) is added and the reaction mixture is stirred overnight. The reaction mixture is neutralized with sat. NH₄Cl to pH=7 and the solvent is removed. The residue is extracted with DCM (3×5 mL) to yield cis-4-(8-Dimethylamino-3-oxo-8-phenyl-2-azaspiro[4.5]decan-2-yl)-2,2-dimethyl-butyric acid as a white solid.

Analogues Syntheses:

The following compounds have been prepared in analogy to cis-4-(8-Dimethylamino-3-oxo-8-phenyl-2-azaspiro[4.5]decan-2-yl)-2,2-dimethyl-butyric acid:

Example SC-1076 cis-4-(8-Dimethylamino-3-oxo-8-phenyl-2-azaspiro[4.5]decan-2-yl)-butyric acid.

Synthesis of cis-2-[(8-Dimethylamino-3-oxo-8-phenyl-2-azaspiro[4.5]decan-2-yl)-methyl]-benzoic acid hydrochloride (Example SC-1107)

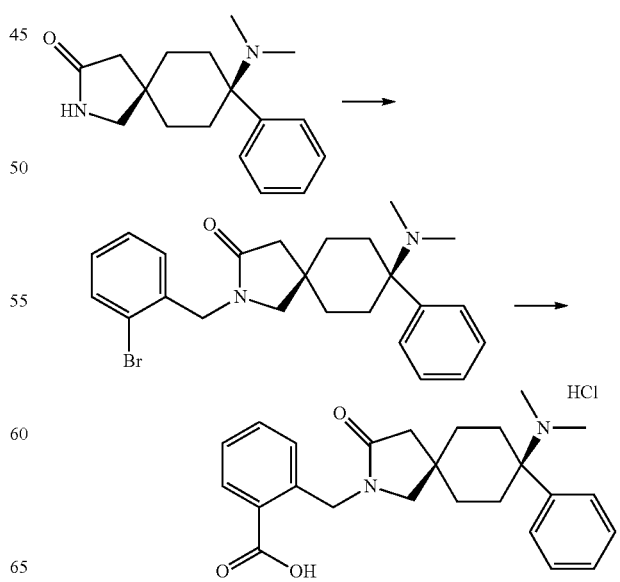

Step 1: cis-2-(2-bromobenzyl)-8-(dimethylamino)-8-phenyl-2-azaspiro[4.5]decan-3-one Cis-8-(dimethylamino)-8-phenyl-2-azaspiro[4.5]decan-3-one (200 mg, 0.74 mmol) was added to a suspension of powdered sodium hydroxide (120 mg, 3 mmol) in anhydrous dmso (5 mL). After stirring for 10 min, 2-bromobenzylbromide (220 mg, 0.88 mmol) was added and the reaction mixture was stirred for another 3 d at RT, then benzylbromide (220 mg, 0.88 mmol) was added again and stirred for further 2 d. Then water (50 mL) was added and the reactions mixture was extracted with ethyl acetate (3×20 mL). the combined organic layers were dried over Na2SO4, concentrated in vacuo and purified by column chromatography to yield cis-2-(2-bromobenzyl)-8-(dimethylamino)-8-phenyl-2-azaspiro[4.5]decan-3-one (166 mg) as a colorless oil.

Step 2: cis-2-[(8-Dimethylamino-3-oxo-8-phenyl-2-azaspiro[4.5]decan-2-yl)-methyl]-benzoic acid hydrochloride A mixture of cis-2-(2-bromobenzyl)-8-(dimethylamino)-8-phenyl-2-azaspiro[4.5]decan-3-one (74 mg, 0.16 mmol), molybdenum hexacarbonyl (11 mg, 0.04 mmol), Na2CO3 (26 mg, 0.24 mmol) and trans-bis(acetato)-bis[o-(di-o-tolyl-phosphino)benzyl]dipalladium(II) (4 mg, 0.0036 mmol) in water (1.5 mL) were heated to 170° C. for 10 min in a microwave. The reaction mixture was filtered off; the filtrate acidified to pH=5 with 0.1 M HCl and then subsequently extracted with DCM (3×3 mL), DCM/iPrOH (9/1, 3×3 mL) and DCM/iPrOH (4:1, 3×3 mL). The combined organic extracts were dried over Na2SO4 and concentrated in vacuo to yield the crude product (10 mg).

The crude product (48 mg) was dissolved in iPrOH (2004) and treated with 4M HCl in 1,4-dioxane (1 mL). After addition of diethylether (5 mL) cis-2-[(8-Dimethylamino-3-oxo-8-phenyl-2-azaspiro[4.5]decan-2-yl)-methyl]-benzoic acid hydrochloride precipitated and was isolated after filtration as a white solid.

Analogues Syntheses:

The following compounds have been prepared in analogy to cis-2-(2-bromobenzyl)-8-(dimethylamino)-8-phenyl-2-azas- piro[4.5]decan-3-one:

methyl 2-((trans-8-(dimethylamino)-3-oxo-8-phenyl-2-azaspiro[4.5]decan-2-yl)methyl)benzoate (Example SC-1202)

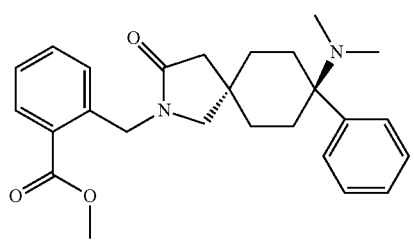 [SMILES: COC(=O)c1ccccc1CN1C[C@]2(CC[C@](c3ccccc3)(N(C)C)CC2)CC1=O]

Synthesis of trans-2-[(8-dimethylamino-3-oxo-8-phenyl-2-azaspiro[4.5]decan-2-yl)-methyl]-benzoic acid hydrochloride (Example SC-1108)

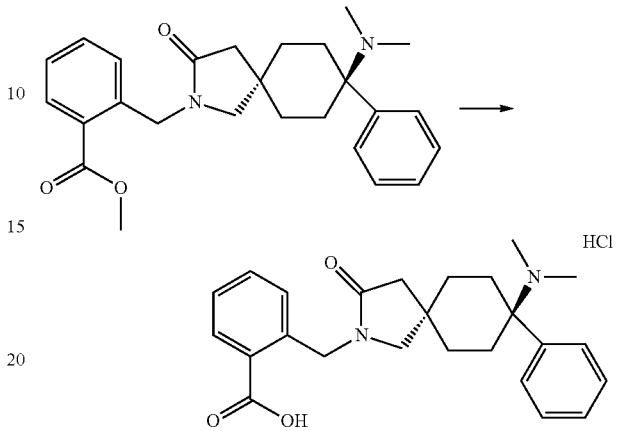

Methyl 2-((trans-8-(dimethylamino)-3-oxo-8-phenyl-2-azaspiro[4.5]decan-2-yl)methyl) benzoate (91 mg, 0.22 mmol) was dissolved in iPrOH (3 mL) and treated with 1M NaOH (500 µL) for 3 days at RT. The reaction mixture was concentrated in vacuo and the residue was dissolved in water (500 µL) and 2M aq. HCl (500 µL). The reaction mixture was concentrated in vacuo and the residue dissolved in ethanol. After filtration from insoluble material, the ethanol layer was concentrated in vacuo to give trans-2-[(8-dimethylamino-3-oxo-8-phenyl-2-azaspiro[4.5]decan-2-yl)-methyl]-benzoic acid hydrochloride (94 mg) as a white solid.

All compounds in the table below were prepared as described earlier within this application or in analogy to examples described earlier within this application. The synthesis of compound building blocks has either been described earlier within this application or can be performed in analogy to the herein described methods or by methods known to the person skilled in the art. Found MS m/z [M+H]$^+$ peaks comply with molecular formula for each example.

| Ex. No. | MS m/z [M + H]$^+$ |
|---|---|
| SC-1001 | 407.5 |
| SC-1002 | 407.5 |
| SC-1003 | 504.7 |
| SC-1004 | 464.6 |
| SC-1005 | 464.6 |
| SC-1006 | 326.5 |
| SC-1007 | 340.5 |
| SC-1008 | 332.4 |
| SC-1009 | 346.4 |
| SC-1010 | 360.5 |
| SC-1011 | 331.4 |
| SC-1012 | 345.5 |
| SC-1013 | 359.5 |
| SC-1014 | 420.6 |
| SC-1015 | 388.5 |
| SC-1016 | 383.5 |
| SC-1017 | 416.6 |
| SC-1018 | 369.5 |
| SC-1019 | 397.5 |
| SC-1020 | 383.5 |
| SC-1021 | 411.6 |

| Ex. No. | MS m/z [M + H]+ |
|---|---|
| SC-1022 | 421.6 |
| SC-1023 | 448.6 |
| SC-1024 | 402.6 |
| SC-1025 | 434.6 |
| SC-1026 | 402.6 |
| SC-1027 | 434.6 |
| SC-1028 | 421.6 |
| SC-1029 | 463.6 |
| SC-1030 | 478.7 |
| SC-1031 | 478.7 |
| SC-1032 | 408.5 |
| SC-1033 | 344.5 |
| SC-1034 | 372.5 |
| SC-1035 | 330.4 |
| SC-1036 | 428.6 |
| SC-1037 | 476.7 |
| SC-1038 | 451.6 |
| SC-1039 | 504.7 |
| SC-1040 | 472.6 |
| SC-1041 | 344.5 |
| SC-1042 | 396.9 |
| SC-1043 | 411.0 |
| SC-1044 | 424.0 |
| SC-1045 | 373.5 |
| SC-1046 | 368.9 |
| SC-1047 | 382.9 |
| SC-1048 | 367.9 |
| SC-1049 | 430.6 |
| SC-1050 | 345.5 |
| SC-1051 | 485.7 |
| SC-1052 | 533.7 |
| SC-1053 | 401.6 |
| SC-1054 | 364.5 |
| SC-1055 | 364.5 |
| SC-1056 | 380.5 |
| SC-1057 | 381.5 |
| SC-1058 | 381.5 |
| SC-1059 | 380.5 |
| SC-1060 | 381.5 |
| SC-1061 | 365.5 |
| SC-1062 | 368.5 |
| SC-1063 | 351.5 |
| SC-1064 | 433.6 |
| SC-1065 | 408.9 |
| SC-1066 | 365.5 |
| SC-1067 | 419.5 |
| SC-1068 | 407.6 |
| SC-1069 | 349.5 |
| SC-1070 | 349.5 |
| SC-1071 | 374.5 |
| SC-1072 | 374.5 |
| SC-1073 | 374.5 |
| SC-1074 | 407.5 |
| SC-1075 | 388.5 |
| SC-1076 | 359.5 |
| SC-1077 | 387.5 |
| SC-1078 | 346.4 |
| SC-1079 | 360.5 |
| SC-1080 | 388.5 |
| SC-1081 | 402.6 |
| SC-1082 | 358.5 |
| SC-1083 | 317.4 |
| SC-1084 | 331.4 |
| SC-1085 | 459.5 |
| SC-1086 | 473.5 |
| SC-1087 | 373.5 |
| SC-1088 | 359.5 |
| SC-1089 | 374.5 |
| SC-1090 | 388.5 |
| SC-1091 | 386.6 |
| SC-1092 | 358.5 |
| SC-1093 | 384.5 |
| SC-1094 | 468.5 |
| SC-1095 | 482.6 |
| SC-1096 | 496.6 |
| SC-1097 | 374.5 |
| SC-1098 | 388.5 |
| SC-1099 | 487.5 |
| SC-1100 | 387.5 |
| SC-1101 | 487.5 |
| SC-1102 | 532.6 |
| SC-1103 | 478.7 |
| SC-1104 | 463.6 |
| SC-1107 | 444.0 |
| SC-1108 | 444.0 |
| SC-1109 | 471.6 |
| SC-1110 | 397.5 |
| SC-1111 | 372.5 |
| SC-1112 | 505.7 |
| SC-1113 | 476.7 |
| SC-1114 | 402.6 |
| SC-1115 | 397.5 |
| SC-1116 | 411.6 |
| SC-1117 | 476.5 |
| SC-1118 | 421.6 |
| SC-1119 | 422.5 |
| SC-1120 | 422.5 |
| SC-1121 | 432.6 |
| SC-1122 | 418.5 |
| SC-1123 | 436.6 |
| SC-1124 | 448.6 |
| SC-1125 | 415.5 |
| SC-1126 | 387.5 |
| SC-1127 | 401.5 |
| SC-1128 | 429.6 |
| SC-1129 | 429.6 |
| SC-1130 | 401.5 |
| SC-1131 | 415.5 |
| SC-1132 | 443.6 |
| SC-1133 | 416.6 |
| SC-1134 | 430.6 |
| SC-1135 | 490.7 |
| SC-1136 | 386.6 |
| SC-1137 | 462.6 |
| SC-1138 | 476.7 |
| SC-1139 | 477.7 |
| SC-1140 | 492.7 |
| SC-1141 | 444.6 |
| SC-1142 | 458.7 |
| SC-1145 | 400.6 |
| SC-1146 | 425.6 |
| SC-1147 | 439.6 |
| SC-1148 | 443.6 |
| SC-1149 | 457.6 |
| SC-1150 | 471.7 |
| SC-1151 | 492.7 |
| SC-1152 | 518.7 |
| SC-1153 | 532.8 |
| SC-1154 | 358.5 |
| SC-1155 | 378.5 |
| SC-1156 | 378.5 |
| SC-1157 | 378.5 |
| SC-1158 | 392.6 |
| SC-1159 | 392.6 |
| SC-1160 | 392.6 |
| SC-1161 | 406.6 |
| SC-1162 | 372.5 |
| SC-1163 | 358.5 |
| SC-1164 | 391.6 |
| SC-1165 | 421.6 |
| SC-1166 | 421.6 |
| SC-1167 | 421.6 |
| SC-1168 | 406.6 |
| SC-1169 | 406.6 |
| SC-1170 | 435.6 |
| SC-1171 | 435.6 |
| SC-1172 | 435.6 |
| SC-1173 | 436.6 |
| SC-1174 | 439.6 |
| SC-1175 | 436.6 |
| SC-1176 | 450.6 |
| SC-1177 | 439.6 |

-continued

| Ex. No. | MS m/z [M + H]+ |
|---|---|
| SC-1178 | 434.6 |
| SC-1179 | 519.7 |
| SC-1180 | 462.6 |
| SC-1181 | 478.7 |
| SC-1182 | 455.6 |
| SC-1183 | 476.7 |
| SC-1184 | 478.7 |
| SC-1185 | 430.6 |
| SC-1186 | 444.6 |
| SC-1187 | 472.7 |
| SC-1189 | 504.7 |
| SC-1190 | 438.5 |
| SC-1191 | 416.6 |
| SC-1192 | 439.6 |
| SC-1193 | 439.6 |
| SC-1194 | 543.6 |
| SC-1195 | 591.7 |
| SC-1198 | 386.6 |
| SC-1199 | 384.5 |
| SC-1200 | 372.5 |
| SC-1201 | 331.4 |
| SC-1202 | 421.2 |

Investigations of the Activity of the Compounds According to the Invention

Measurement of the ORL1 Binding

The compounds were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 µg of membrane protein per 200 µl batch in 50 mM hepes, pH 7.4, 10 mM $MgCl_2$ and 1 mM EDTA. The binding to the ORL1 receptor was determined using in each case 1 mg of WGA-SPA beads (Amersham-Pharmacia, Freiburg) by incubation of the batch at RT for one hour and subsequent measurement in a Trilux scintillation counter (Wallac, Finland). The affinity is stated in Table 1 as the nanomolar $K_i$ value in or % inhibition at c=1 µM.

Measurement of the µ Binding

The receptor affinity for the human µ opiate receptor was determined in a homogeneous set-up in microtitre plates. For this, dilution series of the compound to be tested in each case were incubated with a receptor membrane preparation (15-40 µg of protein per 250 µl of incubation batch) of CHO-K1 cells which express the human µ opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and of 1 mg of WGA-SPA-Beads (wheat germ agglutinin SPA beads from Amersham/Pharmacia, Freiburg, Germany) in a total volume of 250 µl for 90 minutes at room temperature. 50 mmol/l of Tris-HCl supplemented with 0.05 wt. % of sodium azide and with 0.06 wt. % of bovine serum albumin was used as the incubation buffer. 25 µmol/l of naloxone were additionally added for determination of the non-specific binding. After the end of the ninety-minute incubation time, the microtitre plates were centrifuged for 20 minutes at 1,000 g and the radioactivity was measured in a β-counter (Microbeta-Trilux, PerkinElmer Wallac, Freiburg, Germany). The percentage displacement of the radioactive ligand from its binding to the human µ opiate receptor was determined at a concentration of the test substances of 1 µmol/l and stated as the percentage inhibition (% inhibition) of the specific binding. Starting from the percentage displacement by various concentrations of the substances of the general formula I to be tested, $IC_{50}$ inhibitory concentrations which cause a 50 percent displacement of the radioactive ligand were calculated in some cases. By conversion by means of the Cheng-Prusoff relationship, Ki values for the test substances were obtained. In some cases determination of the Ki value was dispensed with and only the inhibition at a test concentration of 1 µM was determined.

Testing of Analgesia in the Tail Flick Test in Rats

The analgesic activity of the test compounds was investigated in the focal ray (tail flick) test in rats in accordance with the method of D'Amour and Smith (J. Pharm. Exp. Ther. 72, 74 79 (1941)). Female Sprague Dawley rats weighing between 130 and 190 g were used for this. The animals were placed individually in special test cages and the base of the tail was exposed to a focused heat ray of a lamp (Tail-flick type 50/08/1.bc, Labtec, Dr Hess). The intensity of the lamp was adjusted such that in the case of untreated animals the time between switching on of the lamp to sudden pulling away of the tail (pain latency) was 2.5-5 seconds. Before administration of a test compound, the animals were pretested twice in the course of 30 minutes and the mean of these measurements was calculated as the pretest mean The pain was measured 20, 40 and 60 min after intravenous administration. The analgesic action was determined as the increase in pain latency (% MPE) according to the following formula: $[(T_1-T_0)/(T_2-T_0)] \times 100$. In this, $T_0$ is the latency period before and $T_1$ the latency period after administration of the substance, $T_2$ is the maximum exposure time (12 sec). To determine the dose dependency, the particular test compound was administered in 3-5 logarithmically increasing doses, which included the threshold and the maximum active dose in each case, and the $ED_{50}$ values were determined with the aid of regression analysis. The $ED_{50}$ calculation was performed at the action maximum, 20 minutes after intravenous administration of the substance.

Chung Model: Mononeuropathy Pain Following Spinal Nerve Ligation

Animals:

Male Sprague Dawley rats (140-160 g), from a commercial breeder (Janvier, Genest St. Isle, France), were kept under a 12:12 h light-dark rhythm. The animals were kept with food and tap water ad libitum. A pause of one week was maintained between delivery of the animals and the operation. After the operation the animals were tested several times over a period of 4-5 weeks, a wash-out time of at least one week being adhered to.

Description of the Model:

The left L5, L6 spinal nerves were exposed under pentobarbital narcosis (Narcoren®, 60 mg/kg i.p., Merial GmbH, Hallbergmoos, Germany) by removing a piece of the paravertebral muscle and a part of the left spinal process of the L5 lumbar vertebra. The spinal nerves L5 and L6 were carefully isolated and tied off with a firm ligature (NC-silk black, USP 5/0, metric 1, Braun Melsungen AG, Melsungen, Germany) (Kim and Chung 1992). After ligation the muscle and adjacent tissue were sewn up and the wound was closed by means of metal clamps.

After a recovery period of one week the animals were placed in cages with a wire floor for measurement of the mechanical allodynia. The withdrawal threshold was determined on the ipsi- and/or contralateral hind paw by means of an electronic von Frey filament (Somedic AB, Malmö, Sweden). The median of five stimulations gave one data point. The animals were tested 30 min before and at various times after administration of the test substance or vehicle solution. The data were determined as % maximum possible effect (% MPE) from the pretesting of the individual animals (=0% MPE) and the test values of an independent sham control group (=100% MPE). Alternatively, the withdrawal thresholds were shown in grams.

Statistical Evaluation:

$ED_{50}$ values and 95% confidence intervals were determined via semilogarithmic regression analysis at the point in time of the maximum effect. The data were analysed via a variance analysis with repeated measurements and a post hoc Bonferroni analysis. The group size was usually n=10.

REFERENCES

Kim, S. H. and Chung, J. M., An experimental model for peripheral neuropathy produced by segmental spinal nerve ligation in the rat, Pain, 50 (1992) 355-363.

Results

| No. | Dia-stereomer | % inhibition (ORL1) [1 μM] | Ki (ORL1) mean [μm] | % inhibition (μ) [1 μM] | Ki (μ) mean [μm] | Tail flick rat, i.v. $ED_{50rat}$ [μg/kg] or % MPE (@μg/kg) | SNL rat, i.v. $ED_{50rat}$ [μg/kg] or % MPE (@μg/kg) |
|---|---|---|---|---|---|---|---|
| 1 | 1 | 33.33 | 0.44 | 80 | 0.1 | nd | nd |
| 2 | 2 | 17.5 | 0.86 | 83 | 0.007 | nd | nd |
| 3 | 2 | 80 | 0.033 | 94.5 | 0.0036 | nd | nd |
| 4 | 1 | 94.5 | 0.0019 | 97.5 | 0.00035 | 25 | 23%@31.6 |
| 5 | 2 | 53.33 | 0.12 | 94 | 0.022 | nd | nd |
| 6 | 1 | 68.5 | 0.044 | 99 | 0.0039 | 30%@100 | nd |
| 7 | 1 | 96 | 0.00064 | 100.5 | 0.0015 | 95%@1000 | nd |
| 8 | 1 | 78 | 0.029 | 98 | 0.0068 | 15%@1000 | nd |
| 9 | 2 | 34.5 | 0.44 | 76.5 | 0.051 | nd | nd |
| 10 | 2 | 32 | 0.31 | 67.5 | 0.052 | nd | nd |
| 11 | 2 | 71.67 | 0.0335 | 93 | 0.023 | 0%@100 | nd |
| 12 | 1 | 73.33 | 0.00056 | 99 | 0.00043 | 35%@100 | nd |
| 13 | 1 | 97 | 0.00495 | 103 | 0.0013 | nd | nd |
| 14 | 1 | 98.67 | 0.00215 | 95.5 | 0.0012 | 3.3 | nd |
| 15 | 2 | 31 | 0.425 | 16 | 1.2 | nd | nd |
| 16 | 1 | 98.5 | 0.00303 | 99.5 | 0.00184 | 0%@100 | nd |
| 17 | 1 | 70.5 | 0.077 | 92 | 0.026 | nd | Nd |
| 18 | 1 | 36 | 0.295 | 56.5 | 0.27 | nd | nd |
| 19 | 1 | 39 | 0.335 | 67.5 | 0.0975 | nd | nd |
| 20 | 1 | 26 | 0.37 | 80.5 | 0.079 | nd | nd |
| 21 | 1 | 63 | 0.0185 | 89 | 0.00685 | nd | nd |
| 22 | 1 | 84 | 0.0117 | 95.5 | 0.0129 | 638 | 36%@464 |
| 23 | 1 | 74 | 0.0395 | 90 | 0.028 | 0%@1000 | nd |
| 24 | 1 | 84.5 | 0.021 | 95 | 0.02 | 77 | 16%@68.1 |
| 25 | 1 | 57 | nd | 60.5 | nd | nd | nd |
| 26 | 1 | 41.5 | nd | 55.5 | nd | nd | nd |
| 27 | 1 | 45 | 0.11 | 77.5 | 0.0795 | nd | nd |
| 28 | 1 | 94 | nd | 99.5 | nd | 3.36 | nd |
| 29 | 1 | 77.5 | 0.0145 | 93.5 | 0.0305 | 31%@1000 | nd |
| 30 | 1 | 90 | 0.0125 | 97 | 0.012 | 1250 | 59.5%@1000 |
| 31 | 1 | 94 | 0.00835 | 100 | 0.0028 | nd | nd |
| 32 | 1 | 79 | 0.0135 | 98.5 | 0.0025 | nd | nd |
| 33 | 1 | 81 | 0.047 | 96.5 | 0.0195 | nd | nd |
| 34 | 1 | 94.5 | 0.0014 | 100.67 | 0.00042 | 100%@100 | nd |
| 35 | 1 | 97.5 | 0.00053 | 99.5 | 0.00083 | nd | nd |
| 36 | 1 | 97 | 0.00049 | 101 | 0.00058 | 11%@100 | nd |
| 37 | 1 | 97 | 0.00081 | 98.5 | 0.00044 | nd | nd |
| 38 | 1 | 91 | 0.0138 | 99.5 | 0.0015 | nd | nd |
| 39 | 1 | 95 | 0.00044 | 103 | 0.00028 | nd | nd |
| 40 | 1 | 97.5 | 0.00065 | 100 | 0.00103 | nd | nd |
| 41 | 1 | 93 | nd | 100 | nd | nd | nd |
| 42 | 1 | 86.5 | nd | 100.5 | nd | nd | nd |
| 43 | 1 | 94 | nd | 96 | nd | nd | nd |
| 44 | 1 | 94.5 | 0.00175 | 100 | 0.0017 | nd | nd |
| 45 | 1 | 82 | 0.015 | 98 | 0.0029 | nd | nd |
| 46 | 2 | 85 | 0.00705 | 96.5 | 0.01535 | nd | nd |
| 47 | 1 | 84.5 | 0.0175 | 96 | 0.0115 | 23%@1000 | nd |
| 48 | 1 | 79.5 | 0.013 | 96.5 | 0.015 | nd | nd |
| 49 | 1 | 21.5 | 0.605 | 46.5 | 1.16 | nd | nd |
| 50 | 1 | 66 | 0.0535 | 88 | 0.039 | nd | nd |
| 51 | 1 | 91 | 0.00129 | 99.5 | 0.00245 | 0%@100 | nd |
| 52 | 1 | 37.5 | 0.22 | 70.5 | 0.16 | nd | nd |
| 53 | 1 | 35 | 0.245 | 51 | 0.39 | nd | nd |
| 54 | 1 | 57 | 0.0895 | 76 | 0.0965 | nd | nd |
| 55 | 1 | 86.5 | 0.008 | 94 | 0.01015 | 0%@100 | nd |
| 56 | 1 | 80 | 0.0155 | 89 | 0.0515 | nd | nd |
| 57 | 1 | 73 | 0.043 | 95.5 | 0.0275 | nd | nd |
| 58 | 3 | 83.5 | 0.0315 | 102 | 0.00325 | nd | nd |
| 59 | 3 | 94.5 | 0.00495 | 100 | 0.0013 | 0%@100 | nd |
| 60 | 3 | 68.5 | 0.0645 | 95.5 | 0.01065 | nd | nd |
| 61 | 1 | 90.5 | 0.0045 | 100 | 0.00225 | nd | nd |

-continued

| No. | Dia-stereomer | % inhibition (ORL1) [1 μM] | Ki (ORL1) mean [μm] | % inhibition (μ) [1 μM] | Ki (μ) mean [μm] | Tail flick rat, i.v. ED$_{50rat}$ [μg/kg] or % MPE (@μg/kg) | SNL rat, i.v. ED$_{50rat}$ [μg/kg] or % MPE (@μg/kg) |
|---|---|---|---|---|---|---|---|
| 62 | 1 | 86 | 0.026 | 90.5 | 0.058 | 165 | nd |
| 63 | 3 | 55.5 | 0.18 | 96.33 | 0.0049 | nd | nd |
| 64 | 3 | 69.5 | 0.099 | 101.5 | 0.0019 | nd | nd |
| 65 | 3 | 64 | 0.13 | 99.5 | 0.017 | nd | nd |
| 66 | 3 | 83 | 0.022 | 99.5 | 0.0055 | nd | nd |
| 67 | 3 | 72 | nd | 96.5 | nd | nd | nd |
| 68 | 3 | 94 | 0.0037 | 100 | 0.0032 | nd | nd |
| 69 | 2 | 54.5 | nd | 81.5 | nd | nd | nd |
| 70 | 1 | 16.5 | 0.46 | 61.5 | 0.465 | nd | nd |
| 71 | 2 | 50 | 0.165 | 76.5 | 0.127 | nd | nd |
| 72 | 1 | 21 | 1.48 | 36 | 0.805 | nd | nd |
| 73 | 1 | 67.5 | 0.135 | 91.5 | 0.0205 | nd | nd |
| 74 | 2 | 17.5 | 1.7 | 41.5 | 0.785 | nd | nd |
| 75 | 1 | 29 | 0.315 | 62 | 0.37 | nd | nd |
| 76 | 2 | 0 | | 19.5 | 2.41 | nd | nd |
| 77 | 1 | 59.5 | 0.0365 | 83 | 0.0665 | nd | nd |
| 78 | 1 | 66 | 0.175 | 92.5 | 0.04 | nd | nd |
| 79 | 2 | 15.5 | 1.61 | 37.5 | 1.87 | nd | nd |
| 80 | 1 | 21.5 | 1.11 | 34.5 | 1.11 | nd | nd |
| 81 | 2 | 1 | nd | 0 | nd | nd | nd |
| 82 | 1 | 65 | 0.1305 | 77.5 | 0.295 | nd | nd |
| 83 | 2 | 31 | nd | 34 | 5.5 | nd | nd |
| 84 | 3 | 27 | 0.915 | 95 | 0.0051 | nd | nd |
| 85 | 3 | 16 | nd | 49.5 | 0.26 | nd | nd |
| 86 | 2 | 12.7 | nd | 11 | 0.42 | nd | nd |
| 87 | 1 | 47.33 | 0.25 | 79.5 | 0.095 | nd | nd |
| 88 | 1 | 38 | 0.126 | 82.5 | 0.0715 | nd | nd |
| 89 | 2 | 31 | 0.26 | 20.5 | 1.11 | nd | nd |
| 90 | 1 | 89 | 0.0081 | 98.5 | 0.00305 | nd | nd |
| 91 | 2 | 36 | 0.23 | 53.5 | 0.37 | nd | nd |
| 92 | 1 | 93.5 | 0.0019 | 100.5 | 0.00038 | nd | nd |
| 93 | 2 | 63.5 | 0.0725 | 50 | 0.285 | nd | nd |
| 94 | 1 | 94.5 | 0.00135 | 99 | 0.00042 | nd | nd |
| 95 | 2 | 65 | 0.0945 | 61.5 | 0.54 | nd | nd |
| 96 | 2 | 69.5 | 0.073 | 98.33 | 0.00086 | nd | nd |
| 97 | 1 | 28.5 | 0.55 | 61 | 0.47 | nd | nd |
| 98 | 2 | 87 | 0.003 | 98.5 | 0.00052 | nd | nd |
| 99 | 1 | 16 | 0.1195 | 39.5 | 0.235 | nd | nd |
| 100 | 2 | 50 | 0.118 | 91.5 | 0.00905 | nd | nd |
| 101 | 2 | 95.5 | 0.00115 | 96.5 | 0.00056 | 100%@100 | nd |
| 102 | 1 | 62.5 | 0.072 | 61 | 0.46 | nd | nd |
| 103 | 2 | 74.5 | 0.0315 | 93 | 0.04233 | 60%@10 | nd |
| 104 | 1 | 59.5 | 0.0865 | 65.5 | 0.42 | nd | nd |
| 105 | 2 | 95 | 0.0022 | 100 | 0.00066 | nd | nd |
| 106 | 1 | 61 | 0.059 | 48.5 | 0.285 | nd | nd |
| 107 | 2 | 97 | 0.0019 | 101.5 | 0.00034 | nd | nd |
| 108 | 1 | 64.5 | 0.0485 | 88 | 0.43 | nd | nd |
| 109 | 2 | 97 | 0.0009 | 98 | 0.00089 | nd | nd |
| 110 | 1 | 91 | 0.0116 | 94.5 | 0.00445 | nd | nd |
| 111 | 1 | 73 | 0.038 | 94.5 | 0.0067 | nd | nd |
| 112 | 1 | 78.5 | 0.0245 | 98 | 0.00255 | nd | nd |
| 113 | 1 | 34 | 0.00903 | 23.5 | 0.00583 | nd | nd |
| 114 | 2 | 75.5 | 0.03467 | 98.5 | 0.00595 | nd | nd |
| 115 | 2 | 62.5 | 0.16 | 94.5 | 0.036 | nd | nd |
| 116 | 2 | 63 | 0.0965 | 95.5 | 0.0195 | nd | nd |
| 117 | 2 | 90 | 0.017 | 98.5 | 0.0077 | nd | nd |
| 118 | 2 | 98 | nd | 98 | nd | nd | nd |
| 119 | 2 | 84 | 0.03 | 96.5 | 0.013 | nd | nd |
| 120 | 1 | 97 | 0.00108 | 100 | 0.00115 | nd | nd |
| 121 | 1 | 97.5 | 0.0013 | 100 | 0.00068 | nd | nd |
| 122 | 1 | 96.5 | 0.00109 | 98.5 | 0.00085 | nd | nd |
| 123 | 1 | 46.5 | 0.17 | 97 | 0.013 | nd | nd |
| 124 | 1 | 6.5 | 1.49 | 23 | 2.97 | nd | nd |
| 125 | 1 | nd | 0.185 | 79 | 0.104 | nd | nd |
| 126 | 1 | 32.5 | nd | 88 | nd | nd | nd |
| 127 | 1 | 71.5 | 0.055 | 93.5 | 0.0265 | nd | nd |
| 129 | 1 | 52 | 0.105 | 93.5 | 0.0155 | nd | nd | nd = not determined

| Example No | ORL1 % Inhibition @ 1 μM | ORL1 Ki [nM] | MOP % Inhibition @1 μM | MOP Ki [nM] |
|---|---|---|---|---|
| SC-1001 | 49 | 61 | 99 | 5.4 |
| SC-1002 | 38 | 250 | 95 | 50 |
| SC-1003 | 48 | 440 | 74 | 390 |
| SC-1004 | 85 | 19.5 | 98 | 5.7 |
| SC-1005 | 74 | 77 | 95 | 5.4 |
| SC-1006 | 1 | nd | 17 | nd |
| SC-1007 | 12 | nd | 15 | nd |
| SC-1008 | 6 | nd | 36 | 2205 |
| SC-1009 | 10 | nd | 46 | 1045 |
| SC-1010 | 4 | nd | 39 | 825 |
| SC-1011 | 9 | 1705 | 30 | 2645 |
| SC-1012 | 19 | nd | 39 | 1760 |
| SC-1013 | 11 | nd | 31 | 2430 |
| SC-1014 | 93 | 3.8 | 101 | 3.1 |
| SC-1015 | 74 | 17.5 | 100 | 9.7 |
| SC-1016 | 73 | 26 | 97 | 7 |
| SC-1017 | 18 | 330 | 90 | 70 |
| SC-1018 | 71 | 27.5 | 97 | 37.5 |
| SC-1019 | 63 | 300 | 87 | 100 |
| SC-1020 | 55 | 235 | 86 | 67 |
| SC-1021 | 43 | 465 | 89 | 56.5 |
| SC-1022 | 74 | 130 | 91 | 28 |
| SC-1023 | 91 | 16.5 | 100 | 4.9 |
| SC-1024 | 56 | 220 | 90 | 36.5 |
| SC-1025 | 78 | 93 | 99 | 8.4 |
| SC-1026 | 65 | 42 | 88 | 33 |
| SC-1027 | 98 | 2.6 | 98 | 0.9 |
| SC-1028 | 69 | 102 | 98 | 72 |
| SC-1029 | 85 | 29.5 | 86 | 8 |
| SC-1030 | 54 | 220 | 90 | 85.5 |
| SC-1031 | 89 | 54 | 96 | 23.5 |
| SC-1032 | 28 | 610 | 70 | 275 |
| SC-1033 | 54 | 825 | 78 | 370 |
| SC-1034 | 55 | 160 | 87 | 56 |
| SC-1035 | 56 | 165 | nd | 265 |
| SC-1036 | 96 | 20.5 | 97 | 51 |
| SC-1037 | 43 | 180 | 93 | 30 |
| SC-1038 | 59 | 225 | 97 | 30 |
| SC-1039 | 26 | 1430 | 58 | 400 |
| SC-1040 | 56 | 220 | 87 | 112.5 |
| SC-1041 | nd | 215.3 | nd | 179.5 |
| SC-1042 | 2 | nd | 6 | nd |
| SC-1043 | 5 | nd | 26 | 3700 |
| SC-1044 | 62 | 270 | 69 | 485 |
| SC-1045 | 36 | 440 | 66 | 430 |
| SC-1046 | −3 | nd | 13 | 5960 |
| SC-1047 | −6 | nd | 14 | 6580 |
| SC-1048 | 27 | 1130 | 31 | 1685 |
| SC-1049 | 60 | 210 | 98 | 31 |
| SC-1050 | 80 | 24.5 | 96 | 29.5 |
| SC-1051 | 8 | 91.5 | 101 | 2.9 |
| SC-1052 | 54 | 142 | 100 | 1.4 |
| SC-1053 | 95 | 8.6 | 98 | 1.4 |
| SC-1054 | 74 | 10 | 99 | 8 |
| SC-1055 | 63 | 37.5 | 95 | 12 |
| SC-1056 | nd | 75 | nd | 150 |
| SC-1057 | nd | 102 | nd | 140 |
| SC-1058 | nd | 170 | nd | 295 |
| SC-1059 | nd | 340 | nd | 1365 |
| SC-1060 | nd | 255 | nd | 2000 |
| SC-1061 | nd | 84.5 | nd | 60 |
| SC-1062 | nd | 117.5 | nd | 89 |
| SC-1063 | nd | 345 | nd | 1545 |
| SC-1064 | nd | 210 | nd | 345 |
| SC-1065 | nd | 1.9 | nd | 1.3 |
| SC-1066 | nd | 58 | nd | 64.5 |
| SC-1067 | nd | 2.2 | nd | 2 |
| SC-1068 | nd | 2.1 | nd | 6.2 |
| SC-1069 | 34 | 250 | 40 | 2280 |
| SC-1070 | 88 | 9.2 | 98 | 4.2 |
| SC-1071 | 32 | 465 | 85 | 175 |
| SC-1072 | 85 | 23 | 99 | 9.7 |
| SC-1073 | 47 | 190 | 96 | 15.5 |
| SC-1074 | 30 | nd | 90 | 420 |
| SC-1075 | 94 | 4.9 | 99 | 2.4 |
| SC-1076 | 13 | 1280 | 42 | 1990 |
| SC-1077 | 79 | 69 | 85 | 117 |
| SC-1078 | 37 | 345 | 58 | 585 |
| SC-1079 | 28 | 490 | 76 | 210 |
| SC-1080 | 79 | 36 | 99 | 8.6 |
| SC-1081 | 43 | 250 | 97 | 43.5 |
| SC-1082 | 25 | 525 | 53 | 755 |
| SC-1083 | 12 | nd | 2 | nd |
| SC-1084 | 4 | nd | 19 | nd |
| SC-1085 | 4 | nd | 27 | nd |
| SC-1086 | 7 | nd | 28 | 4650 |
| SC-1087 | 20 | 1500 | 47 | 1160 |
| SC-1088 | 5 | nd | 22 | nd |
| SC-1089 | 47 | 350 | 77 | 130 |
| SC-1090 | 84 | 23 | 100 | 9.8 |
| SC-1091 | 94 | 18 | 98 | 26 |
| SC-1092 | 52 | 107 | 66 | 125 |
| SC-1093 | 91 | 14.5 | 94 | 14.5 |
| SC-1094 | −2 | nd | 11 | 5900 |
| SC-1095 | 10 | nd | 27 | 2025 |
| SC-1096 | 1 | nd | 32 | 2800 |
| SC-1097 | 10 | 750 | 59 | 975 |
| SC-1098 | 44 | 230 | 61 | 250 |
| SC-1099 | 35 | 560 | 53 | 645 |
| SC-1100 | 57 | 175 | 75 | 270 |
| SC-1101 | −2 | nd | 2 | nd |
| SC-1102 | 87 | 64.5 | 101 | 7.7 |
| SC-1103 | 75 | 33.5 | 101 | 13 |
| SC-1104 | 87 | 8.6 | 98 | 9.3 |
| SC-1107 | 93 | 6.7 | 100 | 4 |
| SC-1108 | 17 | nd | 27 | 2320 |
| SC-1109 | 67 | 96.5 | 99 | 26 |
| SC-1110 | 76 | 31 | 96 | 11.4 |
| SC-1111 | 71 | 82 | 87 | 96.5 |
| SC-1112 | 37 | 275 | 72 | 240 |
| SC-1113 | 44 | 530 | 82 | 150 |
| SC-1114 | 73 | 103 | 78 | 64 |
| SC-1115 | 87 | 40.5 | 94 | 10.3 |
| SC-1116 | 86 | 65.5 | 98 | 10.8 |
| SC-1117 | 44 | 415 | 79 | 180 |
| SC-1118 | 79 | 46.5 | 94 | 52 |
| SC-1119 | 74 | 71 | 94 | 85.5 |
| SC-1120 | 45 | 240 | 91 | 86.5 |
| SC-1123 | 70 | 71.3 | 91 | 61 |
| SC-1124 | 93 | 7.9 | 98 | 1.8 |
| SC-1125 | 52 | 275 | 81 | 150 |
| SC-1126 | 29 | 395 | 72 | 190 |
| SC-1127 | 45 | 245 | 80 | 265 |
| SC-1128 | 32 | 780 | 77 | 210 |
| SC-1129 | 50 | 325 | 87 | 117 |
| SC-1130 | 58 | 265 | 72 | 310 |
| SC-1131 | 75 | 73 | 83 | 86.5 |
| SC-1132 | 34 | 535 | 80 | 145 |
| SC-1133 | 55 | 150 | 78 | 200 |
| SC-1134 | 73 | 79.5 | 68 | 87.5 |
| SC-1135 | 75 | 83.5 | 94 | 69 |
| SC-1136 | 51 | 145 | 85 | 160 |
| SC-1137 | 83 | 23 | 98 | 5.4 |
| SC-1138 | 95 | 4.9 | 94 | 10.8 |
| SC-1139 | 93 | 27.5 | 96 | 31.5 |
| SC-1140 | 67 | 175 | 88 | 52.5 |
| SC-1141 | 59 | 240 | 94 | 70.5 |
| SC-1142 | 58 | 47 | 90 | 78.5 |
| SC-1145 | 74 | 41 | 96 | 36.5 |
| SC-1146 | 83 | 31 | 92 | 27.5 |
| SC-1147 | 67 | 118 | 95 | 34 |
| SC-1148 | 60 | 215 | 83 | 180 |
| SC-1149 | 81 | 43 | 88 | 146.7 |
| SC-1150 | 60 | 165 | 85 | 162.5 |
| SC-1151 | 71 | 205 | 93 | 57.5 |
| SC-1152 | 54 | 215 | 92 | 34 |
| SC-1153 | 56 | 26.5 | 87 | 27 |
| SC-1154 | 66 | 48 | 85 | 68.5 |
| SC-1155 | 95 | 1.3 | 100 | 0.9 |
| SC-1156 | 82 | 23.3 | 101 | 3.1 |
| SC-1157 | 76 | 45.5 | 98 | 25.5 |
| SC-1158 | 76 | 6.7 | 100 | 5.1 |

-continued

| Example No | ORL1 % Inhibition @ 1 μM | ORL1 Ki [nM] | MOP % Inhibition @1 μM | MOP Ki [nM] |
|---|---|---|---|---|
| SC-1159 | 83 | 14.5 | 99 | 35.5 |
| SC-1160 | 87 | 7.8 | 98 | 27.5 |
| SC-1161 | 57 | 52.3 | 101 | 4.9 |
| SC-1162 | 60 | 226.7 | 90 | 69 |
| SC-1163 | 84 | 21 | 96 | 14.5 |
| SC-1164 | 95 | 0.3 | 96 | 1.3 |
| SC-1165 | 88 | 2.2 | 99 | 0.6 |
| SC-1166 | 82 | 28 | 102 | 5.1 |
| SC-1167 | 53 | 283.3 | 90 | 128 |
| SC-1168 | 76 | 6.1 | 100 | 10.1 |
| SC-1169 | 81 | 23 | 99 | 11.9 |
| SC-1170 | 67 | 92.5 | 98 | 24 |
| SC-1171 | 57 | 126 | 93 | 65.7 |
| SC-1172 | 37 | 655 | 80 | 185 |
| SC-1173 | 51 | 205 | 35 | 101.5 |
| SC-1174 | 59 | 125 | 95 | 64 |
| SC-1175 | 45 | 223.3 | 87 | 89 |
| SC-1176 | 34 | 390 | 90 | 36 |
| SC-1177 | 55 | 275 | 88 | 58 |
| SC-1178 | 74 | 59.5 | 95 | 5.6 |
| SC-1179 | 53 | 190 | 83 | 115 |
| SC-1180 | 15 | 1110 | 56 | 595 |
| SC-1181 | 31 | 300 | 72 | 315 |
| SC-1182 | 41 | 255 | 82 | 195 |
| SC-1183 | 15 | nd | 61 | 400 |
| SC-1184 | 28 | 770 | 89 | 320 |
| SC-1185 | 72 | 76.5 | 93 | 31.5 |
| SC-1186 | 56 | 230 | 86 | 81 |
| SC-1187 | 49 | 375 | 85 | 57.5 |
| SC-1189 | 56 | 150 | 89 | 21 |
| SC-1190 | 24 | 885 | 76 | 102.5 |
| SC-1191 | 52 | 150 | 83 | 205 |
| SC-1192 | nd | 53.5 | nd | 56.3 |
| SC-1193 | nd | 180 | nd | 76 |
| SC-1194 | 24 | 1477.5 | 65 | 347.5 |
| SC-1195 | 8 | nd | 88 | 125 |
| SC-1198 | 93 | 2.3 | 101 | 1.4 |
| SC-1199 | 95 | 2 | 101 | 1.2 |
| SC-1200 | 95 | 2.4 | 99 | 1.8 |
| SC-1201 | 34 | 753.3 | 58 | 696.7 |

If the experimental data summarised in the above table give the appearance that individual compounds according to the invention have a comparatively only low receptor affinity, it cannot be concluded from this that these compounds are pharmacologically completely inactive. Rather, these measurement results are connected with the chiefly arbitrarily chosen test concentration of 1 μM. It can be assumed that at a correspondingly higher concentration, e.g. at 10 μM, significantly higher values would also be measured for the receptor affinity.

The invention claimed is:
1. A compound of the general formula (1)

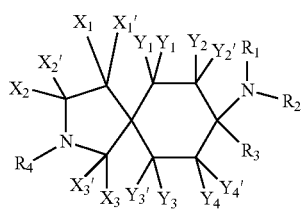

(I)

wherein
$Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —S(=O)$_{1-2}$—NHR$_0$, —S(=O)$_{1-2}$—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; or $Y_1$ and $Y_1'$, or $Y_2$ and $Y_2'$, or $Y_3$ and $Y_3'$, or $Y_4$ and $Y_4'$ together represent =O;

$X_1$, $X_1'$, $X_2$, $X_2'$, $X_3$ and $X_3'$ in each case independently of each other represent —H, —F, —Cl, —Br, —I, —NO$_2$, —CF$_3$, —OR$_5$, —SR$_5$, —SO$_2$R$_5$, —S(=O)$_2$OR$_5$, —CN, —COOR$_5$, —CONR$_5$, —NR$_6$R$_7$, or —R$_0$; or $X_1$ and $X_1'$, or $X_2$ and $X_2'$, or $X_3$ and $X_3'$ together represent =O;

or $X_1$ and $X_2$ or $X_2$ and $X_3$ together represent —(CH$_2$)$_{2-6}$—, wherein individual hydrogen atoms can also be replaced by —F, —Cl, —Br, —I, —NO$_2$, —CF$_3$, —OR$_5$, —CN or —C$_{1-6}$-aliphatic;

or $X_1$ and $X_1'$ or $X_2$ and $X_2'$ or $X_3$ and $X_3'$ in each case together represent a C$_{3-6}$-cycloaliphatic, wherein individual hydrogen atoms can also be replaced by —F, —Cl, —Br, —I, —NO$_2$, —CF$_3$, —OR$_5$, —CN or —C$_{1-6}$-aliphatic;

R$_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

R$_1$ and R$_2$ independently of each other represent —H or —R$_0$; or R$_1$ and R$_2$ together represent —CH$_2$CH$_2$OCH$_2$CH$_2$—, —CH$_2$CH$_2$NR$_8$CH$_2$CH$_2$— or —(OH$_2$)$_{3-6}$—;

R$_3$ represents —R$_0$;
R$_4$ represents —R$_{11}$, —O(=O)R$_{11}$, —O(=O)OR$_{12}$, —C(=O)N(R$_{12}$)$_2$; —O(=O)—O—O(C=O)—R$_{12}$— S(=O)R$_{11}$ or —S(=O)$_2$R$_{11}$;
R$_5$ in each case independently represents —H or —R$_0$;
R$_6$ and R$_7$ independently of each other represent —H or —R$_0$; or R$_6$ and R$_7$ together represent —CH$_2$CH$_2$OCH$_2$CH$_2$—, —CH$_2$CH$_2$NR$_{10}$CH$_2$CH$_2$— or —(OH$_2$)$_{3-6}$—;
R$_8$ represents —H, —R$_0$ or —O(=O)R$_0$;
R$_9$ represents —H, —R$_0$ or —OR$_5$, or —NR$_6$R$_7$;
R$_{10}$ represents —H or —C$_{1-6}$-aliphatic;
R$_{11}$ represents
a) —C$_{1-6}$-alkyl, —C$_{3-6}$-cycloalkyl, or —C$_{1-3}$-alkyl-C$_{3-6}$-cycloalkyl, wherein in the C$_{3-6}$-cycloalkyl group a ring carbon atom can be replaced by an oxygen atom and —C$_{1-6}$-alkyl, —C$_{3-6}$-cycloalkyl or —C$_{1-3}$-alkyl-C$_{3-6}$-cycloalkyl is mono- or polysubstituted by substituents independently of each other selected from the group consisting of —NO$_2$, —CHO, =O, —O(=O)R$_0$, —O(=O)H, —C(=O)—OH, —O(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$R$_0$, —S(=O)$_{1-2}$NH$_2$, —S(=O)$_{1-2}$—NHR$_0$, —S(=O)$_{1-2}$—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$ and —PO(OR$_0$)$_2$;

or b) unsubstituted or mono- or polysubstituted —$C_{7-8}$-alkyl, —$C_{7-12}$-cycloalkyl or $C_{3-12}$-cycloheteroalkyl having up to 3 hetero atoms in the ring selected from the group of O, N and S, with the proviso that heterocycles having only one oxygen atom as a hetero atom are excluded, or c) -aryl, -heteroaryl, —$C_{4-8}$-cycloalkyl-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl, and $R_{12}$ represents H, —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;

wherein

"aliphatic" in each case is a branched or unbranched, saturated or a mono- or polyunsaturated, unsubstituted or mono- or polysubstituted, aliphatic hydrocarbon radical;

"cycloaliphatic" in each case is a saturated or mono- or polyunsaturated, unsubstituted or mono- or polysubstituted, alicyclic, mono- or multicyclic hydrocarbon radical;

wherein with respect to "aliphatic", including —$C_{4-8}$-alkyl, —$C_{7-12}$-alkyl, and "cycloaliphatic" including —$C_{7-12}$-cycloalkyl or $C_{3-12}$-cycloheteroalkyl "mono- or polysubstituted" is understood as meaning substitution once or several times of one or more hydrogen atoms by —F, —Cl, —Br, —I, —CN, —$NO_2$, —CHO, =O, —$R_0$, —O(=O)$R_0$, —O(=O)H, —C(=O)—OH, —O(=O)O$R_0$, —C(=O)$NH_2$, —C(=O)NH$R_0$, —C(=O)N($R_0$)$_2$, —OH, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$$R_0$, —S(=O)$_{1-2}$$NH_2$, —$NH_2$, —NH$R_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)NH$R_0$, —NH—C(=O)N($R_0$)$_2$, —Si($R_0$)$_3$, —PO(O$R_0$)$_2$;

"aryl" in each case independently represents a carbocyclic ring system having at least one aromatic ring, but without hetero atoms in this ring, wherein the aryl radicals can optionally be fused with further saturated, (partially) unsaturated or aromatic ring systems and each aryl radical can be unsubstituted or mono- or polysubstituted, wherein the substituents on aryl can be identical or different and can be in any desired and possible position of the aryl;

"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heterocycle can be unsubstituted or mono- or polysubstituted; wherein in the case of substitution on the heterocycle the substituents can be identical or different and can be in any desired and possible position of the heteroaryl; and wherein the heterocycle can also be part of a bi- or polycyclic system;

wherein with respect to "aryl" and "heteroaryl", "mono- or polysubstituted" is understood as meaning substitution once or several times of one or more hydrogen atoms of the ring system by substituents chosen from the group consisting of —F, —Cl, —Br, —I, —CN, —$NO_2$, —CHO, =O, —$R_0$, —C(=O)$R_0$, —C(=O) H, —C(=O)OH, —C(=O)O$R_0$, —C(=O)$NH_2$, —C(=O)NH$R_0$, —C(=O)—N($R_0$)$_2$, —OH, —O(CH$_2$)$_{1-2}$O—, —O$R_0$, —OC(=O)H, —OC(=O) $R_0$, —OC(=O)O$R_0$, —OC(=O)NH$R_0$, —OC(=O)N ($R_0$)$_2$, —SH, —S$R_0$, —$SO_3$H, —S(=O)$_{1-2}$$R_0$, —S(=O)$_{1-2}$$NH_2$, —$NH_2$, —NH$R_0$, —N($R_0$)$_2$, —$N^+$ ($R_0$)$_3$, —$N^+$($R_0$)$_2$$O^-$, —NHC(=O)$R_0$, —NHC(=O) O$R_0$, —NHC(=O)$NH_2$, —NHC(=O)NH$R_0$, —NHC (=O)N($R_0$)$_2$, —Si($R_0$)$_3$, —PO(O$R_0$)$_2$; wherein N ring atoms optionally present can in each case be oxidised (N-oxide);

in the form of an individual stereoisomer or mixture thereof, the free compounds and/or its physiologically acceptable salts and/or solvates.

2. A compound as claimed in claim 1, wherein $Y_1'$, $Y_2'$, $Y_3'$ and $Y_4'$ each represent —H.

3. A compound as claimed in claim 1, wherein
$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, OH, —$OCH_3$, —$OC_2H_5$ and —N($CH_3$)$_2$.

4. A compound as claimed in claim 1, wherein
$R_3$ represents —$C_{1-8}$-aliphatic, -aryl, -heteroaryl, —$C_{1-3}$-aliphatic-aryl, —$C_{1-3}$-aliphatic-heteroaryl or —$C_{1-3}$-aliphatic-$C_{5-6}$-cycloaliphatic; wherein these are unsubstituted or mono- or polysubstituted by substituents independently of each other chosen from the group consisting of —F, —Cl, —Br, —CN, —$CH_3$, —$C_2H_5$, —$NH_2$, —$NO_2$, —SH, —$CF_3$, —OH, —$OCH_3$, —$OC_2H_5$ and —N($CH_3$)$_2$;

$R_4$ represents —$R_{11}$ or —O(=O)$R_{11}$; and $X_1$, $X_1'$, $X_2$, $X_2'$, $X_3$, $X_3'$ in each case independently of each other represent —H, —F, —Cl, —Br, —I, —$NO_2$, —$CF_3$, —O$R_5$, —S$R_5$, —$SO_2$$R_5$, —S(=O)$_2$O$R_5$, —CN, —COO$R_5$, —CON$R_5$, —N$R_6R_7$, or —$R_0$; or
$X_1$ and $X_1'$, or $X_2$ and $X_2'$, or $X_3$ and $X_3'$ together represent =O.

5. A compound as claimed in claim 1, wherein $Y_1$, $Y_1'$, $Y_2$, $Y_2'$, $Y_3$, $Y_3'$, $Y_4$ and $Y_4'$ each represent —H.

6. A compounds as claimed in claim 1, which has the general formula (3.1)

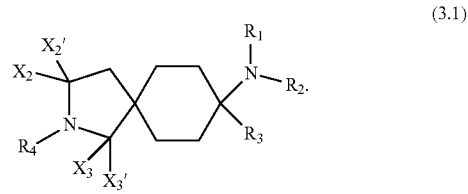

(3.1)

7. A compound as claimed in claim 1, wherein
$X_1$, $X_1'$, $X_2$, $X_2'$, $X_3$ and $X_3'$ represent H; or $X_2$ and $X_2'$, or $X_3$ and $X_3'$ together represent =O;
$R_0$ in each case independently represents —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-}$ 8-aliphatic, —C$_{3-8}$-cycloaliphatic-aryl or —C$_{3-8}$-cycloaliphatic-heteroaryl; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$;

R$_1$ represents CH$_3$;

R$_2$ represents —H or —CH$_3$; or

R$_1$ and R$_2$ together form a ring and represent —(CH$_2$)$_{3-4}$—; and

R$_3$ represents —C$_{1-8}$-aliphatic, -aryl, -heteroaryl, —C$_{1-3}$-aliphatic-aryl, —C$_{1-3}$-aliphatic-heteroaryl or —C$_{1-3}$-aliphatic-C$_{5-6}$-cycloaliphatic; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ and —N(CH$_3$)$_2$;

R$_4$ represents —R$_{11}$ or —O(=O)R$_{11}$;

R$_5$ in each case independently represents —H or R$_0$;

R$_6$ and R$_7$ independently of each other represent —H or R$_0$; or R$_6$ and R$_7$ together represent —CH$_2$CH$_2$OCH$_2$CH$_2$—, —CH$_2$CH$_2$NR$_{10}$CH$_2$CH$_2$— or —(OH$_2$)$_{3-6}$—;

R$_9$ represents —R$_0$, —OR$_5$, or —NR$_6$R$_7$;

R$_{10}$ represents —H or —C$_{1-6}$-aliphatic, and

R$_{11}$ represents C$_{3-12}$-cycloheteroalkyl having up to 3 hetero atoms in the ring selected from the group of O, N and S, with the proviso that heterocycles having only one oxygen atom as a hetero atom are excluded, -aryl, -heteroaryl, —C$_{4-8}$-cycloalkyl-C$_{3-12}$-cycloaliphatic.

8. A compound as claimed in claim 1, wherein R$_1$ and R$_2$ each represent —CH$_3$.

9. A compound as claimed in claim 1, wherein R$_3$ is selected from the group consisting of phenyl, benzyl, pyrazolyl, pyridinyl, pyrazinyl and 2-thienyl, wherein this radical can be unsubstituted or mono- or polysubstituted by substituents independently of each other selected from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$, or R3 is selected from the group consisting of -ethyl, -n-propyl, -n-butyl, -vinyl, or -allyl, unsubstituted or mono- or polysubstituted by —OCH$_3$, —OH or —OC$_2$H$_5$, in particular by —OCH$_3$ or —OC$_2$H$_5$.

10. A compound as claimed in claim 1, which has the general formula (5)

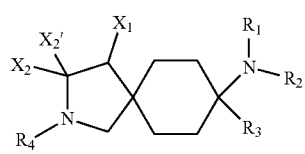

(5)

wherein:

X$_1$ is selected from —H, benzyl or C$_{1-3}$-alkoxy-substituted-C$_{1-4}$-alkyl;

X$_2$ and X$_2$' either are both —H, or together represent =O,

R$_1$ is methyl and R$_2$ is —H or -methyl;

R$_3$ represents —C$_{1-8}$-aliphatic, -aryl, -heteroaryl, —C$_{1-3}$-aliphatic-aryl or —C$_{1-3}$-aliphatic-C$_{5-6}$-cycloaliphatic; wherein these are unsubstituted or mono- or polysubstituted by substituents independently of each other chosen from the group consisting of —F, —Cl, —Br, —CN, —CH$_3$, —C$_2$H$_5$, —NH$_2$, —NO$_2$, —SH, —CF$_3$, OH, —OCH$_3$, —OC$_2$H$_5$ and —N(CH$_3$)$_2$; and R$_4$ is a group according to general formula (6)

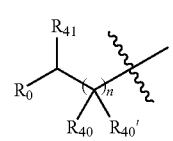

(6)

wherein n=1, 2, 3 or 4

R$_{40}$, R$_{40}$' and R$_{41}$, independently of each other are either H or substituted or unsubstituted C$_{1-3}$-alkyl.

11. A compound as claimed in claim 1, wherein R$_4$ is selected from the group consisting of

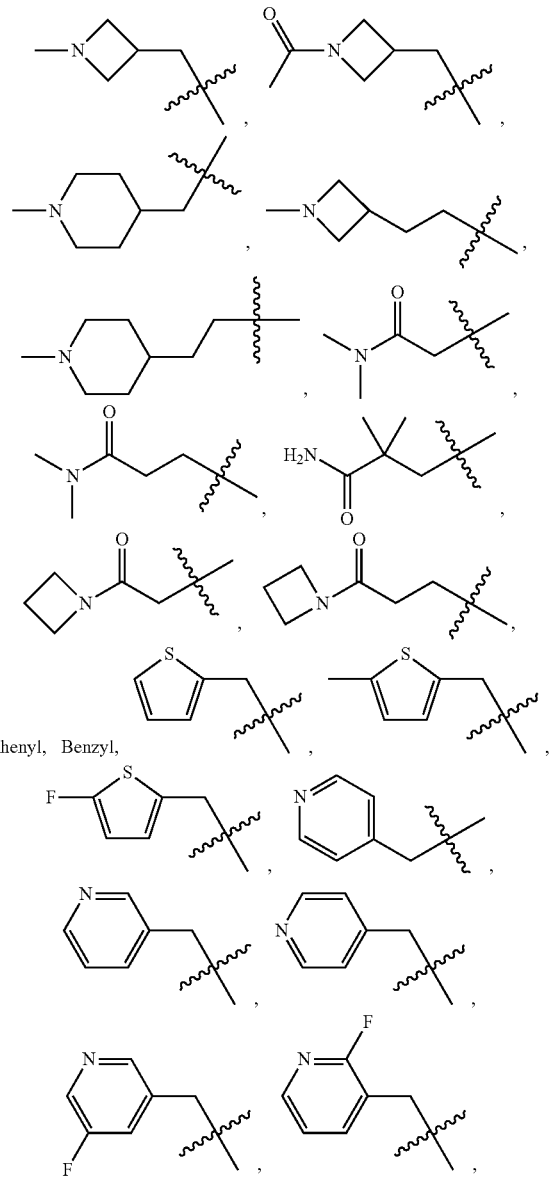

Phenyl, Benzyl,

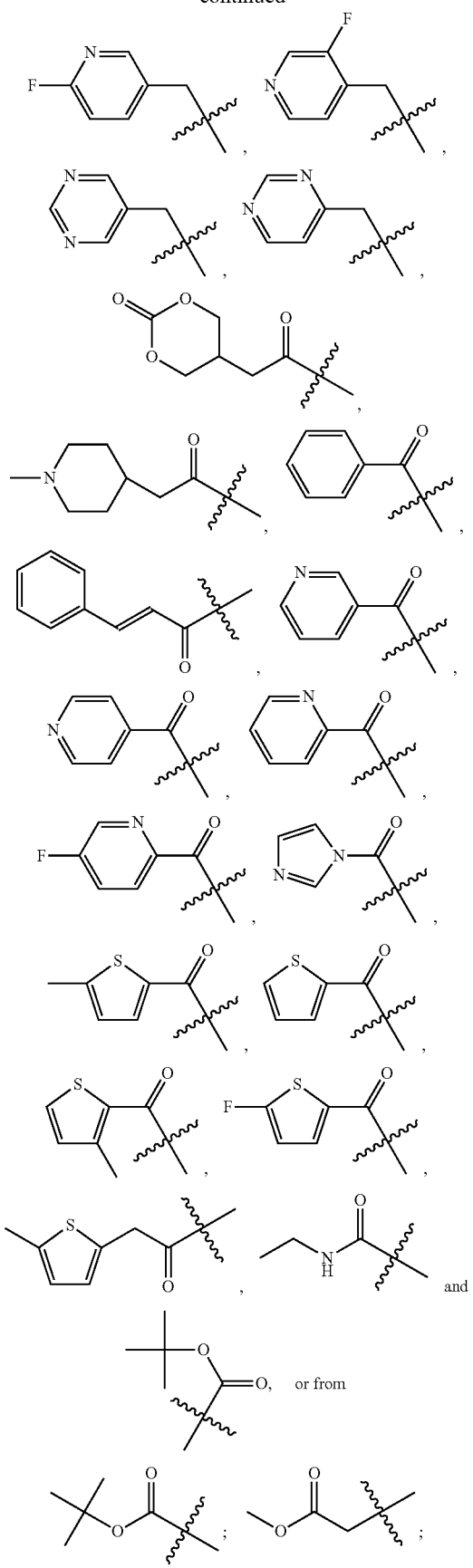
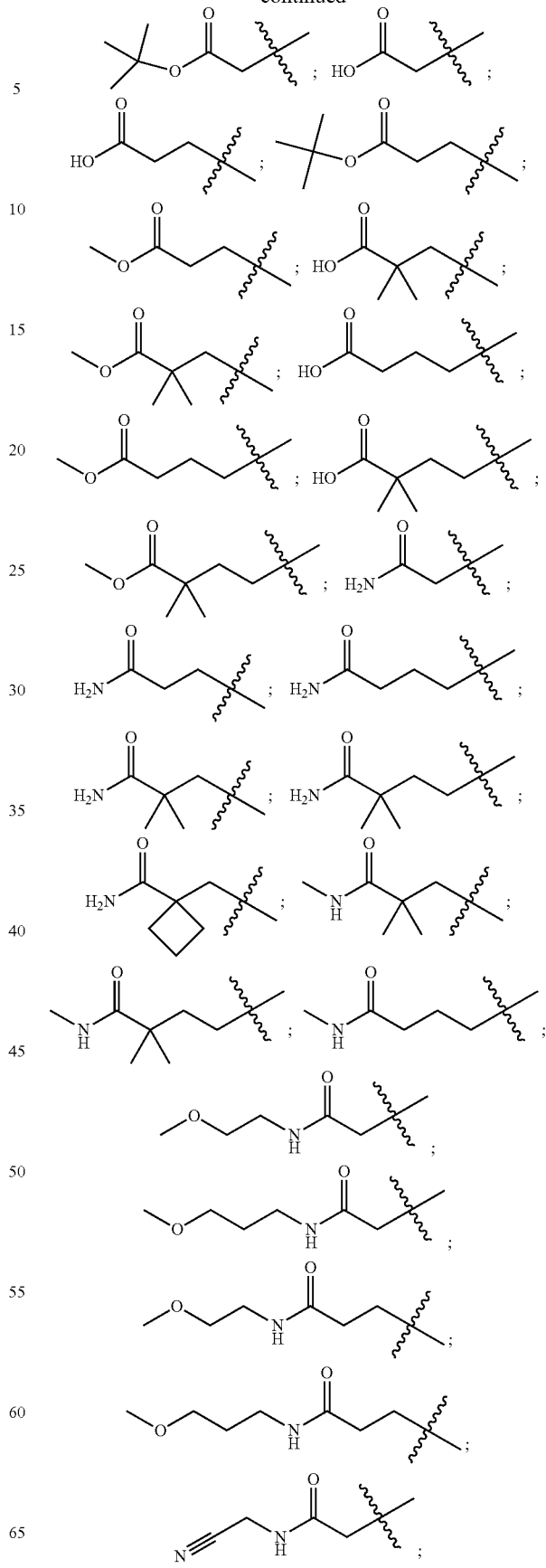

227
-continued
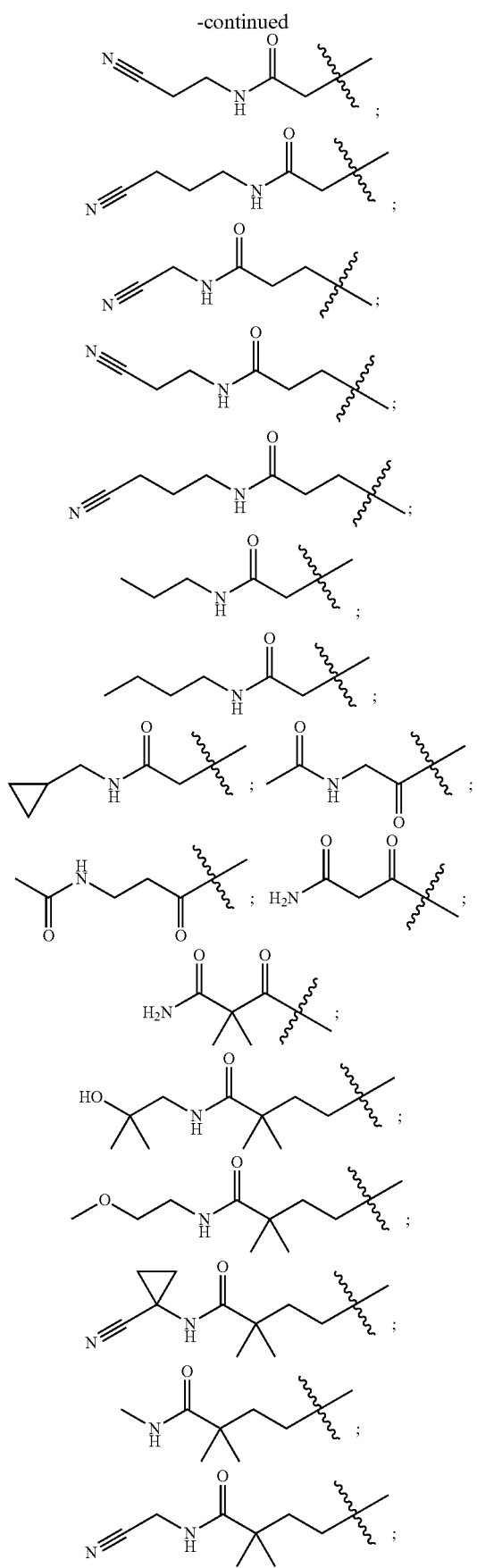
228
-continued
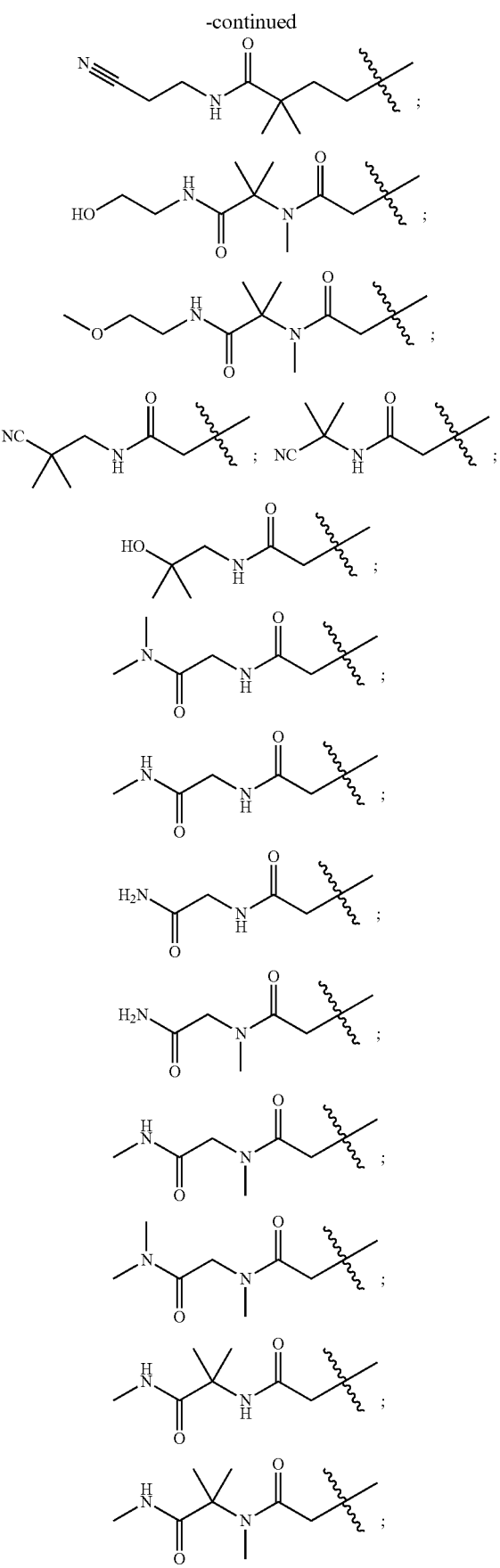

229
-continued
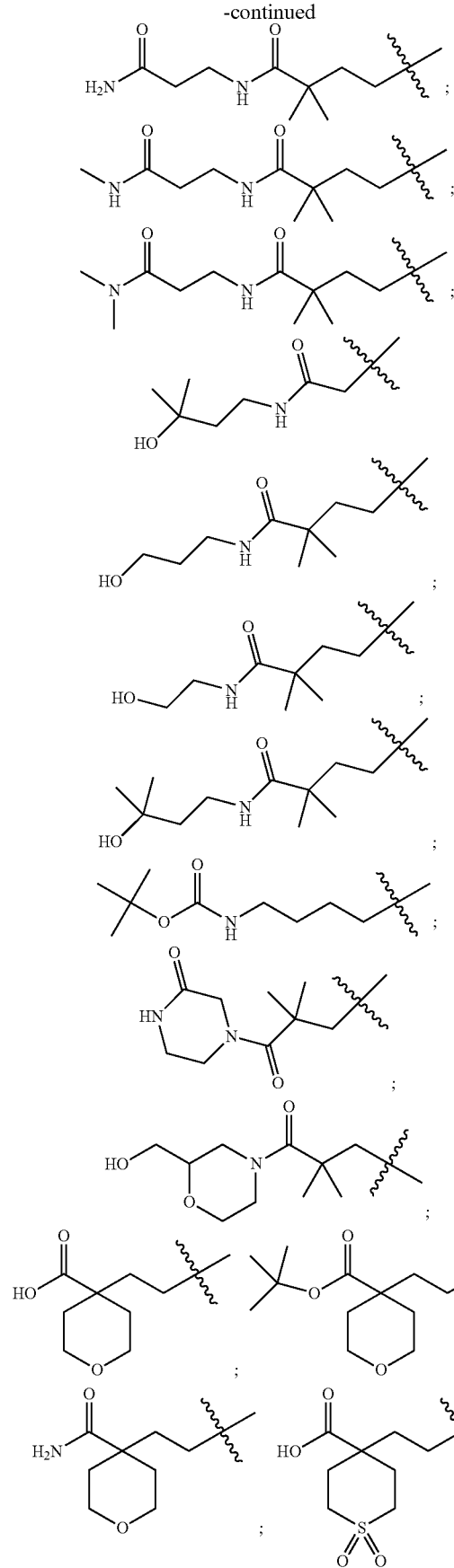
230
-continued
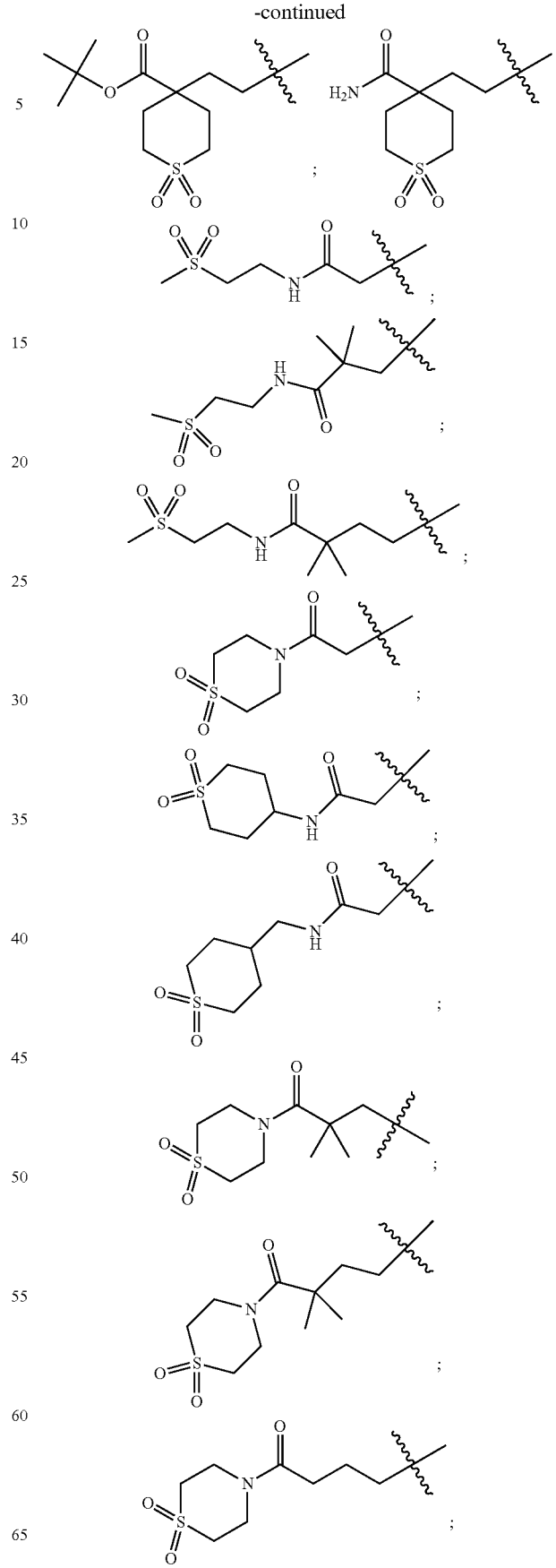

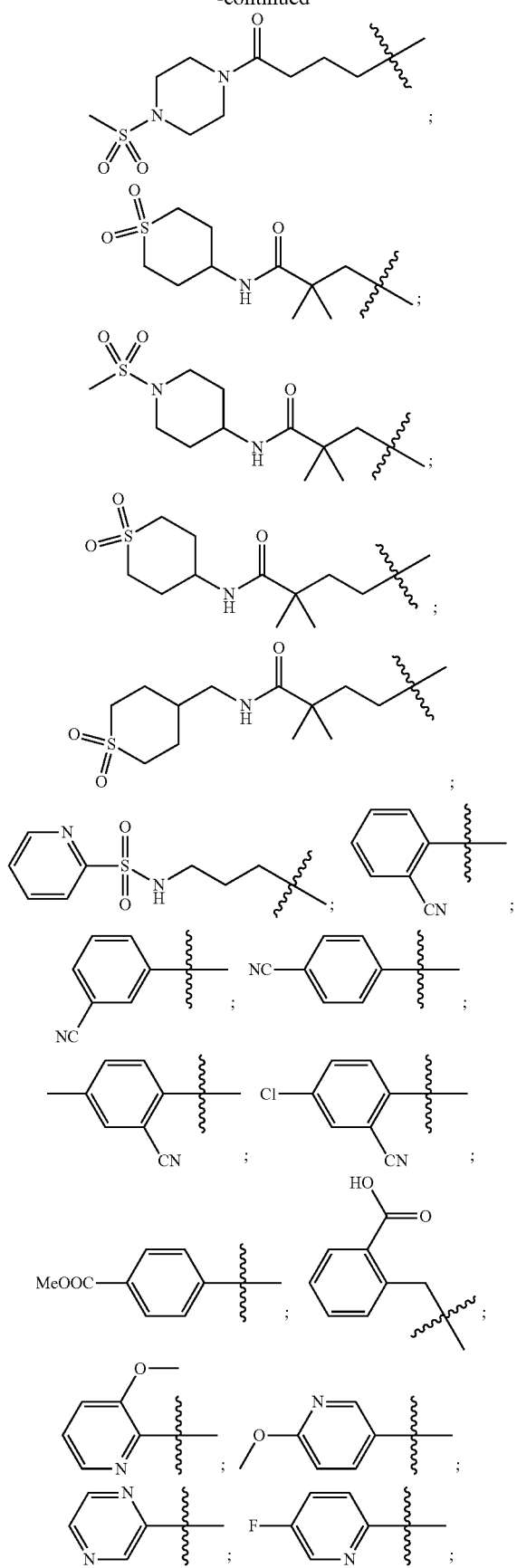
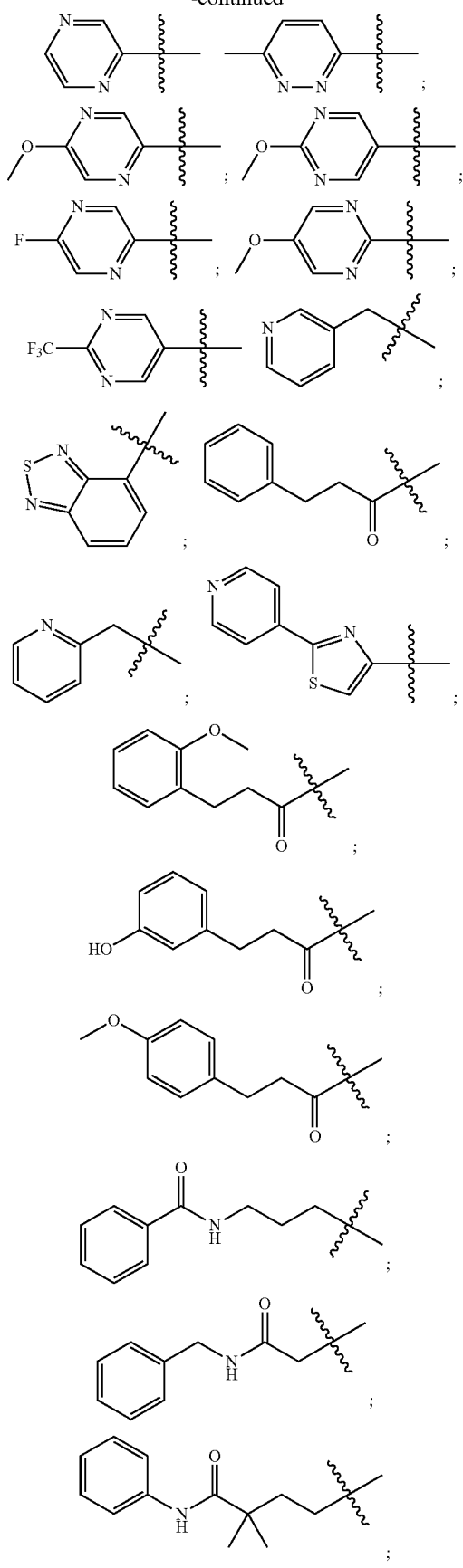

233
-continued
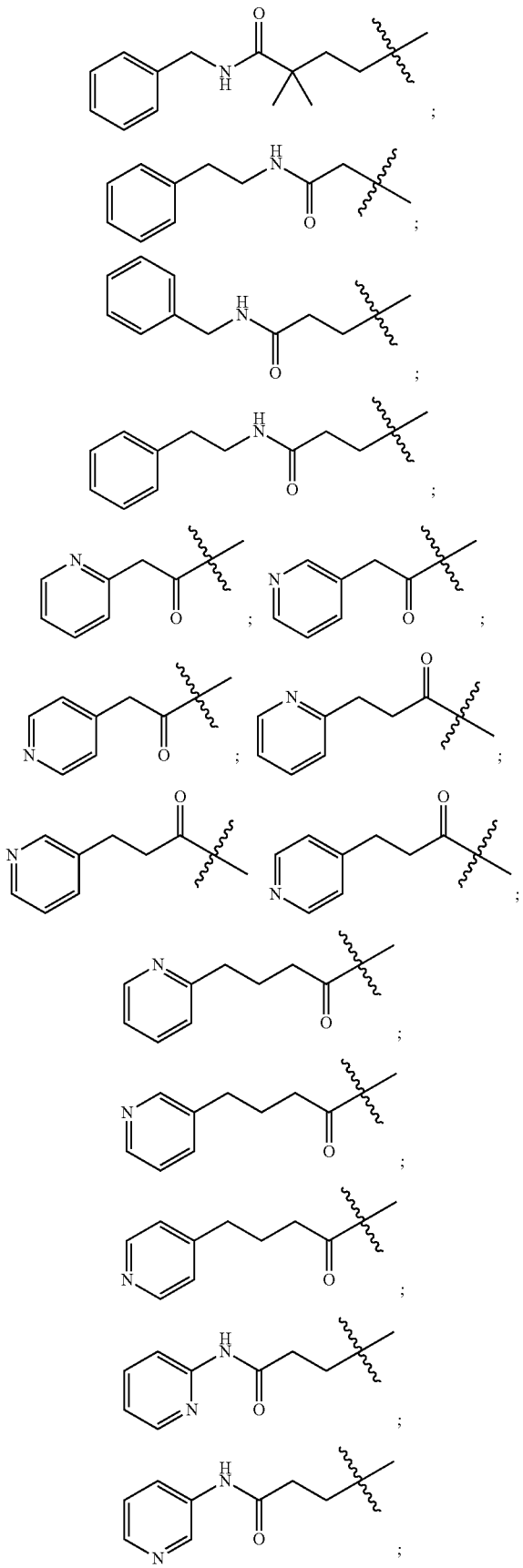
234
-continued
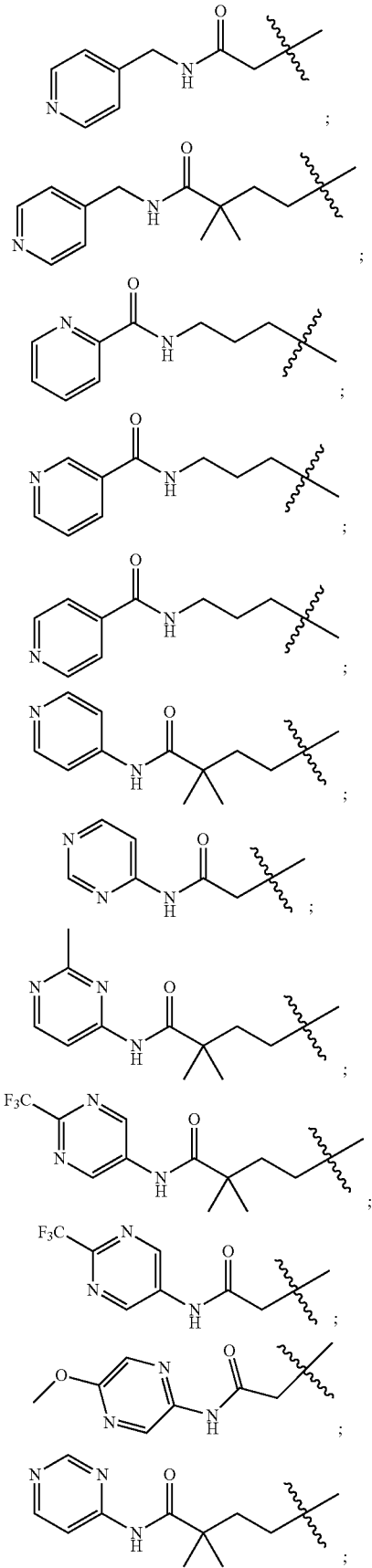

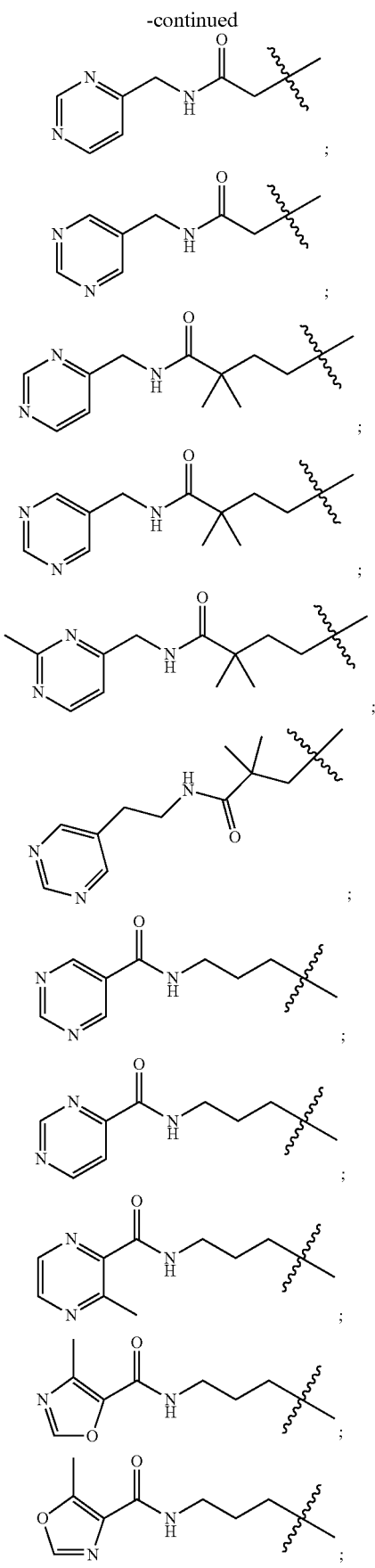

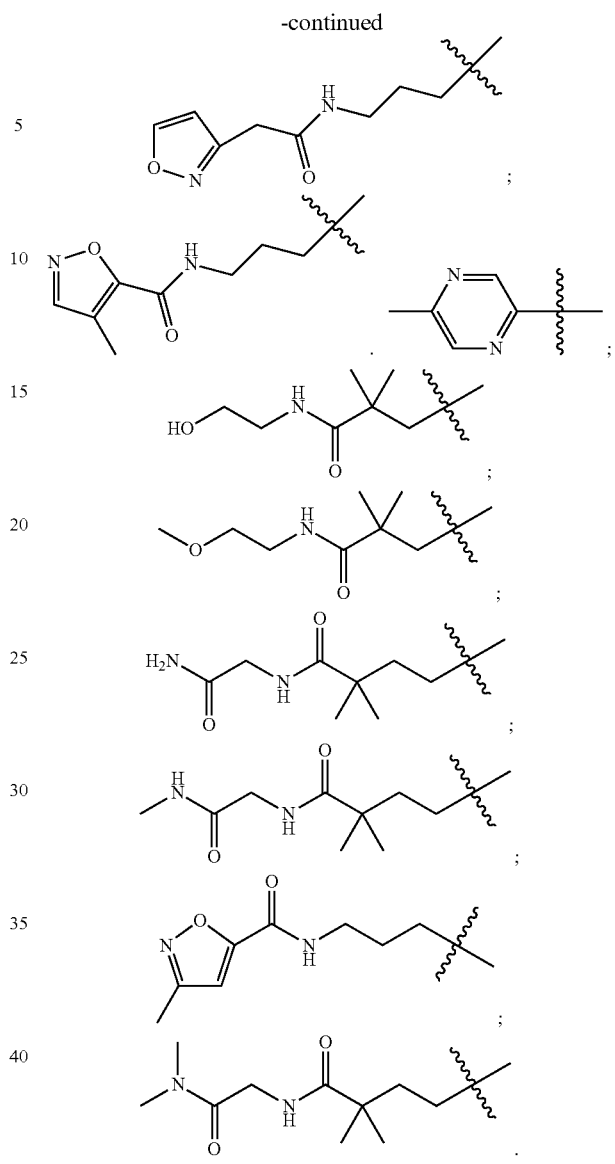

12. A compound as claimed in claim 1 from the group:
(1; 2) (E)-1-[8-Benzyl-8-(dimethylamino)-3-azaspiro[4.5]decan-3-yl]-3-phenylprop-2-en-1-one;
(3) (3,8-Dibenzyl-3-azaspiro[4.5]decan-8-yl)-dimethylamine;
(4; 5) (E)-1-(8-Dimethylamino-8-thiophen-2-yl-3-azaspiro[4.5]decan-3-yl)-3-phenylprop-2-en-1-one;
(6) 8-Dimethylamino-N-ethyl-8-thiophen-2-yl-3-azaspiro[4.5]decane-3-carboxylic acid amide;
(7) (3-Benzyl-8-thiophen-2-yl-3-azaspiro[4.5]decan-8-yl)-dimethylamine;
(8) Dimethyl-[3-(pyridin-4-ylmethyl)-8-thiophen-2-yl-3-azaspiro[4.5]decan-8-yl]-amine;
(9) 8-Benzyl-8-(dimethylamino)-N-ethyl-3-azaspiro[4.5]decane-3-carboxylic acid amide;
(10) [8-Benzyl-3-(pyridin-4-ylmethyl)-3-azaspiro[4.5]decan-8-yl]-dimethylamine;
(11; 12) (E)-1-[8-(Dimethylamino)-8-phenyl-3-azaspiro[4.5]decan-3-yl]-3-phenylprop-2-en-1-one;
(13) (E)-1-[8-(Dimethylamino)-8-(5-methylthiophen-2-yl)-3-azaspiro[4.5]decan-3-yl]-3-phenylprop-2-en-1-one;

(14; 15) 2-Benzyl-8-(dimethylamino)-8-thiophen-2-yl-2-azaspiro[4.5]decan-3-one;
(16) [3-Benzyl-8-(5-methylthiophen-2-yl)-3-azaspiro[4.5]decan-8-yl]-dimethylamine;
(17) [8-(Dimethylamino)-8-(5-methylthiophen-2-yl)-3-azaspiro[4.5]decan-3-yl]-phenylmethanone;
(18) [8-Dimethylamino-8-(5-methylthiophen-2-yl)-3-azaspiro[4.5]decan-3-yl]-pyridin-3-ylmethanone;
(19) [8-Dimethylamino-8-(5-methylthiophen-2-yl)-3-azaspiro[4.5]decan-3-yl]-pyridin-4-ylmethanone;
(20) [8-Dimethylamino-8-(5-methylthiophen-2-yl)-3-azaspiro[4.5]decan-3-yl]-pyridin-2-ylmethanone;
(21) Dimethyl-[8-(5-methylthiophen-2-yl)-3-phenyl-3-azaspiro[4.5]decan-8-yl]-amine;
(22) Dimethyl-[8-(5-methylthiophen-2-yl)-3-(pyridin-3-ylmethyl)-3-azaspiro[4.5]decan-8-yl]-amine;
(23) Dimethyl-[8-(5-methylthiophen-2-yl)-3-(pyridin-4-ylmethyl)-3-azaspiro[4.5]decan-8-yl]-amine;
(24) [8-(Dimethylamino)-8-thiophen-2-yl-3-azaspiro[4.5]decan-3-yl]-phenylmethanone;
(25) [8-(Dimethylamino)-8-thiophen-2-yl-3-azaspiro[4.5]decan-3-yl]-pyridin-4-ylmethanone;
(26) [8-(Dimethylamino)-8-thiophen-2-yl-3-azaspiro[4.5]decan-3-yl]-pyridin-3-ylmethanone;
(27) [8-(Dimethylamino)-8-thiophen-2-yl-3-azaspiro[4.5]decan-3-yl]-pyridin-2-ylmethanone;
(28; 29) Dimethyl-[3-(pyridin-4-ylmethyl)-8-thiophen-2-yl-3-azaspiro[4.5]decan-8-yl]-amine;
(30) Dimethyl-[3-(pyridin-3-ylmethyl)-8-thiophen-2-yl-3-azaspiro[4.5]decan-8-yl]-amine;
(31) Dimethyl-(3-phenyl-8-thiophen-2-yl-3-azaspiro[4.5]decan-8-yl)-amine;
(32) 8-Dimethylamino-8-thiophen-2-yl-3-azaspiro[4.5]decan-3-carboxylic acid tert-butyl ester;
(33) [8-(Dimethylamino)-8-thiophen-2-yl-3-azaspiro[4.5]decan-3-yl]-(1H-imidazol-1-yl)-methanone;
(34) [8-(Dimethylamino)-8-thiophen-2-yl-3-azaspiro[4.5]decan-3-yl]-(5-methylthiophen-2-yl)-methanone;
(35) Dimethyl-[8-thiophen-2-yl-3-(thiophen-2-ylmethyl)-3-azaspiro[4.5]decan-8-yl]-amine;
(36) Dimethyl-[3-[(5-methylthiophen-2-yl)-methyl]-8-thiophen-2-yl-3-azaspiro[4.5]decan-8-yl]-amine;
(37) [8-(Dimethylamino)-8-thiophen-2-yl-3-azaspiro[4.5]decan-3-yl]-thiophen-2-ylmethanone;
(38) [8-(Dimethylamino)-8-thiophen-2-yl-3-azaspiro[4.5]decan-3-yl]-(3-methylthiophen-2-yl)-methanone;
(39) [8-(Dimethylamino)-8-thiophen-2-yl-3-azaspiro[4.5]decan-3-yl]-(5-fluorothiophen-2-yl)-methanone;
(40) [3-[(5-Fluorothiophen-2-yl)-methyl]-8-thiophen-2-yl-3-azaspiro[4.5]decan-8-yl]-dimethylamine;
(41) [3-[(5-Fluoropyridin-3-yl)-methyl]-8-thiophen-2-yl-3-azaspiro[4.5]decan-8-yl]-dimethylamine;
(42) [3-[(2-Fluoropyridin-3-yl)-methyl]-8-thiophen-2-yl-3-azaspiro[4.5]decan-8-yl]-dimethylamine;
(43) [3-[(6-Fluoropyridin-3-yl)-methyl]-8-thiophen-2-yl-3-azaspiro[4.5]decan-8-yl]-dimethylamine;
(44) [3-[(5-Fluoropyridin-2-yl)-methyl]-8-thiophen-2-yl-3-azaspiro[4.5]decan-8-yl]-dimethylamine;
(45) [3-[(3-Fluoropyridin-4-yl)-methyl]-8-thiophen-2-yl-3-azaspiro[4.5]decan-8-yl]-dimethylamine;
(46) (3-Benzyl-8-thiophen-2-yl-3-azaspiro[4.5]decan-8-yl)-dimethylamine;
(47) Dimethyl-[3-(pyrimidin-5-ylmethyl)-8-thiophen-2-yl-3-azaspiro[4.5]decan-8-yl]-amine;
(48) Dimethyl-[3-(pyrimidin-4-ylmethyl)-8-thiophen-2-yl-3-azaspiro[4.5]decan-8-yl]-amine;
(49) (8-Dimethylamino-8-phenyl-3-azaspiro[4.5]decan-3-yl)-pyridin-4-ylmethanone;
(50) (8-Dimethylamino-8-phenyl-3-azaspiro[4.5]decan-3-yl)-phenylmethanone;
(51) (3-Benzyl-8-phenyl-3-azaspiro[4.5]decan-8-yl)-dimethylamine;
(52) (8-Dimethylamino-8-phenyl-3-azaspiro[4.5]decan-3-yl)-pyridin-2-ylmethanone;
(53) (8-Dimethylamino-8-phenyl-3-azaspiro[4.5]decan-3-yl)-pyridin-3-ylmethanone;
(54) Dimethyl-[8-phenyl-3-(pyridin-4-ylmethyl)-3-azaspiro[4.5]decan-8-yl]-amine;
(55) Dimethyl-[8-phenyl-3-(pyridin-2-ylmethyl)-3-azaspiro[4.5]decan-8-yl]-amine;
(56) Dimethyl-[8-phenyl-3-(pyridin-3-ylmethyl)-3-azaspiro[4.5]decan-8-yl]-amine;
(57) 5-[2-[8-(Dimethylamino)-8-phenyl-3-azaspiro[4.5]decan-3-yl]-2-oxo-ethyl]-[1,3]dioxan-2-one;
(58) (E)-1-[8-(5-Chlorothiophen-2-yl)-8-dimethylamino-3-azaspiro[4.5]decan-3-yl]-3-phenylprop-2-en-1-one;
(59) [3-Benzyl-8-(5-chlorothiophen-2-yl)-3-azaspiro[4.5]decan-8-yl]-dimethylamine;
(60) [8-(5-Chlorothiophen-2-yl)-8-dimethylamino-3-azaspiro[4.5]decan-3-yl]-phenylmethanone;
(61) (E)-1-[8-(Dimethylamino)-8-(5-fluorothiophen-2-yl)-3-azaspiro[4.5]decan-3-yl]-3-phenylprop-2-en-1-one;
(62) [8-Dimethylamino-8-(5-fluorothiophen-2-yl)-3-azaspiro[4.5]decan-3-yl]-phenylmethanone;
(63) [8-(Cyclohexylmethyl)-8-dimethylamino-3-azaspiro[4.5]decan-3-yl]-phenylmethanone;
(64) [3-Benzyl-8-(cyclohexylmethyl)-3-azaspiro[4.5]decan-8-yl]-dimethylamine;
(65) [8-(Cyclopentylmethyl)-8-dimethylamino-3-azaspiro[4.5]decan-3-yl]-phenylmethanone;
(66) [3-Benzyl-8-(cyclopentylmethyl)-3-azaspiro[4.5]decan-8-yl]-dimethylamine;
(67) (8-Cyclopentyl-8-dimethyl amino-3-azaspiro[4.5]decan-3-yl)-phenylmethanone;
(68) (3-Benzyl-8-cyclopentyl-3-azaspiro[4.5]decan-8-yl)-dimethylamine;
(69; 70) [3-Benzyl-8-(dimethylamino)-3-azaspiro[4.5]decan-8-yl]-phenylmethanone;
(71; 72) [3-Benzyl-8-(dimethylamino)-3-azaspiro[4.5]decan-8-yl]-thiophen-2-ylmethanone;
(73; 74) (E)-1-[8-(Azetidin-1-yl)-8-thiophen-2-yl-3-azaspiro[4.5]decan-3-yl]-3-phenylprop-2-en-1-one;
(75; 76) [8-(Azetidin-1-yl)-8-thiophen-2-yl-3-azaspiro[4.5]decan-3-yl]-phenylmethanone;
(77) 8-(Azetidin-1-yl)-3-benzyl-8-thiophen-2-yl-3-azaspiro[4.5]decane;
(78; 79) (E)-1-[8-(Azetidin-1-yl)-8-phenyl-3-azaspiro[4.5]decan-3-yl]-3-phenylprop-2-en-1-one;
(80; 81) [8-(Azetidin-1-yl)-8-phenyl-3-azaspiro[4.5]decan-3-yl]-phenylmethanone;
(82; 83) 8-(Azetidin-1-yl)-3-benzyl-8-phenyl-3-azaspiro[4.5]decane;
(84) 3-Benzyl-8-dimethylamino-8-thiophen-2-yl-3-azaspiro[4.5]decan-4-one;
(85) 8-Dimethylamino-3-(pyridin-4-ylmethyl)-8-thiophen-2-yl-3-azaspiro[4.5]decan-4-one;
(86; 87) 3,8-Dibenzyl-8-(dimethylamino)-3-azaspiro[4.5]decan-4-one;
(88; 89) 8-(Dimethylamino)-3-(pyridin-4-ylmethyl)-8-thiophen-2-yl-3-azaspiro[4.5]decan-2-one;
(90; 91) 8-(Dimethylamino)-2-oxo-8-thiophen-2-yl-3-azaspiro[4.5]decan-3-carboxylic acid tert-butyl ester;

(92; 93) 8-(Dimethylamino)-3-[(5-methylthiophen-2-yl)-methyl]-8-thiophen-2-yl-3-azaspiro[4.5]decan-2-one;
(94; 95) 8-(Dimethylamino)-8-thiophen-2-yl-3-(thiophen-2-ylmethyl)-3-azaspiro[4.5]decan-2-one;
(96; 97) 8-(Dimethylamino)-8-(5-methylthiophen-2-yl)-2-oxo-3-azaspiro[4.5]decan-3-carboxylic acid tert-butyl ester;
(98; 99) 3-Benzyl-8-(dimethylamino)-8-(5-methylthiophen-2-yl)-3-azaspiro[4.5]decan-2-one;
(100) 8-(Dimethylamino)-8-(5-methylthiophen-2-yl)-3-(pyridin-4-ylmethyl)-3-azaspiro[4.5]decan-2-one;
(101; 102) 3-Benzyl-8-(dimethylamino)-8-phenyl-3-azaspiro[4.5]decan-2-one;
(103; 104) 8-(Dimethylamino)-8-phenyl-3-(pyridin-4-ylmethyl)-3-azaspiro[4.5]decan-2-one;
(105; 106) 8-(Dimethylamino)-8-phenyl-3-(thiophen-2-ylmethyl)-3-azaspiro[4.5]decan-2-one;
(107; 108) 8-(Dimethylamino)-3-[(5-methylthiophen-2-yl)-methyl]-8-phenyl-3-azaspiro[4.5]decan-2-one;
(109) 8-(Dimethylamino)-3-[(5-fluorothiophen-2-yl)-methyl]-8-phenyl-3-azaspiro[4.5]decan-2-one;
(110) 3-[8-(Dimethylamino)-8-thiophen-2-yl-3-azaspiro[4.5]decan-3-yl]-N,N-dimethylpropionamide;
(111) 2-[8-(Dimethylamino)-8-thiophen-2-yl-3-azaspiro[4.5]decan-3-yl]-N,N-dimethylacetamide;
(112) 1-(Azetidin-1-yl)-2-[8-(dimethylamino)-8-thiophen-2-yl-3-azaspiro[4.5]decan-3-yl]-ethanone;
(113) 1-(Azetidin-1-yl)-3-[8-(dimethylamino)-8-thiophen-2-yl-3-azaspiro[4.5]decan-3-yl]-propan-1-one;
(114) 3-Benzyl-8-cyclopentyl-8-(dimethylamino)-3-azaspiro[4.5]decan-2-one;
(115) 8-(Dimethylamino)-3-[2-(1-methyl-piperidin-4-yl)-ethyl]-8-thiophen-2-yl-3-azaspiro[4.5]decan-2-one;
(116) 8-(Dimethylamino)-3-[(1-methyl-piperidin-4-yl)-methyl]-8-thiophen-2-yl-3-azaspiro[4.5]decan-2-one;
(117) 8-Dimethylamino-3-[2-(1-methyl-azetidin-3-yl)-ethyl]-8-thiophen-2-yl-3-azaspiro[4.5]decan-2-one;
(118) 8-Dimethylamino-3-[(1-methyl-azetidin-3-yl)-methyl]-8-thiophen-2-yl-3-azaspiro[4.5]decan-2-one;
(119) 3-[8-(Dimethylamino)-2-oxo-8-phenyl-3-azaspiro[4.5]decan-3-yl]-2,2-dimethylpropionamide;
(120) [8-(Dimethylamino)-8-phenyl-3-azaspiro[4.5]decan-3-yl]-thiophen-2-ylmethanone;
(121) [8-(Dimethylamino)-8-phenyl-3-azaspiro[4.5]decan-3-yl]-(5-methylthiophen-2-yl)-methanone;
(122) [8-(Dimethylamino)-8-phenyl-3-azaspiro[4.5]decan-3-yl]-(5-fluorothiophen-2-yl)-methanone;
(123) 1-(8-Butyl-8-dimethyl amino-2-azaspiro[4.5]decan-2-yl)-2-(5-methylthiophen-2-yl)-ethanone;
(124; 128) 3-Benzyl-8-butyl-8-(dimethylamino)-3-azaspiro[4.5]decan-2-one;
(125) 1-[8-(Dimethylamino)-8-phenyl-3-azaspiro[4.5]decan-3-yl]-2-(1-methyl-piperidin-4-yl)-ethanone;
(126) 1-[8-(Dimethylamino)-8-thiophen-2-yl-3-azaspiro[4.5]decan-3-yl]-2-(1-methyl-piperidin-4-yl)-ethanone;
(127) 1-[3-[[8-(Dimethylamino)-8-phenyl-3-azaspiro[4.5]decan-3-yl]-methyl]-azetidin-1-yl]-ethanone;
(129) 1-[3-[[8-(Dimethylamino)-8-thiophen-2-yl-3-azaspiro[4.5]decan-3-yl]-methyl]-azetidin-1-yl]-ethanone;
(SC-1001) cis-2-(8-Dimethylamino-3-oxo-8-phenyl-2-azaspiro[4.5]decan-2-yl)-N-pyridin-2-yl-acetamide;
(SC-1002) cis-2-(8-Dimethylamino-3-oxo-8-phenyl-2-azaspiro[4.5]decan-2-yl)-N-pyridin-3-yl-acetamide;
(SC-1003) cis-4-(8-Dimethylamino-3-oxo-8-phenyl-2-azaspiro[4.5]decan-2-yl)-N-[(1,1-dioxo-thian-4-yl)-methyl]-butyramide;
(SC-1004) cis-4-(8-Dimethylamino-3-oxo-8-phenyl-2-azaspiro[4.5]decan-2-yl)-2,2-dimethyl-N-pyrimidin-5-yl-butyramide;
(SC-1005) cis-4-(8-Dimethylamino-3-oxo-8-phenyl-2-azaspiro[4.5]decan-2-yl)-2,2-dimethyl-N-pyrimidin-4-yl-butyramide;
(SC-1006) cis-2-[8-Dimethylamino-8-(3-methoxy-propyl)-3-oxo-2-azaspiro[4.5]decan-2-yl]-acetamide;
(SC-1007) cis-3-[8-Dimethylamino-8-(3-methoxy-propyl)-3-oxo-2-azaspiro[4.5]decan-2-yl]-propionamide;
(SC-1008) cis-2-(8-Dimethylamino-3-oxo-8-pyrazin-2-yl-2-azaspiro[4.5]decan-2-yl)-acetamide;
(SC-1009) cis-3-(8-Dimethylamino-3-oxo-8-pyrazin-2-yl-2-azaspiro[4.5]decan-2-yl)-propionamide;
(SC-1010) cis-4-(8-Dimethylamino-3-oxo-8-pyrazin-2-yl-2-azaspiro[4.5]decan-2-yl)-butyramide;
(SC-1011) cis-2-(8-Dimethylamino-3-oxo-8-pyridin-2-yl-2-azaspiro[4.5]decan-2-yl)-acetamide;
(SC-1012) cis-3-(8-Dimethylamino-3-oxo-8-pyridin-2-yl-2-azaspiro[4.5]decan-2-yl)-propionamide;
(SC-1013) cis-4-(8-Dimethylamino-3-oxo-8-pyridin-2-yl-2-azaspiro[4.5]decan-2-yl)-butyramide;
(SC-1014) cis-N-Benzyl-2-(8-dimethylamino-3-oxo-8-phenyl-2-azaspiro[4.5]decan-2-yl)-acetamide;
(SC-1015) cis-2-(8-Dimethylamino-3-oxo-8-phenyl-2-azaspiro[4.5]decan-2-yl)-N-(2-methoxy-ethyl)-acetamide;
(SC-1016) cis-N-(2-Cyanoethyl)-2-(8-dimethylamino-3-oxo-8-phenyl-2-azaspiro[4.5]decan-2-yl)-acetamide;
(SC-1017) cis-3-(8-Dimethylamino-3-oxo-8-phenyl-2-azaspiro[4.5]decan-2-yl)-N-(3-methoxy-propyl)-propionamide;
(SC-1018) cis-N-(Cyano-methyl)-2-(8-dimethylamino-3-oxo-8-phenyl-2-azaspiro[4.5]decan-2-yl)-acetamide;
(SC-1019) cis-N-(2-Cyanoethyl)-3-(8-dimethylamino-3-oxo-8-phenyl-2-azaspiro[4.5]decan-2-yl)-propionamide;
(SC-1020) cis-N-(Cyano-methyl)-3-(8-dimethylamino-3-oxo-8-phenyl-2-azaspiro[4.5]decan-2-yl)-propionamide;
(SC-1021) cis-N-(3-Cyano-propyl)-3-(8-dimethylamino-3-oxo-8-phenyl-2-azaspiro[4.5]decan-2-yl)-propionamide;
(SC-1022) cis-3-(8-Dimethylamino-3-oxo-8-phenyl-2-azaspiro[4.5]decan-2-yl)-N-pyridin-2-yl-propionamide;
(SC-1023) cis-3-(8-Dimethylamino-3-oxo-8-phenyl-2-azaspiro[4.5]decan-2-yl)-N-(2-phenyl-ethyl)-propionamide;
(SC-1024) cis-3-(8-Dimethylamino-3-oxo-8-phenyl-2-azaspiro[4.5]decan-2-yl)-N-(2-methoxy-ethyl)-propionamide;
(SC-1025) cis-N-Benzyl-3-(8-dimethylamino-3-oxo-8-phenyl-2-azaspiro[4.5]decan-2-yl)-propionamide;
(SC-1026) cis-2-(8-Dimethylamino-3-oxo-8-phenyl-2-azaspiro[4.5]decan-2-yl)-N-(3-methoxy-propyl)-acetamide;
(SC-1027) cis-2-(8-Dimethylamino-3-oxo-8-phenyl-2-azaspiro[4.5]decan-2-yl)-N-(2-phenyl-ethyl)-acetamide;
(SC-1028) cis-3-(8-Dimethylamino-3-oxo-8-phenyl-2-azaspiro[4.5]decan-2-yl)-N-pyridin-3-yl-propionamide;

(SC-1029) cis-4-(8-Dimethylamino-3-oxo-8-phenyl-2-azaspiro[4.5]decan-2-yl)-2,2-dimethyl-N-pyridin-4-yl-butyramide;

(SC-1030) cis-4-(8-Dimethylamino-3-oxo-8-phenyl-2-azaspiro[4.5]decan-2-yl)-2,2-dimethyl-N-(pyrimidin-4-yl-methyl)-butyramide;

(SC-1031) cis-4-(8-Dimethylamino-3-oxo-8-phenyl-2-azaspiro[4.5]decan-2-yl)-2,2-dimethyl-N-(pyrimidin-5-yl-methyl)-butyramide;

(SC-1032) cis-2-(8-Dimethylamino-3-oxo-8-phenyl-2-azaspiro[4.5]decan-2-yl)-N-pyrimidin-4-yl-acetamide;

(SC-1033) cis-3-(8-Dimethylamino-8-phenyl-2-azaspiro[4.5]decan-2-yl)-3-oxo-propionamide;

(SC-1034) cis-3-(8-Dimethylamino-8-phenyl-2-azaspiro[4.5]decan-2-yl)-2,2-dimethyl-3-oxo-propionamide;

(SC-1035) cis-2-(8-Dimethylamino-3-oxo-8-phenyl-2-azaspiro[4.5]decan-2-yl)-acetamide;

(SC-1036) cis-4-[2-(8-Dimethylamino-3-oxo-8-phenyl-2-azaspiro[4.5]decan-2-yl)-ethyl]-tetrahydro-pyran-4-carboxylic acid amide;

(SC-1037) cis-4-[2-(8-Dimethylamino-3-oxo-8-phenyl-2-azaspiro[4.5]decan-2-yl)-ethyl]-1,1-dioxo-thiane-4-carboxylic acid amide;

(SC-1038) cis-N-(1-Cyano-cyclopropyl)-4-(8-dimethylamino-3-oxo-8-phenyl-2-azaspiro[4.5]decan-2-yl)-2,2-dimethyl-butyramide;

(SC-1039) cis-3-(8-Dimethylamino-3-oxo-8-phenyl-2-azaspiro[4.5]decan-2-yl)-N-(1,1-dioxo-thian-4-yl)-2,2-dimethyl-propionamide;

(SC-1040) cis-8-Dimethylamino-2-[3-[2-(hydroxymethyl)-morpholin-4-yl]-2,2-dimethyl-3-oxo-propyl]-8-phenyl-2-azaspiro[4.5]decan-3-one (SC-1041) cis-3-(8-Dimethylamino-3-oxo-8-phenyl-2-azaspiro[4.5]decan-2-yl)-propionamide;

(SC-1042) cis-4-(8-Dimethylamino-3-oxo-8-pyridin-2-yl-2-azaspiro[4.5]decan-2-yl)-butyric acid hydrochloride (SC-1043) cis-3-(8-Dimethylamino-3-oxo-8-pyridin-2-yl-2-azaspiro[4.5]decan-2-yl)-2,2-dimethyl-propionic acid hydrochloride (SC-1044) cis-4-(8-Dimethylamino-3-oxo-8-phenyl-2-azaspiro[4.5]decan-2-yl)-2,2-dimethyl-butyric acid hydrochloride (SC-1045) cis-3-(8-Dimethylamino-3-oxo-8-phenyl-2-azaspiro[4.5]decan-2-yl)-2,2-dimethyl-propionic acid (SC-1046) cis-2-(8-Dimethylamino-3-oxo-8-pyridin-2-yl-2-azaspiro[4.5]decan-2-yl)-acetic acid hydrochloride (SC-1047) cis-3-(8-Dimethylamino-3-oxo-8-pyridin-2-yl-2-azaspiro[4.5]decan-2-yl)-propionic acid hydrochloride (SC-1048) cis-2-(8-Dimethylamino-3-oxo-8-phenyl-2-azaspiro[4.5]decan-2-yl)-acetic acid hydrochloride (SC-1049) cis-[3-(8-Dimethylamino-3-oxo-8-phenyl-2-azaspiro[4.5]decan-2-yl)-propyl]-carbamic acid tert-butyl ester (SC-1050) cis-2-(8-Dimethylamino-3-oxo-8-phenyl-2-azaspiro[4.5]decan-2-yl)-acetic acid methyl ester (SC-1051) cis-4-[2-(8-Dimethylamino-3-oxo-8-phenyl-2-azaspiro[4.5]decan-2-yl)-ethyl]-tetrahydro-pyran-4-carboxylic acid tert-butyl ester (SC-1052) cis-4-[2-(8-Dimethylamino-3-oxo-8-phenyl-2-azaspiro[4.5]decan-2-yl)-ethyl]-1,1-dioxo-thiane-4-carboxylic acid tert-butyl ester (SC-1053) cis-4-(8-Dimethylamino-3-oxo-8-phenyl-2-azaspiro[4.5]decan-2-yl)-2,2-dimethyl-butyric acid methyl ester (SC-1054) cis-8-Dimethylamino-8-phenyl-2-(pyridin-2-yl-methyl)-2-azaspiro[4.5]decan-3-one (SC-1055) cis-8-Dimethylamino-8-phenyl-2-(pyridin-3-yl-methyl)-2-azaspiro[4.5]decan-3-one (SC-1056) trans-8-Dimethylamino-2-(6-methoxy-pyridin-3-yl)-8-phenyl-2-azaspiro[4.5]decan-3-one (SC-1057) trans-8-Dimethylamino-2-(2-methoxy-pyrimidin-5-yl)-8-phenyl-2-azaspiro[4.5]decan-3-one (SC-1058) trans-8-Dimethylamino-2-(5-methoxy-pyrimidin-2-yl)-8-phenyl-2-azaspiro[4.5]decan-3-one (SC-1059) trans-8-Dimethylamino-2-(3-methoxy-pyridin-2-yl)-8-phenyl-2-azaspiro[4.5]decan-3-one (SC-1060) trans-8-Dimethylamino-2-(5-methoxy-pyrazin-2-yl)-8-phenyl-2-azaspiro[4.5]decan-3-one (SC-1061) trans-8-Dimethylamino-2-(5-methyl-pyrazin-2-yl)-8-phenyl-2-azaspiro[4.5]decan-3-one (SC-1062) trans-8-Dimethylamino-2-(5-fluoro-pyridin-2-yl)-8-phenyl-2-azaspiro[4.5]decan-3-one (SC-1063) trans-8-Dimethylamino-8-phenyl-2-pyrazin-2-yl-2-azaspiro[4.5]decan-3-one (SC-1064) trans-8-Dimethylamino-8-phenyl-2-(2-pyridin-4-yl-thiazol-4-yl)-2-azaspiro[4.5]decan-3-one (SC-1065) cis-5-Chloro-2-(8-dimethylamino-3-oxo-8-phenyl-2-azaspiro[4.5]decan-2-yl)-benzonitrile (SC-1066) cis-8-Dimethylamino-2-(6-methyl-pyridazin-3-yl)-8-phenyl-2-azaspiro[4.5]decan-3-one (SC-1067) cis-8-Dimethylamino-8-phenyl-2-[2-(trifluoromethyl)-pyrimidin-5-yl]-2-azaspiro[4.5]decan-3-one (SC-1068) cis-2-([2,1,3]Benzothiadiazol-4-yl)-8-dimethylamino-8-phenyl-2-azaspiro[4.5]decan-3-one (SC-1069) trans-8-Dimethylamino-2,8-diphenyl-2-azaspiro[4.5]decan-3-one (SC-1070) cis-8-Dimethylamino-2,8-diphenyl-2-azaspiro[4.5]decan-3-one (SC-1071) cis-4-(8-Dimethylamino-3-oxo-8-phenyl-2-azaspiro[4.5]decan-2-yl)-benzonitrile (SC-1072) cis-3-(8-Dimethylamino-3-oxo-8-phenyl-2-azaspiro[4.5]decan-2-yl)-benzonitrile (SC-1073) cis-2-(8-Dimethylamino-3-oxo-8-phenyl-2-azaspiro[4.5]decan-2-yl)-benzonitrile (SC-1074) cis-4-(8-Dimethylamino-3-oxo-8-phenyl-2-azaspiro[4.5]decan-2-yl)-benzoic acid methyl ester (SC-1075) cis-2-(8-Dimethylamino-3-oxo-8-phenyl-2-azaspiro[4.5]decan-2-yl)-5-methyl-benzonitrile (SC-1076) cis-4-(8-Dimethylamino-3-oxo-8-phenyl-2-azaspiro[4.5]decan-2-yl)-butyric acid (SC-1077) cis-4-(8-Dimethylamino-3-oxo-8-phenyl-2-azaspiro[4.5]decan-2-yl)-2,2-dimethyl-butyric acid (SC-1078) cis-2-(8-Dimethylamino-3-oxo-8-pyridin-2-yl-2-azaspiro[4.5]decan-2-yl)-acetic acid methyl ester (SC-1079) cis-3-(8-Dimethylamino-3-oxo-8-pyridin-2-yl-2-azaspiro[4.5]decan-2-yl)-propionic acid methyl ester (SC-1080) cis-2-(8-Dimethylamino-3-oxo-8-pyridin-2-yl-2-azaspiro[4.5]decan-2-yl)-acetic acid tert-butyl ester (SC-1081) cis-3-(8-Dimethylamino-3-oxo-8-pyridin-2-yl-2-azaspiro[4.5]decan-2-yl)-propionic acid tert-butyl ester (SC-1082) cis-2,2-Dimethyl-3-(8-methylamino-3-oxo-8-phenyl-2-azaspiro[4.5]decan-2-yl)-propionamide;

(SC-1083) cis-2-(8-Methylamino-3-oxo-8-pyridin-2-yl-2-azaspiro[4.5]decan-2-yl)-acetamide;

(SC-1084) cis-3-(8-Methylamino-3-oxo-8-pyridin-2-yl-2-azaspiro[4.5]decan-2-yl)-propionamide;

(SC-1085) cis-4-(8-Methylamino-3-oxo-8-pyridin-2-yl-2-azaspiro[4.5]decan-2-yl)-butyramide 2,2,2-trifluoro acetate
(SC-1086) cis-2,2-Dimethyl-3-(8-methylamino-3-oxo-8-pyridin-2-yl-2-azaspiro[4.5]decan-2-yl)-propionamide 2,2,2-trifluoro acetate
(SC-1087) cis-2,2-Dimethyl-4-(8-methylamino-3-oxo-8-pyridin-2-yl-2-azaspiro[4.5]decan-2-yl)-butyramide;
(SC-1088) trans-2,2-Dimethyl-3-(8-methylamino-3-oxo-8-pyridin-2-yl-2-azaspiro[4.5]decan-2-yl)-propionamide;
(SC-1089) cis-4-(8-Dimethylamino-3-oxo-8-pyridin-2-yl-2-azaspiro[4.5]decan-2-yl)-butyric acid methyl ester;
(SC-1090) cis-3-(8-Dimethylamino-3-oxo-8-pyridin-2-yl-2-azaspiro[4.5]decan-2-yl)-2,2-dimethyl-propionic acid methyl ester;
(SC-1091) cis-4-(8-Dimethylamino-3-oxo-8-phenyl-2-azaspiro[4.5]decan-2-yl)-2,2-dimethyl-butyramide;
(SC-1092) cis-4-(8-Dimethylamino-3-oxo-8-phenyl-2-azaspiro[4.5]decan-2-yl)-butyramide;
(SC-1093) cis-1-[(8-Dimethylamino-3-oxo-8-phenyl-2-azaspiro[4.5]decan-2-yl)-methyl]-cyclobutane-1-carboxylic acid amide;
(SC-1094) cis-4-[8-Dimethylamino-8-(3-methoxy-propyl)-3-oxo-2-azaspiro[4.5]decan-2-yl]-butyramide 2,2,2-trifluoro acetate
(SC-1095) cis-3-[8-Dimethylamino-8-(3-methoxy-propyl)-3-oxo-2-azaspiro[4.5]decan-2-yl]-2,2-dimethyl-propionamide 2,2,2-trifluoro acetate
(SC-1096) cis-4-[8-Dimethylamino-8-(3-methoxy-propyl)-3-oxo-2-azaspiro[4.5]decan-2-yl]-2,2-dimethyl-butyramide 2,2,2-trifluoro acetate
(SC-1097) cis-3-(8-Dimethylamino-3-oxo-8-pyrazin-2-yl-2-azaspiro[4.5]decan-2-yl)-2,2-dimethyl-propionamide;
(SC-1098) cis-4-(8-Dimethylamino-3-oxo-8-pyrazin-2-yl-2-azaspiro[4.5]decan-2-yl)-2,2-dimethyl-butyramide;
(SC-1099) cis-3-(8-Dimethylamino-3-oxo-8-pyridin-2-yl-2-azaspiro[4.5]decan-2-yl)-2,2-dimethyl-propionamide 2,2,2-trifluoro acetate
(SC-1100) cis-4-(8-Dimethylamino-3-oxo-8-pyridin-2-yl-2-azaspiro[4.5]decan-2-yl)-2,2-dimethyl-butyramide;
(SC-1101) trans-3-(8-Dimethylamino-3-oxo-8-pyridin-2-yl-2-azaspiro[4.5]decan-2-yl)-2,2-dimethyl-propionamide 2,2,2-trifluoro acetate
(SC-1102) cis-4-(8-Dimethylamino-3-oxo-8-phenyl-2-azaspiro[4.5]decan-2-yl)-2,2-dimethyl-N-[2-(trifluoromethyl)-pyrimidin-5-yl]-butyramide;
(SC-1103) cis-4-(8-Dimethylamino-3-oxo-8-phenyl-2-azaspiro[4.5]decan-2-yl)-2,2-dimethyl-N-(2-methyl-pyrimidin-4-yl)-butyramide;
(SC-1104) trans-4-Benzyl-8-dimethyl amino-3-oxo-8-phenyl-2-azaspiro[4.5]decane-2-carboxylic acid tert-butyl ester;
(SC-1107) cis-2-[(8-Dimethylamino-3-oxo-8-phenyl-2-azaspiro[4.5]decan-2-yl)-methyl]-benzoic acid hydrochloride;
(SC-1108) trans-2-[(8-Dimethylamino-3-oxo-8-phenyl-2-azaspiro[4.5]decan-2-yl)-methyl]-benzoic acid hydrochloride
(SC-1109) cis-N-[3-(8-Dimethylamino-3-oxo-8-phenyl-2-azaspiro[4.5]decan-2-yl)-propyl]-pyridine-2-sulfonic acid amide;
(SC-1110) cis-N-(3-Cyano-propyl)-2-(8-dimethyl amino-3-oxo-8-phenyl-2-azaspiro[4.5]decan-2-yl)-acetamide;
(SC-1111) cis-4-(8-Dimethylamino-3-oxo-8-phenyl-2-azaspiro[4.5]decan-2-yl)-N-methyl-butyramide;
(SC-1112) cis-8-Dimethylamino-2-[4-(4-methylsulfonyl-piperazin-1-yl)-4-oxo-butyl]-8-phenyl-2-azaspiro[4.5]decan-3-one;
(SC-1113) cis-8-Dimethylamino-2-[4-(1,1-dioxo-[1,4]thiazinan-4-yl)-4-oxo-butyl]-8-phenyl-2-azaspiro[4.5]decan-3-one;
(SC-1114) cis-2-(8-Dimethylamino-3-oxo-8-phenyl-2-azaspiro[4.5]decan-2-yl)-N-(2-hydroxy-2-methyl-propyl)-acetamide;
(SC-1115) cis-N-(1-Cyano-1-methyl-ethyl)-2-(8-dimethylamino-3-oxo-8-phenyl-2-azaspiro[4.5]decan-2-yl)-acetamide;
(SC-1116) cis-N-(2-Cyano-2-methyl-propyl)-2-(8-dimethylamino-3-oxo-8-phenyl-2-azaspiro[4.5]decan-2-yl)-acetamide;
(SC-1117) cis-2-(8-Dimethylamino-3-oxo-8-phenyl-2-azaspiro[4.5]decan-2-yl)-N-[2-(trifluoromethyl)-pyrimidin-5-yl]-acetamide;
(SC-1118) cis-2-(8-Dimethylamino-3-oxo-8-phenyl-2-azaspiro[4.5]decan-2-yl)-N-(pyridin-4-yl-methyl)-acetamide;
(SC-1119) cis-2-(8-Dimethylamino-3-oxo-8-phenyl-2-azaspiro[4.5]decan-2-yl)-N-(pyrimidin-4-yl-methyl)-acetamide;
(SC-1120) cis-2-(8-Dimethylamino-3-oxo-8-phenyl-2-azaspiro[4.5]decan-2-yl)-N-(pyrimidin-5-yl-methyl)-acetamide;
(SC-1123) cis-2-(8-Dimethylamino-3-oxo-8-phenyl-2-azaspiro[4.5]decan-2-yl)-N-(2-methylsulfonyl-ethyl)-acetamide;
(SC-1124) cis-8-Dimethylamino-2-[2-(1,1-dioxo-[1,4]thiazinan-4-yl)-2-oxo-ethyl]-8-phenyl-2-azaspiro[4.5]decan-3-one;
(SC-1125) cis-2-[[2-(8-Dimethylamino-3-oxo-8-phenyl-2-azaspiro[4.5]decan-2-yl)-acetyl]amino]-N,N-dimethyl-acetamide;
(SC-1126) cis-2-[[2-(8-Dimethylamino-3-oxo-8-phenyl-2-azaspiro[4.5]decan-2-yl)-acetyl]amino]-acetamide;
(SC-1127) cis-2-[[2-(8-Dimethylamino-3-oxo-8-phenyl-2-azaspiro[4.5]decan-2-yl)-acetyl]amino]-N-methyl-acetamide;
(SC-1128) cis-2-[[2-(8-Dimethylamino-3-oxo-8-phenyl-2-azaspiro[4.5]decan-2-yl)-acetyl]amino]-N,2-dimethyl-propionamide;
(SC-1129) cis-2-(8-Dimethylamino-3-oxo-8-phenyl-2-azaspiro[4.5]decan-2-yl)-N-[(dimethyl-carbamoyl)-methyl]-N-methyl-acetamide;
(SC-1130) cis-N-(Carbamoyl-methyl)-2-(8-dimethyl-amino-3-oxo-8-phenyl-2-azaspiro[4.5]decan-2-yl)-N-methyl-acetamide;
(SC-1131) cis-2-(8-Dimethylamino-3-oxo-8-phenyl-2-azaspiro[4.5]decan-2-yl)-N-methyl-N-(methylcarbamoyl-methyl)-acetamide;
(SC-1132) cis-2-[[2-(8-Dimethylamino-3-oxo-8-phenyl-2-azaspiro[4.5]decan-2-yl)-acetyl]-methyl-amino]-N,2-dimethyl-propionamide;
(SC-1133) cis-3-(8-Dimethylamino-3-oxo-8-phenyl-2-azaspiro[4.5]decan-2-yl)-N-(2-hydroxy-ethyl)-2,2-dimethyl-propionamide;
(SC-1134) cis-3-(8-Dimethylamino-3-oxo-8-phenyl-2-azaspiro[4.5]decan-2-yl)-N-(2-methoxy-ethyl)-2,2-dimethyl-propionamide;

(SC-1135) cis-8-Dimethylamino-2-[3-(1,1-dioxo-[1,4]thiazinan-4-yl)-2,2-dimethyl-3-oxo-propyl]-8-phenyl-2-azaspiro[4.5]decan-3-one;

(SC-1136) cis-3-(8-Dimethylamino-3-oxo-8-phenyl-2-azaspiro[4.5]decan-2-yl)-N,2,2-trimethyl-propionamide;

(SC-1137) cis-4-(8-Dimethylamino-3-oxo-8-phenyl-2-azaspiro[4.5]decan-2-yl)-2,2-dimethyl-N-phenyl-butyramide;

(SC-1138) cis-N-Benzyl-4-(8-dimethylamino-3-oxo-8-phenyl-2-azaspiro[4.5]decan-2-yl)-2,2-dimethyl-butyramide;

(SC-1139) cis-4-(8-Dimethylamino-3-oxo-8-phenyl-2-azaspiro[4.5]decan-2-yl)-2,2-dimethyl-N-(pyridin-4-yl-methyl)-butyramide;

(SC-1140) cis-4-(8-Dimethylamino-3-oxo-8-phenyl-2-azaspiro[4.5]decan-2-yl)-2,2-dimethyl-N-[(2-methyl-pyrimidin-4-yl)-methyl]-butyramide;

(SC-1141) cis-4-(8-Dimethylamino-3-oxo-8-phenyl-2-azaspiro[4.5]decan-2-yl)-N-(2-methoxy-ethyl)-2,2-dimethyl-butyramide;

(SC-1142) cis-4-(8-Dimethylamino-3-oxo-8-phenyl-2-azaspiro[4.5]decan-2-yl)-N-(2-hydroxy-2-methyl-propyl)-2,2-dimethyl-butyramide;

(SC-1145) cis-4-(8-Dimethylamino-3-oxo-8-phenyl-2-azaspiro[4.5]decan-2-yl)-N,2,2-trimethyl-butyramide;

(SC-1146) cis-N-(Cyano-methyl)-4-(8-dimethylamino-3-oxo-8-phenyl-2-azaspiro[4.5]decan-2-yl)-2,2-dimethyl-butyramide;

(SC-1147) cis-N-(2-Cyanoethyl)-4-(8-dimethylamino-3-oxo-8-phenyl-2-azaspiro[4.5]decan-2-yl)-2,2-dimethyl-butyramide;

(SC-1148) cis-N-(Carbamoyl-methyl)-4-(8-dimethylamino-3-oxo-8-phenyl-2-azaspiro[4.5]decan-2-yl)-2,2-dimethyl-butyramide;

(SC-1149) cis-4-(8-Dimethylamino-3-oxo-8-phenyl-2-azaspiro[4.5]decan-2-yl)-2,2-dimethyl-N-(methylcarbamoyl-methyl)-butyramide;

(SC-1150) cis-4-(8-Dimethylamino-3-oxo-8-phenyl-2-azaspiro[4.5]decan-2-yl)-N-[(dimethyl-carbamoyl)-methyl]-2,2-dimethyl-butyramide;

(SC-1151) cis-4-(8-Dimethylamino-3-oxo-8-phenyl-2-azaspiro[4.5]decan-2-yl)-2,2-dimethyl-N-(2-methyl-sulfonyl-ethyl)-butyramide;

(SC-1152) cis-4-(8-Dimethylamino-3-oxo-8-phenyl-2-azaspiro[4.5]decan-2-yl)-N-(1,1-dioxo-thian-4-yl)-2,2-dimethyl-butyramide;

(SC-1153) cis-4-(8-Dimethylamino-3-oxo-8-phenyl-2-azaspiro[4.5]decan-2-yl)-N-[(1,1-dioxo-thian-4-yl)-methyl]-2,2-dimethyl-butyramide;

(SC-1154) cis-3-(8-Dimethylamino-3-oxo-8-phenyl-2-azaspiro[4.5]decan-2-yl)-N-methyl-propionamide;

(SC-1155) cis-1-(8-Dimethylamino-8-phenyl-2-azaspiro[4.5]decan-2-yl)-2-pyridin-2-yl-ethanone;

(SC-1156) cis-1-(8-Dimethylamino-8-phenyl-2-azaspiro[4.5]decan-2-yl)-2-pyridin-3-yl-ethanone;

(SC-1157) cis-1-(8-Dimethylamino-8-phenyl-2-azaspiro[4.5]decan-2-yl)-2-pyridin-4-yl-ethanone;

(SC-1158) cis-1-(8-Dimethylamino-8-phenyl-2-azaspiro[4.5]decan-2-yl)-3-pyridin-2-yl-propan-1-one;

(SC-1159) cis-1-(8-Dimethylamino-8-phenyl-2-azaspiro[4.5]decan-2-yl)-3-pyridin-3-yl-propan-1-one;

(SC-1160) cis-1-(8-Dimethylamino-8-phenyl-2-azaspiro[4.5]decan-2-yl)-3-pyridin-4-yl-propan-1-one;

(SC-1161) cis-1-(8-Dimethylamino-8-phenyl-2-azaspiro[4.5]decan-2-yl)-4-pyridin-2-yl-butan-1-one;

(SC-1162) cis-N-[3-(8-Dimethylamino-8-phenyl-2-azaspiro[4.5]decan-2-yl)-3-oxo-propyl]-acetamide;

(SC-1163) cis-N-[2-(8-Dimethylamino-8-phenyl-2-azaspiro[4.5]decan-2-yl)-2-oxo-ethyl]-acetamide;

(SC-1164) cis-1-(8-Dimethylamino-8-phenyl-2-azaspiro[4.5]decan-2-yl)-3-phenyl-propan-1-one;

(SC-1165) cis-1-(8-Dimethylamino-8-phenyl-2-azaspiro[4.5]decan-2-yl)-3-(2-methoxyphenyl)-propan-1-one;

(SC-1166) cis-1-(8-Dimethylamino-8-phenyl-2-azaspiro[4.5]decan-2-yl)-3-(3-methoxyphenyl)-propan-1-one;

(SC-1167) cis-1-(8-Dimethylamino-8-phenyl-2-azaspiro[4.5]decan-2-yl)-3-(4-methoxyphenyl)-propan-1-one;

(SC-1168) cis-1-(8-Dimethylamino-8-phenyl-2-azaspiro[4.5]decan-2-yl)-4-pyridin-4-yl-butan-1-one;

(SC-1169) cis-1-(8-Dimethylamino-8-phenyl-2-azaspiro[4.5]decan-2-yl)-4-pyridin-3-yl-butan-1-one;

(SC-1170) cis-[3-(8-Dimethylamino-3-oxo-8-phenyl-2-azaspiro[4.5]decan-2-yl)-propyl]-pyridine-2-carboxylic acid amide;

(SC-1171) cis-[3-(8-Dimethylamino-3-oxo-8-phenyl-2-azaspiro[4.5]decan-2-yl)-propyl]-pyridine-3-carboxylic acid amide;

(SC-1172) cis-N-[3-(8-Dimethylamino-3-oxo-8-phenyl-2-azaspiro[4.5]decan-2-yl)-propyl]-pyridine-4-carboxylic acid amide;

(SC-1173) cis-N-[3-(8-Dimethylamino-3-oxo-8-phenyl-2-azaspiro[4.5]decan-2-yl)-propyl]-pyrimidine-5-carboxylic acid amide;

(SC-1174) cis-[3-(8-Dimethylamino-3-oxo-8-phenyl-2-azaspiro[4.5]decan-2-yl)-propyl]-5-methyl-oxazole-4-carboxylic acid amide;

(SC-1175) cis-[3-(8-Dimethylamino-3-oxo-8-phenyl-2-azaspiro[4.5]decan-2-yl)-propyl]-pyrimidine-4-carboxylic acid amide;

(SC-1176) cis-N-[3-(8-Dimethylamino-3-oxo-8-phenyl-2-azaspiro[4.5]decan-2-yl)-propyl]-3-methyl-pyrazine-2-carboxylic acid amide;

(SC-1177) cis-N-[3-(8-Dimethylamino-3-oxo-8-phenyl-2-azaspiro[4.5]decan-2-yl)-propyl]-3-methyl-isoxazole-5-carboxylic acid amide;

(SC-1178) cis-N-[3-(8-Dimethylamino-3-oxo-8-phenyl-2-azaspiro[4.5]decan-2-yl)-propyl]-benzamide;

(SC-1179) cis-8-Dimethylamino-2-[2,2-dimethyl-3-(4-methylsulfonyl-piperazin-1-yl)-3-oxo-propyl]-8-phenyl-2-azaspiro[4.5]decan-3-one;

(SC-1180) cis-2-(8-Dimethylamino-3-oxo-8-phenyl-2-azaspiro[4.5]decan-2-yl)-N-(1,1-dioxo-thian-4-yl)-acetamide;

(SC-1181) cis-3-(8-Dimethylamino-3-oxo-8-phenyl-2-azaspiro[4.5]decan-2-yl)-2,2-dimethyl-N-(2-methyl-sulfonyl-ethyl)-propionamide;

(SC-1182) cis-8-Dimethylamino-2-[2,2-dimethyl-3-oxo-3-(3-oxo-piperazin-1-yl)-propyl]-8-phenyl-2-azaspiro[4.5]decan-3-one;

(SC-1183) cis-2-(8-Dimethylamino-3-oxo-8-phenyl-2-azaspiro[4.5]decan-2-yl)-N-[(1,1-dioxo-thian-4-yl)-methyl]-acetamide;

(SC-1184) cis-3-(8-Dimethylamino-3-oxo-8-phenyl-2-azaspiro[4.5]decan-2-yl)-2,2-dimethyl-N-(2-pyrimidin-5-yl-ethyl)-propionamide;

(SC-1185) cis-4-(8-Dimethylamino-3-oxo-8-phenyl-2-azaspiro[4.5]decan-2-yl)-N-(2-hydroxy-ethyl)-2,2-dimethyl-butyramide;

(SC-1186) cis-4-(8-Dimethylamino-3-oxo-8-phenyl-2-azaspiro[4.5]decan-2-yl)-N-(3-hydroxy-propyl)-2,2-dimethyl-butyramide;

(SC-1187) cis-4-(8-Dimethylamino-3-oxo-8-phenyl-2-azaspiro[4.5]decan-2-yl)-N-(3-hydroxy-3-methyl-butyl)-2,2-dimethyl-butyramide;
(SC-1189) cis-8-Dimethylamino-2-[4-(1,1-dioxo-[1,4]thiazinan-4-yl)-3,3-dimethyl-4-oxo-butyl]-8-phenyl-2-azaspiro[4.5]decan-3-one;
(SC-1190) cis-2-(8-Dimethylamino-3-oxo-8-phenyl-2-azaspiro[4.5]decan-2-yl)-N-(5-methoxy-pyrazin-2-yl)-acetamide;
(SC-1191) cis-2-(8-Dimethylamino-3-oxo-8-phenyl-2-azaspiro[4.5]decan-2-yl)-N-(3-hydroxy-3-methyl-butyl)-acetamide;
(SC-1192) cis-N-[3-(8-Dimethylamino-3-oxo-8-phenyl-2-azaspiro[4.5]decan-2-yl)-propyl]-2-isoxazol-3-yl-acetamide;
(SC-1193) cis-N-[3-(8-Dimethylamino-3-oxo-8-phenyl-2-azaspiro[4.5]decan-2-yl)-propyl]-4-methyl-isoxazole-5-carboxylic acid amide;
(SC-1194) cis-4-[2-(8-Dimethylamino-3-oxo-8-phenyl-2-azaspiro[4.5]decan-2-yl)-ethyl]-tetrahydro-pyran-4-carboxylic acid 2,2,2-trifluoro acetate
(SC-1195) cis-4-[2-(8-Dimethylamino-3-oxo-8-phenyl-2-azaspiro[4.5]decan-2-yl)-ethyl]-1,1-dioxo-thiane-4-carboxylic acid 2,2,2-trifluoro acetate
(SC-1198) cis-N-Butyl-2-(8-dimethylamino-3-oxo-8-phenyl-2-azaspiro[4.5]decan-2-yl)-acetamide;
(SC-1199) cis-N-(Cyclopropyl-methyl)-2-(8-dimethylamino-3-oxo-8-phenyl-2-azaspiro[4.5]decan-2-yl)-acetamide;
(SC-1200) cis-2-(8-Dimethylamino-3-oxo-8-phenyl-2-azaspiro[4.5]decan-2-yl)-N-propyl-acetamide;
(SC-1201) cis-2-(8-Dimethylamino-3-oxo-8-phenyl-2-azaspiro[4.5]decan-2-yl)-acetic acid
(SC-1202) methyl 2-((trans-8-(dimethylamino)-3-oxo-8-phenyl-2-azaspiro[4.5]decan-2-yl)methyl) benzoate;
in the form of an individual stereoisomer or mixture thereof, the free compound and/or its physiologically acceptable salt and/or solvate.

13. A medicament containing at least one compound as claimed in claim 1 in the form of an individual stereoisomer or mixture thereof, the free compound and/or its physiologically acceptable salt and/or solvate, and optionally suitable additives and/or auxiliary substances and/or optionally further active compounds, wherein the optionally further active compounds are selected from the group consisting of opioids and anaesthetics.

14. A method of treating pain, comprising administering a therapeutically active dose of a compound as claimed in claim 1 in the form of an individual stereoisomer or mixture thereof, the free compound and/or its physiologically acceptable salt and/or solvate.

15. A method of treating at least one disease or disorder selected from the group consisting of anxiety, stress, syndromes associated with stress, depression, epilepsy, Alzheimer's disease, senile dementia, general cognitive dysfunctions, learning and memory disorders (as a nootropic), withdrawal symptoms, alcohol abuse, drug abuse, medicament abuse, dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, or urinary incontinence, or for administering a compound as a muscle relaxant, anticonvulsive or anaesthetic, or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids, comprising administering to a patient in need thereof a therapeutically effective dose of a compound as claimed in claim 1 in the form of an individual stereoisomer or mixture thereof, the free compound and/or its physiologically acceptable salt and/or solvate.

* * * * *